US007009045B2

(12) United States Patent
Abbas et al.

(10) Patent No.: US 7,009,045 B2
(45) Date of Patent: Mar. 7, 2006

(54) TRANSFORMATION SYSTEMS FOR FLAVINOGENIC YEAST

(75) Inventors: Charles Abbas, Champaign, IL (US);
Andrii Y. Voronovsky, Lviv (UA);
Liubov R. Fayura, Lviv (UA);
Barbara V. Kshanovska, Lviv (UA);
Kostiantyn V. Dmytruk, Lviv (UA);
Kateryna A. Sibirna, Lviv (UA);
Andrii A. Sibirny, Lviv (UA)

(73) Assignee: Archer-Daniels-Midland Company, Decatur, IL (US)

(*) Notice: Subject to any disclaimer, the term of this patent is extended or adjusted under 35 U.S.C. 154(b) by 299 days.

(21) Appl. No.: 09/903,508

(22) Filed: Jul. 13, 2001

(65) Prior Publication Data

US 2003/0082815 A1    May 1, 2003

Related U.S. Application Data

(60) Provisional application No. 60/218,244, filed on Jul. 14, 2000, provisional application No. 60/290,667, filed on May 15, 2001, provisional application No. 60/288,491, filed on May 4, 2001.

(51) Int. Cl.
C07H 21/04    (2006.01)
C12N 1/16     (2006.01)
C12N 15/81    (2006.01)

(52) U.S. Cl. .............. 536/24.1; 435/320.1; 435/440; 435/471; 435/476; 435/483; 435/243; 435/255.1; 435/255.4; 435/255.5; 536/23.1

(58) Field of Classification Search ............ 536/23.1, 536/24.1; 435/320.1, 440, 471, 476, 483, 435/243, 255.1, 255.4, 255.5
See application file for complete search history.

(56) References Cited

U.S. PATENT DOCUMENTS

| 3,932,390 A | 1/1976 | Daigle et al. |
| 4,102,923 A | 7/1978 | Pepperman, Jr. et al. |
| 4,745,057 A | 5/1988 | Beckage et al. |
| 4,794,081 A | 12/1988 | Kawai et al. |
| 4,808,537 A | 2/1989 | Stroman et al. |
| 4,837,148 A | 6/1989 | Cregg |
| 4,855,231 A | 8/1989 | Stroman et al. |
| 4,879,231 A | 11/1989 | Stroman et al. |
| 4,882,279 A | 11/1989 | Cregg |
| 4,885,242 A | 12/1989 | Cregg |
| 4,925,794 A | 5/1990 | Isogai et al. |
| 4,929,555 A | 5/1990 | Cregg et al. |
| 4,935,350 A | 6/1990 | Patel et al. |
| 4,937,193 A | 6/1990 | Hinchliffe et al. |
| 4,943,529 A | 7/1990 | Van den Berg et al. |
| 4,990,446 A | 2/1991 | Oberto et al. |
| 4,997,767 A | 3/1991 | Nozaki et al. |
| 5,041,384 A | 8/1991 | Wilson et al. |
| 5,118,625 A | 6/1992 | Aiba et al. |
| 5,120,655 A | 6/1992 | Foster et al. |
| 5,126,248 A | 6/1992 | Matsuyama et al. |
| 5,135,868 A | 8/1992 | Cregg |
| 5,164,303 A | 11/1992 | Heefner et al. |
| 5,210,023 A | 5/1993 | Grimmer et al. |
| 5,212,087 A | 5/1993 | Fournier et al. |
| 5,231,007 A | 7/1993 | Heefner et al. |
| 5,268,273 A | 12/1993 | Buckholz |
| 5,334,510 A | 8/1994 | Usui et al. |
| 5,460,949 A | 10/1995 | Saunders et al. |
| 5,589,355 A | 12/1996 | Koizumi et al. |
| 5,665,600 A | 9/1997 | Hagenson et al. |
| 5,700,643 A | 12/1997 | Kawasaki |
| 5,716,808 A | 2/1998 | Raymond |
| 5,736,383 A | 4/1998 | Raymond |
| 5,817,503 A | 10/1998 | Chambon et al. |
| 5,821,090 A | 10/1998 | Revuelta Doval et al. |
| 5,837,528 A | 11/1998 | Perkins et al. |
| 5,854,039 A * | 12/1998 | Raymond et al. ........... 435/490 |
| 5,866,404 A | 2/1999 | Bradshaw et al. |
| 5,871,957 A | 2/1999 | Kawasaki et al. |
| 5,891,672 A | 4/1999 | Wang et al. |
| 5,925,538 A | 7/1999 | Perkins et al. |
| 5,932,701 A | 8/1999 | Black et al. |
| 6,001,597 A | 12/1999 | Raymond et al. |
| 6,017,728 A | 1/2000 | Black et al. |
| 6,146,866 A | 11/2000 | Viitanen et al. |

(Continued)

FOREIGN PATENT DOCUMENTS

EP    0 967 287 A2    12/1999

(Continued)

OTHER PUBLICATIONS

Clyne et al. Identification of autonomously replicating sequence (ARS) elements in eukaryotic cells. Methods 13: 221-233, 1997.*

(Continued)

*Primary Examiner*—James Ketter
*Assistant Examiner*—David A. Lambertson
(74) *Attorney, Agent, or Firm*—Craig G. Cochenour; Duane A. Stewart, III; Buchanan Ingersoll PC

(57) ABSTRACT

This invention is directed to the transformation of the flavinogenic yeasts, *Pichia guilliermondii* and *Candida famata*, and mutants thereof, by electroporation (electrotransformation) and by spheroplast transformation. The invention is also directed to nucleic acid constructs such as vectors, plasmids, and ARS sequences which transform flavinogenic yeasts, and mutants thereof, at a high level and in a stable manner so as to result in stably transformed yeast host cells which express/produce recombinant products. This invention also is directed to flavinogenic yeasts, *Pichia guilliermondii* and *Candida famata*, and mutants and temperature sensitive mutants thereof, which produce or overproduce riboflavin.

19 Claims, 40 Drawing Sheets

U.S. PATENT DOCUMENTS 6,376,222 B1     4/2002     Babyak et al.

FOREIGN PATENT DOCUMENTS

WO     WO 91/18103 A1     11/1991
WO     WO 95/26406     10/1995
WO     WO 99/61623     12/1999

OTHER PUBLICATIONS

Seifert, H.S., et al., "Shuttle mutagenesis: A method of transposon mutagenesis for *Saccharomyces cerevisiae*," *Proc. Natl. Acad. Sci. USA 83*:735-739, The National Academy of Sciences (1986).

Tan, X., et al., "The *Hansenula polymorpha* PER8 Gene Encodes a Novel Peroxisomal Integral Membrane Protein Involved in Proliferation," *J. Cell Biol. 128*:307-319, The Rockefeller University Press (1995).

Database EMBL 'Online!, Database Entry SC35112, Database Accession No. U35112 (1995).

Database EMBL 'Online!, Database Entry AF347016, Database Accession No. AF347016 (Mar. 19, 2001).

International Search Report for International Patent Application No. PCT/US01/22083, mailed Oct. 10, 2002.

Becker, D.M., and Guarente, L., "High-Efficiency Transformation of Yeast by Electroporation," *Meth. Enzymol. 194*:182-187, Academic Press, Inc. (1991).

Birnboim, H.C., and Doly, J., "A rapid alkaline extraction procedure for screening recombinant plasmid DNA," *Nucl. Acids Res. 7*:1513-1523, Oxford University Press (1979).

Boretsky, Y., et al., "Identification of an ARS element and development of a high efficiency transformation system for *Pichia guilliermondii*," *Curr. Genet. 36*:215-221, Springer-Verlag (Oct. 1999).

Cannon, R.D., et al., "Isolation and nucleotide sequence of an autonomously replicating sequence (ARS) element functional in *Candida albicans* and *Saccharomyces cerevisiae*," *Mol. Gen. Genet. 221*:210-218, Springer-Verlag (1990).

Clyne, R.K., and Kelly, T.J., "Genetic analysis of an ARS element from the fission yeast *Schizosaccharomyces pombe*," *EMBO J. 14*:6348-6357, Oxford University Press (1995).

Cregg, J.M., et al., "*Pichia pastoris* as a Host System for Transformations," *Mol. Cell. Biol. 5*:3376-3385, American Society for Microbiology (1985).

Dialog File 351, Accession No. 12891639, Derwent WPI English Language abstract for WO99/61623 (Document AN1).

Dialog File 351, Accession No. 10444341, Derwent WPI English Language abstract for WO 95/26406 (Document AL1).

Faber, K.N., et al., 'Highly-efficient electrotransformation of the yeast *Hansenula polymorpha*,' *Curr. Genet. 25*:305-310, Springer-Verlag (1994).

Fayura, L.R., and Kashchenko, V.E., "Thermostable riboflavin kinase in yeast *Pichia guilliermondii*," *Ukr. Biokim. Zh. 69*:21-25, Naukova Dumka (1997). An English language abstract is at the end of the document.

Fedorovych, D., et al., "Hexavalent chromium stimulation of riboflavin synthesis in flavinogenic yeast," *Biometals 14*:23-31, Kluwer Academic Publishers (Mar. 2001).

Iimura, Y., et al., "Yeast Transformation without the Spheroplasting Process," *Agric. Biol. Chem. 47*:897-901, The Agricultural Chemical Society of Japan (1983).

Kasüske, A., et al., "Efficient Electropulse Transformation of Intact *Candida maltosa* Cells by Different Homologous Vector Plasmids," *Yeast 8*:691-697, John Wiley & Sons (1992).

Klinner, U., et al., "Hybridization of *Pichia guilliermondii* by Protoplast Fusion," in *Advances in Protoplast Research: Proceedings of the 5th International Protoplast Symposium*, Ferenczy, L. and G.L. Farkas, eds., Pergamon Press, pp. 113-118 (1980).

Kunze, G., et al., "Transformation of the industrially important yeasts *Candida maltosa* and *Pichia guilliermondii*," *J. Basic. Microbiol. 25*:141-144, Akademie-Verlag (1985).

Kunze, G., et al., "Transformation of *Candida maltosa* and *Pichia guilliermondii* by a plasmid containing *Saccharomyces cerevisiae* ARG4 DNA," *Curr. Genet. 9*:205-209, Springer-Verlag (1985).

Kunze, G., et al., "Transformation of the Industrially Important Yeasts *Candida maltosa* and *Pichia guilliermondii*," *Acta Biotechnol. 6*:28, Akademie-Verlag (1986).

Liauta-Teglivets, O., et al., "Molecular Cloning of the GTP-Cyclohydrolase Structural Gene RIB1 of *Pichia guillermondii* Involved in Riboflavin Biosynthesis," *Yeast 11*:945-952, John Wiley & Sons (1995).

Logvinenko, E.M., et al., "Biosynthesis of 6,7-dimethyl-8-ribityllumazine in Extracts of the Yeast *Pichia guilliermondii*," Biokhimiya (Biochemistry) 47:778-783, Plenum Publishing Corp. Consultants Bureau, Plenum, New York (1982).

Logvinenko, E.M., et al., "Cloning of the RIB7 Gene Encoding the Riboflavin Synthase of the Yeast *Pichia guilliermondii*," *Genetika 29*:922-927, MAIK Nauka (1993). An English language abstract is at the end of the document.

Mauersberger, S., et al., "*Candida maltosa*," Chapter 12; Nonconventional Yeasts in Biotechnology: A Handbook, Wolf, K. ed., Springer-Verlag, pp. 411-580 (1996).

Neilhoc, E., et al., "High Efficiency Transformation of Intact Yeast Cells by Electric Field Pulses," *Bio/Technol. 8*:223-227, Nature Publishing Co. (1990).

Neistat, M.A., et al., "Transformation of *Hansenula polymorpha, Pichia guilliermondii, Williopsis saturnus* Yeasts by a Plasmid Carrying the ADE2 Gene of *Saccharomyces cerevisiae*," *Mol. Gen. Mikrobiol. Virusol. 12*: 19-23, Meditsina, (1986). An English language abstract is at the end of the document.

Piredda S., and Gaillardin, C., "Development of a Transformation System for the Yeast *Yamadazyma (Pichia) ohmeri*," *Yeast 10*:1601-1612, John Wiley & Sons (1994).

Pla, J., et al., "Cloning of the *Candida albicans* HIS1 gene by direct complementation of a *C. albicans* histidine auxotroph using an improved double-ARS shuttle vector," *Gene 165*:115-120, Elsevier Science B.V. (1995).

Prillinger, H., et al., "Phytopathogenic Filamentous (Ashbya, Eremothecium) and Dimorphic Fungi (Holleya, Nematospora) with Needle-Shaped Ascospores as New Members Within the *Saccharomycetaceae*," *Yeast 13*:945-960, John Wiley & Sons (1997).

Reiser, J., et al., "Transfer and Expression of Heterologous Genes in Yeasts Other Than *Saccharomyces cerevisiae*," Adv. Biochem. Engin./Biotech 43:73-102 in *Applied Molecular Genetics*, J. Reiser, Springer-Verlag (1990).

Rose, M.D., and Roach, J.R., "Cloning Genes by Complementation in Yeast," *Meth. Enzymol. 194*:195-230, Academic Press, Inc. (1991).

Scorer, C.A., et al., "Rapid Selection Using G418 of High Copy Number Transformants of *Pichia pastoris* for High-level Foreign Gene Expression," *Bio/Technology 12*:181-184, Nature Publishing Co. (1994).

Shavlovskii, G.M., et al., "Flavinogenous Mutant of the Yeast *Pichia guilliermondii* with Damaged Transport of Iron," *Mikrobiologiia 45*:313-318, Nauka (1976). An English language abstract is at the end of the document.

Shavlovskii, G.M., et al., "Activity of the second step flavinogenesis enzyme, 2,5-diamino-6-hydroxy-4-ribosylaminopyrimidine-5'-phosphate reductase, in the yeast *Pichia guilliermondii*," Mikrobiologiya/Microbiology 50: 752-755, Consultants Bureau, New York, Plenum Publishing Corp. (1981).

Sherman, F., et al., "Laboratory Course Manual for Methods in Yeast Genetics," Cold Spring Harbor Laboratory Press, pp. 91-103,117-122(1986).

Sibirnyi, A.A., et al., "Active Transport of Riboflavin in the Yeast *Pichia guilliermondii*. Detection and Some Properties of the Cryptic Riboflavin Permease," *Biokhimiia 42*:1841-1851, Nauka (1977). An English language abstract is at the end of the document.

Sibirnyi, A.A., et al., "Effect of Glucose and its Derivates on Systems of Riboflavin Uptake and Excretion in Yeast *Pichia guilliermondii*," *Biokhimiia 43*:1414-1422, Nauka (1978). An English language abstract is at the end of the document.

Sibirnyi, A.A., and Shavlovskii, G.M., "On Inhibition of Alkaline Phosphatase I of *Pichia guilliermondii* Yeast in vitro and in vivo," *Ukr. Biokhim. Zh. 50*:212-217, Naukova dumka (1978). An English language abstract is at the end of the document.

Sibirny, A.A., "*Pichia guilliermondii*," in: Nonconventional Yeasts in Biotechnology: A Handbook, Wolf, K., ed., Springer-Verlag, pp. 255-275 (1996).

Sreekrishna, K., and Kropp, K.E., "*Pichia pastoris*," in Nonconventional Yeasts in Biotechnology, K. Wolf, ed., Springer-Verlag, pp. 215-226 (1996).

Stahmann, K.-P., et al., "Three biotechnical processes using *Ashbya gossypii, Candida famata,* or *Bacillus subtilis* complete with chemical riboflavin production," *Appl. Microbiol. Biotechnol. 53*:509-516, Springer-Verlag (May 2000).

Steiner, S., and Philippsen, P., "Sequence and promoter analysis of the highly expressed TEF gene of the filamentous fungus *Ashbya gossypii,*" *Mol. Gen. Genet. 242*:263-271, Springer-Verlag (1994).

Takagi, M., et al., "Construction of a Host-Vector System in *Candida maltosa* by Using an ARS Site Isolated from Its Genome," *J. Bacteriol. 167*:551-555, American Society for Microbiology (1986).

Thompson, J.R., et al., "An Improved Protocol for the Preparation of Yeast Cells for Transformation by Electroporation," *Yeast 14*:565-571, John Wiley & Sons (1998).

Voronovsky, A., and Sybirny, A.A., "Development of cloning and expression transformation systems for nonconventional yeasts," *Biopolymers and Cell 15*:122-132, Naukova Dumka (Mar.-Apr. 1999). An English language summary is at the end of the document.

Voronovsky, A.Y., "Development of Genetic Transformation Systems for the Flavinogenic Yeasts *Pichia guilliermondii* and *Candida famata*," Dissertation, pp. 1-138, Academy of Sciences of the Ukraine (Jun. 2001) (translation attached as document AS15).

Voronovsky, A.Y., "Development of Genetic Transformation Systems for the Flavinogenic Yeasts *Pichia guilliermondii* and *Candida famata*," pp. 1-97, Ralph McElroy Translation Company, Austin, Texas (Jun. 2001).

Yang, C., et al., "Conservation of ARS Elements and Chromosomal DNA Replication Origins on Chromosomes III of *Saccharomyces cerevisiae* and *S. carlsbergensis,*" *Genetics 152*:933-941, Genetics Society of America (Jul. 1999).

Yang, V.W., et al., "High-Efficiency Transformation of *Pichia stipitis* Based on Its URA3 Gene and a Homologous Autonomous Replication Sequence, ARS2," *Appl. Env. Microbiol. 60*:4245-4254, American Society for Microbiology (1994).

Zakalskii, A.E., et al., "Cloning of the RIB1 gene coding for the enzyme of the first stage of flavinogenesis in the yeast *Pichia guilliermondi*, GTP cyclohydrolase, in *Escherichia coli* cells," Genetika 26:614-620, MAIK Nauka (1990). An English language abstract is at the end of the document.

Zvjagilskaia, R.A., et al., "The Respiration System of the Yeast *Pichia guilliermondii* at Different Levels of Flavinogenesis," *Mikrobiologiia 47*: 975-984, Nauka (1978). An English language abstract is at the end of the document.

\* cited by examiner

<400> 1
```
cttgactgat tacgaattcg agctcggtac ccggggatca tgaatgctag tcttttttaca   60
ctgaatattt tttttaacgat ttttttaataa ttttgcaatc atttaagaaa aaccacaaat  120
ggttttccaa aatttaaatt gattttttag aaagtcctaa aaaatagaat cataccaaat  180
aaagaacaac ttaaagtcac tatgacaaat tcagaaatac aatcgtatga tccgttcatg  240
gataaagctg caaagtcaca agcaaggcta actaagatcc tctaggggga tcctctagag  300
tcgactacgt cgttaaggcc gtttctgaca gagtaaaatt cttgagggaa cttttcaccat 360
tatgggaaat ggttcaagaa ggtattgact taaactccat caaatggtca ggtcattgag  420
tgttttttat ttgttgtatt ttttttttttt tagagaaaat cctccaatat ataaattagg  480
aatcatagtt tcatgatttt tagagaaaat cctccaatat ataaattagg aatcatagtt  540
tcatgatttt ctgttacacc taacttttg tgtggngccc tcctccttgt caatattaat  600
ctgttacacc taacttttg tgtgggcccc tcctccttgt caatattaat gttaaagtgc  660
aattcttttt ccttatcacg ttgagccatt agtatcaatt gttaaagtgc aattctttt  720
ccttatcacg ttgagccatt agtatcaatt tgcttacctg tattccttta catcctcctt  780
tttctccttc ttgataaatg tgcttacctg tattccttta catcctcctt tttctccttc  840
ttgataaatg tatgtagatt gcgtatatag tttcgtctac cctatgaaca tattccattt  900
tatgtagatt gcgtatatag tttcgtctac cctatgaaca tattccattt tgtaatttcg  960
tgtcgnttct attatgaatt tcatttataa aggttatgtn tgtaatttcg ggcgtttcta 1020
ttatgaattt catttataaa gtttatgtcc aatatcataa aaaaagagaa tcttttttaag 1080
caanggattt cttaactcaa atatcataaa aaaagagaat cttttttaagc aagggatttt 1140
cttaactttnt tcggggacgc atccccgctt cggnggactg gtggaccct aaatctnttc 1200
ggcgacagca tcccgacttc ggnggnactg tggaaccct aaatcccagt ntgatcctgc 1260
ttccaaanct tttactggtn ttcatgggcc taccccagtt ctgaacctgc atccaaanct 1320
tttactgctc ttcaagggct taccttntca ggcaggtcaa tgacaattca catcntgcnc 1380
anacnaaaaa nggcttttca gcaggtcaan gcaatttcac atcntgcnca aaaananagt 1440
ggcgatnggg tgacctntnt ttggcaacga tngggtgacc tatnttttgca aac        1493
```

FIG.15

```
tatgcacatt cgcacgccga ggtgcagcgt ttaggcgcgg ctcaacggaa gccaacggcc  60
gccacaaatt gtccggaaag tcgccgaaac tgatccactg gtaccacagc cccataagaa 120
ccccctttaa tattaaaaac cgttcttcag ccacttttga tcacattgtt tgcagccgcc 180
cgttgctgcc atccaaacac cacgcgtccc ccgcacccgg ttacggtgcc cactgcattg 240
gaatttgcat aaaacagcct cacgaagtgg attaattttt agagcactca agtcatcatg 300
ctgcaatctc tgcatcatga aatgactccc gttgatacag ggaactcaga ccgcaagcgg 360
cgaagagtca caagagcgtg tgatgtgtgt cgactctaga ggatccccgg gtac       414
```

FIG.16

```
tgattacgaa ttcgagctcg gtacccgggg atcatgaatg ctagtctttt tacactgaat  60
attttttttaa cgattttttta ataattttgc aatcatttaa gaaaaaccac aaatggtttt 120
ccaaaattta aattgatttt ttagaaagtc ctaaaaaata gaatcatacc aaataaagaa 180
caacttaaag tcactatgac aaattcagaa atacaatcgt atgatccgtt catggataaa 240
gctgcaaagt cacaagcaag gctaactaag atcctctaga gtcgactacg tcgttaaggc 300
cgtttctgac agagtaaaat tcttgaggga actttcacca ttatgggaaa tggttcaaga 360
aggtattgac ttaaactcca tcaaatggtc aggtcattga gtgttttttta tttgntgtat 420
tttttttttt ttagagaaaa tcctccaata tataaattag gaatcatagt ttcatgattt 480
tctgtta                                                             487
```

FIG.20

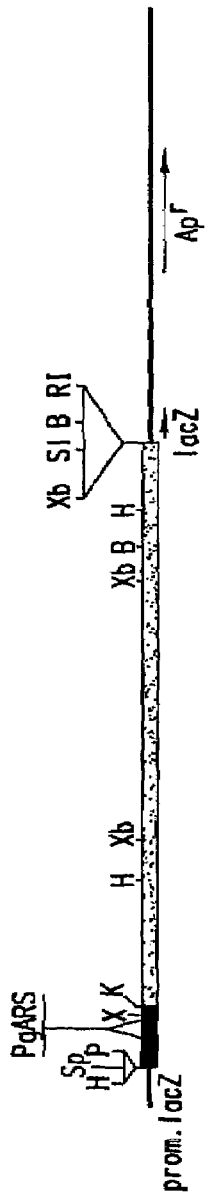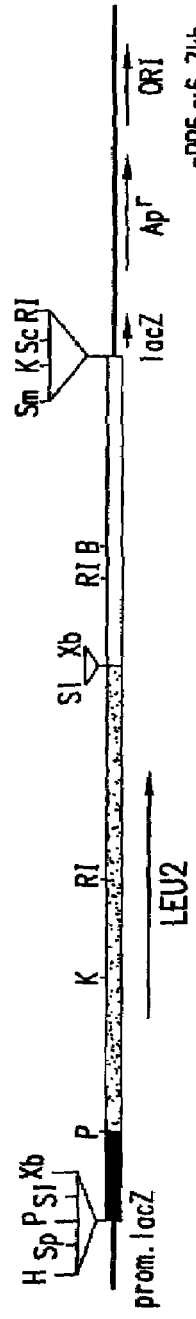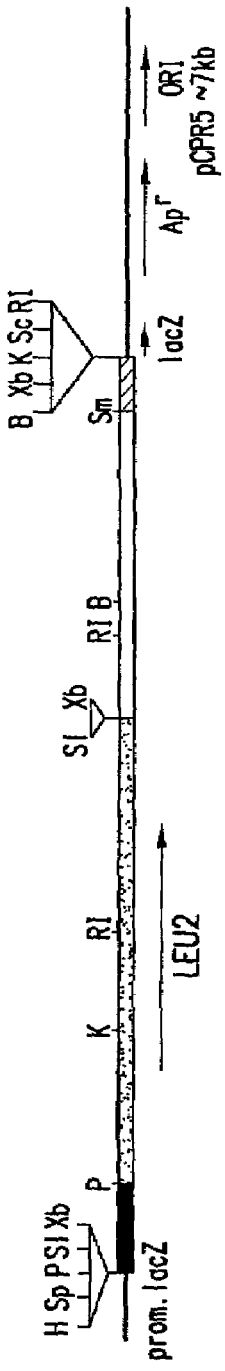

TRANSFORMATION SYSTEMS FOR FLAVINOGENIC YEAST

CROSS-REFERENCE TO RELATED APPLICATIONS

This application claims benefit to the filing dates of U.S. Provisional Application No. 60/218,244, filed Jul. 14, 2000; U.S. Provisional Application No. 60/288,491, filed May 4, 2001; and U.S. Provisional Application No. 60/290,667, filed May 15, 2001, each of which is herein incorporated by reference.

BACKGROUND OF THE INVENTION

1. Field of the Invention

The present invention relates, in general, to the fields of yeast transformation, yeast cells thereby transformed and production of recombinant products therefrom. More specifically, the present invention relates to the transformation of yeast by electroporation and spheroplast formation.

2. Background Art

Riboflavin (vitamin $B_2$) is synthesized by all plants and many microorganisms, but is not produced by higher animals. Because it is a precursor to coenzymes such as flavin adenine dinucleotide and flavin mononucleotide, that are required in the enzymatic oxidation of carbohydrates, riboflavin is essential to basic metabolism. In higher animals, insufficient riboflavin can cause loss of hair, inflammation of the skin, vision deterioration, and growth failure.

The availability of means for the production of recombinant products, such as industrial enzymes, pharmaceutical proteins and products, vitamins, and cofactors, in eukaryotic systems such as yeast, provides significant advantages relative to the use of prokaryotic systems such as *E. coli* for the production of those products encoded by, or synthesized as a result of, recombinant nucleic acids. Yeast can generally be grown to higher cell densities than bacteria and are readily adaptable to continuous fermentation processing.

The development of yeast species as host/vector systems for the production of recombinant products is severely hampered by the lack of knowledge about transformation conditions and suitable means for stably introducing foreign nucleic acids into the yeast host cell. In addition, auxotrophic mutants are often not available, precluding a direct selection for transformants by auxotrophic complementation. New host/vector systems must be devised which facilitate the manipulation of nucleic acids as well as optimize the expression of inserted nucleic acid sequences so that the desired recombinant products can be prepared under controlled conditions and in high yield in yeast.

1. Methods of Transformation a. Transformation by Electroporation

Becker et al. (*Methods in Enzymology* 194: 182–187 (1991)) relates to highly efficient methods of transformation of the yeast *Saccharomyces cerevisiae*. Becker also discloses spheroplast transformation.

Faber et al. (*Curr. Genet.* 25: 305–310(1994)) relates to a highly efficient method for transformation of the methylotropic yeast *Hansenula polymorpha*. Faber also applied the method to *Pichia methanolica*.

Kasütske et al. (*Yeast* 8: 691–697 (1992)) relates to efficient electropulse transformation of intact *Candida maltosa* cells by different homologous vector plasmids.

Meilhoc et al. (*Bio/Technology* 8: 223–227 (1990)) relates to a high efficiency transformation system using intact *Saccharomyces cerevisiae* yeast cells and electric field pulses.

Piredda et al. (*Yeast* 10: 1601–1612 (1994)) relates to development of a transformation system for the yeast *Yamadazyma* (*Pichia*) *ohmeri*.

Scorer et al. (*Bio/Technology* 12: 181–184 (1994)) relates to *P. pastoris* vectors allowing for rapid G418 selection of rare high copy number transformants for high level of expression in *Pichia pastoris* using both electroporation and spheroplast transformation systems.

Sherman et al. (*Laboratory Course Manual for Methods in Yeast Genetics*, pages 91–102, Cold Spring Harbor Laboratory (1986)) relates to a transformation of yeast mutants LEU2 and HIS3.

Thompson et al. (*Yeast* 14:565–571 (1998)) relates to an improved protocol for the preparation of yeast cells such as *Saccharomyces cerevisiae* and *Candida albicans* for transformation by electroporation.

Yang et al. (*Applied and Environmental Microbiology* 60(12): 4245–4254 (1994)) relates to high efficiency transformation of *Pichia stipitis* based on its URA3 gene and a homologous autonomous replication sequence ARS2. The method of transformation is by electroporation.

U.S. Pat. No. 5,716,808 to Raymond relates to methods for preparing *Pichia methanolica* cells containing foreign DNA constructs using electroporation and methods for producing foreign peptides in *Pichia methanolica* cells.

b. Transformation by Spheroplast Formation

Becker et al. (*Methods in Enzymology* 194: 182–187 (1991)) relates to highly efficient methods of transformation of the yeast *Saccharomyces cerevisiae*. Becker also discloses spheroplast transformation.

Scorer et al. (*Bio/Technology* 12: 181–184 (1994) relates to *P. pastoris* vectors allowing for rapid G418 selection of rare high copy number transformants for high level of expression in *Pichia pastoris* using both electroporation and spheroplast transformation systems.

U.S. Pat. No. 4,808,537 to Stroman et al. relates to a method for isolating and cloning methanol inducible gene from *Pichia pastoris* and the regulatory regions useful for the methanol regulation expression of heterologous genes. Stroman used spheroplast transformation.

U.S. Pat. No. 4,837,148 to Cregg et al. relates to autonomous replication sequences which are capable of maintaining plasmids as extra-chromosomal elements in host strains of *Pichia*. The patent further relates to constructs including the DNA sequences as well as transformed organisms produced by spheroplast formation. The patent additionally provides processes for producing the DNA sequences and constructs of the invention, as well as methods for isolating the sequences from any source.

U.S. Pat. No. 4,855,231 to Stroman et al. relates to DNA sequences which are responsive to the presence of methanol, catabolite non-repressing carbon sources and carbon source starvation. The '231 patent demonstrates spheroplast transformation of *Pichia pastoris*.

U.S. Pat. No. 4,879,231 to Stroman et al. relates to a spheroplast transformation method for the yeast such as *Pichia pastoris*.

U.S. Pat. No. 4,882,279 to Cregg et al. relates to a spheroplast transformation technique for yeasts of the genus *Pichia*. The '279 patent specifically embodies *Pichia pastoris*.

U.S. Pat. No. 5,135,868 to Cregg relates to a method for the site specific genomic modification of yeasts of the genus *Pichia*. The '868 patent uses a spheroplast transformation method.

U.S. Pat. No. 5,268,273 to Buckholz relates to a method of spheroplast transformation of *Pichia pastoris*.

U.S. Pat. No. 5,736,383 to Raymond relates to a method of transformation of yeast strains of the genus *Pichia*, particularly *Pichia methanolica*. The '383 patent further relates to a method of spheroplast transformation of yeasts of the genus *Pichia* as well as a method of transformation by electroporation.

c. Other Transformation Systems

Kunze et al. (*Current Genetics* 9(3): 205–209 (1985)) relates to a method of transformation of *Saccharomyces cerevisiae, Candida maltosa* and *Pichia guilliermondii* G266. *Saccharomyces cerevisiae, Candida maltosa* and *Pichia guilliermondii* G266 have been transformed by the plasmid pYe(ARG4)411 which contains the *S. cerevisiae* ARG4 gene inserted into pBR322. Kunze used $CaCl_2$ in the method of transformation.

Kunze et al. (*J. Basic Microbiol.* 25(2): 141–144 (1985)) relates to a method of transformation of the industrially important yeasts *Candida maltosa* and *Pichia guilliermondii* G266 using $CaCl_2$.

Kunze et al. (*Acta Biotechnol.* 6(1): 28 (1986) relates to transformations of the industrially important yeasts *Candida maltosa* and *Pichia guilliermondii*.

Neistat et al. (*Mol. Ge. Mikrobiol. Virusol.* 12: 19–23 (1986))(Abstract only) relates to transformation of *Hansenula polymorpha, Pichia guilliermondii, Williopsis saturnus* yeast by a plasmid carrying the ADE2 gene of *Saccharomyces cerevisiae*. The method of transformation is not disclosed.

U.S. Pat. No. 4,929,555 to Cregg et al. relates to a method for making whole cells of methylotrophic species of genus *Pichia* competent for transformation by DNA and a method for transforming with DNA whole cells of such species, particularly *Pichia pastoris*.

U.S. Pat. No. 5,231,007 to Heefner et al. relates to a method of generating and isolating highly flavinogenic strains of *Candida famata* which produce riboflavin yields of around 7.0 to 7.5 grams per liter per 6 days. The method includes a combination of iterative mutagenizing steps and protoplast fusion steps performed on the parent strain and the descendent strains which are selected following each step according to a screening protocol.

2. Vectors, ARS Elements and Gene Libraries

Clyne, R. K. et al. (*EMBO J.* 14(24): 6348–6357 (1995)) relates to a fine structure analysis of ARS1, an ARS element of the fission yeast *Schizosaccharomyces pombe*. Characterization of a series of nested deletion mutations indicated that the minimal fragment of DNA encompassing ARS1 is large since no fragment under 650 bp retained significant ARS activity.

Liauta-Teglivets, O. et al. (*Yeast* 11(10): 945–952 (1995)) relates to the cloning of the structural gene of GTP-cyclohydrolase involved in riboflavin biosynthesis from a *Pichia guilliermondii* genomic library.

Cannon, R. D. et al. (*Mol. Gen. Genet.* 221(2): 210–218 (1990)) relates to isolation and nucleotide sequence of an autonomously replicating sequence (ARS) element functional in *Candida albicans* and *Saccharomyces cerevisiae*.

Takagi, M. et al. (*J. Bacteriol.* 167(2): 551–555 (1986)) relates to construction of a host-vector system in *Candida maltosa* by using an ARS site isolated from its genome.

Pla, J. et al. (*Gene* 165(1): 115–120(1995)) relates to ARS2 and ARS3 *Candida albicans* DNA fragments with autonomous replicating activity shown to promote non-integrative genetic transformation of both *Candida albicans* and *Saccharomyces cerevisiae*.

U.S. Pat. No. 5,212,087 to Fournier et al. relates to ARS sequences which are efficacious in *Yarrowia lipolytica* as well as plasmids carrying these sequences.

U.S. Pat. No. 5,665,600 to Hagenson et al. relates to *Pichia pastoris* linear plasmids and DNA fragments thereof which contain ARS sequences. The '600 patent used the spheroplast transformation system as described in Cregg et al in U.S. Pat. No. 4,929,555.

U.S. Pat. No. 4,837,148 to Cregg et al. relates to autonomous replication sequences which are capable of maintaining plasmids as extrachromosomal elements in host strains of *Pichia*. The patent further relates to constructs including the DNA sequences as well as transformed organisms therewith. The patent additionally provides processes for producing the DNA sequences and constructs of the invention, as well as methods for isolating the sequences from any source.

3. Yeast Mutants

U.S. Pat. No. 5,120,655 to Foster et al. relates to strains of *Candida famata* which can produce 10 grams of riboflavin per liter in 6 days. The '655 patent also relates to strains having ATCC Accession Nos. 20849 and 20850. The '655 patent reports that riboflavin yields of more than 20 grams per liter in 200 hours have been achieved. The mutants were obtained by chemical or physical mutagenesis methods.

U.S. Pat. No. 5,164,303 to Heefner et al. relates to methods of producing riboflavin by culturing strains of yeast of the species *Candida famata* that produce at least about 10 grams of riboflavin per liter of fermentation medium in six days and culture methods therefore. The mutants were obtained by chemical or physical mutagenesis methods.

4. Riboflavin Production

U.S. Pat. No. 5,589,355 to Koizumi et al. relates to a process for producing riboflavin efficiently wherein riboflavin is formed and accumulated in a medium by culturing a microorganism carrying a recombinant DNA prepared from a microorganism belonging to the genus *Corynebacterium* or *Brevibacterium*. The transformed microorganism belongs to the genus *Corynebacterium* or *Brevibacterium* or *Escherichia*.

Citation of documents herein shall not be construed as an admission that such documents are prior art to the present invention.

None of the above documents teaches methods for efficient transformation of flavinogenic yeast. There remains a need in the art for methods of transforming species of flavinogenic yeast and for using the transformed cells to produce economically important molecules such as enzymes, pharmaceutical and nonpharmaceutical proteins, vitamins, and cofactors. The inventors herein have recognized the problem in the art and developed transformation systems for flavinogenic yeast which have high efficiency of transformation and result in stable transformants.

BRIEF SUMMARY OF THE INVENTION

The invention provides a method for the transformation of flavinogenic yeast.

The invention provides an isolated polynucleotide molecule comprising an ARS nucleotide sequence having at least 95% sequence identity to a nucleotide sequence selected from the group consisting of SEQ ID NO. 1, SEQ ID NO. 2 and SEQ ID NO. 3. In one embodiment, the polynucleotide comprises a nucleotide sequence selected from the group consisting of SEQ ID NO. 1, SEQ ID NO. 2 and SEQ ID NO. 3.

The invention provides a vector comprising the isolated polynucleotide molecule comprising a nucleotide sequence having at least 95% sequence identity to a nucleotide sequence selected from the group consisting of SEQ ID NO. 1, SEQ ID NO. 2 and SEQ ID NO. 3.

The invention further provides a vector comprising an isolated polynucleotide molecule comprising a nucleotide sequence selected from the group consisting of SEQ ID NO. 1, SEQ ID NO. 2 and SEQ ID NO. 3.

The invention provides isolated or purified cells comprising a vector comprising a nucleotide sequence having at least 95% sequence identity to a nucleotide sequence selected from the group consisting of SEQ ID NO. 1, SEQ ID NO. 2 and SEQ ID NO. 3.

The invention provides isolated or purified cells comprising a vector comprising a nucleotide sequence selected from the group consisting of SEQ ID NO. 1, SEQ ID NO. 2 and SEQ ID NO. 3.

The invention provides yeast cells comprising a gene library selected from the group consisting of: a gene library comprising vectors comprising *Pichia guilliermondii* ATCC 9058 DNA segments, PgARS elements, and CfARS elements; and a gene library comprising vectors comprising *Candida famata* VKM Y-9 DNA segments, CfARS elements and PgARS elements.

The invention provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said constructs comprise a nucleotide sequence having at least 95% sequence identity to a nucleotide sequence selected from the group consisting of SEQ ID NO. 1, SEQ ID NO. 2 and SEQ ID NO. 3. In one embodiment, the construct comprises a nucleotide sequence selected from the group consisting of SEQ ID NO. 1, SEQ ID NO. 2 and SEQ ID NO. 3.

The invention provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said field strength is from about 8 to about 15 kV/cm.

The invention provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said cell suspension comprises sucrose.

The invention provides a method for the transformation of yeast cells comprising providing spheroplasts of said yeast cells, contacting a solution comprising said spheroplasts with one or more nucleic acid constructs comprising one or more regulatory sequences and one or more genes or gene segments and with one or more fusion agents, for a time sufficient to transform said spheroplasts, wherein said constructs comprise a nucleotide sequence having at least 95% sequence identity to a nucleotide sequence selected from the group consisting of SEQ ID NO. 1, SEQ ID NO. 2 and SEQ ID NO. 3. In one embodiment, the construct comprises a nucleotide sequence selected from the group consisting of SEQ ID NO. 1, SEQ ID NO. 2 and SEQ ID NO. 3.

The invention provides isolated or purified *Candida famata* cells selected from the group consisting of: a. Leaky rib2 mutants of *Candida famata* VKM Y-9 (leu2⁻rib2⁻) wherein said mutants grow without exogenous riboflavin and in the absence of cobalt addition; b. *Candida famata* ts rib1 mutants which overproduce riboflavin in both iron-sufficient and iron-deficient media; c. *Candida famata* mutants of part (b) which overproduce riboflavin at reduced temperature; d. *Candida famata* ts rib1 mutants which overproduce riboflavin in iron-sufficient media; e. *Candida famata* ts rib1 mutants which overproduce riboflavin in iron-deficient media; f. *Candida famata* leaky rib2 mutants, wherein said mutants grow without exogenous riboflavin and in the presence of $Co^{+2}$ ions; g. *Candida famata* ts rib1 mutants which are prototrophic for riboflavin production at reduced temperatures and which retain riboflavin auxotropy at elevated temperatures; h. *Candida famata* ts rib5/rib6 mutants which are prototrophic for riboflavin production at reduced temperatures and which retain riboflavin auxotrophy at elevated temperatures; i. *Candida famata* leaky rib5/rib6 mutants, wherein said mutants grow without exogenous riboflavin in the presence of exogenous $Co^{+2}$ ions and which are riboflavin auxotrophic in medium without exogenous $Co^{+2}$ ions; j. *Candida famata* ts rib5/rib6 mutants which produce riboflavin in iron sufficient media and which grow in the presence of $Cu^{+2}$ ions; k. Leaky rib2 mutants of *Candida famata* VKM Y-9 (leu2⁻rib2⁻) wherein said mutant comprises sufficient rib2 gene encoded enzyme (reductase) activity to retain riboflavin auxotrophy under conditions of flavinogenesis enzyme repression and simultaneously sufficient reductase activity to produce riboflavin prototrophy under conditions of flavinogenesis enzyme derepression; l. The leaky mutants of (k) wherein said condition of flavinogenesis enzyme repression is growth in iron sufficient media; m. The leaky mutants of (k) wherein said condition of flavinogenesis enzyme derepression is growth in iron deficient media; n. *Candida famata* mutant #105 1-2 (leu2), wherein said mutant grows on ethanol as the sole carbon and energy source and which produces about 70–100 µg riboflavin/ml, having NRRL deposit no. Y-30455; o. *Candida famata* VKM Y-9 L20105 having NRRL deposit no. Y-30292; and, p. *Candida famata* VKM Y-9 (leu2⁻rib⁻) mutants selected from the group consisting of:

1) mutants having a genetic block of the rib1 gene; 2) mutants of (1) transformed with a vector selected from the group consisting of PRp1, pCR1Xb, PRp1Xb and pCR1; wherein said vector comprises a nucleic acid segment which provides complementation of said genetic block when said nucleic acid segment is expressed in said mutant; 3) mutants having a genetic block of the rib2 gene; 4) mutants of (3) transformed with a vector selected from the group consisting of pCR2, pCR2-1, and pR2; wherein said vector comprises a nucleic acid segment which provides complementation of said genetic block when said nucleic acid segment is expressed in said mutant; 5) mutants having a genetic block of the rib3 gene; 6) mutants having a genetic block of the rib5 gene; 7) mutants of (6) transformed with a vector selected from the group consisting of pPR5, pRIV-2, and PRpIV-2; wherein said vector comprises a nucleic acid segment which provides complementation of said genetic block when said nucleic acid segment is expressed in said mutant; 8) mutants having a genetic block of the rib6 gene;

9) mutants of (8) transformed with vector pF; wherein said vector comprises a nucleic acid segment which provides complementation of said genetic block when said nucleic acid segment is expressed in said mutant; 10) mutants having a genetic block of the rib7 gene; and 11) mutants of (10) transformed with a vector selected from the group consisting of pCR7, pPRp7 and pRIB7; and, wherein said vector comprises a nucleic acid segment which provides complementation of said genetic block when said nucleic acid segment is expressed in said mutant.

The invention provides a method comprising: (a) growing a transformed yeast under conditions that provide for synthesis of riboflavin, wherein said transformed yeast comprises one or more nucleic acid constructs comprising one or more copies of one or more genes encoding one or more enzymes involved in riboflavin biosynthesis; wherein said one or more nucleic acid constructs further comprises a nucleotide sequence selected from the group consisting of SEQ ID NO. 1, SEQ ID NO. 2 and SEQ ID NO. 3.; wherein said riboflavin is synthesized by said transformed yeast, said synthesis being greater than that of the corresponding non-transformed yeast(b) recovering said riboflavin from said culture media in which said transformed yeast was cultured. Optionally, the method includes purification of the riboflavin produced.

The invention provides a method comprising: (a) growing a mutant yeast strain under conditions that provide for synthesis of riboflavin, wherein said mutant yeast strain produces riboflavin in both iron sufficient and iron deficient media; wherein said riboflavin is synthesized by said mutant yeast strain, said synthesis being greater than that of the corresponding non-mutant parental yeast strain; and (b) recovering said riboflavin from said culture media in which said mutant yeast was cultured. Optionally, the method includes purification of the riboflavin produced.

The invention provides a method comprising: (a) growing a mutant yeast strain under conditions that provide for synthesis of riboflavin, wherein said mutant yeast strain produces riboflavin in iron sufficient media, and wherein ethanol is the sole energy and carbon source of said mutant; wherein said riboflavin is synthesized by said mutant yeast strain, said synthesis being greater than that of the corresponding non-mutant parental yeast strain; and (b) recovering said riboflavin from said culture media in which said mutant yeast was cultured. Optionally, the method includes purification of the riboflavin produced.

The invention provides a method comprising culturing mutant yeast cells under conditions that provide for synthesis of riboflavin, wherein culturing comprises culture media comprising iron and chromium ions; wherein said mutant yeast cells are *Candida famata* VKM Y-9 L20105; wherein said riboflavin synthesis is greater in said media comprising chromium and iron ions than when said mutant yeast is grown in media lacking chromium ions; and recovering said riboflavin from said culture media in which said mutant yeast was cultured.

The invention provides a method of obtaining flavinogenic yeast cells having one or more altered biological properties as compared to untreated cells comprising treating *Candida famata* NRRL 30292 cells at least once with one or more treatment agents under one or more treatment conditions for a time period sufficient to alter one or more biological properties, wherein one or more biological properties of said treated cells differs from biological properties of untreated cells.

BRIEF DESCRIPTION OF THE DRAWINGS/FIGURES

Restriction sites: H, HindIII, Sp, SphI; P, PstI; Sl, SalI; Hc, HincII; Sc, SacI; X, XhoI; K, KpnI; Xb, XbaI; B, BamHI; Sm, SmaI; RI, EcoRI.

Figure 9:
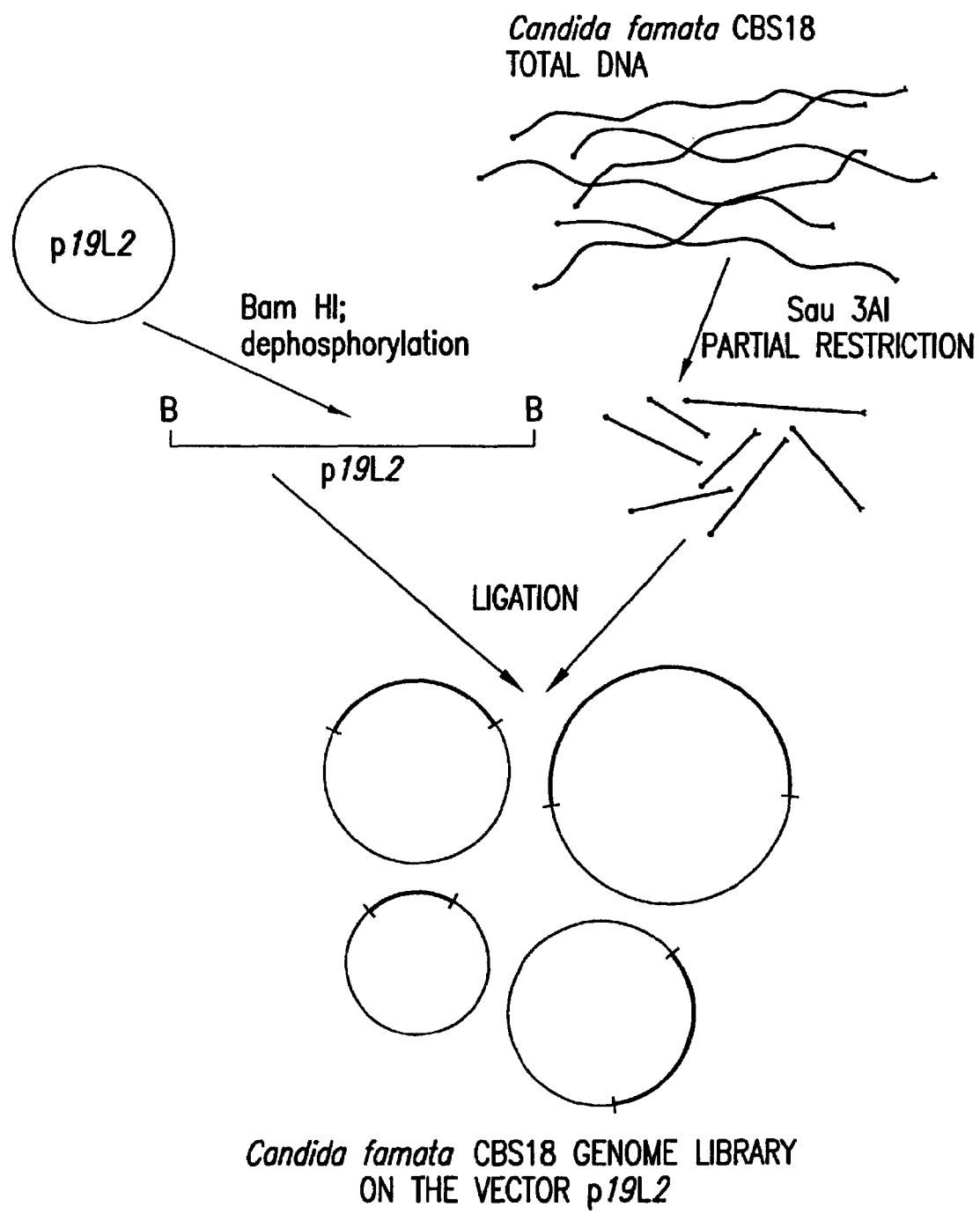

FIG. 9 shows the construction of the *Candida famata* VKM Y-9 genome library on the vector p19L2.

Figure 10:
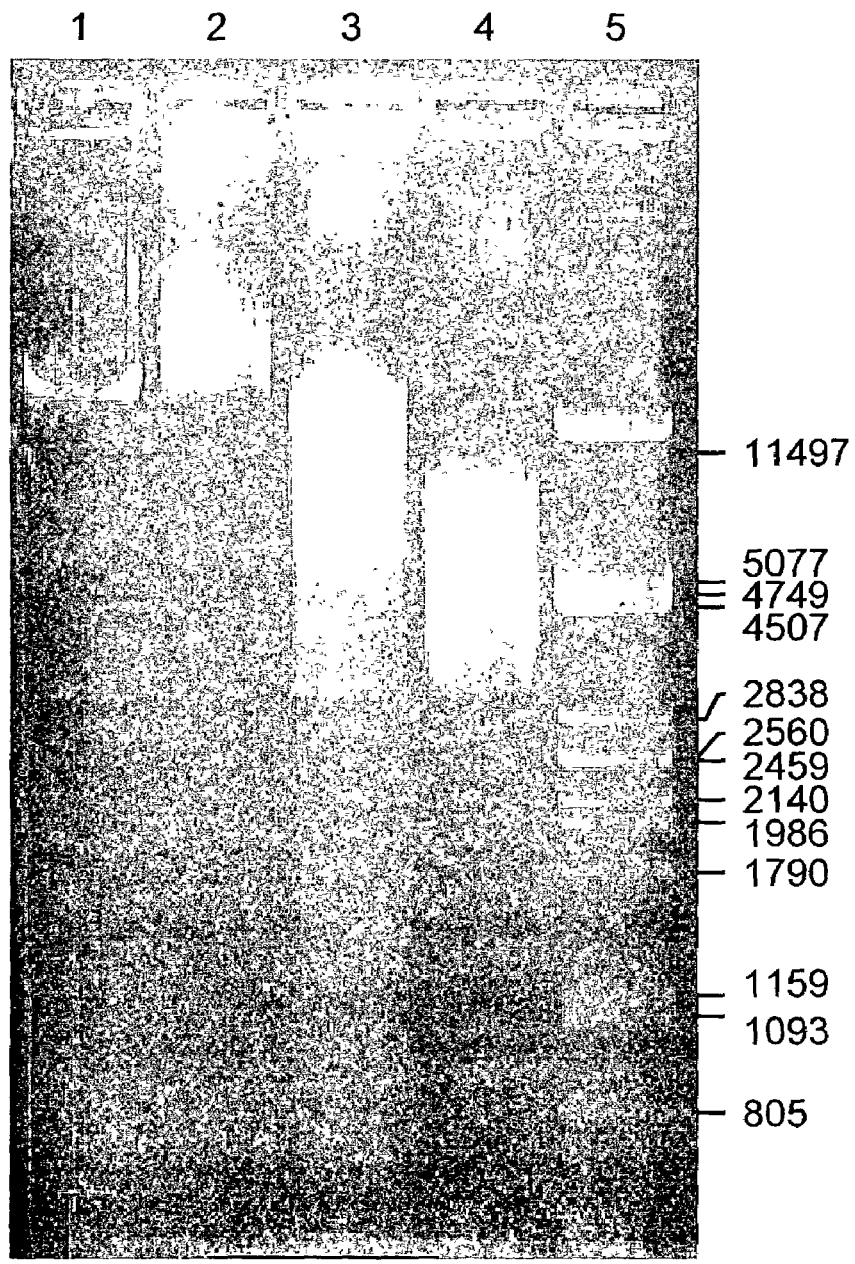

FIG. 10 shows electrophoresis of the yeast *Candida famata* VKM Y-9 total DNA. Track #1—Lambda phage DNA. Track #2—*Candida famata* VKM Y-9 total DNA. Track #3—*Candida famata* VKM Y-9 total DNA after partial digestion by Sau3AI. Track #4—Sau3AI fragments of the *Candida famata* VKM Y-9 total DNA after elution (approximate sizes of the fragments 3 to 10 kb). Track #5—Lambda phage DNA after PstI digestion.

Figure 11:
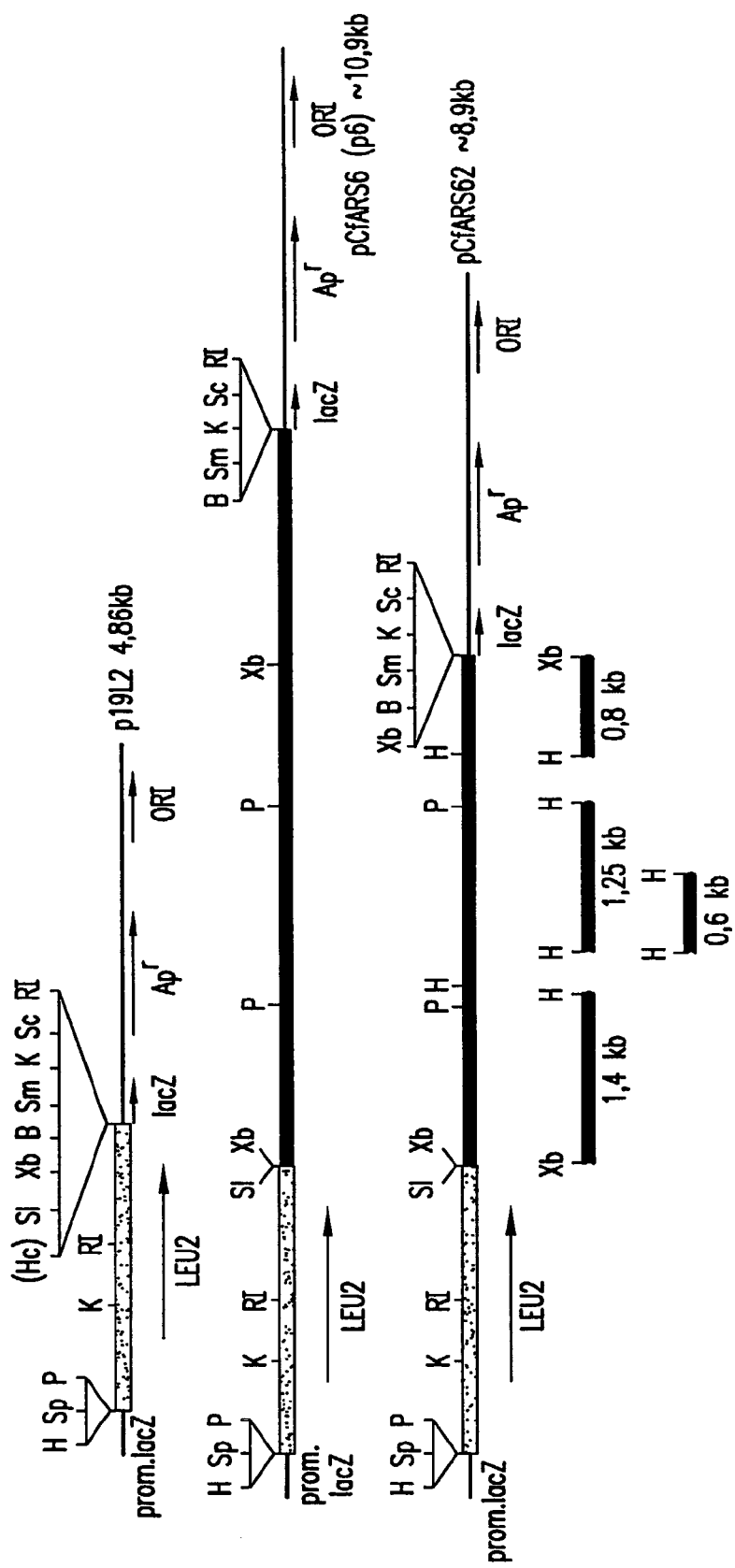

FIG. 11 shows the linear schemes of plasmids p19L2, pCfARS6 and pCfARS62. CfARS6 insert and its subfragments are shown as thick black lines.

Restriction sites: H, HindIII, Sp, SphI; P, PstI; K, KpnI; RI, EcoRI; Hc, HincII; Sl, SalI; Xb, XbaI; B, BamHI; Sm, SmaI; Sc, SacI.

Figure 12:
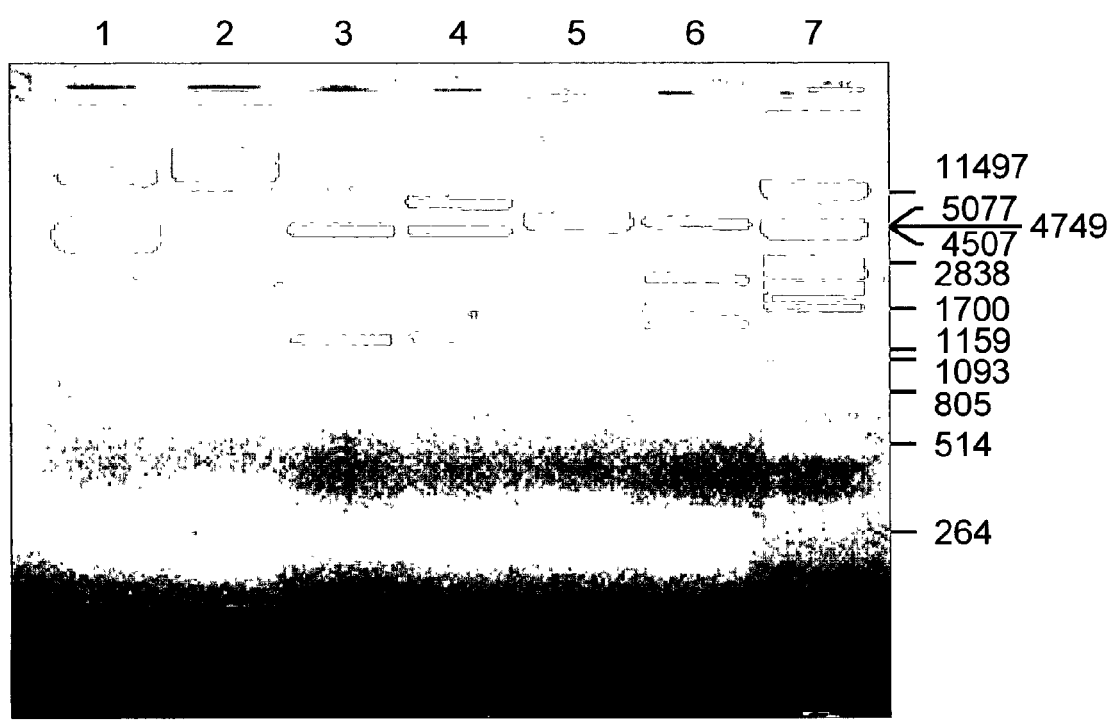

FIG. 12 shows electrophoresis of plasmids pCfARS1614 and pRIV-1. Track #1—plasmid pCfARS1614, native form. Track #2—plasmid pRIV-1, native form. Track #3—pCfARS1614 after EcoRI digestion. Track #4—pRIV-1 after EcoRI digestion. Track #5—pCfARS1614 after XbaI+SmaI digestion. Track #6—pRIV-1 after XbaI+SmaI digestion. Track #7—Marker fragments of Lambda phage DNA digested with PstI. Electrophoresis was performed in 1.5% agarose.

Figure 13:
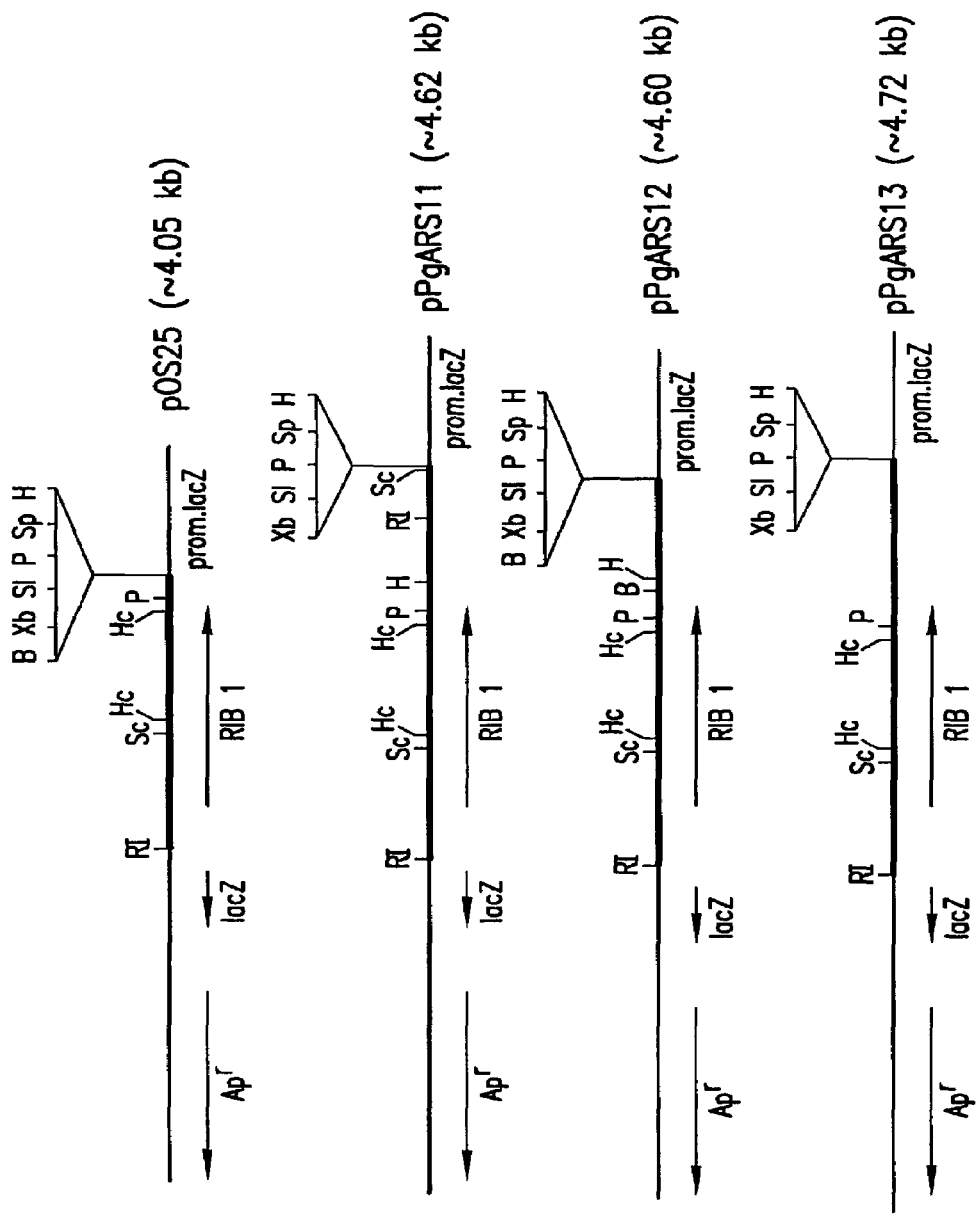

FIG. 13 shows the linear schemes of plasmids pOS25, pPgARS11, pPgARS12, pPgARS13. PgARS insert is shown as a thick black line.

Restriction sites: B, BamHI; H, HindIII; Hc, HincII; P, PstI; R1, EcoRI; Sc, SacI; Sl, SalI; Sp, SphI; Xb, XbaI.

Figure 14:
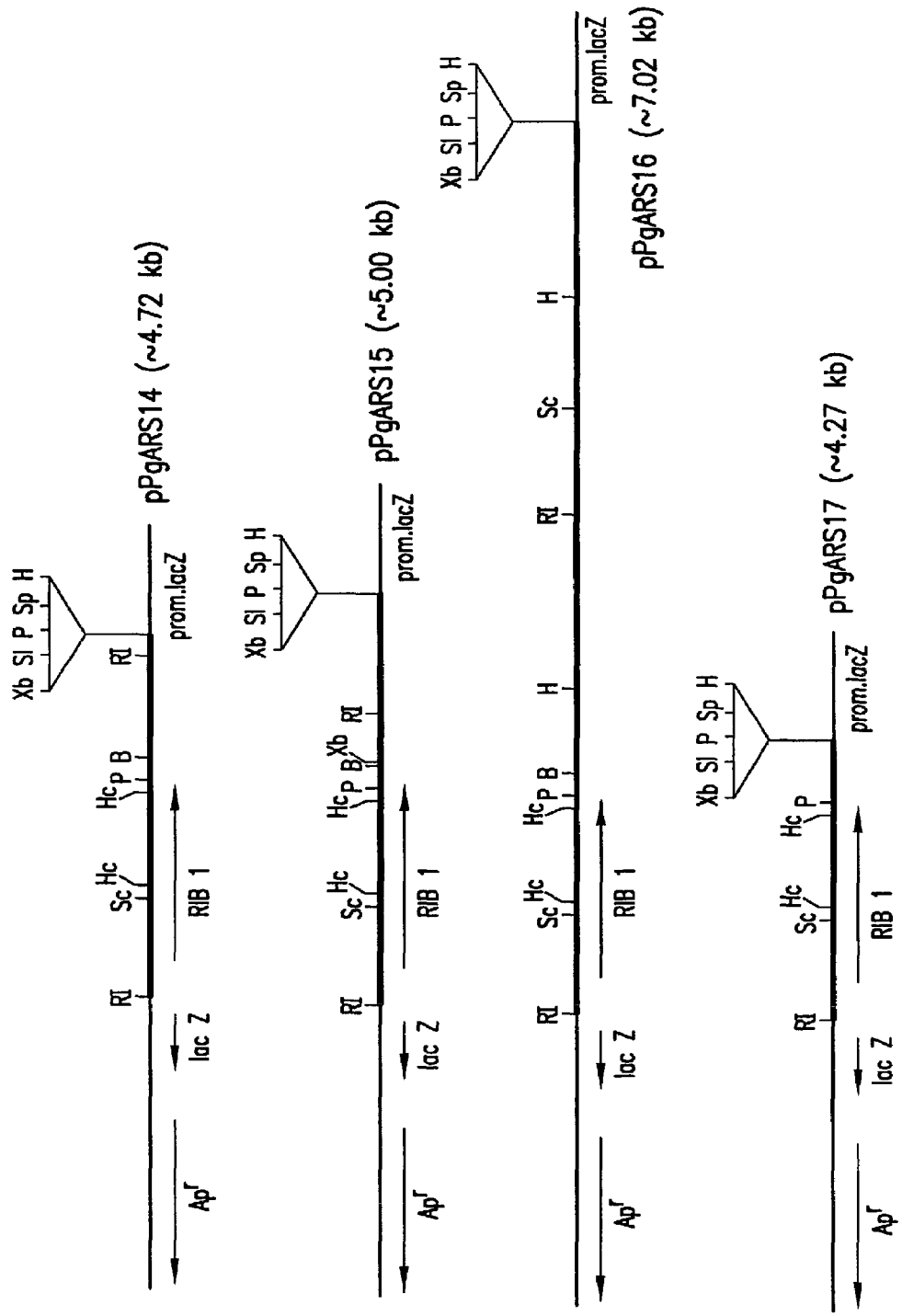

FIG. 14 shows the linear schemes of plasmids pPgARS14, pPgARS15, pPgARS16, pPgARS17. PgARS insert is shown as a thick black line.

Restriction sites: B, BamHI; H, HindIII; Hc, HincII; P, PstI; R1, EcoRI; Sc, SacI; Sl, SalI; Sp, SphI; Xb, XbaI.

FIG. 15 shows the nucleotide sequence (SEQ ID NO. 1) of a *Candida famata* VKM Y-9 ARS element (CfARS).

FIG. 16 shows the nucleotide sequence (SEQ ID NO. 2) of the *Pichia guilliermondii* ARS element (PgARS).

Figure 17:
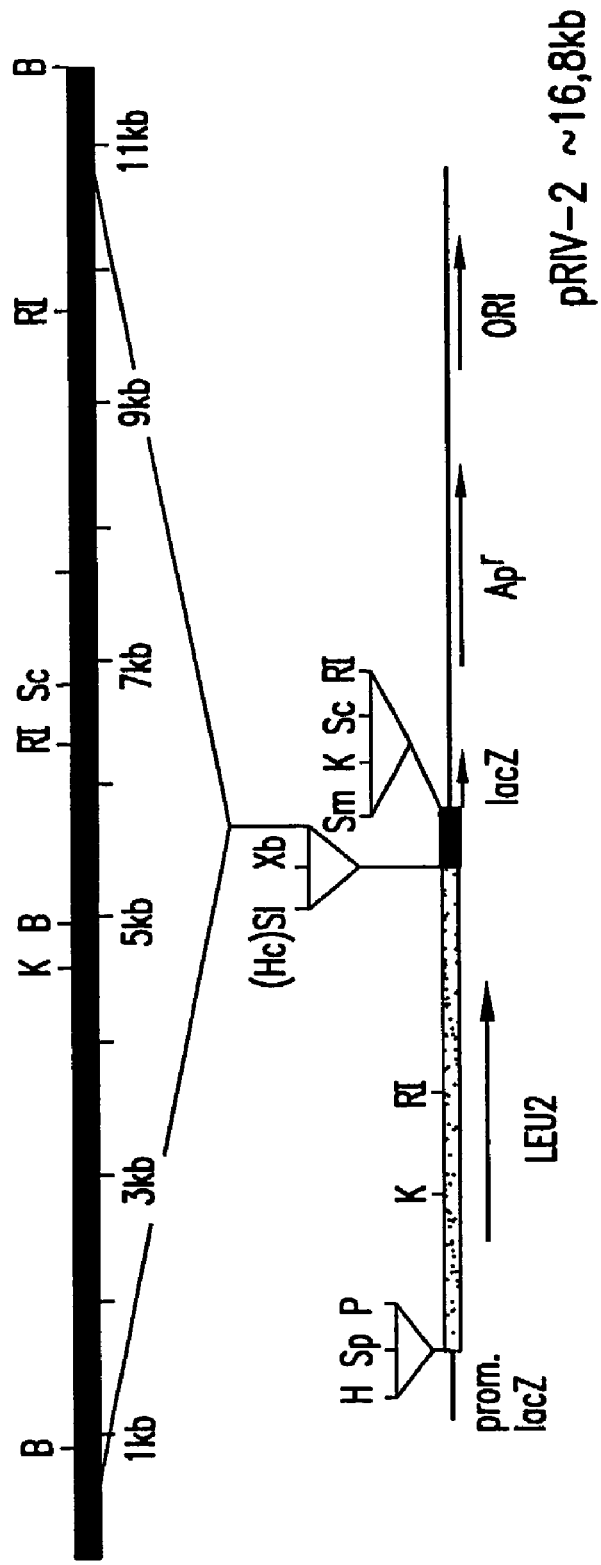

FIG. 17 shows the linear scheme of plasmid pRIV-2.

Figure 18:
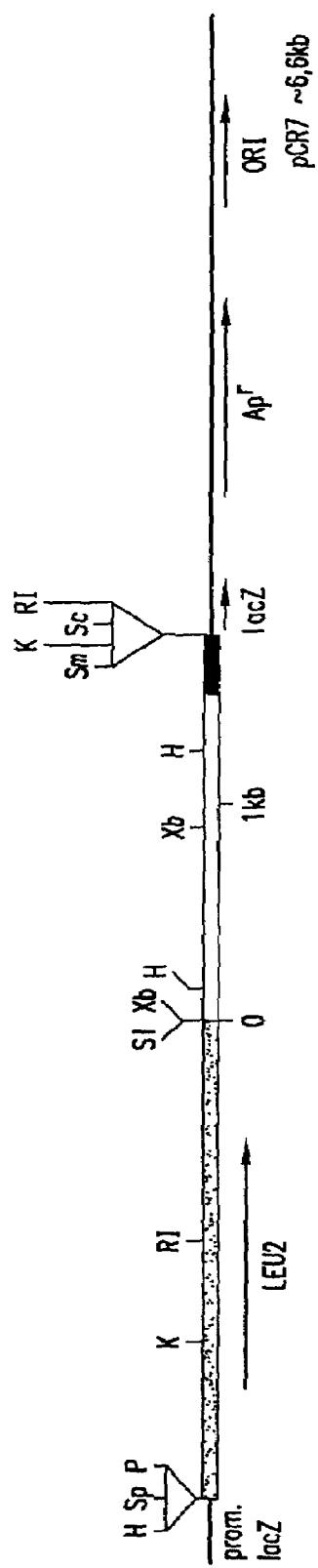

FIG. 18 shows the linear scheme of plasmid pCR7.

Figure 19:
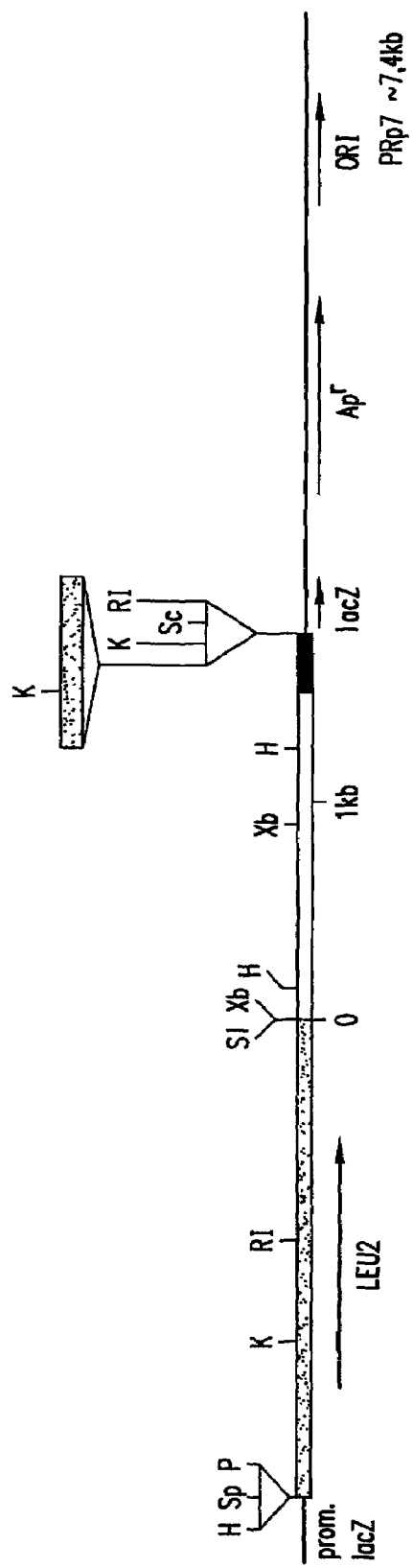

FIG. 19 shows the linear scheme of plasmid pPRp7.

FIG. 20 shows the nucleotide sequence (SEQ ID NO. 3) of a *Candida famata* VKM Y-9 ARS element (CfARS).

Figure 21:
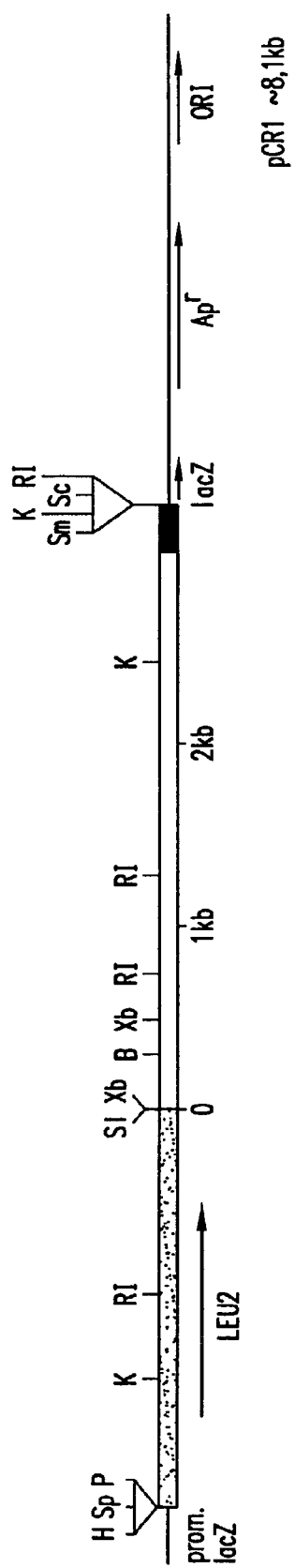

FIG. 21 shows the linear scheme of pCRI. The plasmid is based on pCfARS1614. The ~3 kb insert complementing rib1 mutations of both *Candida famata* and *Pichia guilliermondii* is shown as an open box.

Restriction sites: H, HindIII; Sp, SpI; P, PstI; K, KpnI; RI, EcoRI; Sl, SalI; Xb, XbaI; B, BamHI; Sm, SmaI; Sc, SacI.

Figure 22:
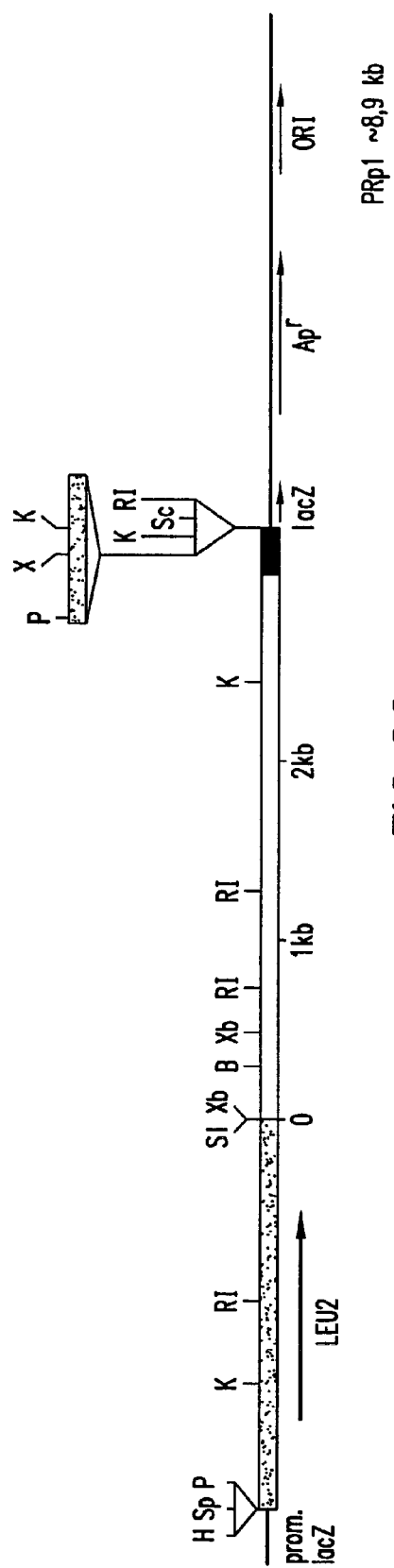

FIG. 22 shows the linear scheme of PRp1. The plasmid is a derivative of pCR1. PRp1 contains a PgARS (separate grey thick line). The ~3 kb insert complementing rib1 mutations of both *Candida famata* and *Pichia guilliermondii* is shown as an open box.

Restriction sites: H, HindIII; Sp, SphI; P, PstI; K, KpnI; RI, EcoRI; Sl, SalI; Xb, XbaI; X, XhoI; B, BamHI; Sm, SmaI; Se, SacI.

Figure 23:
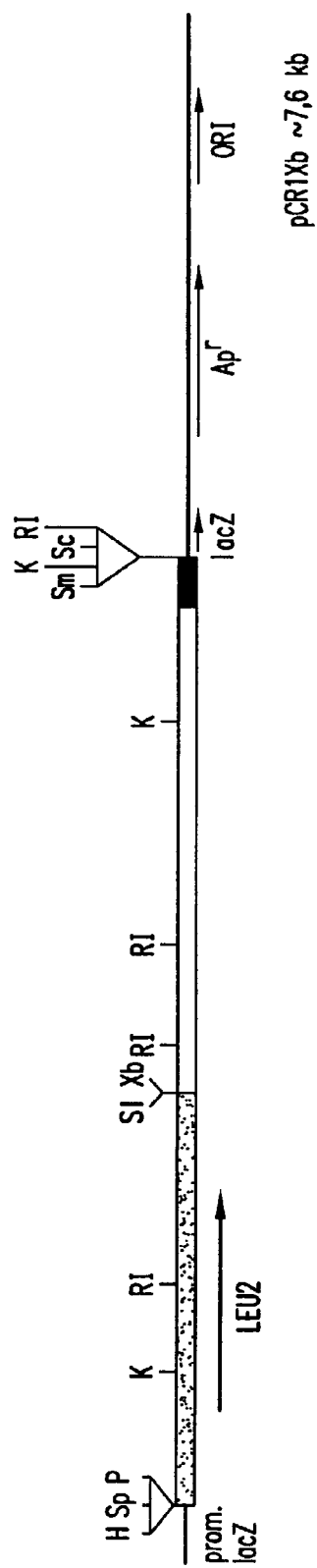

FIG. 23 shows the linear scheme of pCR1Xb. The ~2.5 kb insert complementing the rib1 mutation of *Candida famata* is shown as an open box.

Restriction sites: H, HindIII; Sp, SphI; P, PstI; K, KpnI; RI, EcoRI; Sl, SalI; Xb, XbaI; Sm, SmaI; Se, SacI.

Figure 24:
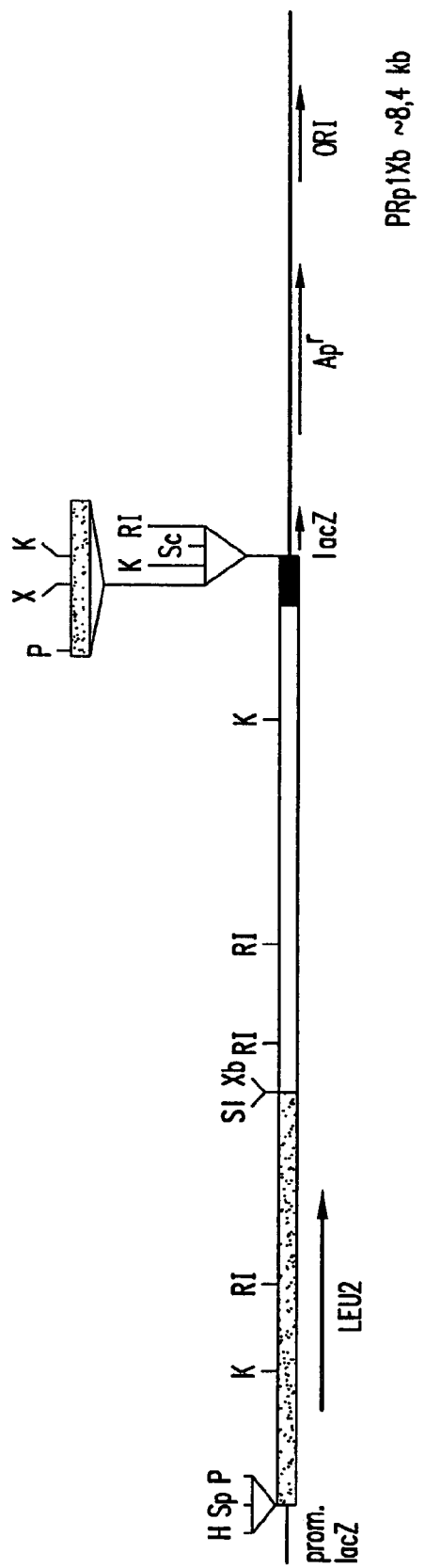

FIG. 24 shows the linear scheme of PRp1Xb. The ~2.5 kb insert complementing the rib1 mutation of *Candida famata* is shown as an open box.

Restriction sites: H, HindIII; Sp, SphI; P, PstI; K, KpnI; RI, EcoRI; Sl, SalI; Xb, XbaI; X, XhoI; B, BamHI; Sm, SmaI; Sc, SacI.

Figure 25:
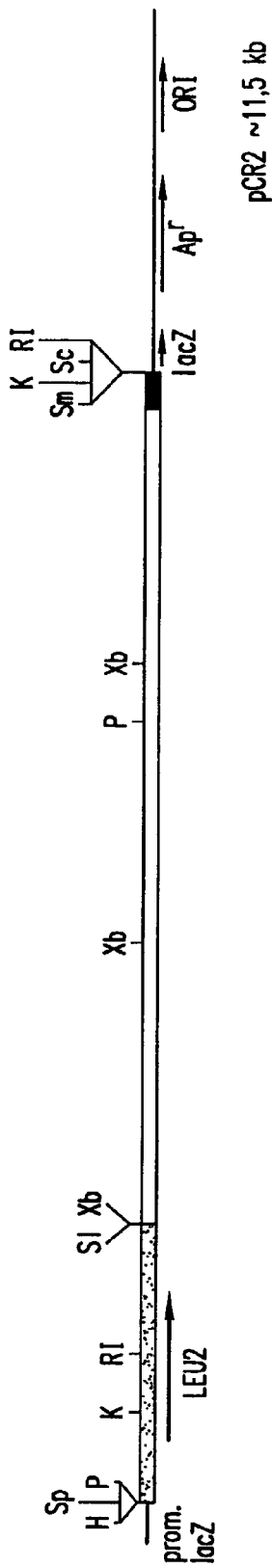

FIG. 25 Shows the linear scheme of pCR2. The plasmid is based on pCfARS1614. The ~6.4 kb insert complementing rib2 mutations of both *Candida famata* and *Pichia guilliermondii* is shown as an open box. Only PstI and XbaI sites are shown on the insert.

Restriction sites: H, HindIII; Sp, SphI; P, PstI; K, KpnI; RI, EcoRI; Sl, SalI; Xb, XbaI; Sm, SmaI; Sc, SacI.

Figure 26:
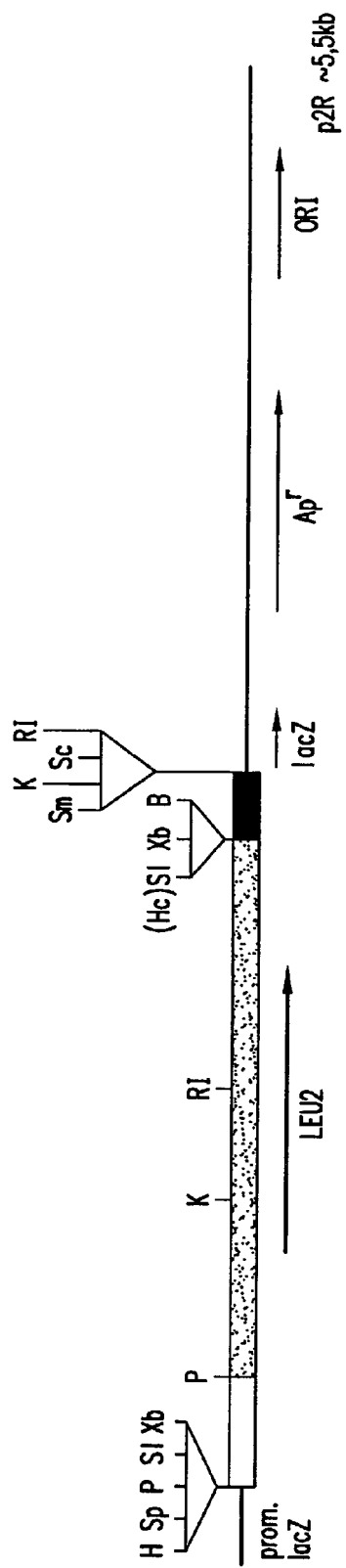

FIG. 26 The linear scheme of plasmid p2R. The ~0.25 kb of CfARS insert is shown as the thick black line. The ~0.4 kb PgARS is shown as the hashed box.

Restriction sites: H, HindIII; Sp, SphI; P, PstI; K, KpnI; RI, EcoRI; Hc, HincII; Sl, SalI; Xb, XbaI; B, BamHI; Sm, SmaI; Sc, SacI.

Figure 27:
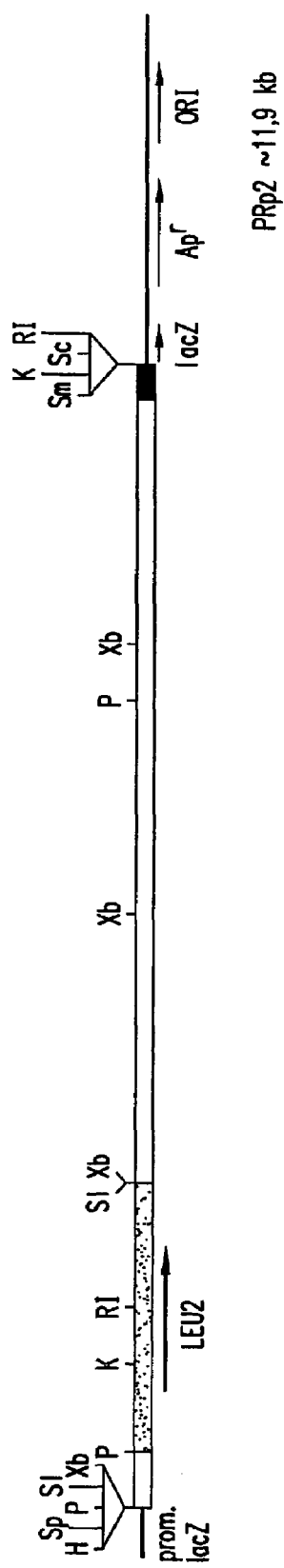

FIG. 27 The linear scheme of PRp2. The plasmid is based on pCfARS1614. The ~6.4 kb insert complementing rib2 mutations of both *Candida famata* and *Pichia guilliermondii* is shown as an open box. Only PstI and XbaI restriction sites are shown on the insert. CfARS is shown as the thick black line; PgARS is shown as the hashed box.

Restriction sites: H, HindIII; Sp, SphI; P, PstI; K, KpnI; RI, EcoRI; Sl, SalI; Xb, XbaI; Sm, SmaI; Sc, SacI.

Figure 28:
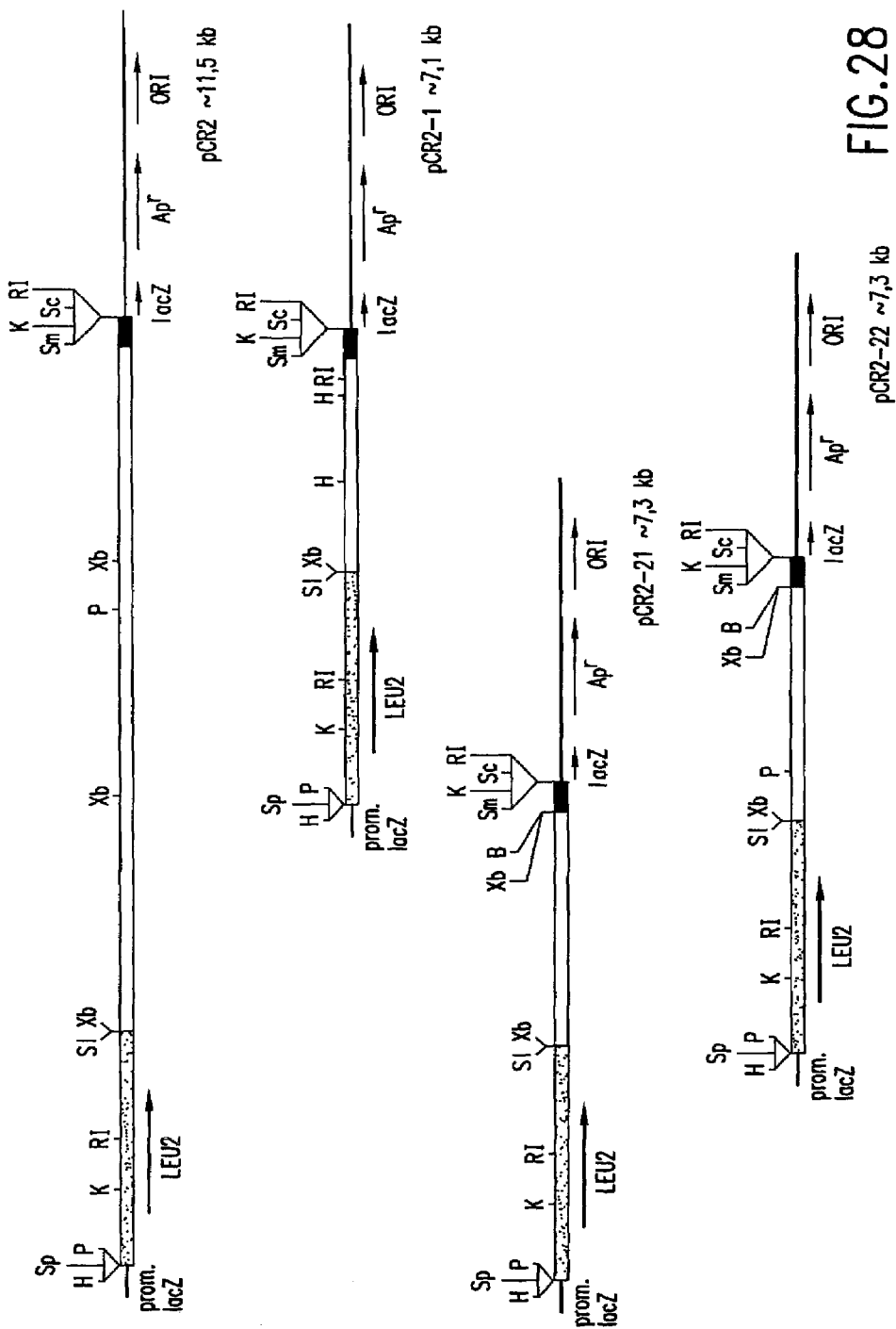

FIG. 28 The linear scheme of pCR2, pCR2-1, pCR2-21 and pCR2-22. The plasmids are based on pCfARS1614.

Restriction sites: H, HindIII; Sp, SphI; P, PstI; K, KpnI; RI, EcoRI; Hc, HincII; Sl, SalI; Xb, XbaI; B, BamHI; Sm, SmaI; Sc, SacI.

Figure 29:
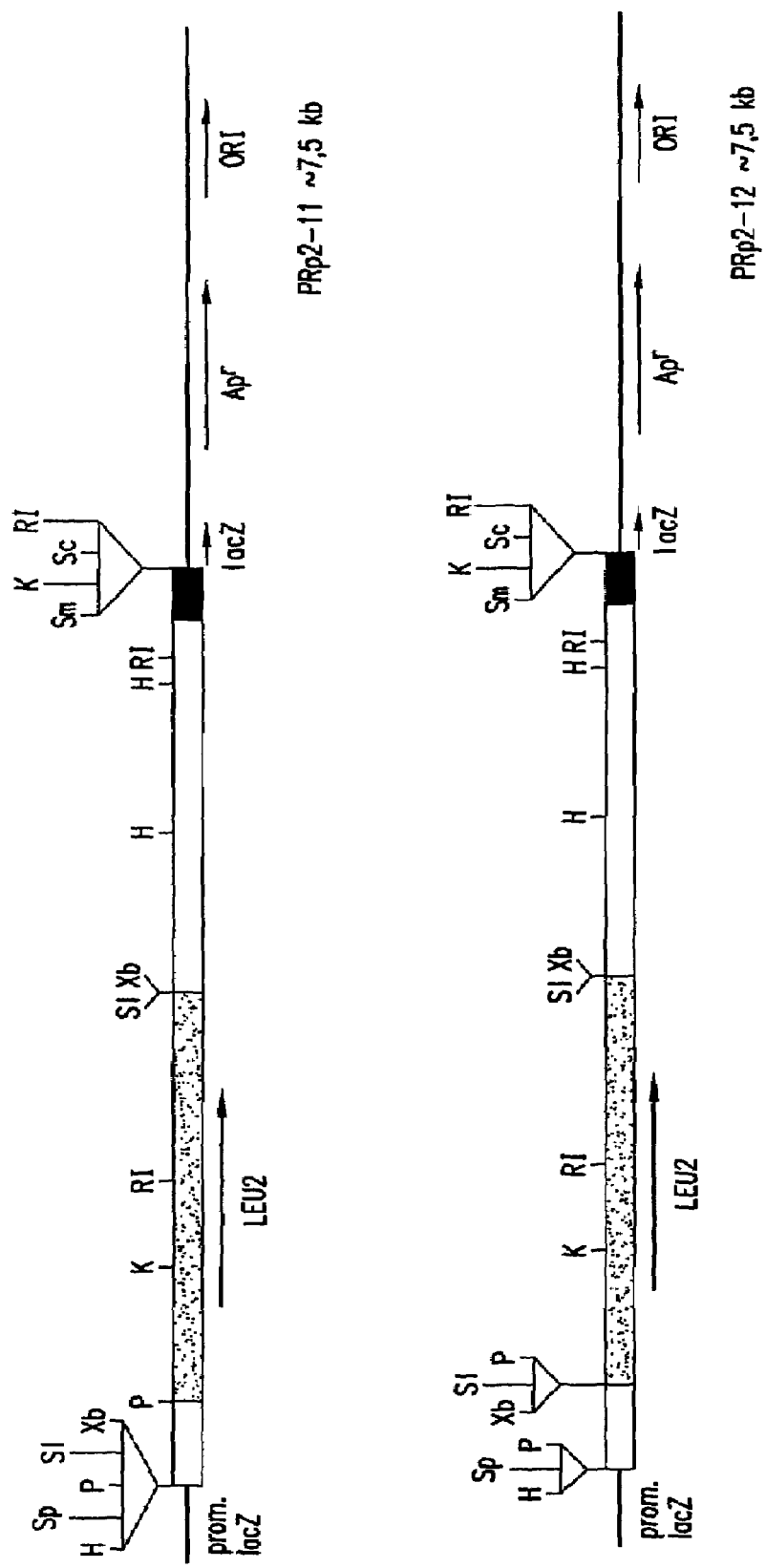

FIG. 29 The linear scheme of PRp2-11 and PRp2-12. The plasmids are based on pCfARS1614. The ~2 kb insert complementing rib2 mutations of both *Candida famata* and *Pichia guilliermondii* is shown as an open box. CfARS is shown as the thick black line; PgARS is shown as the hashed box.

Restriction sites: H, HindIII; Sp, SphI; P, PstI; K, KpnI; RI, EcoRI; Sl, SalI; Xb, XbaI; Sm, SmaI; Sc, SacI.

Figure 30:
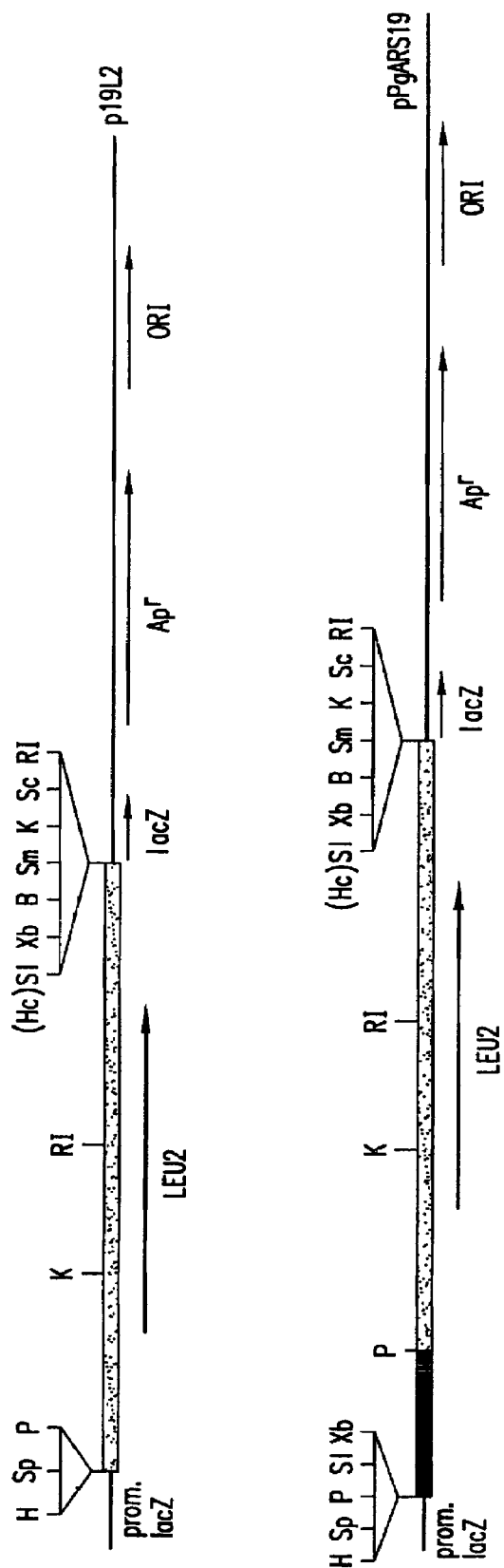

FIG. 30 The linear schemes of plasmids p19L2 (4.86 kb) and pPgARS19 (5.3 kb). The PgARS insert is shown as a thick black line.

Restriction sites: B, BamHI; H, HindIII; Hc, HincII; K, KpnI; P, PstI; RI, EcoRI; Sc, SacI; Sl, SalI; Sm, SmaI; Sp, SphI; Xb, XbaI.

Figure 31:
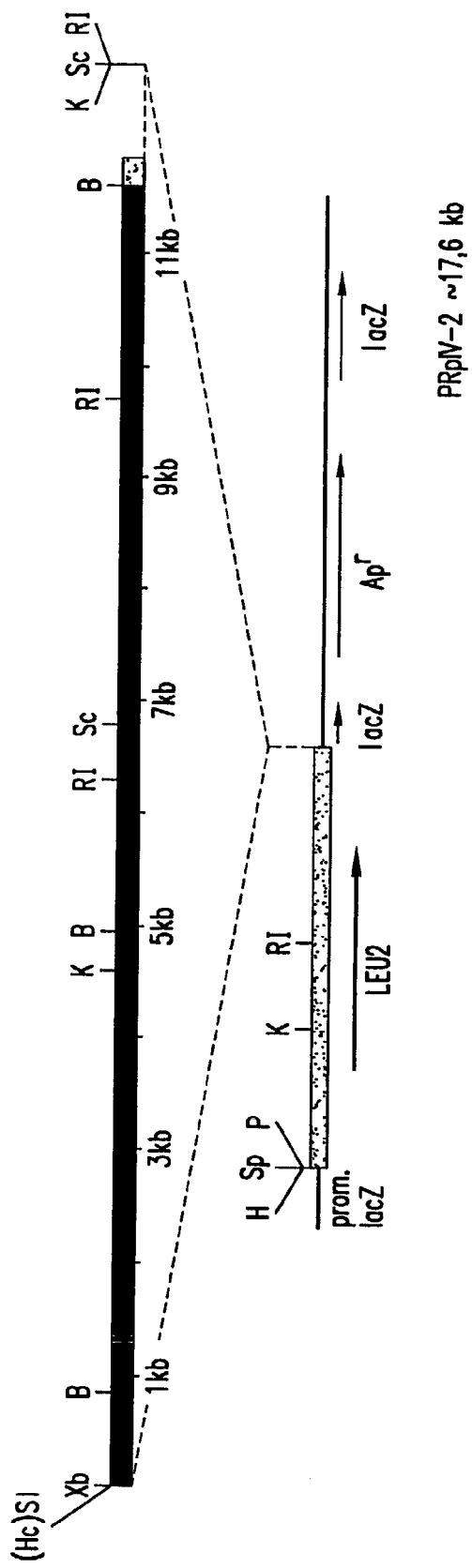

FIG. 31 The linear scheme of the plasmid PRpIV-2. The plasmid is a derivative of pRIV-2. The ~11.7 kb insert complementing the rib6 mutation of both *Candida famata* and *Pichia guilliermondii* and the CfARS are shown as a separate black or grey thick line, respectively. Only BamHI, KpnI, EcoRI and SacI restriction sites are shown on the RIB6 insert. PgARS (~0.8 kb) is shown as an open box.

Restriction sites: H, HindIII; Sp, SphI; P, PstI; K, KpnI; RI, EcoRI; Hc, HincII; Sl, SalI; Xb, XbaI; B, BamHI; Sm, SmaI; Sc, SacI.

Figure 32:
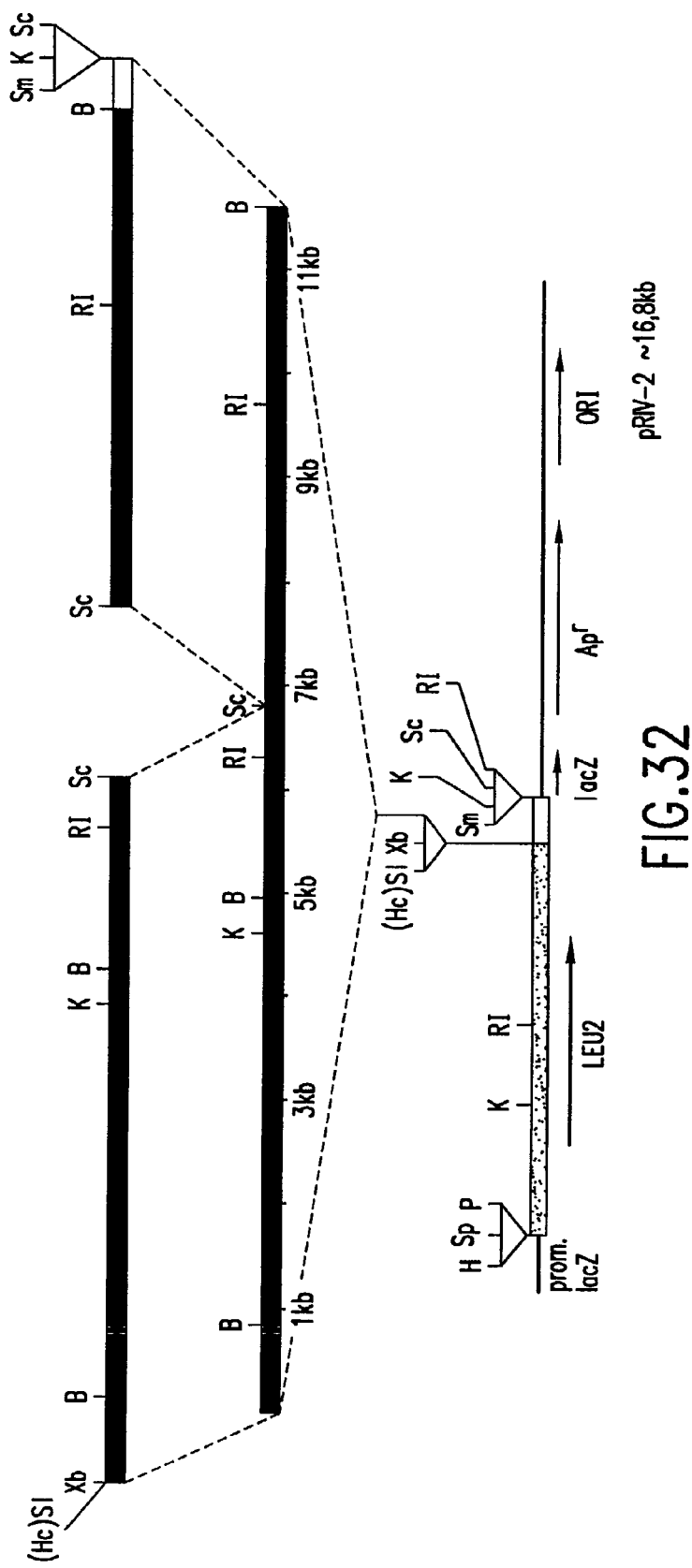

FIG. 32 Separation of the *C. famata* genome insert (carrying the RIB6 gene) of plasmid pRIV-2 on the SacI-SalI and SacI subfragments.

Figure 33:
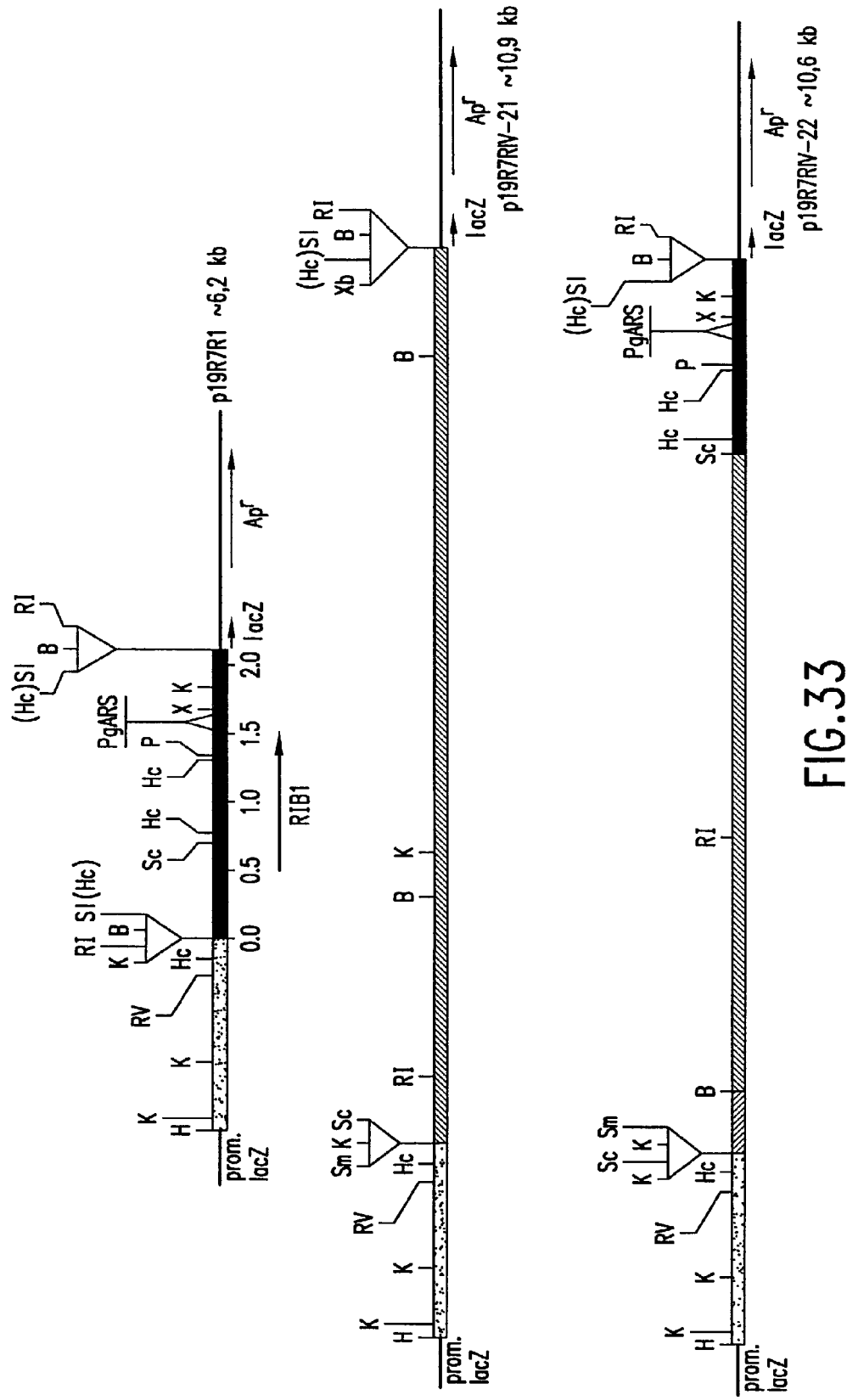

FIG. 33 The linear schemes of plasmids p19R7RI, p19R7RIV-21 and p19R7RIV-22. The *P. guilliermondii* genome fragment carrying the RIB1 gene and PgARS is shown as the thick black line; the *P. guilliermondii* genome fragment carrying the RIB7 gene as the thick grey line; subfragments of the pRIV-2 insert as hashed boxes; and, CfARS as the checked box.

Restriction sites: H, HindIII; RV, EcoRV; P, PstI; K, KpnI; RI, EcoRI; Hc, HincII; Sl, SalI; Xb, XbaI; B, BamHI; Sm, SmaI; Sc, SacI; X, XhoI.

Figure 34:
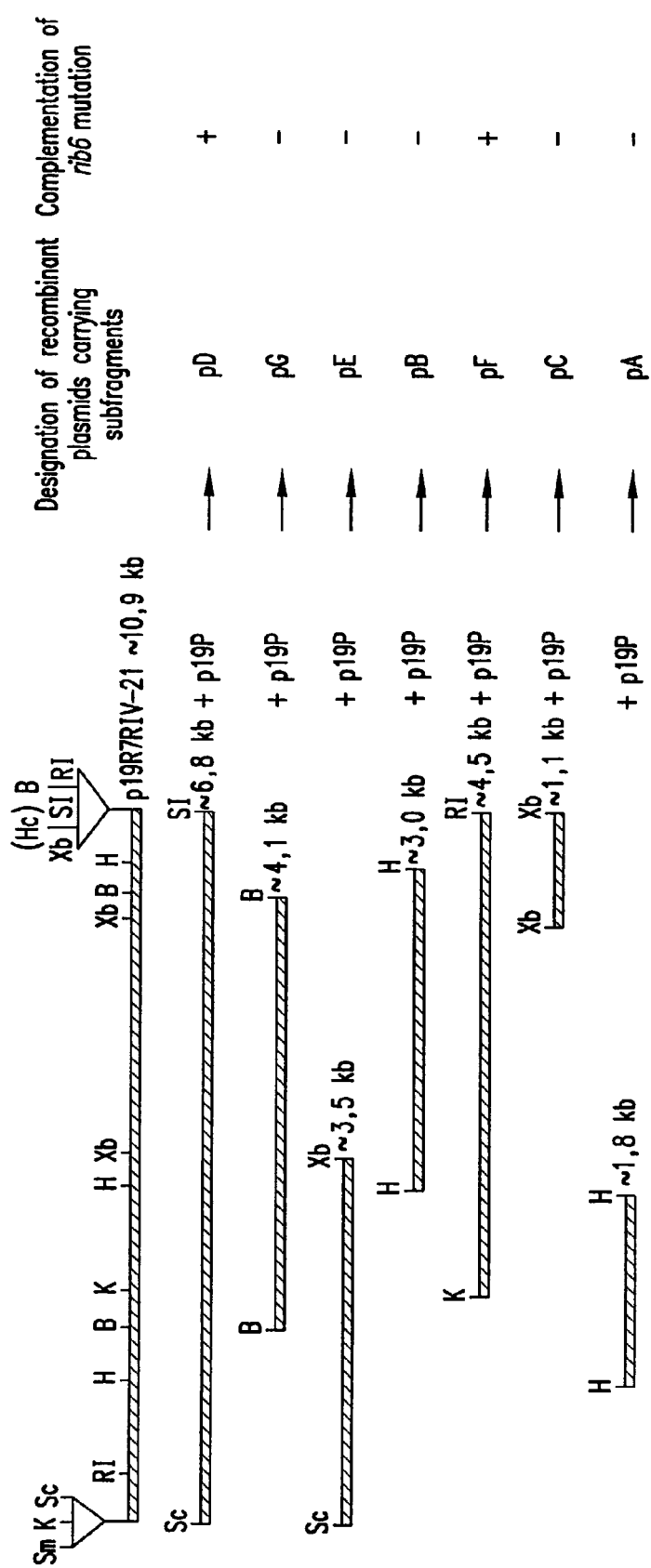

FIG. 34 Subcloning of the ~6.8 kb insert (carrying *C. famata* RIB6 gene) of p19R7RIV-21 in plasmid p19P.

Restriction sites: H, HindIII; K, KpnI; RI, EcoRI; Hc, HincII; Sl, SalI; Xb, XbaI; B, BamHI; Sm, SmaI; Sc, SacI.

Figure 35:
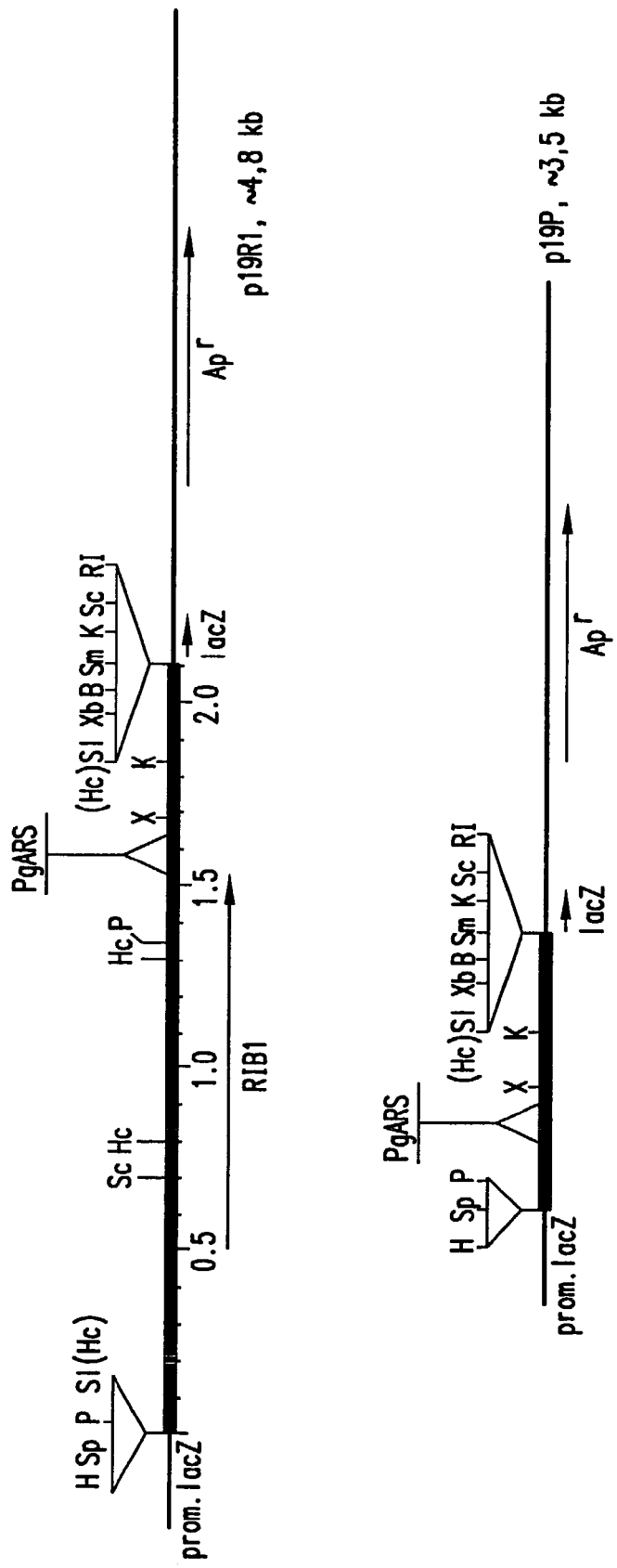

FIG. 35 The linear schemes of plasmids p19R1 and p19P. The plasmid p19P is a derivative of p19R1.

Restriction sites: H, HindIII; Sp, SphI; P, PstI; K, KpnI; RI, EcoRI; Hc, HincII; Sl, SalI; Xb, XbaI; X, XhoI; B, BamHI; Sm, SmaI; Sc, SacI.

FIG. 36 The linear scheme of plasmid pF. The ~4.5 kb insert carrying the *Candida famata* RIB6 gene is shown as a grey thick line and PgARS as a black thick line.

Restriction sites: H, HindIII; Sp, SphI; P, PstI; K, KpnI; RI, EcoRI; Sl, SalI; Xb, XbaI; X, XhoI; B, BamHI.

FIG. 37 The linear scheme of the plasmid pPR5. The plasmid is based on pPgARS19. The ~1.45 kb insert complementing the rib5 mutations of both *Candida famata* and *Pichia guilliermondii* is shown as an open box.

Restriction sites: H, HindIII; Sp, SphI; P, PstI; K, KpnI; RI, EcoRI; B, BamHI; Sl, SalI; Xb, XbaI; Sm, SmaI; Sc, SacI.

FIG. 38 The linear scheme of the plasmid pCPR5. The plasmid is derivative of pPR5. CfARS is shown as a checked box.

Restriction sites: H, HindIII; Sp, SphI; P, PstI; K, KpnI; RI, EcoRI; B, BamHI; Sl, SalI; Xb, XbaI; Sm, SmaI; Sc, SacI.

Figure 39:
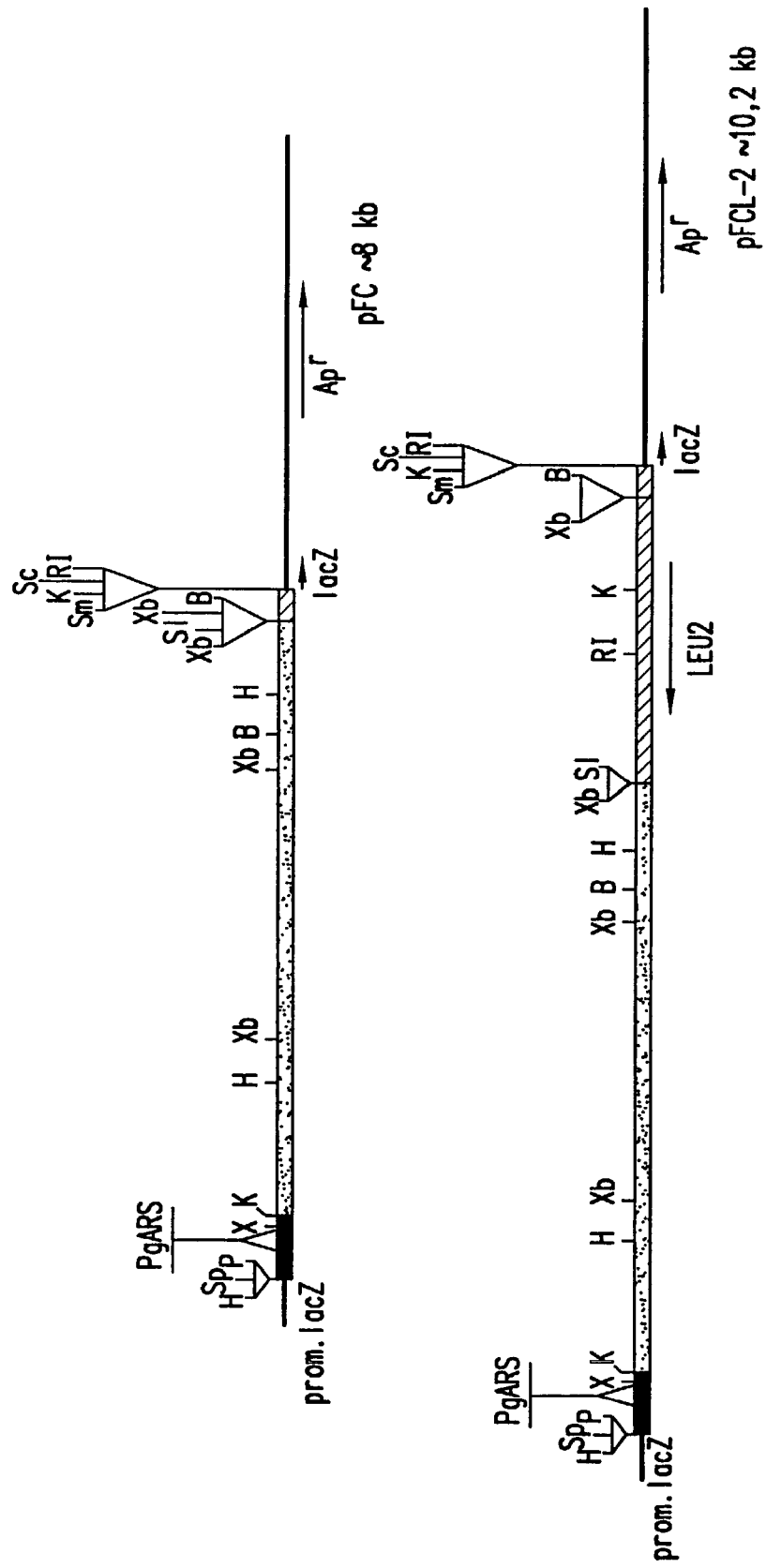

FIG. 39 The linear schemes of plasmids pFC and pFCL-2. They are derivatives of pF. CfARS is shown as a checked box and the *S. cerevisiae* genome fragment containing the LEU2 gene as a hashed box.

Restriction site: H, HindIII; Sp, SphI; P, PstI; K, KpnI; RI, EcoRI; Sl, SalI; Xb, XbaI; X, XhoI; B, BamHI.

Figure 40:
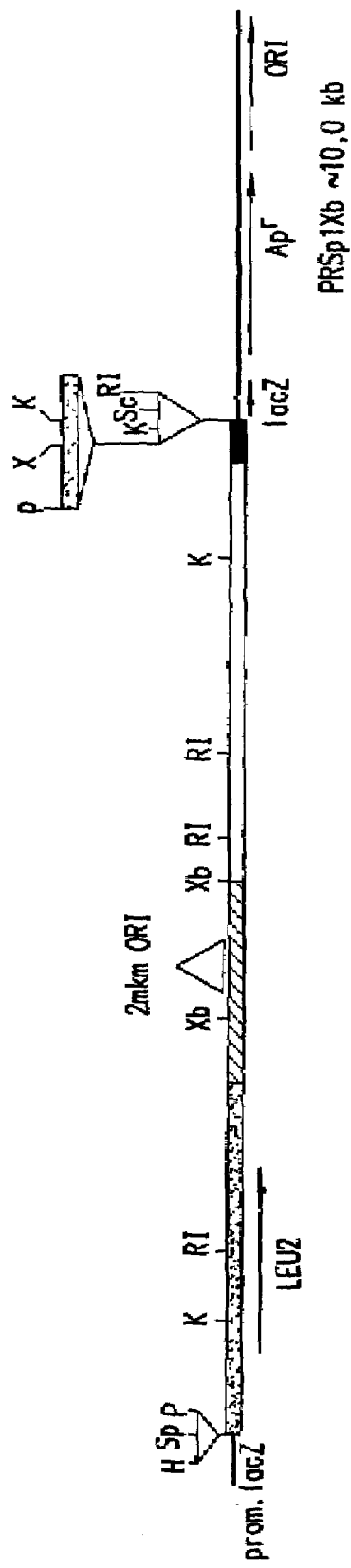

FIG. 40 The linear scheme of PRSp1Xb. The ~2.5 kb insert complementing rib1 mutations of both *Candida famata* and *Pichia guilliermondii* is shown as an open box. Sc2 mkm ORI is shown as a hashed line.

Restriction sites: H, HindIII; Sp, SphI; P, PstI; K, KpnI; RI, EcoRI; Sl, SalI; Xb, XbaI; X, XhoI; B, BamHI; Sm, SmaI; Sc, SacI.

Figure 41:
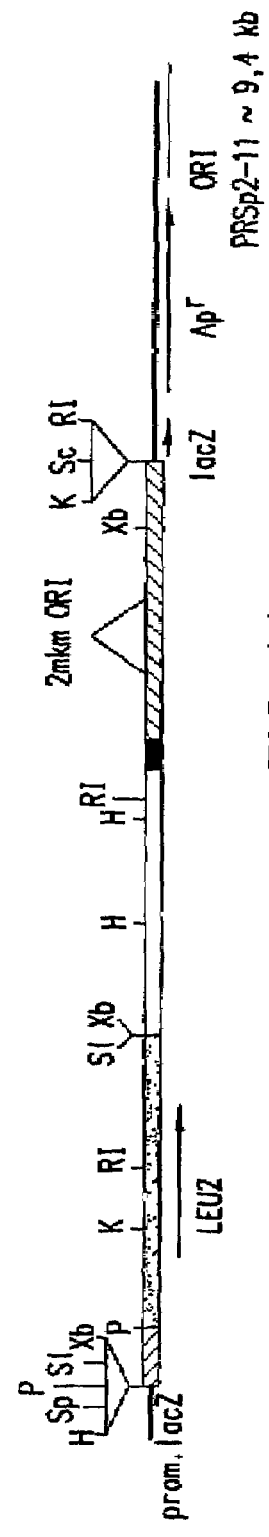

FIG. 41 The linear scheme of PRSp2-11. The plasmid is based on pCfARS1614. The ~2 kb insert complementing rib2 mutations of both *Candida famata* and *Pichia guilliermondii* is shown as an open box. CfARS is shown as the thick black line; Sc2 mkm ORI as a hashed line; PgARS as a checked box.

Restriction sites: H, HindIII; Sp, SphI; P, PstI; K, KpnI; RI, EcoRI; Sl, SalI; Xb, XbaI; Sm, SmaI; Sc, SacI.

Figure 42:
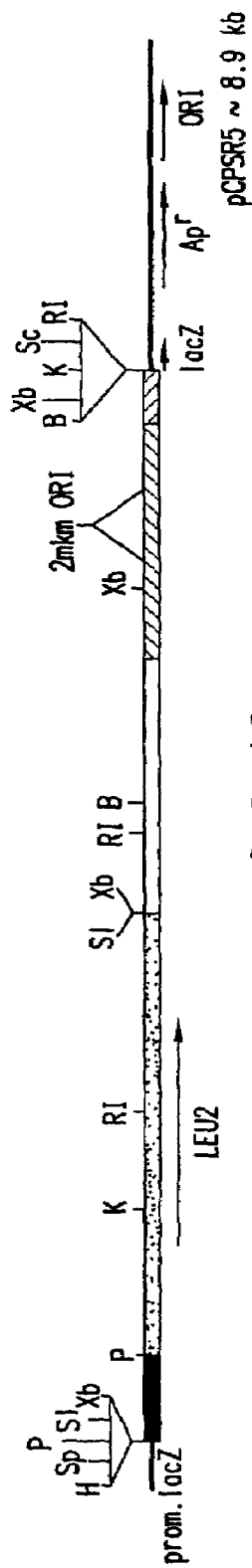

FIG. 42 The linear scheme of the plasmid pCPSR5. The plasmid is a derivative of pCPR5. Sc2 mkm ORI is shown as a hashed line.

Restriction site: H, HindIII; Sp, SphI; P, PstI; K, KpnI; RI, EcoRI; B, BamHI; Sl, SalI; Xb, XbaI; Sm, SmaI; Sc, SacI.

Figure 43:
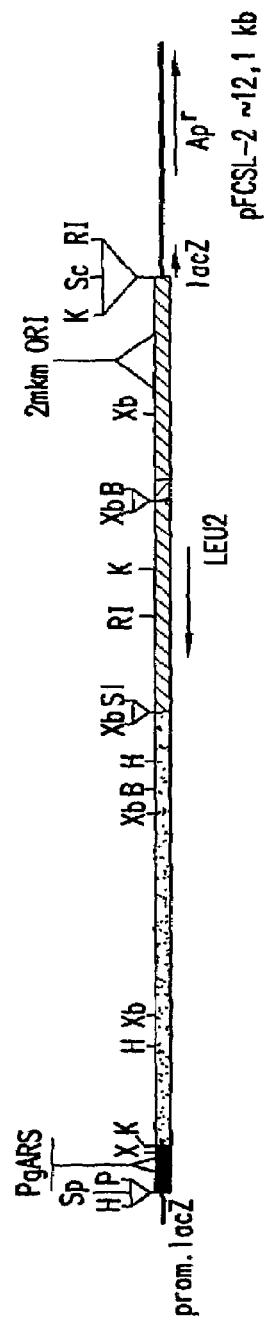

FIG. 43 The linear scheme of plasmid pFCSL-2. The plasmid is a derivative of pFCL-2. Sc2 mkm ORI and a genomic fragment containing LEU2 gene are shown as hashed lines.

Restriction sites: H, HindIII; Sp, SphI; P, PstI; K, KpnI; RI, EcoRI; Sl, SalI; Xb, XbaI; X, XhoI; B, BamHI.

Figure 44:
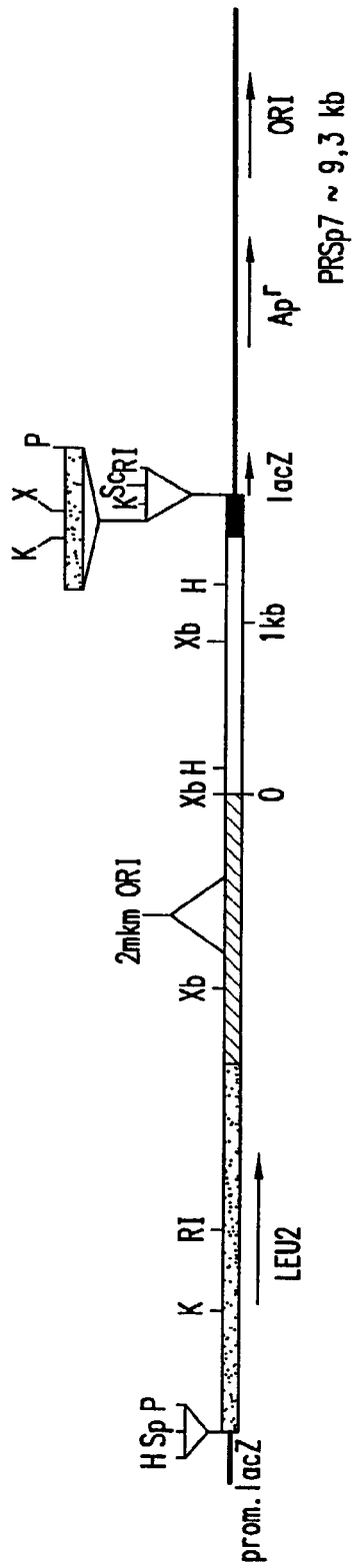

FIG. 44 The linear scheme of PRSp7. The plasmid is a derivative of pCPR7. 2 mkm ORI is shown as a hashed line.

Restriction site: H, HindIII; Sp, SphI; P, PstI; K, KpnI; RI, EcoRI; Sl, SalI; Xb, XbaI; X, XhoI; B, BamHI; Sm, SmaI; Sc, SacI.

Figure 45:
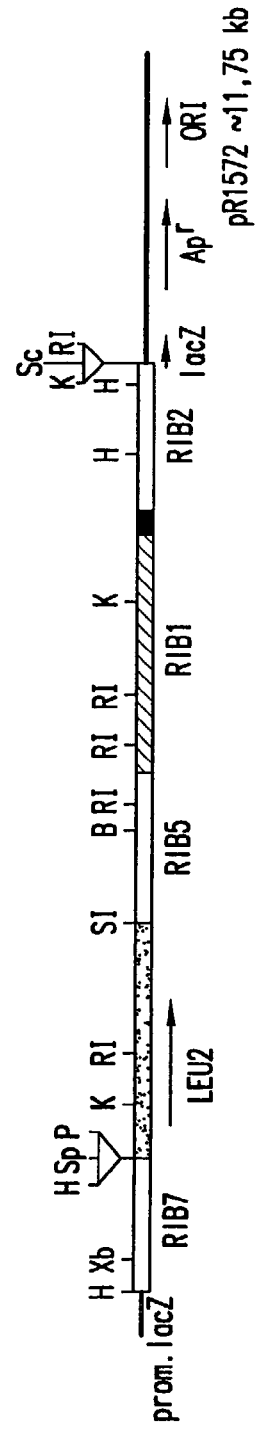

FIG. 45 The linear scheme of plasmid pR1572. The plasmid is a derivative of pCR1Xb. R1B1 is shown as a hashed line. R1B2, R1B5 and R1B7 are shown as open boxes. Restriction sites: H, HindIII; Sp, SphI; P, PstI; K, KpnI; RI, EcoRI; B, BamHI; SI, SalI; Xb, XbaI; Sm, SmaI; Sc, SacI.

DEFINITIONS

In the description that follows, a number of terms used in recombinant DNA (rDNA) technology are extensively utilized. In order to provide a clear and consistent understanding of the specification and claims, the following definitions are provided.

ARS Elements. As used herein, the term "ARS" refers to autonomous replication sequences (elements). ARS sequences enhance the transformation efficiency and the maintenance of vectors as stable extrachromosomal elements in yeast. See, for example, U.S. Pat. No. 4,837,148.

Auxotrophic Mutants. As used herein, auxotrophic mutants are mutant strains which require supplementation with one or more amino acids, vitamins or other nutrients such as purine or pyrimidine bases, in order to grow. Transformation of such a mutant can be readily selected by employing, as part of the recombinant nucleic acid material used to transform the mutant host, nucleic acid sequences which code for the production of the missing gene product. In a preferred embodiment, the nucleic acid sequences are DNA sequences. Mutants are also selected by supplementation with amino acids or vitamins.

Deregulation. As used herein, the term "deregulated or deregulation" refers to an enzyme that is able to convert more substrate to product because, for example, there is an increased amount of the enzyme present in the cell, the enzyme has a higher specific activity, an activity (i.e., an enzyme that competes with the desired enzyme for substrate) is substantially reduced, or combinations thereof. The term "deregulated enzyme" also includes nonenzymatic proteins that influence the enzymatic activity of an enzyme complex containing or interacting with that protein. The amount of an enzyme present in the cell can be increased in a variety of ways including, but not limited to, substantially derepressing synthesis of the enzyme, amplifying the copy number of a nucleic acid sequence encoding the enzyme, and combinations thereof. The specific activity of an enzyme can be increased by modifications of a wild-type enzyme to obtain a deregulated enzyme which is able to convert more substrate to product than essentially the same amount of the wild-type enzyme is able to convert. The specific activity of an enzyme can be increased in a variety of ways including, but not limited to, modifying the catalytic rate of the enzyme, reducing susceptibility of the enzyme to feedback inhibition, and combinations thereof. Methods to increase the specific activity of an enzyme include random or targeted mutagenesis which can be accomplished, for example, by traditional mutation-selection and/or recombinant DNA techniques. See, for example, U.S. Pat. No. 5,445,952.

Derepression. As used herein, the term "derepression" refers to production of greater amounts of an enzyme than are normally produced by wild-type cells such that the amount and/or rate of substrate-to-product conversion is higher than in wild-type cells. In derepressed cells, there is enhanced conversion of substrate to product. Derepression of enzyme synthesis can be accomplished in a variety of ways, including interfering with the regulatory controls that a cell normally exerts over transcription and/or translation of the gene encoding the enzyme and increasing the stability of the messenger RNA (mRNA) corresponding to the enzyme. For example, synthesis of an enzyme which is normally subject to repression may be increased by at least partially inactivating the respective repressor and/or modifying the operator sequence to reduce the ability of the repressor to bind to it. Modification of transcription (e.g., promoter) and/or translation (e.g., Shine Delgarno sequence) control signals (e.g., initiation, elongation, and/or termination signals) can also enhance both the rate and amount of enzyme production. Methods to derepress enzyme synthesis include random or targeted mutagenesis which can be accomplished, for example, by traditional mutation-selection or recombinant DNA techniques. Conditions of derepression may be created, for example, by damaging the controlling gene monitoring the synthesis of the repressor protein, or by damaging the synthesis of the repression cofactor. See, for example, U.S. Pat. Nos. 5,445,952 and 4,278,765.

Expression Vector. As used herein, the term "expression vector" is defined as a DNA construct which includes an autonomous site of replication (ARS), a site of transcription initiation and at least one structural gene coding for a protein which is to be expressed in the host organism. A site of replication, or origin of replication, is any DNA sequence that controls the replication of the cloning and expression vectors. The expression vector usually also contains appropriate control regions such as one or more enhancers and/or promoters, suppressors and/or silencers, and terminators which control the expression of the protein in the host yeast. Expression vectors according to the present invention may also contain a selection marker comprising an essential gene as described herein. The expression vector also optionally contains other selectable markers widely available and well known to those of skill in the art. Expression vectors are one type of vector. Vectors may optionally include one or more ARS sequences (elements) from one or more strains of yeast, such as *Pichia* and *Candida*, for example.

Gene or Gene Segment. As used herein, the term "gene" includes both genomic DNA molecules and the nucleotide sequences encoding the molecules. The term "gene" also includes the corresponding cDNA molecules, naturally occurring DNA molecules, synthetic DNA molecules and the nucleotide sequences encoding the aforementioned molecules. The term "gene segment" includes portions of DNA molecules, the nucleotide sequences thereof and may include upstream and downstream regulatory regions.

Gene Addition. As used herein, the term "gene addition" involves adding the transforming DNA to the endogenous target gene or yeast genome. Depending on the manner in which the modified gene of the transforming DNA was altered, gene addition can result in the presence of either two non-functional copies of the target gene, or one functional and one non-functional copy of the target gene. Each of the two copies consists of a portion of the endogenous gene, and a portion of the transforming DNA. If a functional copy of the target gene remains after gene addition, it can then be removed by homologous recombination between the two copies of the target gene. The combination process of gene addition followed by homologous recombination constitutes the pop-in-pop-out process. Gene addition may occur in both haploid and diploid yeast host cells.

Gene Disruption. As used herein, the term "gene disruption" refers to any manipulation of the target locus that ultimately results in the presence of a gene that does not yield a functional product, or that yields a product with altered function. Disruption can, therefore, result from the presence of added sequence (e.g., by the introduction of auxotrophic marker, or by the introduction of any sequence which causes a shift in the reading frame), the loss of nucleotides from the target gene (e.g., by deletion), or other mutations of the target gene. Gene disruption is achieved by gene addition, gene replacement, or a combination of addition and replacement referred to herein as "pop-in-pop-out".

Gene Replacement. As used herein, the term "gene replacement" refers to the physical removal of the endogenous target gene from the target locus, and replacement with the modified gene or a different gene. This is accomplished by transforming the yeast host with a linear fragment having ends which are homologous to the 5' and 3' ends of the target gene.

Genetic Block. As used herein, the term "genetic block" in the phrase "cells comprising a genetic block" refers to cells comprising one or more mutations in flavinogenesis genes rib1–rib7 or cells comprising a metabolic block due to one or more mutations in genes involved in the biosynthetic pathway of flavinogenesis. "Genetic block" also refers to deficient production of a specific intermediate or end product in the flavinogenic biosynthetic pathway. A genetic block is overcome by complementation or by supplementation of necessary nutrients and/or factors.

Heterologous DNA. As used herein, a "heterologous DNA" is a DNA molecule, or a population of DNA molecules, that does not exist naturally within a given yeast host cell. DNA molecules heterologous to a particular yeast host cell may contain DNA derived from the yeast host cell species so long as that host DNA is combined with non-host DNA. For example, a DNA molecule containing a non-host DNA segment encoding a polypeptide operably linked to a yeast host DNA segment comprising a transcription promoter is considered to be a heterologous DNA molecule.

Integrative transformants. As used herein, "integrative transformants" are yeast cells into which have been introduced heterologous DNA, wherein the heterologous DNA has become integrated into the genomic DNA of the yeast cells.

Linear DNA. As used herein, "linear DNA" is DNA molecules having free 5' and 3' ends, that is non-circular DNA molecules. Linear DNA can be prepared from closed circular DNA molecules, such as plasmids, by enzymatic digestion or physical disruption.

Nucleic acid construct. As used herein, a "nucleic acid construct" is a DNA or RNA molecule, either single- or double-stranded, that has been modified through human intervention to contain segments of nucleic acids combined and juxtaposed in an arrangement not existing in nature. The term "nucleic acid construct" includes clones of nucleic acid molecules which have been so modified. Also included in the term are vectors, expression vectors, and plasmids.

Operably linked. As used herein, the term "operably linked" indicates that DNA segments are arranged so that they function in concert for their intended purposes, e.g., transcription initiates in the promoter and proceeds through the coding segment to the terminator.

Operon. As used herein, the term "operon" refers to a jointly controlled group of genes generally monitoring the synthesis of a single product, such as an enzyme. See, for example, U.S. Pat. No. 4,278,765.

Plasmid. As used herein, the term "plasmid" will have its commonly accepted meaning, i.e., autonomously replicating, usually close-looped, DNA.

Promoter. As used herein, the term "promoter" has its art-recognized meaning, denoting a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. Useful promoters include constitutive and inducible promoters. Many such promoters are known in the art.

Regulate. As used herein, the term "regulate" means that one or more cellular factors can effect the transcriptional activity of a gene that encodes a protein involved in riboflavin synthesis. Thus, one or more cellular factors can regulate the expression of a gene by controlling the transcriptional activity of a gene (i.e., increased or decreased) to a greater or lesser level than occurs in the absence of the cellular factor(s). Up-regulation of a gene can occur, for example, due to induction or to derepression of a gene that is transcriptionally inactive or is expressed at a relatively low level. See, for example, U.S. Pat. No. 5,622,779.

Repression. As used herein, the term "repression" refers to the switching-off of transcription of genes or operons resulting in the termination of synthesis of enzymes. One or more cellular factors also can repress the expression of a gene. The term "repressor" denotes one or more regulating proteins which stop the functioning of genes. Repressor proteins may work in combination with one or more repression cofactors, which may be, but are not always, final products of the biosynthesis or their derivatives. See, for example, U.S. Pat. No. 4,278,765.

Restriction Fragment. As used herein, a "restriction fragment" is any linear DNA generated by the action of one or more restriction enzymes.

Rib Genes. As used herein, by "rib genes" is meant those genes or portions of genes which encode proteins which occur naturally within, or are heterologous to, the organism, or perform a similar function to such proteins, which are involved in the biosynthetic conversion of guanosine triphosphate to riboflavin within the host cell. Generally, the riboflavin biosynthetic proteins are encoded by one or more rib genes, preferably at least seven distinct rib genes (rib1–rib7). An inactivation of one or more rib genes creates a riboflavin auxotroph. Inactivation may be cured by complementation using a heterologous or homologous rib gene.

Riboflavin Biosynthetic Proteins. As used herein, the term "riboflavin biosynthetic proteins" is meant to include those peptides, polypeptides or proteins, and enzymes, which are directly involved in the synthesis of riboflavin from guanosine triphosphate. These proteins may be identical to those which naturally occur within a yeast and are involved in the synthesis of riboflavin within that yeast. Alternatively, there may be modifications of such proteins, for example, the proteins may contain modifications which do not significantly affect the biological activity of the protein. For example, the natural protein may be modified by introducing or substituting one or more amino acids, preferably by conservative amino acid substitution, or by removing nonessential regions of the protein. Such modifications are readily performed by standard techniques. Alternatively, riboflavin biosynthetic proteins may be heterologous to the particular yeast host cell. Such proteins may be from any organism having genes encoding proteins having the same, or similar, biosynthetic roles.

Transformation. As used herein, "transformation" is the introduction of DNA or other nucleic acids into a recipient yeast host cell that changes the genotype.

Transformant. As used herein, a "transformant," or a "transformed cell," is a recipient yeast host cell, and progeny thereof, that has undergone transformation.

DETAILED DESCRIPTION OF THE INVENTION

The invention relates to methods of transformation of flavinogenic yeast.

The invention provides an isolated polynucleotide molecule comprising an ARS nucleotide sequence having at least 95% sequence identity to a nucleotide sequence selected from the group consisting of SEQ ID NO. 1, SEQ ID NO. 2 and SEQ ID NO. 3. In one embodiment, the isolated polynucleotide molecule comprises a nucleotide sequence selected from the group consisting of SEQ ID NO. 1, SEQ ID NO. 2 and SEQ ID NO. 3.

The invention also provides a vector comprising an isolated polynucleotide molecule comprising a nucleotide sequence having at least 95% sequence identity to a nucleotide sequence selected from the group consisting of SEQ ID NO. 1, SEQ ID NO. 2 and SEQ ID NO. 3. In another embodiment, the vector comprises a nucleotide sequence selected from the group consisting of SEQ ID NO. 1, SEQ ID NO. 2 and SEQ ID NO. 3.

In one embodiment, the invention also provides a vector selected from the group consisting of pCfARS6, pCfARS11, pCfARS16, pCfARS1614, pCfARS68, PRpL2, pPgARS11, pPgARS12, pPgARS13, pPgARS14, pPgARS15, pPgARS16, pPgARS17, pRIV-1, pRIV-2, pCR7, PRpRIV-1, pCR1, PRp1, pCR1Xb, pCR2, PRp2, PRp1Xb, pCR2-1, pCR2-21, pCR2-22, PRp2-11, PRp2-12, PgARS19, PRpIV-2, p19R7RIV-2, p19R7RIV-22, pD, pG, pE, pB, pF, pC, pA, pPR5, pCPR5, pPR5, pFC, pFCL-2, PRp7, PRSp1Xb, PRSp2-11, pCPSR5, pFCLS2, PRSp7, pRIB7, p2R, pR15, pR157, pR1572, pR2 and pRIB1.

The invention also provides isolated or purified cells comprising a vector comprising a nucleotide sequence having at least 95% sequence identity to a nucleotide sequence selected from the group consisting of SEQ ID NO. 1, SEQ ID NO. 2 and SEQ ID NO. 3. In one embodiment, the isolated or purified cells comprise a vector comprising a nucleotide sequence selected from the group consisting of SEQ ID NO. 1, SEQ ID NO. 2 and SEQ ID NO. 3. In one embodiment, the cells are yeast cells. In another embodiment, the yeast cells are flavinogenic yeast. In another embodiment, the yeast cells are *Candida* or *Pichia*. In a different embodiment, the yeast cells are *Candida famata* VKM Y-9 L20105 having NRRL deposit number Y-30292.

The invention also provides yeast cells wherein the yeast cells comprise a gene library selected from the group consisting of: a gene library comprising vectors comprising *Pichia guilliermondii* ATCC 9058 DNA segments, PgARS elements, and CfARS elements; and a gene library comprising vectors comprising *Candida famata* VKM Y-9 DNA segments, CfARS elements and PgARS elements.

The invention also provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said constructs comprise a nucleotide sequence having at least 95% sequence identity to a nucleotide sequence selected from the group consisting of SEQ ID NO. 1, SEQ ID NO. 2 and SEQ ID NO. 3. In one embodiment of the method, the construct comprises a nucleotide sequence selected from the group consisting of SEQ ID NO. 1, SEQ ID NO. 2 and SEQ ID NO. 3.

The invention also provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said field strength is from about 8 to about 15 kV/cm. In one embodiment of the method, the resistance is from about 13 ohms to about 720 ohms. In another embodiment of the method, the resistance is about 129 ohms. The invention further contemplates any and all ranges from about 8 to about 15 kV/cm. In one embodiment, the pulse duration is from about 1 ms to about 10 ms.

The invention provides a method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said cell suspension comprises sucrose.

The invention provides a method for the transformation of yeast cells comprising providing spheroplasts of said yeast cells, contacting a solution comprising said spheroplasts with one or more nucleic acid constructs comprising one or more regulatory sequences and one or more genes or gene segments and with one or more fusion agents, for a time sufficient to transform said spheroplasts, wherein said constructs comprise a nucleotide sequence having at least 95% sequence identity to a nucleotide sequence selected from the group consisting of SEQ ID NO. 1, SEQ ID NO. 2 and SEQ ID NO. 3. In one embodiment of the method, the construct comprises a nucleotide sequence selected from the group consisting of SEQ ID NO. 1, SEQ ID NO. 2 and SEQ ID NO. 3.

The invention also provides isolated or purified *Candida famata* cells selected from the group consisting of: a. Leaky rib2 mutants of *Candida famata* VKM Y-9 (leu2⁻rib2⁻)

wherein said mutants grow without exogenous riboflavin and in the absence of cobalt addition; b. *Candida famata* ts rib1 mutants which overproduce riboflavin in both iron-sufficient and iron-deficient media; c. *Candida famata* mutants of part (b) which overproduce riboflavin at reduced temperature; d. *Candida famata* ts rib1 mutants which overproduce riboflavin in iron-sufficient media; e. *Candida famata* ts rib1 mutants which overproduce riboflavin in iron-deficient media; f. *Candida famata* leaky rib2 mutants, wherein said mutants grow without exogenous riboflavin and in the presence of $Co^{+2}$ ions; g. *Candida famata* ts rib1 mutants which are protrophic for riboflavin production at reduced temperatures and which retain riboflavin auxotropy at elevated temperatures; h. *Candida famata* ts rib5/rib6 mutants which are prototrophic for riboflavin production at reduced temperatures and which retain riboflavin auxotrophy at elevated temperatures; i. *Candida famata* leaky rib5/rib6 mutants, wherein said mutants grow without exogenous riboflavin in the presence of exogenous $Co^{+2}$ ions and which are riboflavin auxotrophic in medium without exogenous $Co^{+2}$ ions; j. *Candida famata* ts rib5/rib6 mutants which produce riboflavin in iron sufficient media and which grow in the presence of $Cu^{+2}$ ions; k. Leaky rib2 mutants of *Candida famata* VKM Y-9 (leu2⁻rib2⁻) wherein said mutant comprises sufficient rib2 gene encoded enzyme (reductase) activity to retain riboflavin auxotrophy under conditions of flavinogenesis enzyme repression and simultaneously sufficient reductase activity to produce riboflavin prototrophy under conditions of flavinogenesis enzyme derepression; l. The leaky mutants of (k) wherein said condition of flavinogenesis enzyme repression is growth in iron sufficient media; m. The leaky mutants of (k) wherein said condition of flavinogenesis enzyme derepression is growth in iron deficient media; n. *Candida famata* mutant #105 1-2 (leu2), wherein said mutant grows on ethanol as the sole carbon and energy source and which produces about 70–100 μg riboflavin/ml, having NRRL deposit no. Y-3045 5; o. *Candida famata* VKM Y-9 L20105 having NRRL deposit no. Y-30292; p. *Candida famata* VKM Y-9 (leu2⁻rib⁻) mutants selected from the group consisting of:

1) mutants having a genetic block of the rib1 gene; 2) mutants of (1) transformed with a vector selected from the group consisting of PRp1, pCR1Xb, PRp1Xb and pCR1; wherein said vector comprises a nucleic acid segment which provides complementation of said genetic block when said nucleic acid segment is expressed in said mutant; 3) mutants having a genetic block of the rib2 gene; 4) mutants of (3) transformed with a vector selected from the group consisting of pCR2, pCR2-1, and pR2; wherein said vector comprises a nucleic acid segment which provides complementation of said genetic block when said nucleic acid segment is expressed in said mutant; 5) mutants having a genetic block of the rib3 gene; 6) mutants having a genetic block of the rib5 gene; 7) mutants of (6) transformed with a vector selected from the group consisting of pPR5, pRIV-2, and PRpIV-2; wherein said vector comprises a nucleic acid segment which provides complementation of said genetic block when said nucleic acid segment is expressed in said mutant; 8) mutants having a genetic block of the rib6 gene; 9) mutants of (8) transformed with vector pF; wherein said vector comprises a nucleic acid segment which provides complementation of said genetic block when said nucleic acid segment is expressed in said mutant; 10) mutants having a genetic block of the rib7 gene; and 11) mutants of (10) transformed with a vector selected from the group consisting of pCR7, pPRp7 and RIB7; and, wherein said vector comprises a nucleic acid segment which provides complementation of said genetic block when said nucleic acid segment is expressed in said mutant.

The invention further provides a method comprising: (a) growing a transformed yeast under conditions that provide for synthesis of riboflavin, wherein said transformed yeast comprises one or more nucleic acid constructs comprising one or more copies of one or more genes encoding one or more enzymes involved in riboflavin biosynthesis; wherein said one or more nucleic acid constructs further comprise a nucleotide sequence selected from the group consisting of SEQ ID NO. 1, SEQ ID NO. 2 and SEQ ID NO. 3.; wherein said riboflavin is synthesized by said transformed yeast, said synthesis being greater than that of the corresponding non-transformed yeast; (b) recovering said riboflavin from said culture media in which said transformed yeast was cultured. Optionally, recovering includes purification of the riboflavin produced.

The invention also provides a method comprising: (a) growing a mutant yeast strain under conditions that provide for synthesis of riboflavin, wherein said mutant yeast strain produces riboflavin in both iron sufficient and iron deficient media; wherein said riboflavin is synthesized by said mutant yeast strain, said synthesis being greater than that of the corresponding non-mutant parental yeast strain; and (b) recovering said riboflavin from said culture media in which said mutant yeast was cultured. Optionally, recovering includes purification of the riboflavin produced. In one embodiment of the method, the mutant yeast strain is a *Candida famata* ts rib1 revertant mutant and said parental strain is *Candida famata* VKM Y-9 (leu2rib1) L20105.

The invention also provides a method comprising: (a) growing a mutant yeast strain under conditions that provide for synthesis of riboflavin, wherein said mutant yeast strain produces riboflavin in iron sufficient media, and wherein ethanol is the sole energy and carbon source of said mutant; wherein said riboflavin is synthesized by said mutant yeast strain, said synthesis being greater than that of the corresponding non-mutant parental yeast strain; and (b) recovering said riboflavin from said culture media in which said mutant yeast was cultured.

Optionally, recovering includes purification of the riboflavin produced.

The invention provides a method comprising culturing mutant yeast cells under conditions that provide for synthesis of riboflavin, wherein culturing comprises culture media comprising iron and chromium ions; wherein said mutant yeast cells are *Candida famata* VKM Y-9 L20105; wherein said riboflavin synthesis is greater in said media comprising chromium and iron ions than when said mutant yeast is grown in media lacking chromium ions; and recovering said riboflavin from said culture media in which said mutant yeast was cultured. Optionally, the method includes purification of the riboflavin produced. In another embodiment, the chromium is hexavalent chromium. Optionally, the method includes purification of the riboflavin produced.

The invention provides a method of obtaining flavinogenic yeast cells having one or more altered biological properties as compared to untreated cells comprising treating *Candida famata* NRRL 30292 cells at least once with one or more treatment agents under one or more treatment conditions for a time period sufficient to alter one or more biological properties, wherein one or more biological properties of said treated cells differs from biological properties of untreated cells. In one embodiment, the treatment agents are selected from the group consisting of hexavalent chromium, cadmium ions, cobalt ions, iron ions, copper ions, 2-monofluroacetate, UV light, and nitrosoguanidine. In another embodiment, the treatment conditions are selected from the group consisting of heat shock, cold shock, iron-deficient media, iron-rich media, and alcohol.

The invention provides an efficient method for the transformation of yeast utilizing electroporation. Treatment of cells by electroporation is carried out by applying an electric field to the desired yeast cell suspension between a pair of electrodes. The field strength must be adjusted reasonably accurately so that electroporation of the cells occurs without damage, or at least minimal damage, to any normal or healthy cells. The distance between the electrodes can then be measured and a suitable voltage according to the formula E=V/d can then be applied to the electrodes (E=electric field strength in V/cm; V=voltage in volts; and d=distance in cm).

The various parameters including electric field strengths required for the electroporation of any known cell is generally available from the many research papers reporting on the subject.

Pulse generators for carrying out the procedures described herein are and have been available on the market for a number of years. One suitable signal generator is the ELECTRO CELL MANIPULATOR Model ECM 600 commercially available from BTX, a division of Genetronics, Inc., of San Diego, Calif., U.S.A. The ECM 600 signal generator generates a pulse from the complete discharge of a capacitor which results in an exponentially decaying waveform. The electric signal generated by this signal generator is characterized by a fast rise time and an exponential tail. In the ECM 600 signal generator, the electroporation pulse length is set by selecting one of the timing resistors marked R1 (13 ohms) through R10 (720 ohms). They are active in both High Voltage Mode (HVM) (capacitance fixed at fifty microfarads) and Low Voltage Mode (LVM) (with a capacitance range from 25 to 3,175 microfarads).

The application of an electrical field across the cell membrane results in the creation of transient pores which are critical to the electroporation process. The ECM 600 signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane make-up and individual characteristics of the cell wall itself. For example, mammalian cells typically require between 0.5 and 5.0 kV/cm before cell death and/or electroporation occurs. Generally, the required field strength varies inversely with the size of the cell.

The ECM 600 signal generator has a control knob that permits the adjustment of the amplitude of the set charging voltage applied to the internal capacitors from 50 to 500 volts in LVM and from 0.5 to 2.5 kV in the HVM. The maximum amplitude of the electrical signal is shown on a display incorporated into the ECM 600 signal generator. This device further includes a plurality of push button switches for controlling pulse length, in the LVM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the outside electrodes in an automatic cycle that takes less than five seconds. The manual button may be sequentially pressed to repeatedly apply the predetermined electric field.

The waveforms of the voltage pulse provided by the generator in the power pack can be an exponentially decaying pulse, a square pulse, a unipolar oscillating pulse train or a bipolar oscillating pulse train, for example. The field strength is calculated by dividing the voltage by the distance (calculated for 1 cm separation; expressed in cm) between the electrodes. For example, if the voltage is 500 V between two electrode faces which are ½ cm apart, then the field strength is 500/(½) or 1000 V/cm or 1 kV/cm.

The pulse length can be 100 microseconds ($\mu$s) to 100 milliseconds (ms) and preferably from about 500 $\mu$s to 10 ms. There can be one or more pulses applied to the cells. One skilled in the art would readily be able to determine the appropriate pulse length and number of pulses.

In one embodiment, the resistance is from about R1 (13 ohms) to R10 (720 ohms). In a preferred embodiment, the resistance is about R5 (129 ohms).

The transformed yeasts of the present invention secrete the synthesized riboflavin into the culture medium. This goal is achieved through modification of the metabolism of a desired yeast by introducing and expressing desired heterologous genes, or, deletion or replacement of desired endogenous genes. This goal is also achieved by further modification of the metabolism of certain genes homologous or endogenous to such yeasts in its native state.

The invention will provide a method for the production of riboflavin, the method utilizing a new and novel transformed yeast or in some instances, a mutant yeast, as the producer of the riboflavin. In the invention, the transformed yeast will produce riboflavin either de novo or in enhanced amounts, as a result of the transformation with a vector comprising an ARS sequence and one or more genes encoding one or more enzymes involved in riboflavin synthesis, when compared to the untransformed corresponding yeast.

The invention provides a method for the production of riboflavin using an untransformed yeast, or the transformed yeast as above, the method using the altered riboflavin pathway above, such pathway being altered further by inactivating, using chemically induced mutagenesis or gene disruption or gene addition, of one or more genes encoding any of the enzymes involved in the biosynthesis of riboflavin. In one embodiment of the invention, the inactivated genes are involved in the biosynthetic reactions which produce riboflavin. In another embodiment, the riboflavin biosynthetic gene products are temperature sensitive.

Over-production of riboflavin may be achieved by inserting a gene which codes for an enzyme which is utilized on the route of biosynthesis of riboflavin into a first nucleic acid construct, and inserting a second gene, which codes for an enzyme different from said first enzyme on the route of biosynthesis of said riboflavin into a second nucleic acid construct. The nucleic acid constructs, or vectors, are then introduced into a strain of a yeast to transform said strain which is capable of producing said riboflavin, wherein the enzymes are highly rate determining enzymes for the biosynthesis of riboflavin. Further, insertion of the first and second genes may optionally be followed by insertion of one or more additional genes wherein the additional genes are the same or different genes and are also rate determining enzymes for the biosynthesis of riboflavin. Alternatively, one or more genes encoding one or more different riboflavin biosynthetic pathway enzymes may be inserted into the same vector. Also, the vectors may be the same or different vectors. Additionally, one or more ARS sequences from one or more yeast strains are included in the constructs. In one embodiment, the vector comprises *Candida famata* gene segments, *Candida famata* ARS sequences and *Pichia guilliermondii* ARS sequences. In another embodiment, the vector comprises *Pichia guilliermondii* gene segments, *Pichia guilliermondii* ARS sequences and *Candida famata* ARS sequences.

The invention more particularly relates to the transformation of flavinogenic yeasts, and mutants thereof, by electroporation and by spheroplast transformation. The invention also relates to the transformation of *Pichia guilliermondii* and *Candida famata*, and, mutants of *Pichia guilliermondii* and *Candida famata*. The invention further relates to nucleic acid constructs such as vectors and plasmids comprising ARS and regulatory sequences which transform flavinogenic yeasts at a high level and in a stable manner so as to result in stably transformed yeast host cells.

Electroporation is used within the present invention to facilitate the introduction of DNA into flavinogenic yeast cells. Electroporation is the process of using a pulsed electric field to transiently permeabilize cell membranes, allowing macromolecules, such as DNA, to pass into cells. However, the actual mechanism by which DNA is transferred into the cells is not well understood. For transformation of *Candida famata*, it has been found that electroporation is surprisingly efficient when the cells are exposed to an experimentally decaying pulsed electric field having a field strength of from about 10 to about 13 kV/cm and a resistance value of about R5 (129 ohms), and a time constant of about 4–5 ms. Typically, resistance and capacitance are either present or may be selected by the user, depending on the electroporation equipment selected. In any event, the equipment is configured in accordance with the manufacturer's instructions to provide field strength and decay parameters as disclosed above. Electroporation equipment is available from commercial suppliers.

The invention further relates to transformed flavinogenic yeasts and species thereof, and mutants thereof, produced by the electroporation or spheroplast methods of the invention using the nucleic acid constructs of the invention, or, obtained by any transformation method using the nucleic acid constructs of the invention. The invention more particularly relates to transformed *Pichia* and *Candida* species, especially *Pichia guilliermondii* and *Candida famata*. Within one embodiment of the invention, cells to be transformed by heterologous DNA will have a mutation that can be complemented by a gene (a "selectable marker") on the heterologous DNA molecule. This selectable marker allows the transformed cells to grow under conditions in which untransformed cells cannot multiply ("selective conditions"). The general principles of selection are well known in the art. Commonly used selectable markers are genes that encode enzymes required for the synthesis of amino acids or nucleotides. Yeast cells having mutations in these genes cannot grow in media lacking the specific amino acid or nucleotide unless the mutation is complemented by the selectable marker. Use of such "selective" culture media ensures the stable maintenance of the heterologous DNA within the yeast host cell.

The invention further relates to transformed and non-transformed mutants and nonmutants of flavinogenic yeasts wherein the yeasts overproduce or underproduce riboflavin or over-express or under-express any cofactor or enzyme involved in the synthesis, expression, repression or derepression of riboflavin. The mutants may be obtained by any known chemical or physical mutagenesis method, result from natural biological selection, or result from gene inactivation from using homologous recombination or "knockout" techniques.

When flavinogenic mutant strains are produced by modifying one or more genes, such modifying is carried out, for example, by introducing a modified gene under transformation conditions suitable for the site-directed integration of the modified gene into the genome of the yeast (integrative transformant) at the specific locus of such gene which encodes a protein which influences riboflavin synthesis, riboflavin accumulation, or the synthesis or accumulation of an intermediate in the riboflavin biosynthetic pathway (i.e., the target gene). Integration will replace or alter the yeast endogenous gene, resulting in a yeast host cell which is an integrative transformant. A convenient means to introduce the modified gene into the target locus of a yeast host is to include the modified gene in a linear DNA fragment having ends homologous to two separate portions of the intact gene within the yeast host. This will direct, upon transformation, that homologous recombination occur at the specific locus of the gene whose expression product influences riboflavin production. The endogenous gene is said to be disrupted (gene disruption) when homologous recombination replaces all (gene replacement), or a portion of the endogenous gene, with all or a portion of the modified gene, or, with any nonidentical nucleic acid segment or nucleotide base.

The copy number of one or more genes encoding riboflavin biosynthetic pathway enzymes may also be increased by gene addition. Gene addition can result in the presence of either two non-functional copies of the target gene, or one functional and one non-functional copy of the target gene or two functional copies of the target gene.

Transformants are tested for expression of heterologous genes, either by genetic selection or screening, to find those having a mutation that causes increased expression of the inserted DNA segment resulting in an increase in production of a polypeptide encoded by, or a recombinant product produced as a result of, the inserted DNA segment. Transformants are tested for disruption of endogenous genes, either by genetic selection or screening, to find those having decreased expression of a recombinant product encoded by, or produced as a result of, the inserted DNA segment.

The invention further relates to nucleic acid constructs such as vectors, including expression vectors, and plasmids and to ARS sequences which transform flavinogenic yeasts, and mutants thereof, at a high level and in a stable manner so as to result in stably transformed yeast host cells. The invention also relates to autonomous replicating sequences (ARS) which maintain plasmids as extrachromosomal elements in flavinogenic yeasts. The invention further relates to constructs including the DNA sequences as well as processes for producing the DNA sequences and constructs of the invention. These various plasmids may be used as expression vectors to ensure expression in yeast of heterologous genes suitably positioned upstream of the promoters of the invention. Examples of particular constructs are given as illustrations in the present application, but many other possibilities exist, and various combinations of replication origins, marker genes, control regions and other structural elements which are operably linked may be used to obtain similar results. The various expression vectors which can thus be constructed to express homologous or heterologous genes by virtue of the ARS-containing sequences of the invention must be considered as being within the scope of the invention. The vectors of the present invention contain *Pichia* and *Candida*-derived autonomous replication sequences (ARS elements), which enhance both the transformation frequency and the maintenance of the vectors as stable extrachromosomal elements in yeasts of the genus *Pichia* and *Candida*. These autonomous replication sequences are useful because known yeast ARS elements isolated from *S. cerevisiae* do not function in hosts of the genus *Pichia* and *Candida*.

In general, DNA sequences which have autonomous replication activity in a host of the genus *Pichia* or *Candida* can be isolated by transforming the *Pichia* or *Candida* host with a library of DNA fragments constructed in a vector which contains, among other DNA sequences, a marker gene, but does not contain any DNA sequences with ARS activity in *Pichia* or *Candida*. The marker gene employed will confer a selectable phenotype upon the host yeast strain. The frequency of transformation of the host strain with the vector will be increased by one or more orders of magnitude when DNA sequences with ARS activity are present in the vector compared to the frequency of transformation with an unmodified vector. Thus, selection and isolation of transformed host organisms will provide organisms carrying plasmids with inserted DNA sequences which have ARS activity. In this fashion, DNA sequences from any source which have ARS activity in *Pichia* or *Candida* can be readily isolated.

The invention further relates to highly efficient methods of transformation of yeasts which allow for a high level of expression of any one or more desired endogenous (naturally existing within that yeast cell) or heterologous genes. The method of the invention further relates to a method for isolating and cloning genes and ARS sequences. The method of the invention further relates to the regulatory regions useful for the expression of those genes. When a yeast strain has been induced according to the present invention to produce one or more gene products or riboflavin, it is necessary to multiply the yeast under conditions most favorable to its growth in order to take advantage of this new property. One skilled in the art will easily determine these conditions according to the characteristics peculiar to the yeast strain used as host. As transformed yeast have a tendency to lose artificially-constructed plasmids, it is advantageous to use a culture medium so as to exert a positive selection pressure on them. When the strain is an auxotrophic mutant for an essential metabolite and when the vector plasmid used comprises a marker gene capable of restoring the strain prototrophy, for example, the LEU2 gene mentioned above, this selection pressure may be exerted by omitting the metabolite from the culture medium. Other means exist to obtain the same result and may also be used to practice the invention.

The "nutritionally limiting conditions" required for the increased gene expression of the present invention can be provided either by feeding the yeast limiting amounts of a nutrient or by employing a mutant host which, as a result of the mutation, is nutritionally limited under certain growth conditions.

It is believed that the method for increasing the expression of heterologous gene products described herein is a general method useful in any yeast for which promoters which respond to nutritional limitations exist. Thus, by placing a heterologous gene under the control of such a promoter region, then culturing the yeast under conditions of nutritional limitation with respect to the nutrient(s) which cause the strong promoter to be turned on, increased gene expression should occur. The presently preferred means to provide nutritionally limited growth conditions is to employ a mutant host organism which is partially defective in the ability to metabolize the nutrient(s) which causes some promoters to be expressed at much higher levels than in the non-mutant host.

When transformed yeasts have been grown under conditions ensuring the best production of the product of interest, the product still has to be recovered. In one embodiment, the product of interest is riboflavin. In another embodiment, the product of interest is one or more riboflavin biosynthetic pathway enzymes. In one embodiment, yeast cells will be transformed with one or more copies of one or more genes encoding an enzyme involved in riboflavin biosynthesis. The invention is then directed to a method for over-producing riboflavin comprising: a) growing a transformed yeast under conditions that provide for synthesis of riboflavin, wherein said transformed yeast comprises one or more copies of one or more genes encoding an enzyme involved in riboflavin biosynthesis; wherein said riboflavin is synthesized by said transformed yeast, said synthesis being greater than that of the corresponding non-transformed yeast; b) recovering said riboflavin from said culture media in which said transformed yeast was cultured, and, optionally, c) purifying said riboflavin.

In another embodiment, the invention is directed to a method for over-producing riboflavin comprising: a) growing a mutant yeast strain under conditions that provide for synthesis of riboflavin, wherein said mutant yeast strain produces riboflavin in both iron sufficient and iron deficient media; wherein said riboflavin is synthesized by said mutant yeast strain, said synthesis being greater than that of the corresponding non-mutant parental yeast strain; b) recovering said riboflavin from said culture media in which said mutant yeast strain was cultured, and, optionally, c) purifying said riboflavin.

Many techniques are available which those skilled in the art will combine to obtain in each case the best recovery yield and the greatest purity of the desired product of interest, whether the product is an expression product or an intermediate or end product (riboflavin) of the flavinogenic biosynthetic pathway.

Depending upon the nature of the structural gene of interest, the product or expression product may remain in the cytoplasm of the yeast host cell or be secreted. It has been found that not only the proteins that remain in the cell but also those that are secreted are soluble. Where the product or expression product is to remain in the yeast host cell, it may generally be desirable to have an inducible transcription initiation region, so that until the transformant has reached a high density, there is little or no expression or production of the desired product. After sufficient time for the product or expression product to form, the cells may be isolated by conventional means, e.g., centrifugation, lysis and the product of interest isolated. Depending upon the nature and use of the product, the lysate may be subjected to various purification methods, such as chromatography, electrophoresis, solvent extraction, crystallization, dialysis, ultrafiltration or the like. Methods of chromatography include, but are not limited to, gas chromatography, HPLC, column chromatography, ion exchange chromatography and other methods of chromatography known to those of skill in the art. The degree of purity may vary from about 50%, to 90% or higher, preferably up to about 100%.

Alternatively, the expression product or product of interest may be secreted into the culture medium, and produced on a continuous basis, where the medium is partially withdrawn, the desired product extracted, e.g., by column or affinity chromatography, ultrafiltration, precipitation or the like, and the spent medium discarded or recirculated by restoring essential components. The permeate containing the product from the ultrafiltration can be further subjected to concentration, further by evaporation, followed by crystallization or precipitation using alcohol and/or pH adjustment. Those of skill in the art are aware of the many process options. When the product is to be secreted, normally a constitutive transcriptional initiation region will be employed, although nonconstitutive regions may be used.

Naturally occurring DNA, and synthetic genes may be employed for the production of proteins of interest.

The invention also relates to production of riboflavin using the untransformed or transformed flavinogenic yeast host cells, and mutants thereof, produced by the electroporation transformation method and/or the spheroplast transformation method of the invention. In one embodiment of the invention, the untransformed or transformed flavinogenic yeast host cells, or mutants thereof, are temperature sensitive for riboflavin production.

Unless otherwise indicated, all nucleotide sequences newly described herein were determined using an automated DNA sequencer (such as, for example, the Model 377 from PE Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

In certain embodiments, polynucleotides of the invention comprise a nucleic acid, the sequence of which is at least 90%, 91%, 92%, 93%, 94%, 95%, 96%, 97%, 98% or 99% identical to a sequence selected from the group consisting of SEQ ID NO:1, SEQ ID NO:2; and SEQ ID NO:3, or a complementary sequence thereof.

By a polynucleotide comprising a nucleic acid, the sequence of which is at least, for example, 95% "identical" to a reference nucleotide sequence. It is intended that the nucleic acid sequence is identical to the reference sequence except that the nucleic acid sequence may include up to five mismatches per each 1100 nucleotides of the reference nucleic acid sequence. In other words, to obtain a nucleic acid, the sequence of which is at least 95% identical to a reference nucleic acid sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be any one of the entire nucleotide sequences shown in SEQ ID NO:1, SEQ ID NO:2, or SEQ ID NO:3, or any fragment of any of these sequences, as may be described herein.

As a practical matter, whether any particular nucleic acid sequence is at least 90%, 91%, 92%, 93%, 94%, 95%, 96%, 97%, 98% or 99% identical to, for instance, a nucleotide sequence consisting of SEQ ID NO:1; SEQ ID NO.:2, or SEQ ID NO:3, or a complementary sequence thereof, can be determined conventionally using sequence analysis computer programs such as a OMIGA® Version 2.0 for Windows, available from Oxford Molecular, Ltd. (Oxford, U.K.). OMIGA uses the CLUSTAL W alignment algorithm using the slow full dynamic programming alignment method with default parameters of an open gap penalty of 10 and an extend gap penalty of 5.0, to find the best alignment between two nucleotide sequences. When using CLUSTAL W or any other sequence alignment program to determine whether a particular sequence is, for instance, 95% identical to a reference sequence according to the present invention, the parameters are set, of course, such that the percentage of identity is calculated over the full length of the reference nucleotide sequence such that gaps, mismatches, or insertions of up to 5% of the total number of nucleotides in the reference sequence are allowed. Other sequence analysis programs, known in the art, can be used in the practice of the invention.

This embodiment of the present invention is directed to polynucleotides comprising a nucleic acid, the sequence of which is at least 90%, 91%, 92%, 93%, 94%, 95%, 96%, 97%, 98% or 99% identical to a nucleic acid sequence of SEQ ID NO:1, SEQ ID NO:2, and SEQ ID NO:3, or a complementary sequence thereof, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, are polynucleotides comprising a nucleic acid, the sequence of which is at least 90%, 91%, 92%, 93%, 94%, 95%, 96%, 97%, 98% or 99% identical to a nucleic acid sequence of SEQ ID NO:1, SEQ ID NO:2 or SEQ ID NO:3, or a complementary sequence thereof, which do, in fact, have functional activity in yeast cells, particularly in flavinogenic yeast cells and most particularly in *Candida* or *Pichia* yeast cells.

The present invention is described in further detail in the following non-limiting examples.

EXAMPLES

Example 1

Leucine-deficient Mutants of *C. famata* VKM Y-9

A suspension of a two day culture of *C. famata* VKM Y-9 from a cell wort agar slant was mutagenized with UV light with a dose resulting in 10% cell survival. The cell concentration was $10^7$/ml. The duration of UV irradiation was 35–40 sec. After mutagenesis, the cell suspension was plated, calculating 200–300 viable colonies/plate, on agar containing synthetic modified Burkholder medium with leucine (40 mg/l). The medium contained (per 1 liter): glucose, 20 g; $(NH_4)_2SO_4$, 3 g; $KH_2PO_4$, 0.5 g; $MgSO_4 \times 7H_2O$, 0.2 g; $CaCl_2 \times 6H_2O$, 0.2 g; $Na_2HPO_4$, 0.1 g; biotin, 1 $\mu$g; iron as the Mohr salt, 0.2 mg; trace elements $H_3BO_3$, 56 $\mu$g; $CuSO_4 \times 5H_2O$, 39.3 $\mu$g; $MnSO_4 \times 5H_2O$, 50.4 $\mu$g; $(NH_4)_6Mo_7O_{24} \times 4H_2O$, 120 $\mu$g; $ZnSO_4 \times 7H_2O$, 307.9 $\mu$g; agar, 20 g.

After 4–5 days of the cultivation at 30° C., the grown colonies were replica plated on medium without leucine. The colonies which were unable to grow without leucine, were picked up, streaked on the YPD medium and were tested once more by replica plating on leucine-deficient media. Additionally, the auxotrophy of the mutants was tested in liquid media. Each mutant candidate was inoculated in tubes to grow with and without leucine.

Selection experiments following testing of 45,180 colonies resulted in isolation of 16 leucine defective (leu⁻) mutants of *C. famata*.

Example 2

Identification of *C. famata* VKM Y-9 leu2 Mutants

Figure 4:
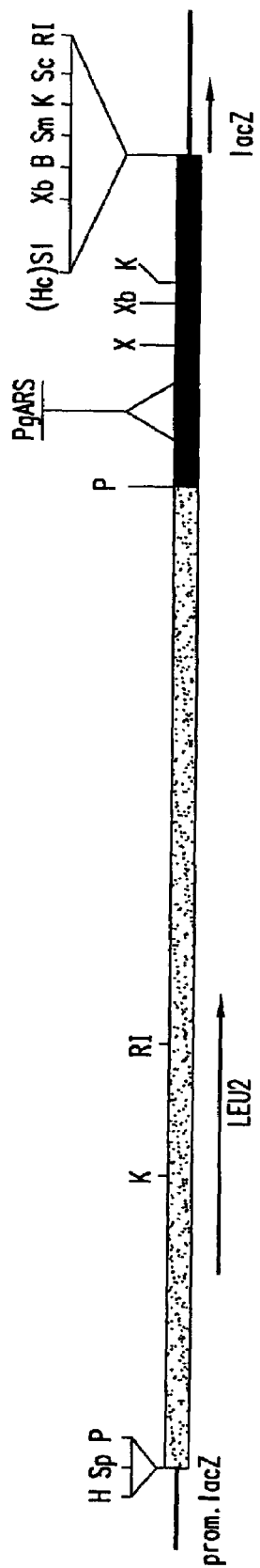
FIG. 4 shows the linear scheme of plasmid PRpL2 (7.66 kb). The *Saccharomyces cerevisiae* LEU2 gene is represented by the thick gray line; the PgARS element, by the thick black line; and pUC19, by the thin line.
Figure 5:
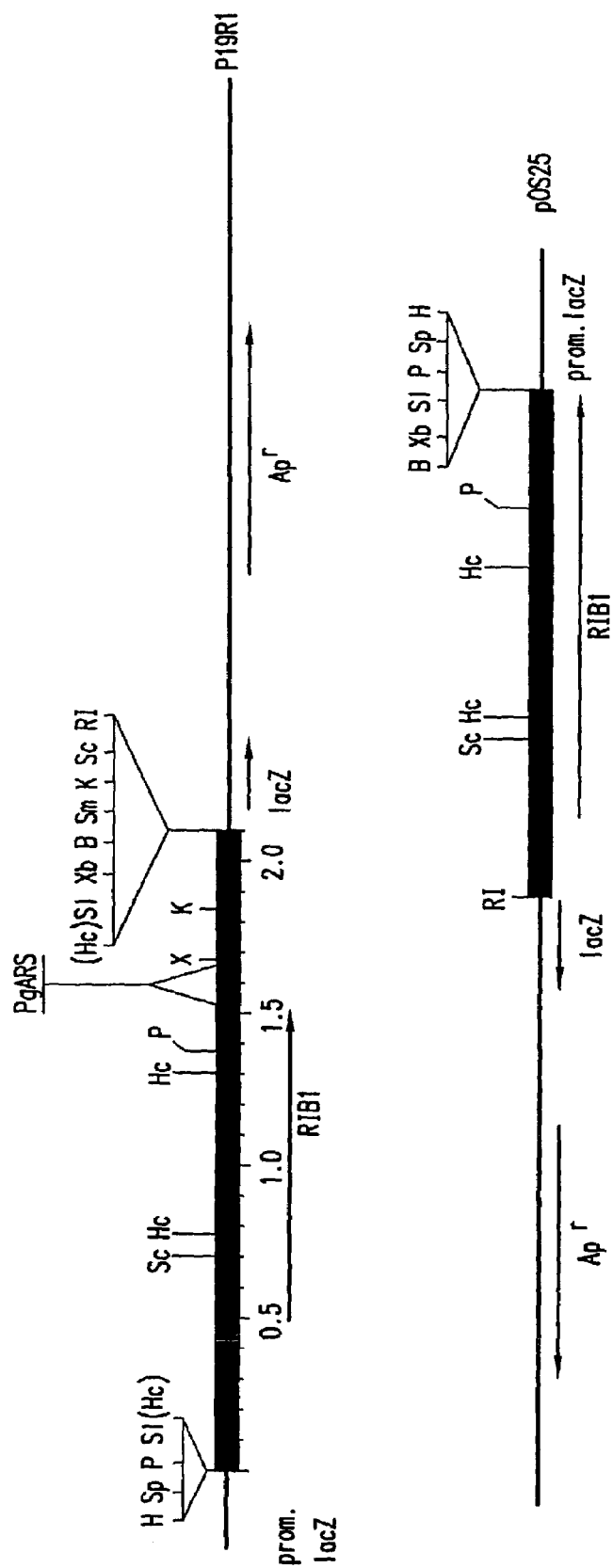
FIG. 5 shows the linear schemes of plasmids p19R1 and pOS25.

Identification of leu2 mutants was conducted by means of transformation of five isolated leu⁻ mutants (## 3, 7, 12, 100, 105) with LEU2 containing plasmids. Two vectors were constructed for this purpose: recombinant plasmid PRpL2 and a standard yeast vector, YEp13. Plasmid PRpL2 (7.66 kb) contains the full sequence of pUC19 (bacterial), a 4.2 kb PstI fragment of *S. cerevisiae* DNA comprising the LEU2 gene and a 0.79 kb fragment of *P. guilliermondii* genomic DNA comprising a PgARS element (see FIG. 4).

Transformation of the selected leu2⁻ mutants was carried out by the spheroplast method as described (Sreekrishna, K. and Kropp, K. E. *Pichia pastoris*. In: K. Wolf (ed.). Nonconventional Yeasts in Biotechnology, 1996, Springer, Berlin, 1996, p.215–226) with some modifications:

1. A fresh colony of leu⁻ mutant was inoculated into 3 ml of YPD and cultivated for approximately 24 h at 30° C. to saturation.
2. 50–100 µl of cell suspension obtained from step 1 was inoculated into 200 ml YPD and cultivated overnight with shaking at 30° C.
3. Next morning the optical density of the cell suspension was measured at 600 nm ($OD_{600}$). The cultures were collected by centrifugation after reaching an $OD_{600}$ of 0.2–0.4.
4. The cells were washed once with 20 ml of sterile water.
5. The cells were washed once with 20 ml of fresh SED solution (sucrose/EDTA/DTT). During *C. famata* transformation, sucrose was used instead of sorbitol, as we have found unexpectedly that sorbitol strongly reduces spheroplast viability.
6. The cells were washed once with 20 ml of 1 M sucrose.
7. The cells were resuspended in 20 ml of sucrose/citrate/EDTA (SCE) buffer and lyticase (Lyticase, crude, "Sigma") (approximately 1,000 U/17 mg of dry weight cells) was added. The cell suspension comprising the lyticase was incubated for 1 h at 30° C. To test protoplasting, 150 µl of cell suspension in SCE buffer was added to 3 ml $H_2O$ before lyticase treatment. The same procedure was carried out during cell incubation with lyticase. The samples were read at $OD_{600}$. Incubation with the enzyme was stopped when the $OD_{600}$ decreased 70–90% from the initial $OD_{600}$.
8. Spheroplasts were collected by gentle centrifugation (750×g) for 10 min at room temperature.
9. Spheroplasts were washed once with 15 ml of 1 M sucrose using gentle centrifugation.
10. Spheroplasts were washed once with 15 ml of CaS (calcium/sucrose) buffer.
11. Spheroplasts were resuspended in 0.5 ml CaS buffer.
12. 5 micrograms of the plasmid DNA (in a volume not exceeding 10 µl) was added to the sample of spheroplasts (100 µl). The sample comprising the spheroplasts and DNA was incubated for 15 min at room temperature. As a control, another sample of protoplasts was treated with TE buffer (10 mM Tris-HCl pH 8.0, 1 mM EDTA) without plasmid DNA.
13. 1 ml PEG 3000 (Ferak) in 10 mM tris-HCl (pH 7.5) with 10 mM $CaCl_2$ was added to the mixture of spheroplasts and DNA, gently mixed and incubated for 15 min at room temperature.
14. The mixture was centrifuged at 750 g for 8 min at room temperature and the supernatant was discarded.
15. The pellet was carefully resuspended in 150 µl of SOS buffer (1 M sorbitol 0.3×YPD medium, 10 mM $CaCl_2$) and incubated for 30 min at room temperature.
16. 850 µl of 1 M sucrose was added as an osmotic stabilizer.
17. Suspensions of transformed spheroplasts were plated on the surface of agar selective medium containing 1 M sucrose as an osmotic stabilizer (0.1 ml to 0.25 ml per plate).
18. The plates were incubated at 30° C. until growing colonies appeared (up to one week).

Leu⁻ mutants of *C. famata* ##3, 12 and 105 were transformed with plasmids comprising the LEU2 gene of *S. cerevisiae* (PRpL2 and YEp13), producing colonies prototrophic for leucine. In these cases, the colonies appeared after 3–6 days of spheroplast plating. The results are presented in Table 1.

TABLE 1

Transformation of leu2 mutants of *Candida famata*

| Strain | Plasmid Used for Transformation | Transformation Frequency; transformants/µg DNA |
|---|---|---|
| 1. #3 (L203) | PRpL2 | 250 |
| 2. #3 (L203) | YEp13 | 106 |
| 3. #12 (L2012) | PRpL2 | 105 |
| 4. #12 (L2012) | YEp13 | 30 |
| 5. #105 (L20105) | PRpL2 | 290 |
| 6. #105 (L20105) | YEp13 | 30 |

The transformation frequency for L203 was 250 and 106 transformants/µg DNA with plasmids PRpL2 and YEp13, respectively; for L2012—105 and 30 transformants, respectively, and for strain L20105—290 and 30 transformants, respectively. The mutants appeared to be very stable and the frequency of their reversion to prototrophy was less than $10^{-7}$. The reversion frequency was maintained at this low level after mutant spheroplasting. Thus, we have identified leu2 mutants of *C. famata* by complementing the corresponding defects with the LEU2 containing plasmids.

Cultures of *C. famata* VKM Y-9 leu2⁻ mutant L20105 were deposited under the terms of the Budapest Treaty on the International Recognition of the Deposit of Microorganisms for Purposes of Patent Procedure on May 5, 2000, at the Agricultural Research Service Culture Collection (NRRL), 1815 North University Street, Peoria, Ill. 61604 USA. The deposit of the culture of the mutant was accepted by that Depository under the terms of that Treaty. The deposit of culture mutant *C. famata* VKM Y-9 leu2⁻ L20105 was assigned NRRL deposit number Y-30292.

Example 3

Construction of a *Candida famata* VKM Y-9 Gene Library

Figure 3:
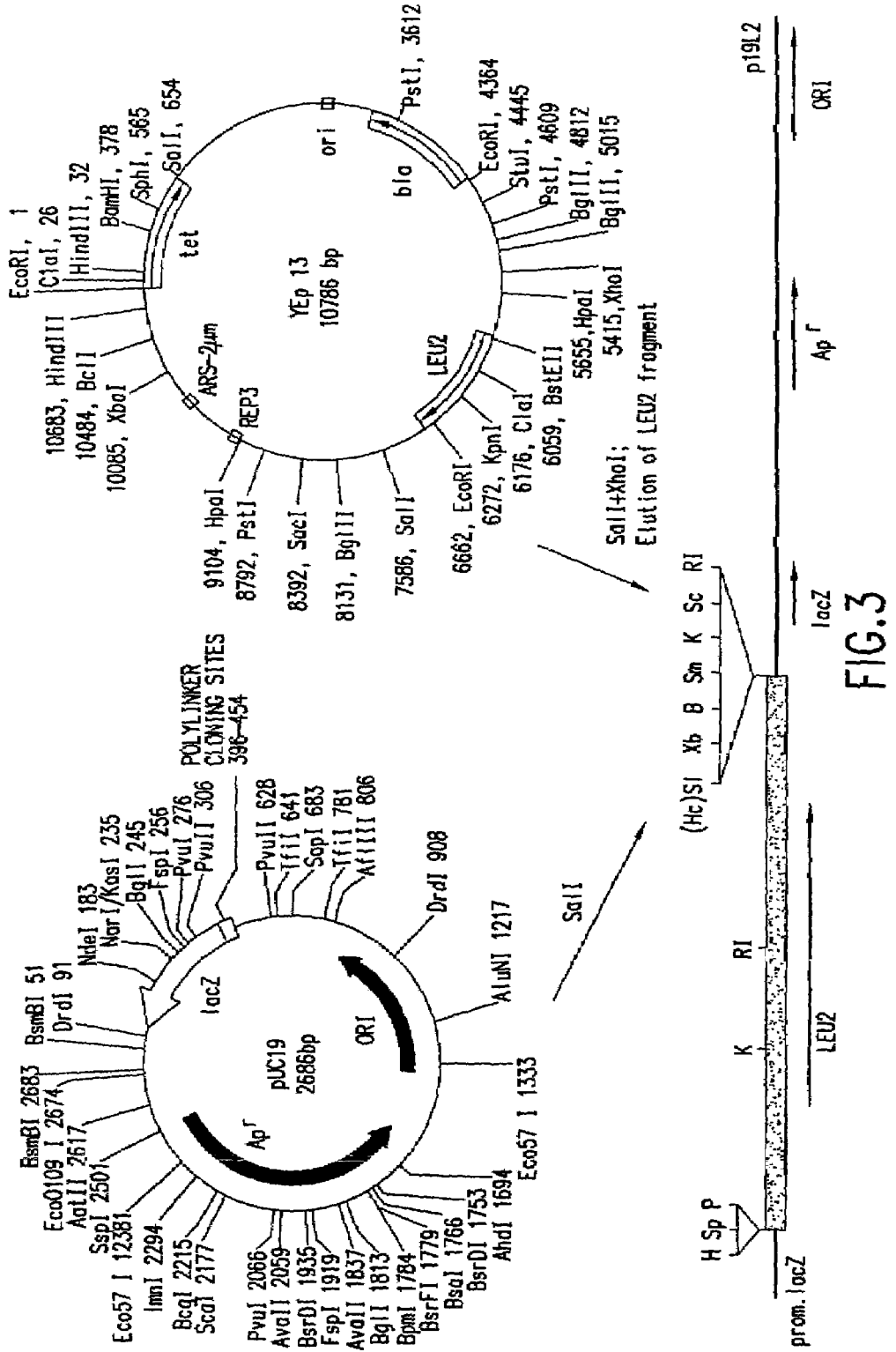
FIG. 3 shows construction of the plasmid 19L2.
Figure 8:
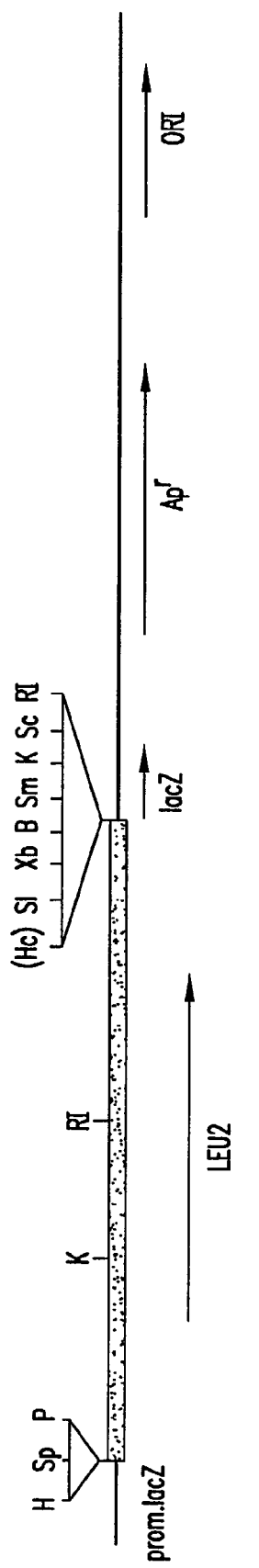
FIG. 8 shows the linear scheme of plasmid p19L2.

The plasmid p19L2 (4.86 kb) (FIG. 3 and FIG. 8) was used as the vector for construction of a *C. famata* VKM Y-9 gene library (FIG. 9). The plasmid was obtained in the following manner: A SalI-XhoI fragment (2.17 kb) was isolated from the YEp13 plasmid of *S. cerevisiae* and was inserted into a SalI fragment of the bacterial plasmid pUC19 (FIG. 3 and FIG. 8). The plasmid p19L2 has been used for transformation of *C. famata* VKM Y-9 leu2 L20105 isolated (Example 1) as above. In the experiment which used the spheroplasts isolated from *C. famata* strain L20105 using the crude preparation of Lyticase ("Sigma"), the frequency of transformation was about 30 transformants per µg DNA whereas the use of the Lyticase preparation which is "partially purified," resulted in a frequency of transformation of approximately $1.5 \times 10^4$ per µg DNA. In both cases more than 98% of the transformant colonies were small and less than 2% of them were large ones. After replica-plating on selective YNB medium, small colonies gradually lost ability to grow and after three consecutive replica platings most of them were eliminated. Approximately 50% of the remaining colonies growing in minimal medium appeared to be large ones and are expected to be the integrants.

Thus, inefficient transformation was observed using the p19L2 plasmid, since a stable Leu$^+$ phenotype is maintained only in a small proportion of the transformants.

For gene library construction, p19L2 plasmid (30 μg) was linearized with the endonuclease BamHI. The enzyme ("Fermentas," Lithuania) was added at a concentration of 6 units per 1 μg of plasmid DNA. The completeness of the plasmid linearization was tested using the *Escherichia coli* transformation system as previously described (Rose et al. (1991)).

20 μg of the BamHI linearized p19L2 plasmid was dephosphorylated by means of alkaline phosphatase (Boehringer Mannheim, Germany) which was used at the concentration of 0.4 U per 1 μg of plasmid DNA. The amount of alkaline phosphatase was chosen using the protocol of Rose et al. (1991).

Total high molecular weight DNA was isolated from *C. famata* VKM Y-9 cells using the previously described method (Cregg, J. M. et al., *Mol. Cell. Biol.* 5:3376–3385 (1985)) with some modifications. The cells were cultivated in 1.2 liters of YPD medium to an optical density 1.5 (540 nm, 3 mm cuvette). The cells were sedimented by centrifugation (2,000 g, 7 min), washed with 120 ml of water, then washed with 60 ml of SED solution (1 M sucrose, 25 mM EDTA, 50 mM dithiothreitol) and then washed with 60 ml 1 M sucrose. The cells were then resuspended in 60 ml ST buffer (1 M sucrose, 75 mM tris-HCl, pH 8.0), and 15,000 units of lyticase (Sigma, "partially purified") was added. The suspension was incubated for 1 h 20 min for cell wall digestion. Protoplasting was monitored by suspension lysis after transfer into osmotic non-stabilized medium. Cells were suspended in 10 ml SCE and absorbance was checked after dilution of 100–150 μl of cell suspension in 3 ml of water. During incubation with lyticase, absorbance was checked at 5 minute intervals. Protoplasting resulted in an absorbance decrease to 10–20% of the initial value.

Spheroplasts were centrifuged at 750 g for 10 min and were resuspended in 7 ml of buffer (1 M sucrose, 50 mM tris-HCl, pH 8.0, 50 mM EDTA). 50 ml of lysis buffer (0.5% sodium dodecyl sulfate, 10 mM tris-HCl, pH 8.0, 10 mM EDTA, 50 mM NaCl) was then added and the suspension was incubated for 20 min at 65° C. After cooling to room temperature, proteinase K (50 μg/ml) and RNAse (100 μg/ml) was added and incubated for 40 min at 37° C. DNA was deproteinized with an equal volume of phenol saturated with buffer. The water phase was separated by centrifugation (10,000×g, 25 min). The treatment with phenol was repeated. The water phase was withdrawn and 2–3 volumes of 96% ethanol were added. After gentle mixing, the DNA was picked up by spooling on a glass rod. Isolated DNA was dissolved in 5 ml of TE buffer (10 mM Tris-HCl, pH 8.0, 1 mM EDTA) and dialyzed against 100 volumes of TE buffer overnight at 4° C.

Partial digestion of the total DNA isolated from *C. famata* VKM Y-9 was conducted using endonuclease Sau3AI according to methods known in the art (T. Maniatis, E. F. et al., *Molecular Cloning: a Laboratory Manual*. Cold Spring Harbor Laboratory, Cold Spring Harbor, N.Y. (1982)). The Sau3AI enzyme ("Fermentas," Lithuania) was used at 25 U/μg DNA. Partial digestion of 30 μg DNA was conducted in a total volume of 500 μl. DNA was incubated with Sau3AI for 15 min at 37° C. Reaction was stopped by putting the mixture on the ice and EDTA was added to a final concentration of 20 mM. The sample of DNA was extracted by phenol, washed with 70% ethanol and dissolved in 150 μl of TE buffer. The concentration of the obtained DNA fragments is ~0.2 μg/μl. Electrophoresis analysis revealed most of the restriction fragments possessed molecular sizes in the range of 0.5 kb to 8 kb.

Linearized dephosphorylated vector p19L2 was ligated with the Sau3AI fragments of the total DNA of *C. famata* VKM Y-9. Ligation was carried out as was previously described (Rose et al. (1991)). The vector DNA was mixed with fragments in the ratio 1:1 in a 1 ml ligation reaction volume. Ligation was carried out in the water bath in the refrigerator overnight. In such conditions, the temperature gradually decreased from room temperature to 4° C. DNA ligase ("Fermentas," Lithuania) was added at 8 U of the enzyme/μg total DNA. The resulting ligate was used for transformation of *E. coli* DH5α. Altogether, more than 30,000 bacterial transformants resulted. The transformant colonies were washed out from the plates with sterile LB medium containing ampicillin (50 μg/ml), grown in 2 l of this medium for 3.5 h on a shaker at 37° C. Plasmid DNA was isolated using alkaline lysis (Birnboim, H. C. and J. Doly, *Nucleic Acid Res.* 7:1513–1523 (1979)). The obtained plasmid DNA (the gene library of VKM Y-9) was used for transformation of *C. famata* VKM Y-9 L20105. The transformation frequency was $5.5 \times 10^4$ transformants/μg DNA, which is 3.6 times higher than the frequency of transformation obtained with the vector p19L2 alone without genomic DNA inserts. The majority of transformants isolated after transformation with the VKM Y-9 gene library retained the Leu$^+$ phenotype under conditions of selective growth. After 3 replica platings on selective YNB medium, more than 80% of transformant colonies remain leucine prototrophic. Under the same conditions, more than 95% of Leu$^+$ transformants obtained with the use of the p19L2 vector without inserts lose prototrophy. Thus both factors, the increased transformation frequency and stable maintenance of the Leu$^+$ phenotype by the transformants, suggested the presence of ARS elements among the inserts comprising the *C. famata* VKM Y-9 constructed gene library. In Example 14, a *C. famata* VKM Y-9 gene library on CfARS1614, comprising the ARS element having SEQ ID NO. 1, was constructed in *Escherichia coli*.

Example 4

Construction of a Gene Library from *Pichia guilliermondii* ATCC 9058

Strains of *Pichia guilliermondii* ATCC 9058 are available from the American Type Culture Collection (Manassas, Va.) and other repositories. The plasmid pOS25 (4.05 kb) was used for construction of a *P. guilliermondii* gene library for isolation of ARS elements. The plasmid contains a *P. guilliermondii* DNA fragment of 1.35 kb which contains a RIB1 gene inserted into a pUC19 polylinker. The plasmid pOS19 does not contain an ARS element.

40 μg of plasmid pOS25 was linearized with endonuclease BamHI and dephosphorylated with alkaline phosphatase. These procedures were the same as used for digestion and dephosphorylation of the plasmid p19L2 (see above).

Total high molecular weight DNA isolated from *P. guilliermondii* ATCC 9058 (40 μg) was partially digested with endonuclease Sau3AI. Isolation and partial restriction was conducted under the same conditions as was described above for *C. famata*. Linearized dephosphorylated vector pOS25 was ligated with restriction digests of total DNA isolated from *P. guilliermondii* ATCC 9058. The ligation method was the same as was used for *C. famata*. The ligation product was used for transformation of *E. coli* DH5α. 28,000 colonies of bacterial transformants were obtained. The colonies were washed out from the plates with liquid sterile LB medium supplemented with ampicillin (50 µg/ml). The colonies were grown and plasmid DNA was isolated (see above, the protocol for *C. famata*). The isolated plasmid DNA, comprising the genomic library of *P. guilliermondii*, was used for the transformation of *P. guilliermondii* strain RG21 (rib1) to study the frequency of transformation and for isolation of the corresponding ARS elements from the gene library. After transformation of spheroplasts isolated from strain RG21 (rib1) using a crude preparation of "Sigma" lyticase with the plasmid pOS25, the transformation frequency was 18 transformants/µg DNA. This transformation frequency is 2 orders of magnitude lower than the transformation frequency obtained using plasmid p19R1 (contains PgARS, SEQ ID NO. 2).

Example 5

Isolation of Riboflavin Dependent Mutants from leu2 Mutants of *C. famata* VKM Y-9

The strain *C. famata* L20105 was used for generation of riboflavin deficient mutants as it shows satisfactory frequency of transformation and is stable. UV irradiation and N-methyl-N'-nitro-N-nitrosoguanidine (1 mg/ml) were used as mutagens.

The cells were cultivated in a modified Burkholder medium. After mutagenesis, the cells were plated on agar medium containing riboflavin (200 µg/ml), leucine (40 µg/ml) and uracil (40 µg/ml) (for isolation of leu2 ura⁻ mutants). Resulting colonies were replica plated on minimal medium with leucine without riboflavin. Together, 8 experiments using nitrosoguanidine and 2 experiments using UV irradiation have been conducted for isolation of riboflavin deficient mutants. Altogether, 145,598 colonies have been tested. Seventy leu2rib⁻ mutants have been isolated (transformation frequency 0.048%).

Isolated riboflavin deficient mutants were used for biochemical identification of accumulated intermediates of riboflavin biosynthesis and, thus, for identification of the corresponding genetic block. See Example 8 and Example 12.

In addition, 17 leu2 ura⁻ mutants have been isolated after analysis of 68,735 colonies. These mutants will be used for checking for leu2 ura3 double mutants which can be used for transformation with URA3 containing vectors.

Example 6

Cloning of the ARS Elements from the *Candida famata* VKM Y-9 Gene Library

As has been shown, above, insertion of genomic DNA in plasmid p19L2 confers an increase in transformation frequency of *C. famata* leu2 mutants (as compared to the vector p19L2 alone), and stable maintenance of Leu⁺ phenotypes in the transformants during growth using selective medium.

For cloning of the recombinant constructs containing ARS elements, plasmid DNA was isolated from *C. famata* transformants obtained after transformation with plasmid DNA comprising the gene library (See, Example 3).

Transforming DNA was isolated using modified methods described before for other species of non-conventional yeast, *Candida maltosa* (Mauersberger S., et al., *Candida maltosa*. In: Nonconventional Yeasts in Biotechnology. Ed. by K. Wolf. Springer, Berlin, 1996, p.411–580). The colonies of transformants were washed out from the plates (approximately 50,000 yeast transformants) with sterile YNB minimal medium. The culture was grown in this medium in a total volume of 300 ml for approximately 18 h to obtain approximately 190 mg of dry weight. Cells were sedimented by centrifugation (2,000 g during 7 min) and resuspended in 8.5 ml of TS buffer (50 mM tris-HCl, pH 8.0, 1 M sucrose). 170 µl of 2-mercaptoethanol was added to this suspension. Then lyticase was added to achieve 19 U of enzymatic activity per 1 mg (dry weight) of cells. The mixture was incubated at 30° C. for 80 min. The obtained spheroplasts were collected by centrifugation (1,000 g, 10 min) and were resuspended in 3 ml of SE lysis buffer (0.5% sodium dodecyl sulfate, 50 mM EDTA, pH 8.0). The mixture was incubated for 15 min at 65° C. The lysate was cooled to room temperature. Proteinase K (5 mg/ml) was added to a final concentration of 0.05 mg/ml. RNAse (10 mg/ml) was added to a final concentration of approximately 0.3 mg/ml. The resulting mixture was incubated for 40 min at 37° C. Then 1.5 ml of 5 M potassium acetate was added to the lysate. The lysate was incubated for 30 min on ice. The sediment was separated by centrifugation (4,500 RPM, 15 min). The supernatant was transferred to another tube, an equal volume of phenol saturated with Tris-HCl was added and mixed. The mixture was centrifuged (5,000 RPM, 20 min). The water phase was removed, and 0.6 volumes of isopropanol was added and mixed. The resulting pellet was centrifuged (5,000 RPM, 10 min), washed with 70% ethanol, dried and dissolved in 1.5 ml of TE buffer. 0.75 ml of 7.5 M ammonium acetate was added, mixed and the mixture incubated on ice for 30 min. The mixture was centrifuged (8,000 RPM, 10 min). The supernatant was withdrawn and the DNA precipitated with two volumes of ethanol. After centrifugation, the pellet was washed with 70% ethanol and dried.

The resulting DNA isolated from the *C. famata* transformants was dissolved in 1 ml of TE buffer (10 mM Tris-HCl, pH 8.0, 1 mM EDTA). This DNA was used for transformation of *Escherichia coli* DH5α. After addition of 1 µl of DNA isolated from *C. famata* transformants, approximately 100 colonies of *E. coli* DH5α ampicillin resistant transformants were recovered.

Approximately 200 colonies of bacterial transformants were isolated from plates with sterile LB medium containing ampicillin (100 µg/ml) and cultivated in a total volume of 400 ml for approximately 14 h. Plasmid DNA was isolated using the alkaline lysis method. Thus, a genomic library of *C. famata* VKM Y-9, enriched with recombinant constructs able to confer autonomous maintenance in *C. famata* cells was obtained.

At the next step, isolation of plasmid DNA from 16 separate clones of the *E. coli* DH5α transformants was carried out. Electrophoretic analysis revealed the vectors can be divided into five groups by their sizes. One plasmid was picked from each group for further studies. Restriction of the plasmids was carried out using endonuclease EcoRI and the results compared to the restriction digest of the vector p19L2. The results are shown in Table 2.

TABLE 2

Transformation of the L20105 strain of Candida famata by plasmids containing CfARS inserts

| Plasmid used for transformation | Length of CfARS insert; kb | Transformation frequency; transformants/µg DNA |
|---|---|---|
| 1. pCfARS1 (p1) | 3.4 | 850 |
| 2. pCfARS6 (p6) | 6.0 | 1100 |
| 3. pCfARS11 (p11) | 3.6 | 1060 |
| 4. pCfARS7 (p7) | 1.9 | 580 |
| 5. pCfARS16 (p16) | 0.26 | 1780 |
| 6. p19L2 | — | 83* |

*L20105/p19L2 colonies were small and eliminated during passages on selective medium.

Figure 6:
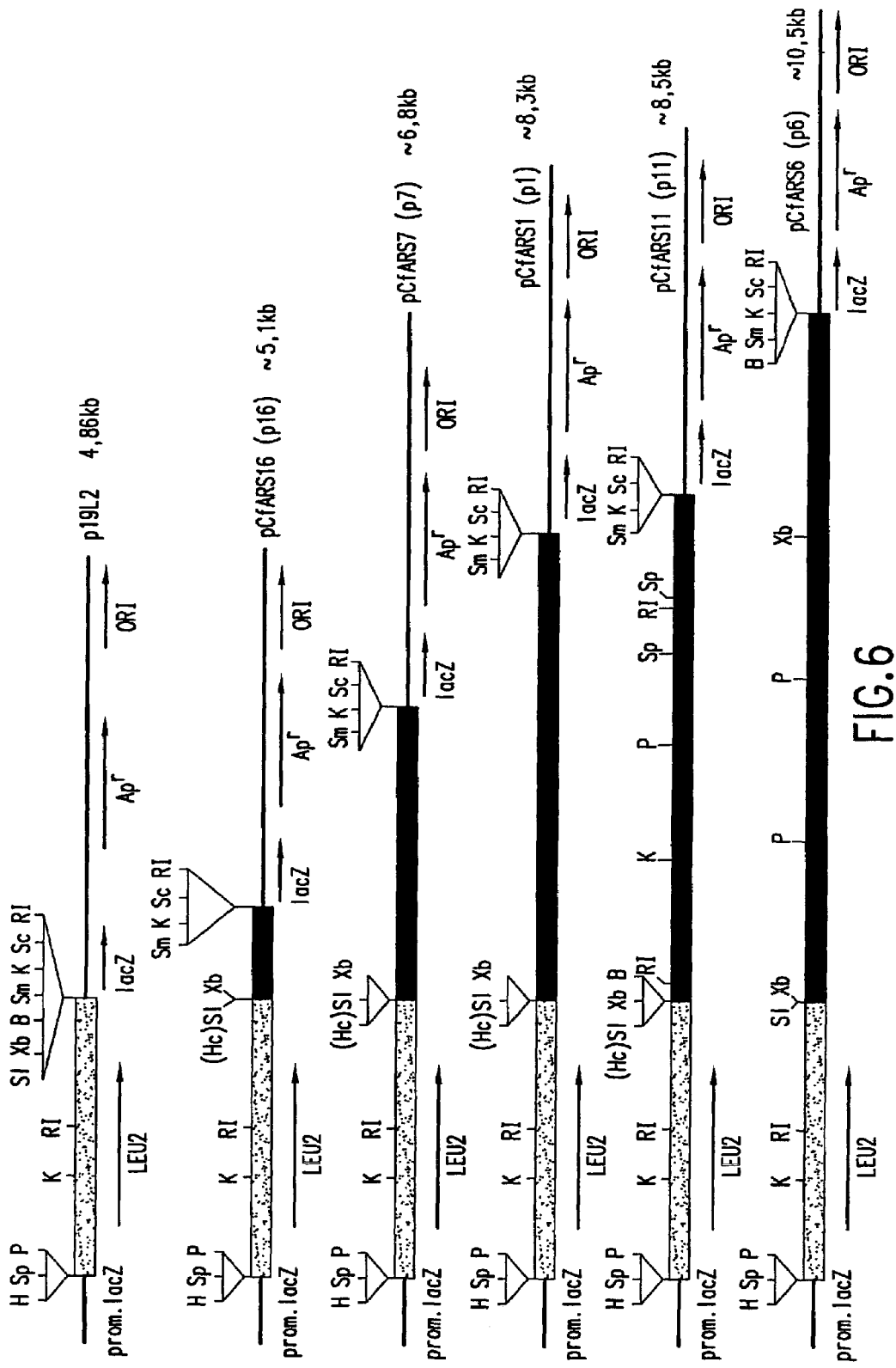
FIG. 6 shows the linear schemes of plasmids p19L2, pCfARS16 (p16), pCfARS7 (p7), pCfARS1 (p1), pCfARS11 (p11) and pCfARS6 (p6) containing the CfARS inserts. The CfARS inserts are shown as the thick black line.
Figure 7:
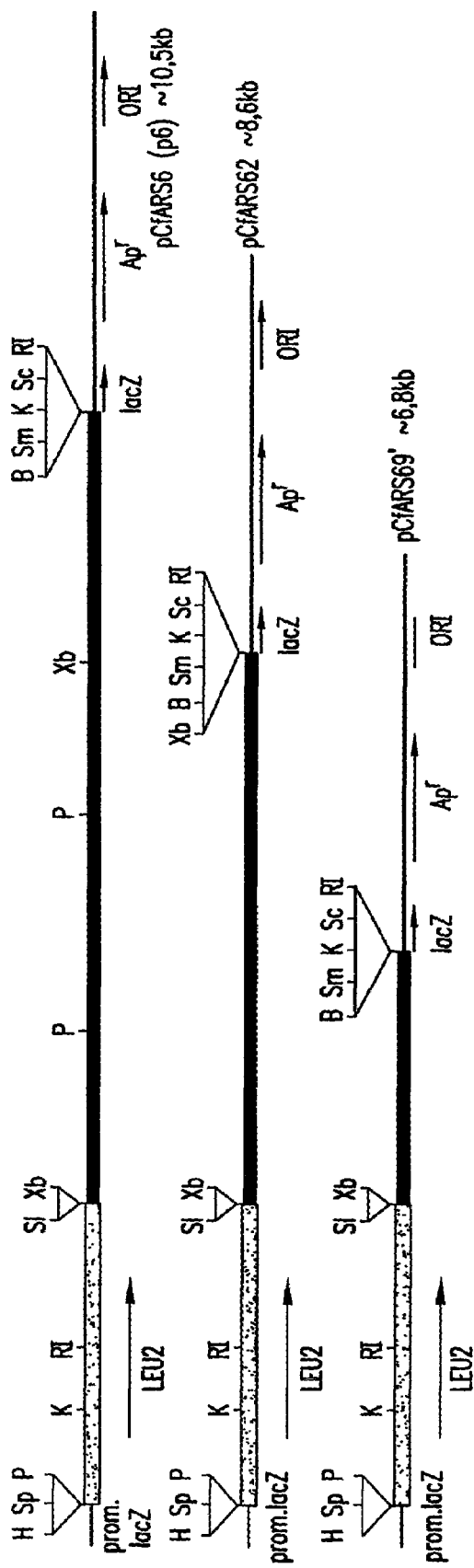
FIG. 7 shows the linear schemes of the plasmid pCfARS6 and of its derivatives pCfARS62 and pCfARS69'. The CfARS insert is shown as the thick black line.

The approximate length of the inserts was identified: plasmid p1 possessed an insert of 3.4 kb (total length is 8.3 kb); p6 had an insert of 6.0 kb (total length—10.9 kb); p7 had an insert of 1.9 kb (total length—6.8 kb); p11 had an insert of 3.6 kb (total length—8.5 kb); and p16 had an insert of 0.26 kb (total length—5.12 kb) (see FIG. 6). The nucleotide sequence (SEQ ID NO. 3) of the ARS element of p16 is shown in FIG. 20.

Transformation of the spheroplasts isolated from strain C. famata VKM Y-9 L20105 with plasmids was carried out. The frequency of transformation by plasmids containing these inserts appeared to be approximately 13 times greater than the frequency obtained using the vector p19L2 containing no insert. The frequency of transformation in this experiment was lower than average for plasmid p19L2 and was only 83 transformants per 1 µg of plasmid DNA. An average transformation frequency for plasmids containing the inserts was 1074 transformants per 1 µg DNA. In these experiments, lyticase used for spheroplasting was used after long term storage. Long term storage may be the reason for the decrease in transformation frequency. The insert-containing vectors showed the following transformation frequencies: for p1—850; p6—1100; p11—1060, p7—580 and p16—1780 transformants per 1 µg DNA. The transformants obtained using the above mentioned plasmids stably maintained the Leu$^+$ phenotype under selective growth condition. These transformants differ from those transformants containing the p19L2 plasmid, in that the p19L2 containing colonies were very small and eliminated during passage on selective medium.

Detailed restriction analysis of three plasmids, p6, p11 and p16, conferring the highest transformation frequency of C. famata VKM Y-9 L20105 was carried out. The p11 plasmid possesses an insert of 3.6 kb length. Thus, the p11 plasmid consists of vector p19L2 (4.86 kb) having a 3.6 kb insert located in the BamHI site. Thus, the total length of the plasmid is approximately 8.5 kb. This plasmid contains the following unique restriction sites: HindIII, SalI, XbaI, BamHI, SmaI, SacI. All mentioned sites are absent in the insert. Plasmid p11 possesses two PstI restriction sites, one of which is in the insert; three KpnI restriction sites (one located in the insert); three SphI restriction sites (two in the insert) and four EcoRI sites (two in the insert). Plasmid p11 does not possess restriction sites for XhoI.

Plasmid p6 (10.9 kb) consists of vector p19L2 (4.86 kb) having a 6.0 kb insert located in the BamHI site. The plasmid contains the following unique restriction sites: SalI, BamHI, SmaI, SacI. All mentioned sites are absent in the insert. The plasmid p6 possesses two KpnI restriction sites (absent in the insert), two XbaI sites (one in the insert), three PstI sites (two in the insert), five HindIII sites (four in the insert), and six EcoRI sites (four in the insert). This plasmid does not contain XhoI sites.

Plasmid p16 (5.12 kb) consists of vector p19L2 and has a 0.26 kb insert. This plasmid possesses the following unique restriction sites: HindIII, SphI, PstI, SalI, XbaI, SmaI, and SacI. Two sites are available for endonucleases KpnI and EcoRI. All mentioned sites are absent in the insert. Plasmid p16 does not contain restriction sites for XhoI and BamHI.

Thus, segments of C. famata VKM Y-9 genomic DNA have been isolated which show characteristics of ARS elements, such as an increase in transformation frequency and stabilization of the resulting transformants. The corresponding inserts were isolated and three inserts were characterized by use of restriction analysis. The nucleotide sequence of a C. famata ARS element (SEQ ID NO. 1) carried on plasmid pCfARS 1614 is shown in FIG. 15. The nucleotide sequence of another C. famata ARS element (SEQ ID NO: 3) carried on plasmid pCfARS16 (p16) is shown in FIG. 20.

Example 7

Nucleotide sequences were obtained using an ABI Prism® 377 DNA Sequencer (PE Applied Biosystems, Inc., Foster City, Calif. 94404). The samples were prepared using the Big Dye™ Terminator Cycle Sequencing Ready Reactions Kit available from PE Applied Biosystems, Inc., Foster City, Calif. 94404. Sequencing was carried out at a commercial sequencing facility, the University of Illinois, DNA Services, Champaign, Ill.

The optimal amount of a template for standard sequencing reactions was 500 ng and 4 picomoles of primer. Thermal cycler conditions were: 1-95° C. for 1 min; 2-95° C. for 15 seconds; 3-45° C. for 5 seconds; 4-60° C. for 4 minutes; 5-go back to step 2, repeat thirty four times; 6-hold at temperature of step 4.

Following the reactions, the DNA was precipitated using 75 µl of 0.3 mM MgSO$_4$ for 15 minutes. The DNA was then centrifuged for 15 minutes.

The sample was resuspended in 3 µl loading buffer. The gel was a 4.25% 29:1 polyacrylamide gel in 6M urea. The plate was flipped and centrifuged for 1 minute, then dried for 10 minutes. The run time was 8 hours.

The nucleotide sequences set forth here and throughout the specification may also be obtained using other sequencing methods well known in the art.

Example 8

Characterization of Candida famata VKM Y-9 Riboflavin Deficient Mutants (Groups I–IV)

Biochemical characterization of the riboflavin deficient mutants previously isolated (Example 5) from Candida famata VKM Y-9 strain L20105 was carried out. Characterization included identification of the intermediates of riboflavin biosynthesis which are accumulated in culture medium of the corresponding mutants during incubation in iron deficient medium. Iron deficient medium is used for derepression of the available enzymes of riboflavin biosynthesis.

Iron deficient media was obtained after removal of metals using 8-hydroxyquinoline. Yeast were cultivated in synthetic Burkholder medium. Urea (1 g/l) was used as the nitrogen source and sucrose (20 g/l) was used as the carbon source. Yeast were cultivated in 500 ml Erlenmeyer flasks containing 100 ml of medium on a shaker (200 rpm) at 30° C. for 3–4 days with addition of riboflavin (200 mg/l) and leucine (40 mg/l). Then the cells were washed and transferred into fresh iron deficient medium containing leucine but without riboflavin. The cells were grown on a shaker for 16–20 h. The cells were separated from the media by centrifugation and the culture medium incubated with and without diacetyl (800 mg/l) at 30° C. for 24 h. In the presence of diacetyl unstable pyrimidine precursors of riboflavin are non-enzymatically transformed into fluorescent pteridines. Depending on the color of the fluorescent compounds which were accumulated in the culture media of riboflavin defective mutants grown with and without diacetyl, and on the basis of growth tests in media containing diacetyl (100 mg/l) or 6,7-dimethyl-8 ribityllumazine (200 mg/l) instead riboflavin, all mutants were divided into five biochemical groups.

The mutants of biochemical group I (16 strains) did not accumulate fluorescent products in the medium during incubation with and without diacetyl. They did not grow in the medium with diacetyl but grew with 6,7-dimethyl-8 -ribityllumazine. These mutants appear to possess a genetic block of the first enzyme of riboflavin synthesis, GTP cyclohydrolase (the corresponding gene of *P. guilliermondii* is designated as RIB1.)

The mutants of biochemical group II (10 strains) accumulated 2,4,5 triaminopyrimidine in the medium. Condensation of 2,4,5 triaminopyrimidine with diacetyl resulted in formation of 2-amino-4-hydroxy-6,7-diaminopterine, which displayed intense blue fluorescence. The mutants of this group appear to have a genetic block of the reductase, the second enzyme of the pathway (the corresponding gene of *P. guilliermondii* is designated RIB2).

The mutants of biochemical group III (5 strains) accumulated 2,5diamino-6-hydroxy-4-ribitylaminopyrimidine in the culture medium. Incubation with diacetyl resulted in production of 4-hydroxy-6,7-dimethyl-8-ribityllumazine. This compound showed blue-green fluorescence. This suggests a genetic block of the deaminase third enzyme of the pathway (the corresponding gene of *P. guilliermondii* is designated RIB3). Mutants having this genetic block will be isolated.

Mutants of biochemical group IV (6 strains) accumulated 2,6-dihydroxy-5amino-4-ribitilaminopyrimidine in the medium. Condensation with diacetyl resulted in the production of 6,7-dimethyl-8-ribityllumazine which gave a green fluorescence. These mutants appear to have a genetic block of 6,7-dimethyl-8-ribityllumazine synthetase (*P. guilliermondii* gene RIB5) or a block in the synthetase of aliphatic precursors of riboflavin (*P. guilliermondii* gene RIB6). These mutants grew in medium without riboflavin and containing diacetyl.

Mutants of biochemical group V (7 strains) accumulated 6,7-dimethyl-8-ribityllumazine in the medium (green fluorescence). These mutants cannot grow in medium without riboflavin and containing diacetyl. These mutants possess a genetic block of the last enzyme of the pathway, riboflavin synthase (*P. guilliermondii* gene RIB7).

Some mutants accumulated significant amounts of flavins during incubation in iron deficient media. One may assume partial genetic block of riboflavin biosynthesis in such mutants. Some mutants (5 strains) appeared to be hypersensitive to iron deficiency as they failed to grow under such conditions.

Temperature sensitive *C. famata* riboflavin biosynthesis regulatory mutants were isolated. The temperature maximum for growth of *C. famata* mutants of biochemical group I was determined. It was discovered that for most of the mutants the maximal growth temperature was 37° C. and for several strains was 35° C.

The sensitivity of *C. famata* to cobalt was studied. It is known that cobalt at subinhibitory concentrations stimulates *C. famata* flavinogenesis. It was discovered that 25 μg/ml of $CoCl_2$ is the maximal subinhibitory concentration which stimulates flavinogenesis (plate experiments). Higher concentrations tested (50 and 100 μg/ml) inhibited plate growth.

Example 9

Electrotransformation (Electroporation) of *C. famata* L20105

Cells from a fresh colony of strain L20105 were inoculated in 3 ml liquid YPD and were cultivated at 30° C. on a shaker approximately one day to reach stationary phase. This culture was used as the inoculating suspension. Approximately 0.75 ml of inoculating suspension was added to 500 ml of YPD medium and cultured overnight at 30° C. to an optical density of 1.7 (540 nm, cuvette 3 mm). This optical density corresponded to a cell concentration of ~2.5×10$^7$ cells/ml.

The cells were spun down and resuspended in 100 ml (0.2 volume) of 50 mM phosphate buffer, pH7.5, containing 25 mM dithiothreitol and incubated for 15 min at 30° C.

The cells were spun down and washed twice with sterile double distilled water, first with 500 ml and then 250 ml. The cells were then washed once with 20 ml of cold sterile solution of 1 M sucrose.

The cells were then resuspended in 2 ml of cold sterile solution of 1 M sucrose. 0.1–0.4 μg of plasmid DNA was added to 100 μl of cell suspension containing 7.5×10$^8$ cells. The mixture is added to the bottom of the electroporation cuvette having a slot thickness of 2 mm. Electroporation was carried out using an electroporator, ECM 600 produced by the "BTX" company. The parameters used were: resistance: R5—129 Ω; field strength: 11.5 kV/cm (for pCfARS16) and 11.5 kV/cm (for pCfARS6); and at a pulse duration of 4–5 ms.

After electroporation, a cold sterile solution of 1 M sucrose was quickly added to the sample directly in the cuvette to a final volume of 1 ml. A suspension of transformed cells was spread onto plates with selective medium containing 0.3 M sucrose (YNB+1 M sucrose). The plates were incubated at 30° C. The colonies of transformants appeared after 3–5 days.

Using the above protocol, the frequency of electrotransformation was 1×10$^5$ transformants/μg DNA for plasmid pCfARS16 and 8×10$^4$ transformants/μg DNA for plasmid pCfARS6.

Figure 1:
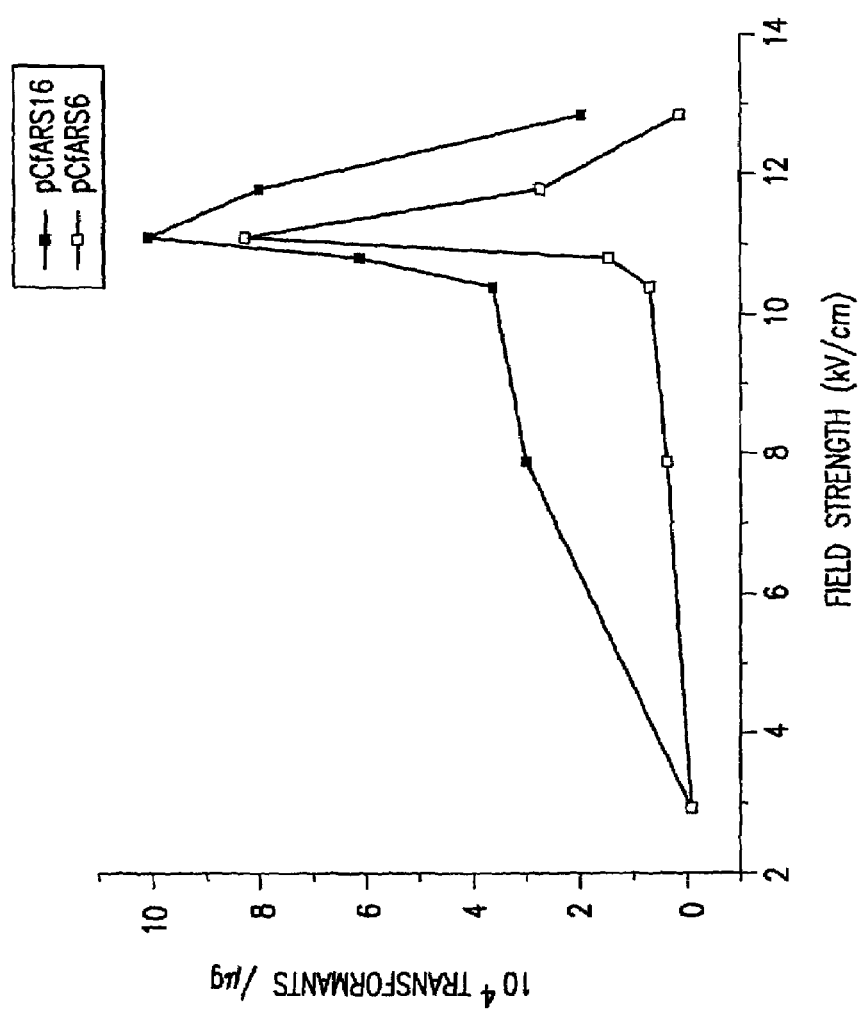
FIG. 1 shows the effect of field strength on transformation frequency of *Candida famata* L02015. Cells were grown and treated prior to the electric pulse as described in the text. 0.35 µg of pCfARS6 or pCfARS16 were used for each transformation -■-pCfARS16; -□-pCfARS6.

The optimal field strength for plasmids pCfARS16 and pCfARS6 was determined after comparison of the influence of the different field strengths on transformation efficiency (FIG. 1). FIG. 1 shows the optimal electric field strength for plasmid pCfARS16 is 11.5 kV/cm, and is 11.5 kV/cm for plasmid pCfARS6. Plasmid pCfARS16 comprises the ARS element having the nucleotide sequence set forth in SEQ ID NO. 3.

Optimal cell concentration in the sample for electrotransformation of *C. famata* L20105 was ~7.5×10$^8$ cells/ml. A further increase in cell concentration reduced transformation frequency.

Transformation of *C. famata* L20105 was conducted at a resistance of 129Ω (R5), which in combination with a capacitance of 50 μF, gave a pulse duration of ~5 ms. Different resistance values in the range from R1 to R10 were checked and R5 was found optimal for *C. famata* L20105.

Example 10

Spheroplast Transformation in C. famata

Spheroplast transformation is efficient, as the method results in a transformation frequency with an average of $6.3\times10^4$ transformants/µg DNA for plasmids pCfARS6 and pCfARS16. A very important factor influencing the spheroplast transformation frequency appeared to be the purity and specific activity of the enzyme used for cell wall hydrolysis. The above transformation frequency of the strain L20105 was obtained by using the enzyme Lyticase ("Sigma," "partially purified"). Lyticase ("Sigma," "crude") resulted in decreased spheroplast transformation frequency by one order of magnitude. The long storage of the enzyme, as a rule, decreases its activity which negatively influences transformation efficiency.

The other important factor influencing spheroplast transformation efficiency is the quality and/or supplier of polyethylene glycol (PEG). We have found that the best for transformation are PEG 4,000 ("Merck", Germany) and PEG 3,000 ("Ferak", Germany). The use of PEG 3,350 "Carbowax" ("Fisher", USA) has been found to provide a transformation frequencies 10 times lower than the PEGs mentioned above.

Example 11

Electrotransformation of the Flavinogenic Yeast P. guilliermondii

Electrotransformation was conducted using the same protocol as were used for C. famata (see, above). Riboflavin deficient mutant RG21 was used as the recipient host strain. The transformation was conducted with plasmid p19R1 containing P. guilliermondii gene RIB1. After two experiments it was determined that the optimal electric field strength for electrotransformation of P. guilliermondii is 11 kV/cm. Resistance used during transformation was 129Ω (R5) and the capacitance was 50 µF which gave a pulse duration of approximately 4–5 ms. Electrotransformation was conducted in 2 mm cuvettes. The average transformation frequency was $5.9\times10^4$ transformants/µg DNA.

Example 12

Biochemical Classification of C. famata VKM Y-9 leu2 Riboflavin Deficient Mutants C. famata VKM Y-9 leu2 riboflavin mutants, generated as in Example 5 and Example 8 were used for identification of the intermediates accumulating in the culture media of the riboflavin deficient mutants of C. famata. Removal of iron ions from the media was conducted with 8-hydroxyquinoline.

53 leu2 riboflavin deficient mutants were used for analysis.

16 mutants did not accumulate fluorescent products and were characterized by one or more defects in the first reaction of flavinogenesis (GTP cyclohydrolase). 10 mutants accumulated 2,4,5-triaminopyrimidine due to one or more defects in the second reaction (reductase). 5 mutants accumulated 2,5-diamino-6-hydroxy-4-ribitylaminopyrimidine due to one or more defects in the third reaction (deaminase). 6 mutants accumulated 2,6-dihydroxy-5-amino-4-ribitylaminopyrimidine due to one or more defects either in the 6,7-dimethyl-8-ribitylumazine synthase reaction or in the biosynthesic reactions of the aliphatic riboflavin precursors. 7 mutants accumulated 6,7-dimethyl-8-ribityllumazine due to one or more defects in the riboflavin synthase reaction. The remaining 9 mutants accumulated small amounts of riboflavin in the medium, apparently as a result of an incomplete defect in the reactions which prevented identification of the genetic block of such mutants.

Example 13

Isolation of Regulatory rib2 Mutants of C. famata Having Derepressed Enzymes of Riboflavin Biosynthesis Several methods successfully developed and used earlier for Pichia guilliermondii were adapted for use in C. famata. One method for isolation of regulatory mutants of C. famata with derepressed enzymes of riboflavin biosynthesis is based on preliminary selection of the leaky rib2 mutants which possess sufficient RIB2 gene coded enzyme (reductase) activity to retain riboflavin auxotrophy under conditions of flavinogenesis enzyme repression (iron sufficient media) and simultaneously sufficient reductase activity to ensure riboflavin prototrophy under conditions of flavinogenesis enzyme derepression (iron deficient media). It is assumed that in iron deficient media the amount of the product of the GTP cyclohydrolase reaction will be high enough to be able to pass the limiting reductase step in leaky rib2 mutants for subsequent conversion to riboflavin. Of course, the amounts of synthesized riboflavin in iron deficient media will be very small, and no riboflavin oversynthesis will be observed. Such leaky rib2 mutants will be used in the next selection step as the parental ones for the generation and isolation of mutants able to grow in the iron sufficient media (repressing conditions) without exogenous riboflavin. During the first step of the selection, the iron-sensitive mutants (leaky rib2 revertants) will be isolated whereas during the second selection step, the iron-resistant mutants will be isolated. Such second-step iron-resistant mutants can evolve either as the result of reversion of a leaky rib2 mutation to the wild-type allele or due to regulatory mutations which ensure derepression of riboflavin biosynthetic enzymes under repressive conditions (iron sufficient media). Discrimination between these two possibilities would be accomplished by the genetic crossing of the second-step mutants with the wild-type strain and subsequent substitution of the leaky rib2 allele for the wild-type RIB2 allele.

For C. famata, the second-step mutants will be tested for their ability to overproduce riboflavin under derepressing conditions (iron deficient media). In the case of reversion of the leaky rib2 allele to the wild-type RIB2 allele, the second-step mutants will overproduce riboflavin under such conditions whereas in the case of evolved regulatory mutations the second-step mutants will be unable to overproduce this vitamin due to very low reductase activity as the result of the remaining leaky rib2 allele. The regulatory mutants can accumulate the product of the GTP cyclohydrolase reaction in the medium, especially under derepressing conditions. The product of the GTP cyclohydrolase reduction, a derivative of pyrimidine, after incubation with diacetyl can be non-enzymatically converted to blue-colour fluorescing 6,7-dimethylpterine.

As the testing of thousands of the first-step mutants (parental strain) and the second-step regulatory mutants in liquid iron-deficient media is a time and labor consuming procedure, a simple method for creation of iron deficiency on Petri dishes was developed. It is known that cobalt ions ($Co^{2+}$) derepress flavinogenesis, apparently due to competition with iron ions for penetration into yeast cells. It was discovered that a cobalt concentration of 15 µg/ml was non-toxic for yeast growth and stimulates riboflavin synthesis. Higher concentrations of $CoCl_2$ inhibited yeast growth. In Example 8, 25 µg/ml of $CoCl_2$ were shown to be the maximal subinhibitory concentration.

For selection of the first-step leaky rib2 mutants (parental strains for regulatory mutant isolation), the conditions of UV and nitrosoguanidine mutagenesis of available leu2 rib2 mutants for leu2 Rib+ revertant isolation were studied. For mutagenesis, a high density yeast suspension (OD 3.0 at 540 nm) was used. Cells were UV irradiated for 10 sec or incubated with nitrosoguanidine (1 mg/ml) for 10 min. Cells were twice washed out of the mutagen and 0.1 ml of such suspension (without dilution) was spread on Petri dishes without riboflavin and with cobalt (15 µg/ml).

Four leu2rib2 mutants (4-68, 4-126, 5-128, 3-30) were used in this work. Strain 4-68 did not form riboflavin revertants at all. UV light appeared to be a nonefficient mutagen. Using nitrosoguanidine, it was discovered that the frequency of reversion to riboflavin prototrophy of the 4-126 mutant was $1 \times 10^{-5}$, of the 5-128 mutant was $2.5 \times 10^{-5}$ and for the 3-30 mutant was $4.8 \times 10^{-4}$. Two hundred fifty riboflavin prototrophs isolated from mutant 4-126, 750 riboflavin prototrophs isolated from mutant 5-128 and 7215 riboflavin prototrophic colonies isolated from mutant 3-30 were tested for their ability to grow without riboflavin in the absence of cobalt in the medium. Practically all revertants appeared to be riboflavin prototrophs both on the plates with $CoCl_2$ (15 µg/ml) and without it. Only two revertants (isolated from mutant 3-30) have been found which grew on the agar medium with cobalt ions without exogenous riboflavin and grew only after addition of riboflavin (0.2 mg/ml) if the agar medium did not contain $CoCl_2$. Only one of these two leaky rib2 mutants displayed the same phenotype during growth in liquid media. This mutant failed to grow in iron sufficient media without exogenous riboflavin although the mutant grew well without exogenous riboflavin in iron deficient medium obtained by purification with 8-hydroxyquinoline. These data show that ability of this mutant to grow without riboflavin is not dependent upon the availability of cobalt in the medium but depends on iron deficiency. This leaky rib2 strain was used in further selection of revertants growing in iron sufficient medium. Cells were UV irridated and plated onto medium without cobalt. Growing colonies were isolated (frequency was $3.0 \times 10^{-3}$). Two hundred of such revertants were tested for growth and production of fluorescent products in liquid iron deficient medium with $CoCl_2$ (15 µg/ml). Only one strain was found accumulating large amount of blue-color fluorescent pteridine, which is produced after endogenous condensation with the C4 compound, the immediate product of the GTP cyclohydrolase reaction. Other mutants either did not accumulate any fluorescent products, or accumulated riboflavin. Apparently, in these latter mutants, reversion of leaky rib2 mutation to wild-type RIB2 allele occured.

Example 14

Construction of Gene Libraries Containing C. famata VKM Y-9 ARS Elements

Construction of a Gene Library on pCfARS1614

Figure 2:
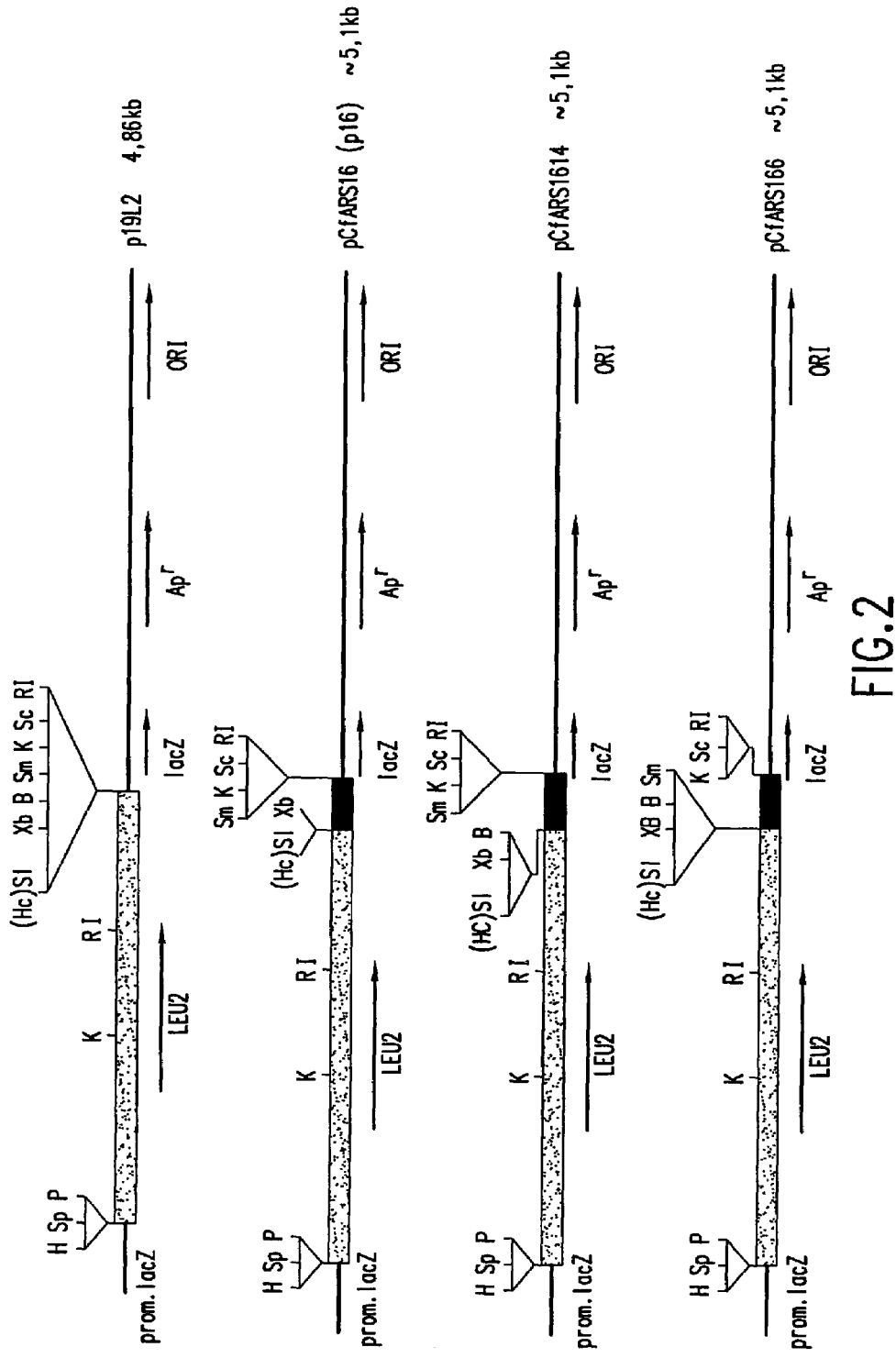
FIG. 2 shows the linear schemes of plasmids p19L2, pCfARS16 (p16), pCfARS1614 and pCfARS166 containing a 0.26 kb CfARS insert. The CfARS insert is shown as the thick black line.

For construction of a C. famata gene library, the replicative plasmid pCfARS1614 was used (FIG. 2). This plasmid is the derivative of the plasmid pCfARS16 (described in Example 6). Plasmid pCfARS16 was used for isolation of a XbaI-SmaI fragment with size of approximately 0.25 kb which contains a CfARS element. The XbaI sticky end of the fragment was blunted using deoxynucleotides and Klenow fragment following the protocol of Maniatis et al. (Maniatis, et al., Molecular Cloning: A Laboratory Manual. Cold Spring Harbor Laboratory Press, Cold Spring Harbor, N.Y. (1982)). The sequence with a C. famata ARS element, flanked by blunted ends, was inserted into a SmaI site of the plasmid p19L2. Thus, the vector of pCfARS1614 (5.1 kb) bears a fragment of S. cerevisiae with the LEU2 gene, CfARS (0.25 kb) (SEQ ID NO. 1) and a bacterial fragment pUC19 (FIG. 2). The plasmid pCfARS1614 contains a unique BamHI site. Preparative amounts of this plasmid were accumulated.

For isolation of the genomic library, pCfARS1614 (30 µg) was linearized with endonuclease BamHI. The enzyme (Promega) was added at 2.5 U/µg of plasmid DNA. This amount was enough for total linearization of the plasmid; the sticky ends remained intact during this procedure. The extent of plasmid linearization and retention of the sticky ends was tested by E. coli transformation, essentially as described (Rose et al.(1991)).

Twenty µg of linearized pCfARS1614 was dephosphorylated using calf intestine alkaline phosphatase (Promega). The phosphatase was added at 0.02 U/µg plasmid DNA. This amount of the enzyme was enough to eliminate plasmid self-ligation by 97%. The ratio of alkaline phosphatase to amount of plasmid DNA was selected according to the method of Rose et al. (see above).

The total high-molecular weight DNA of C. famata VKM Y-9 was isolated using the modified method of Cregg et al., Mol. Cell. Biol. 5:3376–3385 (1985). Partial restriction of total DNA of C. famata VKM Y-9 was conducted using endonuclease Sau3AI according to Maniatis et al. The endonuclease (New England Biolabs) was added at 0.24 U/µg DNA. The partial restriction of 100 µg DNA was carried out in the total volume of 2,500 µl. DNA was incubated with Sau3AI for 18 min at 37° C. Reaction was stopped by shifting the mixture to ice and adding EDTA to final concentration of 20 mM. The DNA sample was extracted with phenol and precipitated with 96% ethanol. The DNA sample was twice washed out with 70% ethanol and dissolved in 170 µl TE buffer. The concentration of resulting Sau3AI DNA fragments was approximately 0.8 µg/µl. Gel electrophoresis showed that the size of the majority of the obtained fragments was from 3 kb to 30 kb (FIG. 10).

Elution of Sau3AI DNA fragments by size of ~3–10 kb was carried out according to Maniatis et al. with some modifications. The sample of Sau3AI fragments of the total DNA (~90 µg) was separated by gel electrophoresis. The gel slice containing Sau3AI DNA fragments of the desired size (~3–10 kb) was cut and put in a dialysis bag containing 0.5×TAE buffer. This bag was put in the electrophoresis chamber containing the same 0.5×TAE buffer. Electrophoresis was carried out for ~1.5 h at 100 v. Then, the direction of current was changed for 2 min. The dialysis bag was pierced with a pipette tip and solution withdrawn (total volume 1.3 ml). tRNA (70 µg), and ⅒ volume of 3 M sodium acetate (pH 5.2) were added to the sample. The sample was precipitated with 70% ethanol. The sample was dissolved in 400 µl of double distilled water, extracted twice with phenol, precipitated with 96% ethanol and washed twice with 70% ethanol. Finally, the sample with fragments of chromosomal DNA of C. famata VKM Y-9 was dissolved in 80 µl TE buffer. DNA concentration in the sample was approximately 0.15 µg/µl. Gel electrophoresis of the sample in 0.8% agarose showed that the size of eluted Sau3AI DNA fragments was, as expected, from about 3 to 10 kb (FIG. 10, lane 4).

Linearized and dephosphorylated vector pCfARS1614 was ligated with the eluted Sau3AI fragments of total DNA of C. famata VKM Y-9. Ligation was carried out using the method of Rose et al. (1991). The vector DNA was mixed with Sau3AI chromosomal fragments in a ratio of 1:2. Altogether, 4 µg of vector DNA was mixed with 8 µg of chromosomal fragments in 400 µl of ligation mixture. Ligation was carried out overnight in the water bath put into the refrigerator. During such conditions, the temperature was gradually decreased from room temperature to 4° C. DNA ligase (Sigma) was added at 0.5 U/µg DNA. The resulting ligate was used for E. coli DH-5α transformation. Transformation of E. coli was conducted by the electroporation method according to "Electro Cell Manipulator ECM 600," in Electroporation System Operation Manual (1998). After electroporation, more than 90,000 ampicillin resistant bacterial colonies were isolated.

The extent of fragment representation in the obtained gene library of C. famata is presented in Example 17. This ARS containing gene library is used for cloning of riboflavin structural gene by complementation of the corresponding formerly isolated and identified mutations of C. famata.

Construction of a C. famata Gene Library on pCfARS62

Another vector was prepared which can be used for construction of another gene library of C. famata VKM Y-9. The subcloning of the CfARS element of the plasmid pCfARS6 was carried out (p6 in FIG. 11). Preliminary restriction analysis of the C. famata CfARS fragment bearing ARS activity on the plasmid pCfARS6 showed its size as ~5.7 kb. Later the size of this fragment was more precisely identified as near 6.0 kb. The total size of pCfARS6 vector was determined as ~10.9 kb. By means of functional analysis, ARS activity was localized in the CfARS XbaI subfragment (size of ~4 kb) but not in the XbaI-BamHI subfragment (size of ~2 kb). The XbaI subfragment containing ARS activity was inserted in the corresponding site of the p19L2 plasmid. This plasmid (size ~8.9 kb) was designated as pCfARS62 (FIG. 11). The CfARS sequence of this plasmid possessed three HindIII restriction sites. Two of them are shown in FIG. 11. Localization of the third HindIII site which lies between two others, shown at the Figure, is not precisely localized yet. As a result treating the CfARS sequence (flanked by XbaI sites) of the plasmid pCfARS62 with endonuclease HindIII, four fragments are obtained (FIG. 11): two XbaI-HindIII fragments with a size of ~0.8 kb and ~1.4 kb and two HindIII fragments with a size of ~0.6 kb and ~1.25 kb.

Each of these four fragments having the CfARS sequence of pCfARS62 was isolated by elution from agarose gel and subcloned as in Example 22. The recombinant plasmid bearing ARS activity, pCfARS68, was used as the vector for construction of an alternative gene library of C. famata VKM Y-9 as in Example 17.

Example 15

Cloning of ARS Elements from the P. guilliermondii Gene Library

For cloning of P. guilliermondii ARS elements, transformation of P. guilliermondii RG21 with the formerly constructed gene library (See Example 4) of this species was carried out. The transformation protocol for electroporation was as described in Example 11. In these experiments, ~20,000 colonies of yeast transformants were obtained. These colonies have been used for isolation of total DNA. DNA isolation was conducted using the method described formerly for an alkane-utilizing yeast, Candida maltosa, Mauersberger, et al., "Candida maltosa," in Nonconventional Yeasts in Biotechnology, Wolf, K., ed., Springer, Berlin (1996), pp. 411–580). Isolated total DNA was used for transformation of Escherichia coli DH-5α using the calcium method according to Maniatis et al. (1982). 210 colonies of bacterial transformants were used for isolation of plasmid DNA. Plasmid DNA was isolated using the method of rapid alkaline lysis (Birnboim, H. C. & Doly, J., Nuc. Acids Res. 7:1513–1523 (1979)).

E. coli DH-5α was transformed with the isolated plasmid DNA. Plasmid DNA was isolated from 24 individual E. coli colonies of transformants using the above rapid alkaline lysis method. Isolated plasmids were restricted using endonuclease EcoRI. Obtained fragments were analyzed using electrophoresis in 0.8% agarose gel. According to the presence and the size of inserts in the isolated plasmids, the inserts were distributed into 7 groups. The size of inserts were as follows: #1—0.2 kb; #2—0.7 kb; #3—1.0 kb; #4—0.7 kb; #5—5.08 kb; #6—2.8 kb. Inserts #2 and #4 apparently are different, as the corresponding vectors showed different restriction patterns. Two additional plasmids were identified which did not contain any insert DNA.

Transformation by electroporation of P. guilliermondii RG21 was carried out with each isolated group of insert-containing plasmids. The frequency of yeast transformation was found to be #1—6.8×10$^4$; #2—9.3×10$^4$; #3—7.4×10$^4$; #4—7.2×10$^4$; #5—8.5×10$^4$; #6—6.8×10$^4$. For comparison, the frequency of transformation of strain RG21 with plasmid pOS25 (does not contain an ARS element) using electroporation was 66 transformants/µg DNA. Transformation frequency of RG21 strain with the formerly isolated (Voronovsky, A. Y., unpublished) ARS-containing plasmid of P. guilliermondii p19R1 was 6.2×10$^4$ transformants/µg DNA. The ARS element (SEQ ID NO:2) of p19R1 apparently is adjacent to the RIB1 gene (Voronovsky, A. Y., unpublished) which hampers the use of this vector for cloning of structural genes involved in riboflavin biosynthesis.

The accumulated data suggest that the isolated plasmids contain sequences which render high frequency of transformation of P. guilliermondii (up to 1.5 times higher than that with formerly-isolated ARS-containing plasmid p19R1 and 1400 times higher than that with plasmid pOS25 which does not contain an ARS sequence).

One additional group of plasmid-containing 0.22 kb inserts was isolated.

In another experiment, transformation of the mutant strain P. guilliermondii RG21 was carried out with isolated plasmid PgARS17. The electroporation frequency was 8.3×10$^4$ transformants/µg DNA. For comparison, the frequency of this strain transformation using plasmid pOS25 (does not contain PgARS) was only 50 transformants/µg DNA and with plasmid p19R1 (contains the PgARS (SEQ ID NO:2) of the RIB1 gene) was 6.1×10$^4$ transformants/µg DNA. These data show that the isolated plasmid PgARS17 indeed contains the sequence which renders high frequency of transformation (1660 fold higher than the transformation frequency obtained with plasmid pOS25 which does not contain an ARS element and 1.4 times higher than that obtained with previously isolated ARS-containing plasmid p19R1).

Thus, seven plasmids have been constructed which contain ARS sequences which supply high transformation frequencies. These plasmids have been isolated in preparative quantities. The plasmids are designated pPgARS11, pPgARS12, pPgARS13, pPgARS14, pPgARS15, pPgARS16, and pPgARS17.

Restriction analysis was carried out for more precise identification of the molecular mass and for mapping of the restriction sites of the isolated plasmids. For this, 9 restrictive endonucleases have been used: BamHI, XbaI, HincII, HindIII, PstI, EcoRI, SacI, SalI, SphI. The sizes of the obtained restriction fragments are shown in Table 3.

Isolation of rib1 ts Mutants

C. famata leu2 rib1 mutants can serve as parental strains for isolation of temperature-sensitive (ts) riboflavin prototrophic revertants which would be able to grow in the medium without riboflavin at reduced temperature and retain riboflavin auxotrophy at elevated temperature. Such mutations can evolve due to change in structure of the RIB1 gene product, GTP cyclohydrolase, in such a way that the resulting enzyme reacquires activity and simultaneously acquires thermolability. The ts revertants will be tested for ability to overproduce riboflavin at lower (permissive) temperature and those of them capable of oversynthesis will be used for the next step of selection. The leu2rib1$_{ts}$ mutants will be tested for identification of a non-permissive temperature which stops cell growth without exogenous riboflavin. Then,

TABLE 3

Restriction Analyses of Plasmids Containing *Pichia guilliermondii* ARSs

|  | BamHI kb | XbaI kb | Hinc I kb | HindIII kb | PstI kb | EcoRI kb | SacI kb | SalI kb | SphI kb | MW, kb | Insert, kb |
|---|---|---|---|---|---|---|---|---|---|---|---|
| pOS25 | 4.05 | 4.05 | 3.28 + + 0.54 + + 0.23 | 4.05 | 3.83 + + 0.22 | 4.05 | 4.05 | 4.05 | 4.05 | 4.05 | — |
| pPgARS11 | — | 4.62 | 3.28 + + 0.80 + + 0.54 | 4.05 + + 0.57 | 3.83 + + 0.79 | 3.05 + + 1.57 | 3.27 + + 1.35 | 4.62 | 4.62 | 4.62 | 0.57 |
| pPgARS12 | 4.05 + + 0.55 | 4.60 | 3.28 + + 0.78 + + 0.54 | 4.10 + + 0.50 | 3.83 + + 0.77 | 4.60 | 4.60 | 4.60 | 4.60 | 4.60 | 0.55 |
| pPgARS13 | — | 4.72 | 3.28 + + 0.90 + + 0.54 | 4.72 | 3.83 + + 0.89 | 4.72 | 4.72 | 4.72 | 4.72 | 4.72 | 0.67 |
| pPgARS14 | 4.72 | 4.72 | 3.28 + + 0.90 + + 0.54 | 4.72 | 3.83 + + 0.89 | 2.80 + + 1.92 | 4.72 | 4.72 | 4.72 | 4.72 | 0.67 |
| pPgARS15 | 5.00 | 3.85 + + 1.15 | 3.28 + + 1.18 + + 0.54 | 5.00 | 3.83 + + 1.17 | 3.38 + + 1.62 | 5.00 | 5.00 | 5.00 | 5.00 | 0.95 |
| pPgARS16 | 7.02 | 7.02 | 3.28 + + 3.20 + + 0.54 | 4.27 + + 2.20 + + 0.55 | 3.83 + + 3.19 | 4.22 + + 2.80 | 4.22 + + 2.80 | 7.02 | 7.02 | 7.02 | 2.97 |
| pPgARS17 | — | 4.27 | 3.28 + + 0.54 + + 0.45 | 4.27 | 3.83 + + 0.44 | 4.27 | 4.27 | 4.27 | 4.27 | 4.27 | 0.22 |

For identification of the location of the BamHI restriction site in the plasmids pPgARS14-16, double restriction with endonucleases BamHI and XbaI was carried out. Electrophoretic analysis of the restriction fragments showed the presence of the fragments whose size is close to the size of the insert in the analyzed plasmids. The data suggest preservation of BamHI restriction sites at the distance of the insert size from the polylinker localization. For localization of restriction sites of HindIII in pPgARS16, double restriction with endonucleases SacI and HindIII was carried out. The data obtained permitted construction of the linear schemes of the cloned plasmids (FIG. 13, FIG. 14).

Example 16

Isolation of *C. famata* Mutants with Impaired Regulation of Flavinogenesis

Isolation of *C. famata* regulatory mutants from rib1 and leaky rib2 mutants was carried out as described below. Simultaneously, a new approach for selection of *C. famata* mutants impaired in regulation of flavinogenesis, starting from rib1$_{ts}$ mutants, was developed.

the leu2 rib1$_{ts}$ mutants will be mutagenized and plated on the medium without exogenous riboflavin at the minimal non-permissive temperature. The grown colonies will be tested for riboflavin production at the permissive temperature. The mutants which accumulate sufficiently more riboflavin than the parental rib1$_{ts}$ strain can evolve either due to restoration of GTP cyclohydrolase with normal thermosensitivity or due to one or more regulatory mutations leading to overexpression of still thermolabile GTP cyclohydrolase. To discriminate between these two possibilities, the ability of isolated riboflavin overproducers to grow at elevated (restrictive) temperature was tested. The regulatory mutants would retain thermosensitivity for growth at elevated temperature without exogenous riboflavin.

The following experimental work was conducted. The strains *C. famata* 3-53, 8-58 and 8-24 (all leu2 rib1) were used as the parental ones for selection. Cell suspensions of the mutants were mutagenized with UV light or nitrosoguanidine with dose supplying 10% cell survival. Mutagenized cells were spread on the plates with leucine but without riboflavin and incubated at 28° C. for 10–12 days. Among three tested rib1 mutants, only one, 8-58, reverted to rib1$_{ts}$ variants (frequency of reversion was 8.3×10$^{-5}$). The colonies grew very slowly and were of small size. The colonies were replica-plated onto two media: with riboflavin (200 μg/ml) and without it (both media contained leucine at 40 μg/ml) and incubated at 28° C. and 35° C. for 5 days. The strains which were riboflavin prototrophs at 28° C. and still retained riboflavin auxotrophy at 35° C. were picked up. Altogether, 5390 revertants which were riboflavin prototrophs at 28° C. have been analyzed. Only 4 of them were found to retain riboflavin auxotrophy at 35° C. Thus, the frequency of $rib1_{ts}$ revertants appeared to be $7.4 \times 10^{-4}$ to the total number of analyzed riboflavin revertants and $6.1 \times 10^{-8}$ to the total number of surviving rib1 mutagenized cells.

For further selection, two $rib1_{ts}$ revertants, 8-58/1 and 8-58/4, were used. The minimal restrictive (non-permissive) temperature for plate growth of both strains in the medium without riboflavin was 32° C. Cells of both ts revertants were mutagenized with nitrosoguanidine (10% survival), plated on the medium without riboflavin and incubated at 32° C. After 6–7 days of incubation, small colonies appeared. Approximately 400 of them were picked up, streaked onto plates and tested for riboflavin overproduction after incubation at 28° C. No mutants able to overproduce riboflavin were found. Rib2 mutants will be used for isolation of conditional temperature-sensitive revertants. Use of rib2 mutants will aid in easier discrimination of regulatory mutants due to accumulation of the blue-colored fluorescent product of the GTP cyclohydrolase reaction in their cultures.

Isolation of rib2 Mutants

Regulatory mutants from leaky rib2 strains which grew without exogenous riboflavin only under condition of iron deficiency (cobalt-containing media) were isolated. One of such leaky strains was used for further selection of revertants growing in iron sufficient medium. Cells were UV irradiated and plated onto medium without cobalt. Growing colonies were isolated (frequency was $3.0 \times 10^{-3}$). 200 of such revertants were tested for growth and production of fluorescent products in liquid iron-deficient medium containing $CoCl_2$ (15 μg/ml). Only one strain was found accumulating large amount of blue-color fluorescent pteridine, which is produced after endogenic condensation with the C4 compound, the immediate product of the GTP cyclohydrolase reaction. Other mutants either did not accumulate any fluorescent products, or accumulated riboflavin. Apparently, in the latter mutants, reversion of the leaky rib2 mutation to the wild-type RIB2 allele occurred.

The isolated revertant accumulating the blue-color fluorescent product appeared to be unstable. For this reason, a new round of selection starting from leaky rib2 mutant 3-30 was undertaken. Altogether, 2715 revertants were tested. Eight of them appeared to be leaky as they grew without exogenous riboflavin only under the condition of iron deficiency (presence of $Co^{+2}$ ions). The frequency of such leaky mutants in this experiment was $2.9 \times 10^{-3}$. Testing of these strains showed that some of them resumed growth in iron-sufficient medium after prolonged incubation. Only one leaky revertant had a clear-cut phenotype and did not give any growth on iron-sufficient plates. This revertant was UV irradiated and plated on iron-sufficient medium. The frequency of appearance of such iron-resistant mutants was $1.8 \times 10^{-3}$. See example 20 for isolation of C. famata mutants able to over produce riboflavin.

Example 17

Isolation of Preparative Quantities of Plasmid DNA from the C. famata VKM Y-9 Gene Library Construction of an alternative gene library of C. famata VKM Y-9 in pCfARS68 was carried out. See Example 14.

The presence of inserts was tested in this library. Plasmid DNA was isolated from 30 individual colonies of *Escherichia coli* containing the library of C. famata. A rapid alkaline extraction procedure was used for such extraction (Birnboim, H. C. & Doly, J., *Nucl. Acids Res.* 7:1513–1523 (1979)). The presence of inserts in each of the isolated plasmids was assayed. Fifteen of the plasmids contained inserts. Thus, 50% of 90,000 isolated bacterial colonies contain C. famata gene library inserts.

Preparative amounts of plasmid DNA which represent the genomic library of C. famata VKM Y-9 have been obtained. For this, the cells of 75,000 bacterial colonies, carrying the library, were washed out and cultivated for 4 h in LB liquid medium (2.2 l) containing ampicillin (100 μg/ml). Plasmid DNA was extracted using rapid alkaline lysis method. Finally, the isolated plasmid DNA of C. famata gene library was dissolved in 2.5 ml of sterile TE buffer. Agarose gel electrophoresis of this DNA showed an approximate concentration of 3 μg/μl.

Example 18

Transformation of C. famata Riboflavin-deficient Mutant (group IV) 5-109 with C. famata VKM Y-9 Gene Library Plasmid DNA Mutant C. famata 5-109 is a double auxotroph for leucine (leu2) and riboflavin (biochemical group IV), possibly having defects either in synthesis of the aliphatic precursor of riboflavin, 3,4-dihydroxy-2-butanone-4-phosphate (DBP), or in the lumazine synthase reaction. In other words, the mutants have defects in the structural genes corresponding to *P. guilliermondii* genes rib5 (encodes lumazine synthase) or rib6 (encodes D6P synthase).

The cells of mutant 5-109 were transformed with plasmid DNA containing the gene library of C. famata VKM Y-9 on pCfARS1614 (see Example 14). Transformation was conducted using the electroporation method as in Example 9. For the control experiment, the strain was transformed with parental vector pCfARS1614. The transformation frequencies were the same for the control vector ($1.5 \times 10^5$/μg DNA) and for the vector containing the gene library ($1.3 \times 10^5$/μg DNA). After electroporation the cells of strain 5-109 were plated on minimal medium without leucine and riboflavin. One colony was found which appeared to be $Leu^+Rib^+$. This one colony appeared from approximately 12,000 colonies which were prototrophs only for leucine but not for riboflavin.

The $Leu^+Rib^+$ transformant was used for isolation of plasmid DNA. Plasmid DNA was isolated by *E. coli* retransformation as described before for *Candida maltosa* (Mauersberger, S., et al., in *Nonconventional Yeasts in Biotechnology*, Wolf, K., ed., Springer, Berlin (1996), pp. 411–580). *E. coli* transformation was conducted by electroporation as described in the Manual for ECM 600. The plasmid DNA, designated as pRIV-1, appeared to be much larger than the vector pCfARS1614 (FIG. 12). The preliminary restriction analysis of pRIV-1 plasmid was carried out using endonucleases EcoRI and simultaneously XbaI and SmaI. After treatment with endonuclease EcoRI, the plasmid gave three fragments, with sizes ~7 kb, 3.9 kb (similar to that of the parental vector) and ~1.25 kb. After simultaneous treatment with restrictive endonucleases XbaI and SmaI, the plasmid was digested into 7 fragments: 4.86 kb (identical to that obtained with parental vector), ~2.2 kb, ~1.6 kg, ~1.4 kb, ~0.85 kb, ~0.75 kb, ~0.55 kb. Thus, the total length of the plasmid pRIV-1 is ~12.2 kb and the length of the insert is ~7.1 kb. The data suggest that the insert of pRIV-1 plasmid contains one restriction site for EcoRI and after simultaneous treatment with nucleases XbaI and SmaI, the insert is cleaved into 5 fragments.

The electroporation of the strain C. famata 5-109 (leu2rib⁻) with plasmid pRIV-1 was carried out. The double Leu⁺Rib⁺ transformants appeared after three days. Transformation frequency was $3.25 \times 10^4$/µg DNA. Thus, the insert of ~7.1 kb, which is located on the plasmid pRIV-1, provides complementation of riboflavin auxotrophy of the mutant 5-109. As the strain belongs to biochemical group IV, one may assume that the insert of pRIV-1 plasmid contains (i) a gene encoding lumazine synthase or DBP synthase, or, (ii) a gene-suppressor. To identify whether the insert contains the structural gene of flavinogenesis or a gene-suppressor, this insert, or its subfragments, was transformed into the genome of the rib5 and rib6 mutants of flavinogenic species *P. guilliermondii*. If the plasmid 5-109 bears some structural gene of flavinogenesis, the corresponding riboflavin auxotroph of *P. guilliermondii* will acquire riboflavin prototrophy.

To study whether plasmid pRIV-1 complemented the rib5 or rib6 mutation of *P. guilliermondii*, corresponding auxotrophs of rib5 and rib6 were electroporated with this plasmid. Results are presented in Example 21.

Example 19

Construction of the *P. guilliermondii* ATCC 9058 Gene Library on pCfARS1614

For construction of *P. guilliermondii* gene library, the replicating plasmid of pCfARS1614 (size 5.1 kb) (FIG. 2) was used (see Example 14). The most convenient method for *P. guilliermondii* riboflavin structural gene cloning would be the heterologous complementation of both leucine and riboflavin auxotrophies by the gene library of *P. guilliermondii* constructed on previously isolated *C. famata* replicating vector CfARS1614.

Preparative amounts of this plasmid were accumulated. The plasmid (30 µg) was linearized with endonuclease BamHI. The enzyme (Promega, USA) was added at 2.5 U/µg of plasmid DNA. The amount of endonuclease was adjusted empirically for total plasmid linearization. The enzymatic treatment preserved sticky ends. The extent of linearization and sticky ends preservation was controlled by means of *E. coli* transformation (Rose et al., 1991).

The dephosphorylation of the linearized vector and the isolation of the total high molecular weight yeast *P. guilliermondii* DNA was carried out. See, Example 23.

Example 20

Isolation of rib1$_{ts}$ C. famata Mutants Able to Overproduce Riboflavin

Four temperature sensitive rib1 (rib1$_{ts}$) mutants (8-58/1; 8-58/2; 8-58/3 and 8-58/4) were isolated from C. famata rib1 mutant 8-58 (See Example 16). The mutants retained riboflavin auxotrophy at 35° C. and grew without exogenous riboflavin at 28° C. These four conditional mutants were tested for ability to overproduce riboflavin in tubes containing 2 ml of iron deficient medium obtained after 8-hydroxyquinoline treatment at 28° C. It was found that the mutants accumulated from 1.4 to 4.7 µg riboflavin/ml after a 5 day cultivation whereas partial strain C. famata leu2 accumulated 3.0 µg/ml under the same conditions. At 35° C. ts mutants did not grow in iron deficient medium at all.

UV and nitrosoguanidine derivative mutants of ts rib1 strains were isolated which were able to grow and overproduce riboflavin at 32–33° C. in iron sufficient medium. Several hundred such mutants were isolated from each corresponding ts strain. They were cultivated in test tubes at 28° C. containing iron sufficient medium with leucine (40 µg/ml). Altogether, 900 colonies were analyzed. Only one of them, the revertant RL8-58-tr1 isolated from strain ts1, appeared to be a riboflavin overproducer in the iron sufficient medium. This strain overproduced riboflavin in both iron sufficient (7 g/ml) and iron deficient (9 µg/ml) media. In contrast, the parental strain L20105 accumulated 1 µg/ml of riboflavin in iron sufficient and 3 µg/ml in iron deficient media. All other temperature resistant riboflavin prototrophic revertants did not accumulate more than 1 µg of riboflavin/ml in iron sufficient medium. See Table 4.

TABLE 4

Contents of Flavins and Blue Flourescent Product in the Culture Medium and in Cells of *Candida famata* VKM Y-9 Parental Strain leu2 L20105 and mutants "resistant to iron ions", µg/U O.D.

| Strain | Concentration iron in the medium µg/ml | flavins | blue flourescent product |
|---|---|---|---|
| leu2 L20105 | 0.01 | 12.0 | 1.2 |
| | 0.2 | 1.8 | 0.4 |
| 9-2 | 0.01 | 5.0 | 1.1 |
| | 0.2 | 6.2 | 1.7 |
| 8-2 | 0.01 | 8.6 | 1.4 |
| | 0.2 | 6.8 | 1.7 |
| 6-10 | 0.01 | 3.6 | 1.2 |
| | 0.2 | 0 | 0.4 |
| 9-7 | 0.01 | 3.3 | 1.2 |
| | 0.2 | 4.2 | 1.9 |
| *Pichia guilliermondii* rib 81 | 0.01 | 96.0 | 9.6 |
| | 0.2 | 96.0 | 11.4 |

Ts conditional revertants from other biochemical groups of *C. famata* riboflavin auxotrophs will be isolated.

Previously isolated iron-resistant mutants isolated from leaky rib2 auxotrophs were tested for ability to accumulate fluorescent products during cultivation in iron deficient medium (after addition of Co$^{+2}$ ions for a final concentration of 15 µg/ml) in tubes for 5–7 days. Among 215 analyzed mutants 20 accumulated blue fluorescent products, 50 accumulated green fluorescent products (apparently lumazine), 55 accumulated mixed blue-green fluorescence products, 22 accumulated riboflavin (yellow fluorescence) and 69 failed to grow. 140 such mutants were also cultivated in iron sufficient medium which did not contain cobalt ions. Under these culture conditions, 15 strains accumulated blue fluorescing products, 25-green fluorescent products, 65-accumulated products of "foggy" blue fluorescence and 18 mutants accumulated riboflavin. Seventeen mutants did not grow in this medium.

Accumulation of the blue fluorescing compound by 4 mutants has been quantitatively analyzed. The mutants were cultivated in Erlenmeyer flasks containing iron sufficient (0.2 mg/l) and iron deficient (0.01 mg/l) medium. Three mutants accumulated elevated amounts of flavins and blue fluorescent products. The mutants accumulated up to 2 µg of pteridines/ml of culture medium in iron sufficient medium which was 4 times greater than the amount accumulated by the parental strain.

It is known that $Cu^{2+}$ ions totally inhibit growth of the *P. guilliermondii* riboflavin overproducing mutants which overproduce this vitamin due to defects in iron transport. The sensitivity of the isolated mutants to $CuSO_2$ (0.05–0.1 mM) on Petri dishes was tested. The isolated *C. famata* mutants were able to overproduce blue fluorescing products in iron sufficient medium and appeared to be resistant to $Cu^{+2}$ ions. Therefore these mutants may bear defects in one or more regulatory genes involved in riboflavin synthesis. Mutants able to produce higher amounts of blue fluorescing compounds from a leaky rib2 strain will be isolated.

Example 21

Cloning of Structural Genes of Flavinogenesis Involved in 6,7-Dimethyl-8-ribityllumazine (DMRL) Synthesis (Group IV)

Additional *C. famata* genome DNA fragments which complement riboflavin auxotrophy of the mutants belonging to biochemical group IV were cloned. Mutants of biochemical group IV (6-10, 5-26-1,8-48) were transformed by electroporation with plasmid DNA of a *C. famata* gene library as prepared in Example 14.

Biochemical group IV includes two types of mutants: those with defective DMRL synthase (*P. guilliermondii* gene rib5) or dihydroxybutanone phosphate synthase (*P. guilliermondii* gene rib6). Identification of which mutation complemented each cloned DNA fragment was undertaken. Such identification was conducted in the heterologous *P. guilliermondii* system as mutations rib5 and rib6 have been identified.

Additional restriction analysis of the pRIV-1 plasmid (~12.1 kb, FIG. 12) was carried out. This plasmid appeared to possess a unique restriction site for BamHI which flanks the genome sequence of *C. famata* in the plasmid. pRIV-1 possesses two KpnI restriction sites (no sites on the insert) and four HindIII restriction sites (three sites on the insert).

Plasmid pRIV-1 was used for electrotransformation of *C. famata* strains 6-10 and 8-15 (both are leu2 rib⁻). These mutants, similar to the 5-109 mutant, belong to biochemical group IV. Plasmid pRIV-1 transformed both strains (6-10 and 8-15) simultaneously to leucine and riboflavin prototrophy with frequencies of $8\times10^3$ and $4\times10^4$ transformants/μg DNA, respectively.

To determine which mutation was complemented by plasmid pRIV-1 (*P. guilliermondii* rib 5 or rib 6), transformation of the corresponding mutants of *P. guilliermondii* RG8 (rib 5) and RG68 (rib 6) was conducted. To efficiently transform *P. guilliermondii*, the ARS element of this species (PgARS) was introduced into plasmid pRIV-1. A BamHI fragment (size ~0.82 kb) which possessed PgARS was removed from plasmid p19R7-7 and eluted from an agarose gel. The eluted fragment was ligated into plasmid pRIV-1 linearized with BamHI. The resulting ligate was used for electroporation of *Escherichia coli* DH5α. Separate colonies of bacterial transformants were used for plasmid DNA isolation. The obtained plasmid was further analyzed for presence of the necessary fragments. Seven of 12 analyzed bacterial transformants possessed new plasmid pRIV-1 with an inserted BamHI sequence bearing the PgARS sequence (FIG. 31). The resulting construct was designated as PRpRIV-1 (~12.9 kb). This plasmid contains origin of replication sequences for the two yeast species, *C. famata* and *P. guilliermondii*.

Plasmids pRIV-1 and PRpRIV-1 were used for transformation of two *P. guilliermondii* mutants, RG8 (rib 5) and RG68 (rib 6). However, neither plasmid was able to complement riboflavin auxotrophy of either rib 5 or rib 6 mutants after spheroplast transformation or electroporation. This result has several possible explanations:

(i) the construct PRpRIV-1, for one or more reasons cannot be expressed in *P. guilliermondii*, e.g., that the cloned genes of *C. famata* are not expressed in a heterologous *P. guilliermondii* system; or, (ii) the plasmid comprising the cloned genome fragment of *C. famata* contains a gene-suppressor of flavinogenesis rather than the structural gene of riboflavin synthesis.

Riboflavin-deficient mutant *C. famata* 6-10 (biochemical group IV) was transformed with the genomic library of this species as obtained in Example 17. The electrotransformed cells were plated on minimal medium without leucine and riboflavin. Five colonies of yeast prototrophs were obtained. Plasmid DNA was isolated from three of them. Such isolation was conducted through *E. coli* retransformation (by electroporation). Restriction analysis showed that plasmid DNA isolated from two of three yeast transformants was the same as formerly isolated plasmid pRIV-1. These plasmids transformed not only strain 6-10 but also strains 5-109 and 8-15 to the Leu+ Rib+ phenotype. Plasmid DNA isolated from a third yeast transformant contained a much longer insert than that of pRIV-1. Preliminary restriction analysis showed that this plasmid, designated as pRIV-2, bears an insert of ~11.7 kb. This plasmid was cut by numerous restriction endonucleases: SalI, KpnI, EcoRI, BamHI, SacI, PstI, SphI, and HincII. Nuclease SalI linearized pRIV-2 which suggests the only site for this enzyme exists in the vector polylinker. Endonuclease KpnI produced three fragments of ~6.9 kb, ~6.0 kb and ~3.5 kb. The pRIV-2 insert contains one KpnI site. Treatment with nuclease EcoRI gave four fragments of ~7.0 kb, ~4.0 kb, ~3.3 kb, ~2.16 kb. Two sites are located in the insert. Plasmid digested with BamHI resulted in three fragments of ~6.5 kb, ~6.0 kb and ~3.9 kb. Digestions with SacI gave two fragments of ~11.3 kb and ~5.1 kb. One fragment is located on the insert. PstI digestion gave four fragments of ~6 kb, ~4.7 kb, ~3.4 kb, and ~2.3 kb. Three sites are on the insert. SphI digestion produced three fragments of ~6.2 kb, ~6 kb and ~4.2 kb. Two sites are located on the insert. Digestion with HincII gave eight fragments of ~4.8 kb, ~4.4 kb, ~2.7 kb, ~1.1 kb, ~0.97 kb, ~0.93 kb, ~0.83 kb and ~0.6 kb. Seven sites are located on the insert.

This DNA was used for *E. coli* DH5α transformation. No ampicillin resistant colonies were obtained. Thus, none of the 10 yeast colonies contained plasmid.

Plasmid pRIV-2 bears the ~11.7 kb *C. famata* fragment. To subclone the fragment which renders complementation of *C. famata* mutants of biochemical group IV, it is important to know the location of restriction sites in the insert. We were able to determine preliminary location of several restriction sites, BamHI, KpnI, EcoRI and SacI, using endonucleases (FIG. 17).

Plasmid pRIV-2 transformed not only strain 6-10 but also mutant 8-15 to the Leu+ Rib+ phenotype. The electrotransformation frequency in both cases was approximately $1\times10^3$ transformants/μg DNA.

To determine which mutation is complemented by plasmid pRIV-2, transformation of *P. guilliermondii* rib 5 (RG8) and rib 6 (RG68) mutants was carried out. To efficiently transform *P. guilliermondii*, a PgARS was inserted into plasmid pRIV-2. A HincII fragment of ~0.82 kb, which contains a PgARS, was obtained from plasmid p19R7-7 and eluted. Plasmid pRIV-2 was linearized with SmaI. The plasmid contains a unique site for this enzyme (FIG. 17). Digestion with SmaI produced blunt ends. Plasmid pRIV-2 was linearized with SmaI and dephosphorylated with alkaline phosphatase (Promega). The linearized and dephosphorylated plasmid will be ligated with the 0.82 HincII fragment of P. guilliermondii which bears a PgARS.

C. famata 5-26-1 (Group IV) was transformed with a gene library obtained from C. famata as described in Example 17. After electroporation, cells were plated on minimal medium without leucine and riboflavin. The prototrophic colonies were obtained and plasmid DNA was isolated from one of them. The plasmid transformed not only strain 5-26-1 but also mutant 8-15 to the Leu+ Rib+ phenotype. In both cases the transformation frequency was approximately 600 transformants/µg DNA. Restriction analysis of the recombinant plasmid isolated from Leu$^+$ Rib$^+$ transformants of the 5-26-1 strain was carried out. The isolated plasmid appears to be identical to pRIV-2.

C. famata riboflavin deficient mutant 8-48, also of biochemical group IV, was transformed with the C. famata gene library as obtained above in Example 17. Transformed cells were plated on minimal medium. Ten leucine and riboflavin prototrophic colonies were picked up. Total DNA was isolated from all ten Leu$^+$ Rib$^+$ colonies.

Thus, two fragments of the C famata genome, which complement riboflavin auxotrophy of the strains 6-10 and 5-26-1, were cloned. One of these fragments (~11.4 kb; in pRIV-2) was able to complement riboflavin deficiency of strains 6-10, 5-109 and 8-15. The other fragment (isolated from transformant 5-26-1) complemented mutations in strains 5-26-1 and 8-15. Thus, strains 6-10, 5-109, 8-15 and 5-26-1 may bear mutations in the same gene of riboflavin synthesis. To identify in P. guilliermondii which mutation (rib5 or rib6) complements the cloned fragment in plasmid pRIV-1, we constructed the recombinant PrpRIV-1 plasmid comprising PgARS. In the future, plasmid pRIV-2 comprising PgARS will be constructed.

Strain 8-48 and other mutants of biochemical group IV may have mutations in the same gene or other genes of biochemical group IV.

Example 22

Subcloning the CfARS Element from pCfARS62

Plasmid pCfARS62 was previously constructed as in Example 14. Four fragments of this CfARS sequence (two XbaI-HindIII fragments of ~0.8 kb and 1.4 kb and two HindIII fragments of ~0.6 kb and 1.25 kb) were isolated. To identify which of these fragments bears ARS activity, the fragments were inserted in plasmid YEp13. By means of functional analysis based on determining the transformation frequency, ARS activity was localized to a ~0.8 kb XbaI-HindIII fragment. A plasmid containing this fragment was designated pCfARS68 (~10.9 kb). The plasmid includes the XbaI-HindIII fragment of YEp13 (~10.1 kb) which bears the LEU2 gene of S. cerevisiae, a replicator of the 2µ plasmid, the bacterial gene for ampicillin resistance, Apr, an E. coli ori sequence as well as the XbaI-HindIII fragment of ~0.8 kb with CfARS activity. pCfARS68 is a trireplicon vector which can be used in E. coli, S. cerevisiae and C. famata systems.

Example 23

Construction of a P. guilliermondii ATCC 9058 Gene Library on pCfARS1614

A gene library of P. guillermondii ATCC 9058 was constructed in the replicative plasmid pCfARS1614 (~5.1 kb). Preparative amounts of this plasmid were linearized with endonuclease BamHI. 20 µg of the linearized plasmid was dephosphorylated with calf intestine alkaline phosphatase (CIP). Enzyme was added at 0.03 U/µg plasmid DNA. This amount was enough for elimination of 95% of vector self-ligation. The efficiency of dephosphorylation and the retention the sticky ends was checked by E. coli transformation (Rose et al. (1991)).

Total high-molecular weight DNA of P. guilliermondii ATCC 9058 was isolated using the modified method of Cregg et al., 1985. The molecular weight of the isolated total DNA was ~50–60 kb. Partial restriction of the native DNA was conducted with endonuclease Sau3AI (New England Biolabs) according to Maniatis et al., 1982. The quantity of the endonuclease was 0.042 U/g DNA. The preparative restriction of 100 µg DNA was conducted in 1500 µl of the restrictive mixture for 18 min at 37° C. The reaction was stopped by cooling in an ice-bath and addition of EDTA to a final concentration 20 mM. The DNA samples were twice extracted with phenol and sedimented by ethanol. The DNA pellet was twice washed with 70% ethanol and dissolved in 250 µl TE buffer. The concentration of the obtained DNA restriction fragments was 0.3 µg/ml. Using agarose gel electrophoresis the size of the DNA fragments was determined to be from ~2 to 25 kb.

Elution of Sau3AI DNA fragments with a size between 3 and 10 kb was conducted according to Maniatis et al., 1982, with some modifications. Electrophoresis of Sau3AI fragments was conducted in 0.8% agarose gel containing ethidium bromide. Restriction fragments of that size were cut from the gel. The 0.6% low-melting agarose, containing the fragments with a size between about 3 and 10 kb, was poured into the slit before the gel lane. The low-melting agarose was prepared in 2× concentrated electrophoresis buffer containing ethidium bromide. After agarose polymerization, electrophoresis was carried out (temperature 4° C., voltage 100 v, duration 3 hours). DNA fragments of between 3 and 10 kb were localized in the low-melting agarose. Pieces of agarose, containing the DNA fragments, were washed with 2 volumes of TE buffer and melted at 65° C. The samples were cooled for 15 min at −20° C. and centrifuged. About ~20 µl of tRNA (80 µl) and ¹/₁₀ volume of 3 M sodium acetate (pH 5.2) were added to the samples. The fragments were then precipitated from the samples by ethanol.

The DNA precipitate was dissolved in 400 µl TE buffer, twice was extracted with phenol, precipitated with ethanol and twice washed with 70% ethanol. The precipitate of eluted Sau3AI fragments was dissolved in 100 µl TE buffer. DNA concentration was 0.17 µg/ml in the sample. Electrophoresis of the obtained sample in 0.8% agarose gel showed that the size of the eluted fragments, according to expectations, was ~3 to 10 kb.

Ligation of the linearized dephosphorylated vector pCfARS1614 with the eluted Sau3AI fragments of total P. guilliermondii DNA was carried out. Ligation was conducted overnight at 8° C. The mass ratio between vector and Sau3AI chromosomal fragments was adjusted experimentally to 1:5. The final concentration of DNA in the ligation mixture was 0.5 µg/ml. Efficiency of ligation was checked by means of E. coli transformation with subsequent plasmid DNA isolation from the separate bacterial transformant colonies. The presence of the inserts in the plasmids was tested electrophoretically.

Example 24

Isolation of Quantitative Amounts of Plasmid Containing P. guilliermondii Gene Library in pCFARS1614

In the next experiments, the ligation of the preparative amounts of the vector/insert was carried out. The obtained ligate was used for E. coli DH5α electroporation. The representation of the library was determined. For this, plasmid DNA was isolated from 24 individual bacterial colonies. The presence of the inserts was determined in each of the isolated plasmids by means of native plasmid electrophoresis as well as by electrophoresis of the restriction fragments isolated from these plasmids. Ten of the studied plasmids contained the inserts. Thus, of 110,000 obtained bacterial transformants, 42% contained inserts of genomic P. guilliermondii DNA.

Preparative amounts of P. guilliermondii ATCC 9058 plasmid DNA have been isolated. For this, 110,000 bacterial colonies of the described above library were washed out and cultivated for 3 h in liquid LB medium (volume 2.5 l) containing ampicillin (100 mg/l). Plasmid DNA was isolated using the rapid alkaline lysis method. The DNA precipitate was dissolved in 300 µl of sterile TE buffer. The DNA concentration of this plasmid DNA, determined by electrophoresis, was 1.5 µg/µl.

Example 25

Isolation of ts rib5 or rib6 C. famata Mutants Defective in Regulation of Flavinogenesis Isolation of C. famata mutants defective in regulation of riboflavin synthesis (riboflavin overproducers in iron-rich medium) was successfully exploited in P. guilliermondii using two approaches. One approach is based on isolation of leaky riboflavin deficient mutants able to grow in the medium without riboflavin only during iron starvation and subsequent isolation of riboflavin prototrophs in iron-rich medium. Another approach included selection of temperature sensitive riboflavin auxotrophs followed by isolation of riboflavin auxotrophs more temperature resistant. Both methods can be successfully used in the C. famata system. However, most of the isolated regulatory mutants appeared to be unstable. Therefore, isolation of the regulatory mutants from other initial riboflavin defective mutants was undertaken in order to obtain more stable regulatory mutants.

One approach included isolation of regulatory mutants from the mutants of biochemical group IV (strains 5-26, 6-10 and 8-48). As the first step, the riboflavin prototrophs were selected. Cells were mutagenized with UV light and plated on the medium with leucine without riboflavin. The frequencies of the reversion to riboflavin prototrophy were $4.5 \times 10^{-5}$, $7.0 \times 10^{-4}$ and $6.4 \times 10^{-4}$, respectively. The grown colonies were replica-plated on the media with riboflavin (200 µg/ml) and without it and incubated at 28° C. and 35° C. for 5 days. The riboflavin colonies prototrophic at 28° C. and simultaneously auxotrophic at 35° C. colonies were picked up.

The selected ts rib mutants were tested for regulation of flavinogensis by iron. The mutants were cultivated in tubes at 28° C. with leucine and cobalt ions (15 µg/ml), which induces iron deficiency. Flavinogenic activity was tested for 24 ts mutants isolated from strain 5-26, 48 ts mutants isolated from strain 6-10 and 100 ts mutants isolated from strain 8-48. All selected clones appeared very sensitive to cobalt ions, grew very weakly and accumulated green and blue-green fluorescent products in the culture medium. Several such representatives were picked up from the each strain and were tested for their flavinogenic activity in iron-free medium. The tested colonies accumulated 0.2–12 µg of fluorescent compounds/ml in the iron-free medium. Those mutants which accumulated the highest amounts of fluorescent compounds were used in the next stage of selection.

The ts mutants isolated from strain 8-48 (ts 5, 9, 12, 17) and from 6-10 (ts 5, 7, 20) were plated on medium without riboflavin and incubated at the minimum restrictive temperature (33° C.). Temperature resistant clones grown under those conditions were incubated at 28° C. in the medium with regular iron concentration. Together 766 such clones were analyzed. Most of them accumulated not more than 0.4 µg fluorescent product/ml. One temperature resistant revertant isolated from mutant 8-48, ts17, accumulated 1–8 µg riboflavin/ml. Copper ions (0.1 mM) did not inhibit growth of this strain whereas citrate suppressed flavinogenesis.

Another approach was directed to the introduction of leaky mutations into riboflavin auxotrophs. Again, the mutants belonging to biochemical group IV were used (strains 8-15, 8-28, 8-48). Using mutant 8-48, two leaky revertants were isolated which were able to grow without exogenous riboflavin in the medium with cobalt ions (5.5 µg/ml) and remained as riboflavin auxotrophs in the medium without cobalt. They were used for isolation of "iron-resistant" mutants. The frequency of transformation was $1.9 \times 10^{-3}$ for strain 8-48-1 and $2.4 \times 10^{-3}$ for strain 8-48-9.

330 iron-resistant mutants were studied for riboflavin synthesis in iron-rich liquid medium. As a result, 5 mutants were isolated which accumulated 13–20 µg of riboflavin/ml medium. Copper ions did not inhibit growth of these mutants suggesting that they are not mutants defective in cellular iron uptake. Apparently these are mutants with impaired iron regulation of riboflavin synthesis.

Example 26

Isolation of rib7 C. famata Mutants

Mutant 8-33 (leu2⁻ rib7⁻) was transformed with C. famata gene library plasmid DNA by electrotransformation. Two colonies were isolated which were both prototrophs for leucine and riboflavin. Plasmid DNA from these cells was isolated through E. coli retransformation. This plasmid, designated pCR7 (FIG. 18), was used for electroporation of the strain 8-33. Leu⁺ Rib⁺ transformants were appeared with frequency of $1 \times 10^3$ transformants/µg DNA. Using E. coli retransformation, plasmid DNA was isolated from these transformants which appeared to be identical to pCR7. Thus, this plasmid complements both leucine and riboflavin auxotrophies of the 8-33 mutant and is autonomously maintained in the cells of yeast transformants.

Restriction analysis of pCR7 was carried out. The plasmid was linearized with several restriction endonucleases: PstI, SmaI, SalI, SacI, SphI, KpnI, EcoRI, XbaI, HindIII, BamHI, and HincII. Endonucleases PstI, SmaI, SalI and SphI linearized pCRI. Each endonuclease possesses only one unique site in the vector polylinker (FIG. 21). After treatment with nuclease KpnI, two fragments, ~3.5 kb and ~3.1 kb, are produced. The pCR7 insert does not contain a KpnI site.

Treatment with EcoRI gives also two fragments of ~3.9 kb and ~2.7 kb. The pCR7 insert does not contain an EcoRI site. XbaI cuts the plasmid into two fragments of ~5.7 kb and ~0.9 kb. The XbaI site is localized in the insert. Treatment with HindIII produces three fragments of ~3.2 kb, ~2.3 kb and ~1.16 kb; two HindIII sites are localized in the insert (FIG. 18). Treatment with HincII gives four fragments of about 3.6 kb, 0.95 kb, 0.9 kb and 0.7 kb. BamHI sites are absent on the pCR7 plasmid. These data show that the total length of pCR7 is approximately 6.6 kb and the length of the insert is approximately 1.5 kb (FIG. 18).

The possibility of the complementation of the rib 7 mutation in another yeast species, P. guilliermondii, by pCR7 was studied. To achieve efficient transformation of P. guilliermondii, PgARS was introduced into plasmid pCR7 in the following way: pCR7 was linearized with endonuclease SmaI which produces blunt ends. Linearized plasmid was ligated with the 0.82 kb HincII fragment of P. guilliermondii carrying PgARS. The obtained ligate was used for E. coli DH5α electroporation. Plasmid DNA was isolated from 11 such ampicillin resistant transformants. DNA from 5 such samples was identical and contained a new construct carrying both plasmid (pCR7) and insert (PgARS). The new plasmid was designated as pPRp7. The size of the pPRp7 plasmid is approximately 7.4 kb (FIG. 19).

Plasmid pPRp7 was used for electrotransformation of P. guilliermondii mutant RG162 (his rib7). The conditions for electroporation were substantially the same as those described for P. guilliermondii strain RG21 (see Example 11). No riboflavin prototrophic transformants were found. Riboflavin prototrophic transformants were also not isolated using plasmid p19R7-7, which contains a homologous RIB7 gene of P. guilliermondii and a PgARS. RG162 cells reverted to riboflavin prototrophy during the electroporation procedure. Thus, it was clear that strain RG162 is not suitable for electrotransformation.

Another P. guilliermondii strain, a P. guilliermondii rib7 mutant, RG130, was transformed by the spheroplast method. This strain is efficiently transformed with plasmids bearing PgARS and the RIB7 gene of P. guilliermondii. The transformation frequency was $10^{3-10^5}$ transformants/µg DNA. After transformation of this strain with plasmids pCR7 and PRp7, riboflavin prototrophic transformants were obtained in both cases with frequencies of 2 and 110 transformants/µg DNA, respectively. Transformants RG130/pCR7 and RG130/PRp7 were used for isolation of the corresponding plasmids using E. coli retransformation. Both plasmids are maintained extrachromosomally in P. guilliermondii. Plasmid PRp7, apparently due to the presence of a PgARS element, transforms RG130 strain 55 times more efficiently than pCR7. Thus, the pCR7 and PRp7 plasmids, comprising the isolated C. famata genomic fragment(s), bear the RIB7 gene.

The attempts to clone genomic fragments of C. famata which would complement rib1 mutations of this species was carried out. The mutants 8-77, 3-25 and 8-80 (all: leu2 rib1) were electrotransformed with plasmid DNA of the C. famata VKM Y-9 gene library. The electroporated mutant cells were plated in minimal medium. Only in the case of the 8-80 strain was one Leu⁺ Rib⁺ colony obtained. Plasmid DNA was isolated from this colony through E. coli retransformation. Preliminary restriction analysis of this plasmid showed that it represents the pCfARS1614 vector carrying a ~3 kb insert. The total length of this plasmid, designated as pCR1, is approximately 8.1 kb. This vector will be used to retransform rib1 mutants of C. famata.

Example 27

Transformation of C. famata Riboflavin Auxotrophs with Plasmids of P. guilliermondii ATCC 9058 Gene Library The gene library of P. guilliermondii ATCC 9058, constructed on C. famata plasmid pCfARS1614, was used for cloning the structural genes of riboflavin synthesis in the heterologous system of C. famata.

Mutant C. famata 5-109 (leu2, riboflavin auxotroph of biochemical group IV) was electrotransformed with plasmid DNA of the P. guilliermondii gene library. In the control experiment, this mutant was transformed with plasmid pCfARS1614 as the control. The transformation frequency for isolation of leucine prototrophs was $2.1 \times 10^4$ transformants/µg DNA for the gene library and $3.2 \times 10^4$ transformants/µg DNA for the control vector. The transformed cells of C. formata 5-109 were also plated on the medium without leucine and riboflavin. Altogether, 15 such colonies were isolated. However, rare prototrophic revertants were found on the control plates (non-transformed cells).

Total DNA was isolated from each of 15 colonies and the plasmid DNA was isolated after bacterial retransformation. Restriction analysis of the isolated plasmids using endonucleases EcoRI, PstI, and HindIII showed 13 of 15 plasmids were the control plasmid pCfARS1614. Two other plasmids contained inserts. However, plasmids with these inserts do not provide complementation of riboflavin auxotrophy of C. famata strain 5-109.

In the second round of experiments, another C. famata strain of biochemical group IV, 6-10, was used as the recipient strain for transformation with the P. guilliermondii gene library. Again, electroporation was used as the transformation method. Transformation frequency for one marker, leucine prototrophy, appeared to be $1.0 \times 10^4$ transformants/µg DNA for the library and $1.8 \times 10^4$ tranformants/µg DNA for the initial vector pCfARS1614. Among 10,500 transformants plated on the minimal medium, 10 prototrophs for both leucine and riboflavin were picked up. Only two of them maintained ability to grow in the minimal medium. Plasmid DNA will be isolated.

In another experiment, C. famata riboflavin auxotroph 4-68 (leu2 rib2) was used as the recipient strain. Transformation frequency for one marker (selection for leucine prototrophy) using electroporation was $6.2 \times 10^4$ transformants/µg DNA. Among 21,000 transformants, plated on minimal medium, four colonies were able to grow without both leucine and riboflavin. Plasmid DNA will be isolated from these transformants for subsequent analysis. Transformation of other C. famata riboflavin auxotrophs of biochemical groups II and IV will be conducted in order to clone the corresponding P. guilliermondii genes of riboflavin biosynthesis by heterologous complementation.

Example 28

C. famata Gene RIB1 Cloning

The gene fragment C. famata carried by recombinant plasmid pCR1, which complements riboflavin auxotrophy of the 880 mutant (leu2 rib1), was cloned. See Example 26. Plasmid pCR1 has size of ~8.1 kb and was obtained by ligating the vector pCfARS1614 with the insert of ~3 kb.

Plasmid pCR1 was used for electroporation of independently obtained mutants of C. famata 8-80, 8-77 and 3-25 (all leu2 rib1). Double prototrophic transformants were obtained. The frequencies of transformation were 8.3×10³/µg DNA (strain 8-80), 1×10⁴/µg DNA (8-77) and 2.7×10³/µg DNA (strain 3-25). Thus, pCR1 complements both leucine and riboflavin auxotrophies in all three above mentioned mutants of C. famata. Transforming plasmid pCR1 can be isolated from yeast transformants through E. coli retransformation.

Restriction analysis of pCR1 was conducted. The plasmid was treated with the following restriction endonucleases: HindIII, SphI, PstI, SalI, SmaI, SacI, KpnI, BamHI, XbaI and EcoRI. Enzymes HindIII, SphI, PstI, SalI, SmaI and SacI linearized pCR1 which means that each of them possesses only one unique site located in the vector polylinkers (FIG. 21). After treatment of pCR1 with endonuclease XbaI, two fragments of ~7.6 kb and ~0.5 kb were produced. Treatment of the plasmid with KpnI gave three fragments of ~3.7 kb, ~3.5 kb and ~0.9 kb. One site for KpnI is located in the insert of pCR1 plasmid. Treatment with EcoRI gave four fragments of ~3.9 kb, ~2.1 kb, ~1.6 kb and ~0.55 kb; two sites are located in the plasmid insert (FIG. 21). The total size of the pCR1 plasmid is ~8.1 kb and the size of the insert is ~3 kb (FIG. 21).

The ability of plasmid pCR1 to complement rib1 mutations of Pichia guilliermondii, was tested. To achieve efficient transformation in the heterologous system of P. guilliermondii, a PgARS element was inserted into plasmid pCR1 as follows. pCR1 was linearized with endonuclease SmaI which produces blunt ends. The linearized plasmid was ligated with 0.82 kb HincII fragment of P. guilliermondii PgARS isolated earlier from the plasmid p19R1. The ligate produced was used for electrotransformation of E. coli DH5 α. Plasmid DNA was isolated from 6 independent ampicillin resistant bacterial transformants. DNA of all 6 samples was identical and contained a new construction comprising pCR1 and the PgARS insert. New recombinant plasmid was designated as PRp1 and has a size of approximately 8.9 kb (FIG. 22).

The new plasmid PRp1 was used for spheroplast transformation of P. guilliermondii hisX rib1 mutant RG21. This strain is efficiently transformed to Rib⁺ phenotype with plasmids bearing PgARS and RIB1 gene of P. guilliermondii (transformation frequency was $10^{3-105}$ transformants/µg DNA). After transformation of RG21 with plasmid PRp1, the Rib⁺ transformants appeared with a frequency of 160 transformants/µg DNA. PRp1 is maintained extrachromosomally in P. guilliermondii cells; it was isolated from RG21/PRp1 transformants through retransformation of E. coli.

PRp1 also effectively transforms leu2 rib1 mutants of C. famata to the Leu⁺Rib⁺. The transformation frequency using electroporation was 2.8×10³, 1.9×10³ and 1.2×10³ transformants/µg DNA for mutants 8-80, 8-77 and 3-25, respectively. These data suggest that the pCR1 plasmid bears the RIB1 gene.

Subcloning of C. famata DNA Fragment Bearing RIB1 Gene

For subcloning the DNA fragment bearing the C. famata RIB1 gene, plasmids pCR1 and PRp1 were digested with XbaI endonuclease. The XbaI fragments of pCR1 and PRp1 plasmids of ~7.6 and ~8.4 kb, respectively, were eluted. As a result, new recombinant constructs pCR1Xb (FIG. 23) and PRp1Xb (FIG. 24) deleted for ~0.5 kb RIB1 containing insert of the size of ~2.5 kb were isolated. The obtained plasmids pCR1Xb and PRp1Xb were used for electroporation of the mutant C. famata 8-77 (leu2 rib1). Both plasmids complemented the rib1 mutation. The frequencies of transformation were approximately the same as those obtained using the parental plasmids pCR1 and PRp1: 5×10³ transformants/µg DNA for pCR1Xb and 7×10³ transformants/µg DNA for PRp1Xb. Thus, the size of the subcloned DNA fragment containing the RIB1 gene of C. famata is ~2.5 kb.

Example 29

Cloning of C. famata Gene RIB7

Whether the vector fragment bearing the C. famata RIB7 gene, carried by recombinant plasmids pCR7 and PRp7 (See Example 26), complemented rib7 mutations in two leu2 C. famata mutants, 3-24 and 8-70, was investigated. These strains were isolated independently from 8-33 which was used for cloning of the RIB7 fragment.

Cells of the strain 3-24 reverted with high frequency during the electroporation procedure to riboflavin prototrophy. Thus this strain cannot be used as the recipient one for transformation. Another strain, 8-70, retained riboflavin auxotrophy during the electroporation procedure and was used as the recipient. This strain (leu2rib7) was electrotransformed with plasmids pCR7 and PRp7. Double prototrophic transformants were isolated with a frequency of 3.4×10³ transformants/µg DNA in the case of pCR7 plasmid and 2.4×10³ transformants/µg DNA in the case of plasmid PRp7. Using Escherichia coli retransformation, the corresponding plasmid DNA was isolated from transformants 8-70/pCR7 and 8-70/PRp7. Thus, the cloned RIB7-containing fragment of C. famata DNA complemented the rib 7 mutation in two independent mutants, 8-33 and 8-70. This is additional proof that the cloned fragment bears the RIB7 gene.

Example 30

Isolation of C. famata Regulatory Mutants Overproducing Riboflavin and Study of Their Properties Regulatory mutants have now been isolated which overproduce riboflavin. The properties of these mutants were studied.

C. famata strain #105 (leu2) was UV irradiated and plated on the minimal medium with leucine. After testing 6250 colonies one mutant was isolated, #105-1, which accumulated elevated amounts of riboflavin. Cultivation of this mutant in test tubes in synthetic Burkholder medium with optimal conditions for growth (riboflavin concentration (0.2 µg/ml)) for 5 days showed that it produces 25 µg riboflavin/ml whereas the parental strain #105 produced only 1.4 µg/ml. Strain #105-1 was used for isolation of more productive riboflavin mutants. Cells were again UV irradiated and plated on leucine (40 µg/ml) containing Burkholder medium. Colonies were tested for riboflavin production after cultivation for 5 days in tubes optimal for growth having an iron concentration 0.2 µg/ml. Under these conditions, the best clones produced up to 70 µg/ml. One such strain (#105 1-2) produced 70–100 µg riboflavin/ml. This strain grew on ethanol as its sole carbon and energy source.

Cultures of this strain (#105 1-2) were deposited under the terms of the Budapest Treaty on the International Recognition of the Deposit of Microorganisms for Purposes of Patent Procedure on Mar. 22, 2001, at the Agricultural Research Service Culture Collection (NRRL), 1815 North University Street, Peoria, Ill. 61604 USA. The deposit of the strain was accepted by that Depository under the terms of that Treaty. The deposit was assigned NRRL deposit number Y-30455.

The next step of the work was directed to isolation of derived mutants producing even higher quantities of riboflavin. Mutants which accumulated up to 250 μg riboflavin/ml after 5 days cultivation in tubes containing Burkholder medium with leucine were successfully isolated. Unfortunately, this strain appeared to be leucine prototrophic. Isolation of leucine auxotrophs from the mutant was undertaken. Isolation was unsuccessful after screening 1585 colonies (UV treatment) and 7780 colonies (nitrosoguanidine treatment). No leucine auxotrophs were isolated. In contrast to the parental strain, this strong riboflavin overproducer does not grow on ethanol as the sole carbon and energy source.

It is known that *P. guilliermondii* mutants defective in iron transport are sensitive to growth inhibition by $Cu^{2+}$ ions whereas mutants defective in regulation of riboflavin synthesis are normally resistant to copper ions. All isolated *C. famata* mutants overproducing riboflavin are normally resistant to copper ions. Thus, riboflavin oversynthesis apparently is not due to a defect in iron uptake into the cell.

Example 31

Cloning of *C. famata* Gene RIB2

The strategy of RIB2 gene cloning was based on isolation of the fragment of chromosomal DNA from a *C. famata* gene library. Previously isolated and identified rib2 mutants were transformed by plasmid DNA containing this library. After testing five available rib2 mutants, only one, 33-1n, which did not revert after transformation either by electroporation or spheroplast transformation, was used for the following experiments.

Plasmid DNA from a *C. famata* gene library was used for transformation of the strain 33-1n (leu2 rib2). Both methods (electroporation and spheroplasting) were used for transformation. Two colonies of double $Leu^+Rib^+$ transformants were obtained. The transformants were used for isolation of transforming plasmid DNA (through *Escherichia coli* retransformation). The obtained transforming plasmid DNA appeared to be identical in both cases. Restriction analysis of this plasmid (designated pCR2) (FIG. 25) showed that it comprises the pCfARS1614 vector and the insert of ~6.4 kb (FIG. 25). Plasmid pCR2 was cut with several restriction endonucleases: BamHI, SalI, SacI, SmaI, KpnI, XbaI, PstI, HindIII, EcoRI. The plasmid does not contain BamHI sites. Endonucleases SalI and SmaI linearized the plasmid indicating only one unique site in the vector polylinkers. Endonuclease KpnI gave two fragments of ~8.0 and ~3.5 kb; the insert did not possess a KpnI site. Nuclease XbaI cleaved the plasmid in three fragments of ~7.1, ~2.2 and ~2.2 kb (these two last fragments are not separated by electrophoresis); two XbaI sites are located in the insert. Endonuclease SacI produced three fragments of ~6.2, ~4.4 and 0.9 kb; two SacI sites are located in the insert. Treatment with enzyme PstI gave two fragments of ~6.5 and ~5.0 kb; one PstI site is located in the insert. Treatment with EcoRI produced five fragments of ~3.9, ~2.8, ~1.8, ~1.8 and ~0.65 kb; three EcoRI sites are located in the insert. The insert contains HindIII sites. The total length of plasmid pCR2 is approximately 11.5 kb and the length of the insert is ~6.4 kb.

Plasmid pCR2 was used for electrotransformation of strain 33-1n. Transformants of $Leu^+Rib^+$ phenotype appeared with a frequency of $6.5 \times 10^3$ transformants/μg DNA. Using *E. coli* retransformation, plasmid DNA identical to pCR2 was isolated. Thus, plasmid pCR2 complements both leucine and riboflavin auxotrophies of the mutant 33-1n and is autonomously maintained in the cells of the yeast transformants.

The possibility of complementing the rib2 mutation of another species of flavinogenic yeast, *P. guilliermondii*, with the *C. famata* insert carried in the pCR2 plasmid, was studied. To achieve efficient transformation of *P. guilliermondii*, a plasmid bearing the cloned *C. famata* RIB2-fragment and an ARS element of *P. guilliermondii* was constructed. For this, the earlier isolated plasmid p2R (FIG. 26) was cleaved with endonuclease KpnI and a fragment of ~3.9 kb was eluted. This ~3.9 kb fragment contains the total sequence of bacterial vector pUC19, the ARS element of *P. guilliermondii*, part of the *S. cerevisiae* LEU2 gene, the RIB2-fragment of *C. famata* and a CfARS (FIG. 26). Two obtained fragments were ligated and the resulting ligate was used for *E. coli* DH5α transformation. Plasmid DNA was isolated from 20 bacterial transformants. Ten transformants contained an insert and the remaining 10 appeared to be the product of self-ligation of the p2R KpnI-fragments. Restriction analysis of plasmids containing an insert showed that 5 contained an insert in proper orientation in view of the restored LEU2 gene functions; the other five plasmids contained an insert in the inverted orientation. Constructs restoring LEU2 gene functions were named PRp2 (FIG. 27). Thus, plasmid PRp2 has a size of ~11.9 kb and carries a RIB2-fragment of *C. famata* and an ARS of *P. guilliermondii*.

Spheroplast transformation of *P. guilliermondii* RG2 strain (rib2) was carried out with plasmid PRp2. $Rib^+$ transformants appeared with a frequency of 40 transformants/μg DNA. Plasmid PRp2 was isolated from yeast transformants (through *E. coli* retransformation). Thus, the genomic DNA fragment of *C. famata*, carried by the pCR2 and PRp2 plasmids, contains the RIB2 gene.

Subcloning of the RIB2-containing insert of *C. famata* was carried out. Plasmid pCR2 was treated with nuclease XbaI and the XbaI fragment of ~7.1 k. was self-ligated. As a result, new recombinant construct pCR2-1 (FIG. 28) lacking the RIB2-insert of ~2 kb was isolated. Plasmid pCR2-1 was used for electrotransformation of strain *C. famata* 33-1n (leu2 rib2). This plasmid was shown to complement the rib2 mutation of the strain 33-1n. The transformation frequency appeared to be higher than when plasmid pCR2 was used: $1.3 \times 10^4$ transformants/μg DNA. Plasmid pCR2-1 is maintained autonomously in the yeast transformants. In parallel, transformation was carried out with plasmids pCR2-21 and pCR2-22 (FIG. 28) which bear two other XbaI fragments. Neither pCR2-21 nor pCR2-22 complement the rib2 mutation of strain 33-1n. Only the ~2 kb subfragment of *C. famata* RIB2-fragment in the plasmid pCR2-1 contains two HindIII and one EcoRI site (FIG. 28).

The ability of the RIB2 *C. famata* subfragment in the pCR-1 plasmid to complement the *P. guilliermondii* rib2 mutation was studied. An ARS from *P. guilliermondii* was inserted into pCR2-1 using the following method: (i) a *P. guilliermondii* ARS was obtained by using nuclease PstI on plasmid p2R (FIG. 26) and eluted from a gel; (ii) pCR2-1 was linearized with the same enzyme and then dephosphorylated; (iii) the fragments from the restriction digest were ligated. The resulting recombinant constructs, identified as PRp2-11 and PRp2-12, appeared to be plasmid pCR2-1 comprising a *P. guilliermondii* ARS. The ARS element is located in PRp2-11 and PRp2-12 in opposite orientations (FIG. 29).

Plasmids PRp2-11 and PRp2-12 were used for spheroplast transformation of *P. guilliermondii* strain RG2 (rib2).

Rib+ transformants appeared at a frequency of 110 transformants/μg DNA. Thus, genomic fragments of *C. famata* having a size of ~2 kb complemented the rib2 mutation of *P. guilliermondii*. These data additionally prove that the subcloned fragment bears the RIB2 gene.

Example 32

Isolation of Leucine Deficient Mutants of the Yeast *P. guilliermondii* with Impaired Regulation of Flavinogenesis Previously, regulatory mutants rib80 and rib81 of ascosporogenous species *P. guilliermondii* overproducing riboflavin were isolated. Unfortunately, these mutants as well as all other available strains of *P. guilliermondii* do not contain a leu2 (or any other convenient) marker for transformation. Therefore, leucine auxotrophs of rib80 and rib81 regulatory mutants were isolated. Subsequently, the mutants were used to identify leu2 mutations among them using heterologous transformation with plasmids bearing a *Saccharomyces cerevisiae* LEU2 gene.

Regulatory mutant 1-13 (rib81) was used in these experiments. An exponentially growing culture of mutant 1-13 (rib 81) was UV irradiated or treated with nitrosoguanidine and plated on sugar-mineral Burkholder medium with leucine (40 μg/ml). Altogether, 80823 mutagenized colonies were checked and seven leucine defective mutants were isolated. The frequency of mutation was $8.7 \times 10^{-5}$. Identification of leu2 mutants was carried out by transformation with plasmid PRpL2 containing the LEU2 gene of *S. cerevisiae*, an ARS of *P. guilliermondii* (PgARS), plasmid p2r containing the LEU2 gene of *S. cerevisiae*, PgARS and additionally an ARS of *C. famata* (CfARS) (FIG. 29). Transformation using the lithium chloride method appeared to be inefficient as revertants appeared on control plates without plasmid DNA. Leucine defective mutants 9-20 and 20-2, transformed by the spheroplasting method, were obtained. Transformants were selected on agar medium with 1 M sucrose without leucine. Transformation frequency for strain 9-20 was 110 transformants/μg DNA (plasmid PRpL2) and 28 transformants/μg DNA (plasmid p2R). For strain 20-2, the transformation frequency was 105/μg DNA (plasmid PRpL2) and 66/μg DNA (plasmid p2R). Strain *C. famata* 105 (leu2) was used in these experiments as the control. Transformation frequency for this strain was 26 transformants/μg DNA (plasmid PRpL2) and 18 transformants/μg DNA (plasmid p2R).

Total DNA isolated from leucine prototrophic transformants of rib81 mutants was used for electrotransformation of *Escherichia coli* DH5α. Plasmid DNA isolated from bacterial transformants was electrophoretically identical to either transforming plasmid PRpL2 or 2R. Thus, *P. guilliermondii* mutants 9-20 and 20-2 were shown to contain mutations homologous to the *S. cerevisiae* LEU2 gene.

Hybridization of the isolated mutants 9-20 and 20-2 with strains of *P. guilliermondii* genetic lines of opposite mating types L1 (mat+) and L2 (mat−) showed that the leu2 rib81 mutants have mating type mat+.

Isolation of leu2 (or ura3) mutants from another complementation group of flavinogenesis regulatory mutants, the rib80 mutants, was conducted. After testing 2505 mutagenized colonies of one of them, strain 80-2, two uracil defective mutants, 2-1 and 2-9, were isolated. No leucine defective mutants were isolated in these experiments. Isolated leucine defective mutants have mating type mar. Uracil auxotrophy was used as the selective marker for diploid hybrid selection. In the next experiment mutant 9-20 (mat+ leu2 rib81) was crossed with mutant 2-9 (mat− uraX rib80) and prototrophic hybrids were selected on minimal medium. Hybrids did not overproduce riboflavin. Hybrids were sporulated on acetate medium and the spore progeny analyzed. Only leu2 segregants overproducing riboflavin were analyzed. Mutants of rib80 were identified by backcrossing with rib80 and rib81 tester strains. For further experiments, the segregant 20 (mat+ leu2 rib80) was used. Confirmation of the leu2 mutation bearing strain was done by the spheroplast transformation method using plasmids PRpL2 and p2R (above). Both plasmids transformed strain 20 to leucine prototrophy with frequencies of 46 and 23 transformants/μg DNA for plasmids PRpL2 and p2R, respectively.

Example 33

Construction of *C. famata* VKM Y-9 Gene Library on the Vector Comprising a *P. guilliermondii* ARS Sequence There are several approaches to cloning *C. famata* regulatory genes of riboflavin synthesis. One approach is based on homologous transformation of *C. famata* regulatory mutants using a *C. famata* gene library and selection of transformants showing a restored wild-type phenotype. Another approach uses previously isolated and better characterized regulatory mutants of the sporogenous flavinogenic species, *P. guilliermondii* rib 80 and rib 81. The last approach is the preferred approach because homologous genes were already identified and the properties of the corresponding mutations were described. During cloning of the structural genes of flavinogenesis, heterologous transformation of corresponding *P. guilliermondii* mutants with isolated *C. famata* gene fragments containing the gene of interest was successfully conducted.

The next step involved constructing a gene library of *C. famata* VKM Y-9 suitable for efficient transformation of *P. guilliermondii* cells. First the plasmid containing the ARS of *P. guilliermondii* and markers for selection in bacteria (ampicillin resistance) and yeast (*S. cerevisiae* LEU2 gene) was constructed. This was done using plasmid p19L2 which possesses both selective markers (FIG. 30). Restriction digestion of 20 μg of p19L2 vector was done with endonuclease PstI. Efficiency of linearization was checked electrophoretically and by *E. coli* transformation with linearized vector. 15 μg of linearized plasmid was dephosphorylated with CIP (calf intestine phosphatase), added at 2 U/μg plasmid DNA (30 min at 37° C.). Efficiency of dephosphorylation was tested by *E. coli* transformation.

For isolation of a *P. guilliermondii* ARS containing fragment, 30 μg of plasmid pPgARS17 was treated with nuclease PstI. A fragment of 0.44 kb, containing an ARS, was isolated by elution from an agarose gel. Elution was conducted according to Maniatis et al., 1982, with some modifications. After electrophoresis in a 1.5% agarose gel containing ethidium bromide, a slot was cut off from the gel just in front of the location of the 0.44 kb fragment. The slot was poured with 0.6% low-melting agarose in 2× concentrated electrophoretic buffer containing ethidium bromide. Electrophoresis was carried out for 30 min at 100 V at room temperature. The low melting point agarose section comprising the desired fragment was combined with 2 volumes of TE buffer and melted at 65° C. The sample was cooled for 15 min. at −70° C. and centrifuged. Then glycogen and 0.1 volume of 3 M sodium acetate (pH 5.2) was added to the eluate after which the DNA was precipitated by ethanol.

DNA was dissolved in 100 µl of TE buffer, twice extracted with phenol, precipitated with ethanol and twice washed with 70% ethanol. DNA concentration in the obtained sample was 0.1 µg/ml.

In the next experiment ligation of the linearized desphosphorylated vector p19L2 with the *P. guilliermondii* ARS-containing fragment was carried out overnight at room temperature. Reaction efficiency was tested by *E. coli* DH5α transformation with the obtained ligate. Subsequently the plasmid was isolated and analyzed by electrophoresis. The conditions for optimal ligation were determined. The optimal ratio of vector to insert is 1:2 (w/w) at a total DNA concentration in the ligate of 0.03 µg/µl. Efficiency of ligation was 91%.

Preparative amounts of constructed plasmid DNA were isolated from individual colonies of *E. coli* transformants. The resulting plasmid was designated as pPgARS19. Insert orientation in the plasmid was identified by restriction analysis with XbaI and SalI endonucleases. The scheme of the constructed plasmid pPgARS19 is presented in FIG. 30.

Plasmid pPgARS19 was used for subsequent construction of the *C. famata* VKM Y-9 genomic library. The plasmid (40 µg) was linearized with BamHI. The amount of endonuclease was carefully adjusted in order to retain the sticky ends. Restriction efficiency and retention of the sticky ends was checked by comparison of *E. coli* transformation with linearized and recyclized vector. Linearized plasmid (30 µg) was dephosphorylated with CIP (2 U/µg plasmid DNA). This amount prevented 95% of self-ligation. Efficiency of dephosphorylation was also checked using *E. coli* transformation.

Total high-molecular weight DNA of *C. famata* VKM Y-9 was isolated using the modified method of J. Cregg, et al., *Mol. Cell. Biol.* 5:3376–3385 (1985). Molecular weight of isolated *C. famata* DNA was estimated, using electrophoretic mobility in 0.3% agarose gel, by comparing with mobility of the DNA with the mobility of phage X marker DNA. The molecular weight appeared to be about 50–60 kb.

Next, the partial restriction of isolated native *C. famata* DNA was conducted using Sau3AI endonuclease. Enzyme was added at 0.06 U/µg DNA. Preparative restriction (100 µg DNA) was conducted in 1.5 ml of reaction mixture for 15 min at 37° C. Reaction was stopped by cooling the mixture in an ice bath. EDTA was added to final concentration of 20 mM. Samples of DNA were twice washed with 70% ethanol and dissolved in 150 µl of TE buffer. The molecular weight of the obtained DNA fragments appeared to be from about 0.5 to about 20 kb. Fragments of 2 to 10 kb were eluted from the agarose gel according to Maniatis et al., 1982 with some modifications. Electrophoresis was conducted in 0.8% agarose containing ethidium bromide. After clear-cut separation of the fragments having the desired sizes, the gel sections bearing DNA fragments bigger than 10 kb and smaller than 2 kb were cut off. In front of the remaining gel, containing fragments of 2–10 kb, low melting point 0.6% agarose containing ethidium bromide in 2x electrophoretic buffer was poured. Electrophoresis was run at 4° C. and 100 V for 3 h to achieve transfer of the 2–10 kg DNA fragments to the low melting point agarose. DNA extraction from low melting point agarose was conducted as described above. The obtained DNA precipitate was dissolved in 80 µl of TE buffer. Agarose gel electrophoresis of this sample confirmed that the size of the eluted fragments was from about 2 to about 10 kb.

The isolated fragments of *C. famata* chromosomal DNA were ligated with linearized dephosphorylated vector pPgARS19 overnight at room temperature. Optimal ratio of the vector to insert was found to be 1:2 (w/w) at a final DNA concentration in the ligate of 0.04 µg/µl (total 0.8 µg DNA in 20 µl of the ligation mixture). Ligation efficiency was checked by transformation of *E. coli* DH5α with the obtained ligate. Subsequently, plasmid DNA was isolated from individual bacterial colonies. The presence of the inserts in plasmids was checked electrophoretically. Ten of twenty-four tested plasmids contained inserts. Thus ~42% of bacterial transformants contained inserts of *C. famata* VKM Y-9 genomic DNA.

Preparative amounts of the obtained ligate were used for *E. coli* DH5α electrotransformation. In total, ~70,000 bacterial transformants have been obtained. Plasmid DNA was isolated from these transformants and dissolved in 1.2 ml of sterile TE buffer. DNA concentration in the resulting solution was 1.5 µg/µl. The obtained *C. famata* gene library can be used for efficient heterologous transformation of *P. guilliermondii* and subsequent isolation of *C. famata* genes by heterologous complementation (Example 34).

Example 34

Heterologous Transformation of *P. guilliermondii* rib80 and rib81 Regulatory Mutants with *C. famata* VKM Y-9 Gene Library Rib80 and rib81 regulatory mutants additionally comprising the leu2 marker have been used as host stains for transformation. The mutants produced elevated amounts of riboflavin during cultivation in iron rich medium. Both host strains were transformed with the obtained *C. famata* gene library. Transformation was conducted using spheroplast and electroporation methods. After transformation, cells were plated on minimal medium without leucine. Leucine prototrophic transformants were selected. Using the spheroplast method of transformation, the transformation frequency of *P. guilliermondii* regulatory mutants 9-20 and 20-2 (both: leu2 rib 81) was rather low (80–100 transformants/µg plasmid DNA). Therefore the electroporation method was used for transformation. Field strengths of 5–11.5 kV/cm have been compared and the highest transformation frequency was found at field strength of 11 kV/cm. This field strength resulted in 1.0 to 1.2×10³ transformants/µg DNA.

Plating of transformants was conducted so as to obtain 50–100 transformants (leucine prototrophs) per plate. The colonies which visually do not accumulate elevated amounts of riboflavin were picked up. As the rule, such colonies are slightly bigger by size and do not fluoresce under a UV lamp. Altogether, ~20,000 transformants of *P. guilliermondii* leu2 rib81 mutants 9-20 and 20-2 and ~5,000 transformants of the strain 20 (leu2 rib80) were checked for riboflavin overproduction.

Colonies suspected of lower riboflavin production (altogether ~1500 colonies) were streaked on plates with minimal medium (25–30 streaks per plate) and checked for flavinogenesis. As the result of these experiments 7 transformants have been picked up from *P. guilliermondii* rib81 mutants 20-2 and 9-20. No such transformants were isolated until now from the rib80 mutant. Two of the 7 transformants showing better growth characteristics were tested for riboflavin accumulation in the culture medium (Table 5). These two transformants were cultivated in liquid minimal medium (YNB) in tubes for 5 days on the shaker at 30° C. Cells of the transformant (#12) accumulated riboflavin at the level of the wild type strain ATCC 9058 (Table 5).

In the case of regulatory gene cloning, all leucine prototrophic transformants will display inability to overproduce riboflavin in iron rich medium.

TABLE 5

| Strain | P.g. ATCC9058 | P.g. 9-20 rib 81 | P.g. 9-20/ pPgARS19 | Transformant #12 | Transformant #26 |
|---|---|---|---|---|---|
| Biomass, mg/ml | 2.21 | 2.25 | 1.59 | 0.36 | 1.21 |
| Riboflavin in culture medium, µg/ml | 1.05 | 62.0 | 22.0 | 1.0 | 0.4 |
| Productivity, µg of riboflavin per mg of dry weight | 0.48 | 27.6 | 13.8 | 2.8 | 0.33 |

Example 35

Subcloning of C. famata Genomic Fragment Bearing the RIB6 Gene

Earlier the C. famata DNA fragment of ~11.7 kb (as a part of the pRIV-2 plasmid) was cloned which complemented riboflavin auxotrophy in some C. famata mutants, representants of the $4^{th}$ biochemical group. To identify mutations in which one gene complements plasmid pRIV-2, rib5 or rib6, heterologous transformation of the corresponding mutants of P. guilliermondii was carried out. To achieve efficient transformation of P. guilliermondii, a PgARS sequence was inserted into plasmid pRIV-2. For this, plasmid pRIV-2 was linearized with SmaI. This endonuclease possesses a unique site in this plasmid and gives blunt ends. Linearized plasmid was dephosphorylated with alkaline phosphatase and ligated with the 0.82 kb HincII fragment of P. guilliermondii which bears a PgARS. The resulting plasmid was designated PRpIV-2 (FIG. 31). Its size is approximately 17.6 kb.

Plasmid PRpIV-2 was used for spheroplast transformation of P. guilliermondii strains RG8 (rib5) and RG68 (rib6). The plasmid was found to complement riboflavin auxotrophy only of strain RG68 (rib6) but not that of strain RG8 (rib5). The frequency of RG68 spheroplast transformation with plasmid PRpIV-2 to riboflavin prototrophy is $1\times10^3$ transformants/µg DNA. Thus, PRpIV-2 bears the DNA fragment of C. famata containing gene RIB6 (encoding dihydroxybutanonephosphate synthase).

As the cloned fragment is rather big (11.7 kb), the 11.7 kb fragment was subcloned. The insert of PRpIV-2 was digested into two parts: a SacI SalI fragment of ~6.8 kb and a SacI fragment of ~5.1 kb (FIG. 32). The SacI fragment, in addition to containing part of the insert, also contains a CfARS (FIG. 32). For subcloning both fragments, plasmid p19R7R1 was used (FIG. 33) because it possesses convenient restriction sites. As the result of such subcloning, two recombinant plasmids were constructed: p19R7RIV-21 (~10.9 kb) and p19R7RIV-22 (~10.6 kb) (FIG. 33). These two constructs were used for transformation of P. guilliermondii RG68 (rib6) spheroplasts. The rib6 mutation was found to be complemented by p19R7RIV-21 (transformation frequency was $1.8\times10^2$ transformants/µg DNA) but not by plasmid p19R7RIV-22.

Further work was conducted with the SacI-SalI fragment of ~6.8 kb carried by plasmid p19R7RIV-21. Restriction analysis permitted identification of the quantity and approximate order of the location of restriction sites of endonucleases XbaI, HindIII, KpnI, EcoRI and BamHI (FIG. 34). The fragment was digested into 6 subfragments: BamHI fragment (~4.1 kb), SacI-XbaI fragment (~3.5 kb), HindIII fragment (~3 kb), KpnI-EcoRI fragment (~4.5 kb), XbaI fragment (~1.1 kb), and HindIII fragment (~1.8 kb) (FIG. 34). All these fragments were recloned in plasmid p19P (FIG. 35). Plasmid p19P was constructed by cutting the 1.3 kb PstI fragment of P. guilliermondii chromosomal DNA and subsequent self-ligating the second PstI fragment of plasmid p19R1 (FIG. 35). As the result of recloning the above subfragments and the initial entire fragment in p19P, seven recombinant constructs have been obtained: pD, pG, pE, pB, pF, pC and pA (FIG. 34). All these recombinant plasmids bear, in particular, a PgARS, and are based on p19P. All obtained plasmids were used for spheroplast transformation of P. guilliermondii rib6 mutant RG68. Two plasmids were found to transform strain RG68 to riboflavin prototrophy: plasmid pD, containing a full SacI-SalI fragment of ~6.8 kb as well as plasmid pF. Plasmid pF bears a KpnI-EcoRI fragment of ~4.5 kb. The transformation frequencies were 40 transformants/µg DNA (plasmid pD) and $1\times10^2$ transformants/µg DNA (plasmid pF).

Thus, these data suggest the RIB6 gene is located between the KpnI-EcoRI sites in the ~4.5 kb fragment. The linear scheme of plasmid pF is presented in FIG. 36. The insert of plasmid pF which bears RIB6 gene contains one BamHI site and two sites of both HindIII and XbaI endonucleases.

The ability of plasmid pF to complement the rib6 mutation in C. famata was tested. Plasmid pF transformed rib6 mutants with a frequency of $7.7\times10^4$ transformants/µg DNA using the electroporation method. Thus, the RIB6 gene of C. famata contained in the 11.7 kb genomic fragment was further subcloned, and carried by the ~4.6 kb fragment by the pF plasmid.

Example 36

Cloning of a C. famata Genomic Fragment Which Complements the rib5 Mutation in the Heterologous P. guilliermondii System To identify C. famata rib5 mutants, representants of the $4^{th}$ biochemical group of riboflavin auxotrophs were electrotransformed with plasmids pRIV-2 and PRpIV-2. In total, five strains have been tested: 6-33n, 4-32n, 6-29n, 42-6n and 5-133. Only one strain, 5-133, was transformed by the mentioned plasmid toprototrophy. Thus, mutants 6-33n, 4-32n, 6-29n and 42-6 n may bear mutations in the RIB5 gene.

Cloning of the genomic fragment of C. famata which bears the RIB5 gene, was done first in the P. guilliermondii heterologous system. For this, the gene library of C. famata constructed on the vector pPgARS19, was used (Example 33). The P. guilliermondii rib5 mutant RG5 was used as the recipient strain. Transformation was conducted by the spheroplasting method. 20 colonies of Rib+ transformants were obtained. Total DNA was isolated from the cells of 8 randomly selected P. guilliermondii Rib+ transformants and used for E. coli retransformation. Total yeast DNA was isolated using method of Yang et al. (1999) described for S. cerevisiae (Yang C., Theis J. F., Newlon C. S., Genetics, 1999, v.152, p.933–941). Retransformation of E. coli with total DNA of the yeast transformants showed the presence of plasmid DNA in four transformants. In all cases, the plasmid DNA was identical. The corresponding plasmid was designated as pPR5. Preliminary restriction analysis showed that pPR5 is the pPgARS19 vector with the insert of ~1.45 kb.

Plasmid pPR5 was tested for complementation of the P. guilliermondii and C. famata rib5 mutation. For this, spheroplasts of mutants P. guilliermondii RG8 and C. famata 6-29n were transformed with plasmid pPR5. pPR5 was shown to transform to riboflavin prototrophy strains RG8 and 6-29n with frequencies of $3 \times 10^3$ and $4 \times 10^2$ transformants/µg DNA, respectively. Thus, the results suggest that the cloned fragment of C. famata carried by the pPR5 plasmid bears gene RIB5.

Detailed restriction analysis of pPR5 plasmid was carried out. The plasmid was digested with following endonucleases: HindIII, SalI, PstI, XbaI, KpnI, EcoRI, SmaI, SacI, and BamHI. Nucleases HindIII, SmaI, SacI and BamHI linearized plasmid pPR5. Thus, each of them possess unique restriction site: HindIII, SmaI and SacI sites in the vector polylinkers and a BamHI site—in the insert (FIG. 37). After treatment with nucleases SalI and XbaI, two similar fragments were produced in both cases with sizes of ~4.2 kb and ~2.6 kb. Insert pPR5 does not contain sites for these enzymes. Endonuclease PstI splits the plasmid into two fragment of ~6.4 kb and ~0.4 kb. Insert pPR5 does not possess a site for PstI. Treatment with endonuclease KpnI also gives two fragments of ~4 kb and ~2.8 kb; again no site is located in the insert. Treatment with nuclease EcoRI produced three fragments of ~4.4 kb, ~1.2 kb and ~1.1 kb; one EcoRI site is located in the insert (FIG. 37). Thus, the total size of plasmid pPR5 is approximately 6.7 kb.

Thus, the RIB5 gene of C. famata was cloned from the genomic fragment of ~1.45 kb carried on plasmid pPR5.

Example 37

Construction of the Three-replicon Vectors

The three-replicon vectors contain replicators from E. coli, C. famata and P. guilliermondii. The availability of three-replicon vectors permits manipulation of genetic material which is located in the recombinant constructs from the three mentioned microorganisms.

The following three-replicon plasmids were constructed:
Plasmids which bear the RIB1 gene of C. famata (PRp1 and PRp1Xb);
Plasmids which bear the C. famata RIB2 gene (PRp2, PRp2-11, pRP2-12);
The plasmid which comprises the C. famata RIB5 gene (pCPR5; FIG. 38). This plasmid is the derivative of plasmid pPR5. pCPR5 is ~7 kb by size and comprises ori, the Ap$^r$ gene of E. coli (bacterial part), PgARS19, CfARS, the LEU2 gene of S. cerevisiae and the fragment of C. famata DNA comprising the RIB5 gene.
Plasmids comprising the C. famata RIB6 gene: PRpIV-2 (FIG. 31), pFC and pFCL-2 (FIG. 39). The two last constructions are the derivatives of the pF plasmid. The size of pFC is ~8 kb; it contains the bacterial part (ori and Ap$^r$ gene of E. coli), PgARS, CfARS, and the C. famata genomic fragment comprising the RIB6 gene (FIG. 39). Plasmid pFCL-2 contains the same parts as plasmid pFC; additionally, it contains the LEU2 gene of S. cerevisiae (FIG. 39).
Plasmids comprising the C. famata RIB7 gene (PRp7).

Example 38

Transformation of Regulatory Mutant P. guilliermondii rib81 with the Gene Library of C. famata VKM Y-9

7 colonies of transformants were picked up of P. guilliermondii strains 20-2 and 9-20 (rib81) which accumulated riboflavin at the level of the wild type (near 1 µg/ml). These transformants were used for total DNA isolation. Using E. coli retransformation (by electroporation) with total yeast DNA, the plasmid DNA was isolated and characterized. 4 transformants did not contain plasmid DNA and 3 transformants contained initial plasmid without any insert. Apparently the isolated yeast colonies are the revertants or integrative transformants.

In the next experiments, heterologous transformation was conducted by electroporation. Among grown colonies, both small colonies (apparently revertants for leucine synthesis) and large colonies appeared. Transformation frequency calculated by the number of large colonies was 300–500 transformants/µg DNA. The colonies which did not accumulate elevated amounts of riboflavin were picked up. After screening of ~75,000 transformants, ~6,000 colonies were streaked on the minimal plates and their flavinogenic activity tested. 25–30 transformants were streaked on each plate. Later their flavinogenic activity was checked in liquid medium after 5 days of cultivation in tubes on the shaker. After such selection, 22 Leu+ transformants of P. guilliermondii 20-2 and 9-20 rib81 mutants have been picked up. They accumulated riboflavin at the level of the wild-type strain (1–3 µg/ml). Total DNA was isolated from 19 such transformants. After E. coli retransformation, plasmid DNA was isolated. The 12 picked up yeast colonies did not possess plasmid DNA at all, and 5 transformants contained initial plasmid vector without any insert. Two of these transformants were used for isolation of the plasmids which contained initial vector pPgARS19 with inserts of 2.5 kb and 5 kb. These plasmids were used for retransformation P. guilliermondii rib81 mutants 20-2 and 9-20. However, these plasmids did not complement the regulatory mutations.

The plasmid DNA of 3 more transformants will be analyzed.

Example 39

Isolation of Regulatory Mutants of C. famata Unable to Overproduce Riboflavin in Iron-deficient Medium Isolation of C. famata mutants unable to overproduce riboflavin in iron-deficient medium (mutants having defective genes involved in the regulation of derepression of riboflavin production) was conducted using several approaches.

In the first approach, earlier isolated C. famata riboflavin overproducers 2-5, 4-48, 75 were used as the parental strains for selection. In liquid iron rich media they accumulated (test tubes) 80–100 µg riboflavin/ml after 5 days of cultivation. They were prototrophs and efforts to introduce auxotrophic markers into them were unsuccessful. After UV or nitrosoguanidine mutagenesis, they were plated on minimal medium and the grown colonies were tested for ability to overproduce riboflavin. Mutant 75 apparently had a partially impaired system for riboflavin excretion from cells. Cells of these mutants produced yellow-orange colored colonies.

After mutagenesis, 410 "white" (did not produce elevated amounts of riboflavin) colonies were picked up, derivatives of strain 75; 260 "white" colonies, derivatives of strain 2-5; and 300 "white" colonies, derivatives of strain 4-48. After 1–2 days, plates with the corresponding streaks were checked under the UV lamp for riboflavin synthesis. Mutants which do not overproduce riboflavin were tested in tubes with liquid media containing $CoCl_2$ (15 μg/ml) for creation of the iron-deficiency. In total, 160 mutants were tested in liquid medium with cobalt. It was unexpectedly found out that most of such mutants appeared to be super sensitive to cobalt ions and did not grow after 7–10 days of cultivation. Some of the mutants "suspected" as having the non-ability to overproduce riboflavin in iron deficient medium were cultivated during 5 days in shake flasks containing medium depleted of iron using 8-hydroxyquinoline. Five such mutants synthesized 5–15 μg riboflavin/ml whereas parental strains in the same conditions produced 100–150 μg riboflavin/ml.

In addition, selection of the mutants unable to overproduce riboflavin in iron-deficient medium was conducted using *C. famata* riboflavin overproducing mutant 105-6 (leu2). The cells of the strain 105-6 were mutagenized with UV light or nitrosoguanidine and plated on synthetic medium. After testing 4360 colonies, 50 colonies were picked up which did not secrete riboflavin to the medium. Then they were streaked on plates containing $CoCl_2$ (12.5 μg/ml). 36 strains did not produce riboflavin in such conditions compared to parental strain 105-6 (riboflavin overproducer) and parental for 105-6 mutant strain L20105 (leu2). All 36 mutants were tested in liquid iron deficient medium. It was found that they did not accumulate elevated amounts of riboflavin under such conditions. Some of the mutants were tested for riboflavin accumulation both in iron-rich and iron-deficient media. Data on riboflavin accumulation are presented in Table 6.

TABLE 6

Biosynthesis of riboflavin by non-flavinogenic mutants and the parental strains after growing in medium containing normal or low iron concentrations

| Strain | Iron concentration in the medium, μg/ml | Riboflavin | |
|---|---|---|---|
| | | μg/ml | μg/mg of dry weight |
| L20105 | 0.01 | 18.0 | 18.9 |
| | 0.2 | 2.2 | 1.6 |
| #105-6 | 0.01 | 36.0 | 48.0 |
| | 0.2 | 48.0 | 32.0 |
| #105-6-33 | 0.01 | 3.5 | 8.8 |
| | 0.2 | 7.5 | 7.5 |
| #105-6-11 | 0.01 | 2.0 | 3.3 |
| | 0.2 | 3.0 | 3.3 |
| #105-6-34 | 0.01 | 1.9 | 3.2 |
| | 0.2 | 3.6 | 5.5 |
| #105-6-2 | 0.01 | 1.7 | 4.8 |
| | 0.2 | 3.4 | 3.7 |
| #105-6-26 | 0.01 | 0.11 | 0.55 |
| | 0.2 | 2.0 | 4.4 |
| #105-6-18 | 0.01 | 1.6 | 3.5 |
| | 0.2 | 5.0 | 4.0 |
| #105-6-21 | 0.01 | 10.0 | 11.1 |
| | 0.2 | 12.0 | 8.0 |
| #105-6-6 | 0.01 | 1.4 | 2.3 |
| | 0.2 | 3.0 | 3.0 |

Another method for selection of riboflavin non-overproducing mutants was based on creation of conditions where the mutants unable to oversynthesize riboflavin retained viability whereas wild-type strains died. Riboflavin deficient mutants of the second biochemical group 4-126 and fourth biochemical group 5-133 were used in selection work. First, leaky reversion mutations were introduced in each of these mutants. Such mutations permitted them to grow without riboflavin only in iron-deficient media due to derepression of the enzymes of flavinogenesis. Suspensions of leaky mutants, strains 4-126-1 (derivative of 4-126), 5-133-6 and 5-133-9 (derivatives of 5-133), were UV irradiated and cultivated in iron deficient medium for 4, 22 and 31 h. At indicated intervals, cells were withdrawn, incubated at 54° C. for 7 min and plated on synthetic medium with $CoCl_2$ (12.5 μg/ml). In these conditions (temperature shock), cells unable to derepress enzymes of flavinogenesis did not grow and remained viable whereas parental mutants derepressing enzymes of flavinogenesis, grew and were killed by elevated temperature.

Using this approach, 15 mutants from strain 4-126-1, 15 mutants from strain 5-133-6 and 49 mutants from strain 5-133-9 were isolated. 15 mutants isolated from each strain (totally 45 strains) were cultivated in liquid iron deficient medium and fluorescent compounds were visualized under UV lamp after 3–5 days of cultivation. All 45 tested strains were unable to overproduce riboflavin or fluorescent riboflavin intermediates under cultivation in iron-deficient media. The study of their properties is under way.

Example 40

*C. famata* RIB3 Gene Cloning by Complementation

The attempts to clone the genomic fragment of *C. famata* which bears the RIB3 gene (encoding the specific deaminase) by complementation of the corresponding auxotrophic mutation in the homologous system were unsuccessful as the available rib3 mutants of *C. famata* appeared to be highly unstable. Therefore it was decided to clone the RIB3 gene by complementation in the heterologous *P. guilliermondii* system as the corresponding rib3 mutants appeared to be more stable. For this, the plasmid DNA of the *C. famata* gene library constructed on the vector pPgARS19 containing the *C. famata* ARS sequence was used. The *P. guilliermondii* mutant RG1 (hisX rib3) was used as the recipient strain for transformation. Transformation was conducted by the spheroplasting method. After several experiments, 25 colonies of Rib+ transformants of *P. guilliermondii* were obtained. Plasmid DNA with some inserts, however, was found only in the cells of two such transformants. In one, the size of the insert was of ~0.3 kb and in the other the size was ~0.6 kb. These recombinant plasmids did not complement the rib3 mutation of *P. guilliermondii* strain RG1.

There can be several reasons for unsuccessful attempts of RIB3 gene cloning by heterologous complementation. One can be the absence of the fragment in the gene library used which contains the complete RIB3 gene of *C. famata*. (It is known that the RIB3 gene is the largest among all structural genes of riboflavin synthesis). Therefore work began on construction of a new genomic library of *C. famata*. The recombinant plasmid p2R was used. The plasmid p2R contains the selective marker LEU2 gene of *S. cerevisiae*, PgARS, CfARS and the complete sequence of the bacterial vector pUC 19. Plasmid p2R was linearized with endonuclease BamHI and dephosphorylated with alkaline phosphatase. High molecular weight total DNA of *C famata* VKM Y-9 was isolated. Subsequently, the partial digestion of the isolated total DNA was conducted with endonuclease Sau3AI and elution of the obtained fragments of ~3–10 kb by size was carried out. It is planned:

1. to conduct the ligation of linearized and dephosphorylated vector p2R with eluted Sau3AI fragments of total *C. famata* DNA;
2. to transform *E. coli* DH5α with the obtained lysate and to isolate Ap$^r$ transformants. Further the isolation of plasmid DNA from such transformants is planned for obtaining preparative amounts of the new gene library of *C. famata*;
3. to conduct a new series of *P. guilliermondii* rib 3 mutant transformations with isolated plasmid DNA of the *C. famata* gene library in order to clone the *C. famata* RIB3 gene.

Example 41

Attempts to Clone the RIB3 Gene of *C. famata* Using a PCR-based Approach

To isolate a putative homologue of the *Saccharomyces cerevisiae* RIB2 gene (ScRib2p) (DRAP deaminase) from the yeast *Candida famata* (RIB3), a PCR-based approach was utilized. First, genomic databases were searched for strong homologues of the ScRib2p. Several sequences were retrieved. They included: hypothetical protein encoded by Yd1036c from *S. cerevisiae* with unknown function (77% similarity), SPAC181311.02 cp from fission yeast *Schizosaccharomyces pombe* (63% similarity), and several other proteins from higher eukaryotes that displayed less than 50% overall homology. Only one protein from databases, namely *S. pombe* SPCC4G3.16 (unknown function) exhibited significant homology to the ScRib2p in the C-terminal region (61%), where the putative deaminase domain is predicted to reside. The above mentioned protein sequences were aligned and conserved amino acid repeats determined. Nine degenerate PCR primers were designed, specific for corresponding DNA regions, 4 forward (F) and 5 reverse (R). PCRs were set with different combinations of the F and R primers using plasmid DNA of *C. famata* genomic library and its isolated total DNA as templates. PCRs were optimized in respect of template concentration, MgCl$_2$ concentration and cycle parameters. At this stage, several pairs were shown to produce DNA fragments of an appropriate length, i.e. 1 F-5R, 4F-5R, 2F-5R, and the same F primers with 8R. The best result, in respect of product yield, was obtained with 2F-5R and 2F-8R pairs of primers, with resulting fragments of approx. 1.1 kb and 1.9 kb, respectively. Next, these fragments will be isolated, purified and utilized as templates for analytical PCRs (for example, 2F-5R fragment should be amplified from the bigger 2F-8R fragment). To further analyze the isolated fragments, they have to be sequenced and compared to ScRIB2. Subsequently, a *C. famata* mutant having a disruption in the corresponding gene can be constructed and assayed for riboflavin auxotrophy. Having verified the mutant's phenotype, the remaining portion of a putative *C. famata* RIB3 gene can be isolated from the genomic library by a variety of methods: "PCR walking," *E. coli* colony hybridization or functional complementation of a disrupted strain.

Example 42

Subcloning the Structural Genes of Riboflavin Biosynthesis from *C. famata*

Subcloning of all available gene fragments which bear the structural genes of riboflavin biosynthesis was achieved.

1. The fragment which bears gene RIB1. The initial fragment of ~3 kb in the content of the pCR1 plasmid was shortened to ~2.5 kb. The shortened fragment is carried by plasmid pCR1Xb and PRp1Xb.
2. The fragment which bears gene RIB2. The initial fragment of ~6.4 kb carried by plasmid pCR2 was shortened to ~2 kb. This shortened fragment is carried by plasmids pCR2-1, PRp2-11 and PRp2-12.
3. The fragment which bears gene RIB5. The initial fragment of ~1.5 kb is carried by plasmids pPR5 and pCPR5. As the size of the cloned fragment is really small, further subcloning was not undertaken.
4. The fragment which bears gene RIB6. The initial fragment of ~11.7 kb carried by plasmid pRIV-2, was shortened to ~4.5 kb. This shortened fragment is carried by plasmids pF, pFC and pFCL-1.
5. The fragment which bears gene RIB7. The initial fragment of ~1.5 kb is carried by plasmids pCR7 and PRp7. Due to small size of the cloned fragment, further subcloning was not undertaken.

Example 43

Construction of the Four-replicon Vectors

Four-replicon vectors are recombinant constructs which contain replicators and are maintained in the cells of four different hosts: *E. coli*, *C. famata*, *P. guilliermondii* and *S. cerevisiae*. The availability of such four-replicon vectors permits manipulation of genetic materials present in the recombinant constructs in all four mentioned hosts.

To carry out this work, previously constructed three-replicon vectors were used: PRp1Xb (bears gene RIB1), PRp2-11 (bears gene RIB2), pCPR5 (bears gene RIB5), pFCL-2 (bears gene RIB6) and PRp7 (bears gene RIB7). The plasmids PRp2-11, pCPR5 and pFCL-2 were linearized with endonuclease SmaI (this enzyme produces blunt ends). Plasmids PRp1Xb and PRp7 were linearized with endonuclease SalI. The sticky ends of linearized plasmids PRp1Xb and PRp7 were blunted with T4 DNA polymerase. All linearized plasmids were treated with alkaline phosphatase to prevent self-ligation.

The shuttle vector Yep 13 which bears ORI from 2$\mu$ plasmid DNA was used as the source of the *S. cerevisiae* replicator. A PstI-HindIII fragment from the 2$\mu$ plasmid of 1.9 kb (contains ORI element) was cut from Yep13 plasmid and blunted with T4 DNA polymerase.

Subsequently, ligation of linearized dephosphorylated vectors with the insert excised from Yep13 which contains 2$\mu$ DNA ORI from *S. cerevisiae*, was carried out. The resulting ligates were used for electroporation of *E. coli* DH5α. Obtained bacterial Ap$^r$ transformants were used for plasmid DNA isolation which were analyzed by serial endonuclease digestion for the presence of the inserts. To determine the orientation of the DNA fragment bearing the *S. cerevisiae* ORI sequence, additional restriction analysis was carried out. As a result, five recombinant constructs were obtained which contained one structural gene of riboflavin synthesis (RIB1, RIB2, RIB5, RIB6 or RIB7) and replicators of four hosts: *E. coli, C. famata, P. guilliermondii* and *S. cerevisiae* (FIGS. 40–45). The plasmid PRSp1Xb (FIG. 40) has a total size ~10 kb; it contains the *C. famata* RIB1 gene. The plasmid PRSp2-11 (FIG. 41) has a total size of ~9.4 kb; it contains the *C. famata* RIB2 gene. The plasmid pCPSR5 (FIG. 42) has the size of ~8.9 kb; it contains the *C. famata* RIB5 gene. The plasmid pFCLS2 (FIG. 43) has a size of ~12.1 kb; it bears the *C. famata* RIB6 gene. The plasmid PRSp7 (FIG. 44) has size of ~9.3 kb; it bears the *C. famata* RIB7 gene.

Example 44

Transformation of *P. guilliermondii* rib81 Regulatory Mutants with *C. famata* VKM Y-9 Gene Library The cells transformed by the electroporation method were plated on minimal medium and leucine prototophic transformants were analyzed for complementation of rib81 regulatory mutations. Colonies which, in contrast to rib81 riboflavin overproducers, do not synthesize elevated amounts of riboflavin were sought. In addition to large colonies of transformants, the plates inoculated either with transformed DNA cells or with cells electroporated according with the protocol but without adding the plasmid DNA, contain a lot of smaller colonies. The transformation frequency calculated after counting only large colonies, appeared to be 200–500 transformants/µg DNA. However, the appearance of slowly growing transformants among small colonies can not be excluded. Only large colonies which, according to visual observation, did not accumulate elevated amounts of riboflavin were picked up. As the small colonies secreted riboflavin into the medium, discrimination of riboflavin non-overproducing colonies was rather complicated. To overcome this problem, smaller amounts of transformants were plated as it was found that analysis of 15–30 large colonies of transformants was possible directly on the initial plates. The search for riboflavin non-overproducing colonies among small colonies was impossible to conduct, however.

Altogether, we tested ~70,000 colonies of rib81 transformants. 8,000 of them were picked up for additional testing. The streaks of some of them, which did not overproduce riboflavin during growth in minimal medium, were studied for riboflavin production in liquid cultures after 5 days of cultivation. Finally, 24 transformants were selected which accumulated riboflavin on the level of the wild-type strain of *P. guilliermondii* (1–5 µg/ml). Total DNA was isolated from 22 such transformants. Such total DNA was used for retransformation of *E. coli* DH5α by electroporation. Subsequently, the plasmid DNA isolated from *E. coli* transformants was studied by restriction analysis. 10 analyzed colonies do not possess plasmid DNA at all, 8 transformants contained plasmid-vector without any insert. The remaining 4 transformants contained vectors with inserts of the size of ~1.3 kb, ~1.7 kb, ~1.9 kb and ~2.4 kb. These plasmids were used for transformation *P. guilliermondii* rib81 mutant 9-20.

However, they did not complement this regulatory mutation. Finally the plasmid DNA of the remaining two transformants will be analyzed.

The possibility for positive selection of *P. guilliermondii* rib81 transformants unable to overproduce riboflavin in minimal medium was studied. For this, the toxicity of $K_2Cr_2O_7$ ($Cr^{+6}$) was compared for the *P. guilliermondii* wild-type strain ATCC 9058 and regulatory mutants *P. guilliermondii* rib81 9-20 and 20-2. The cells were pregrown in liquid YPD to OD 1.5–2.0 (540 nm) and electroporated according to the protocol described (Example 34). Electroporated cells were washed three times with 10×volume of 0.6 M KCl and then the volume was adjusted to 1 ml. Then the cells were plated at 0.2 ml suspension per plate which contained 0.5% glycerol, 0.6 M KCl and $K_2Cr_2O_7$ (50–1000 µM). At $Cr^{+6}$ concentrations of 250–350 µM, the growth of *P. guilliermondii* rib81 was severely inhibited whereas the growth of wild-type strain *P. guilliermondii* ATCC 9058 was only slightly depressed compared with that in the medium without chromium.

Example 45

Study of the Properties of the Regulatory Mutants Unable to Overproduce Riboflavin in Iron-deficient Media A strain of *C. famata* unable to overproduce riboflavin in iron-deficient media was used.

The growth of such mutants on ethanol as the sole carbon and energy source as well as their susceptibility to copper ions during growth on synthetic agar medium with leucine (40 µg/ml) was studied. It was determined that the cells grow well, similarly to the wild-type strain VKM Y-9, in agarized medium with 1% ethanol as the sole carbon source. $Cu^{+2}$ at 0.05 mM and 0.1 mM did not inhibit their growth.

In further experiments, the influence of the aconitase inhibitor, 2-monofluoroacetate (MFA), on the growth of *C.famata* regulatory mutants unable to overproduce riboflavin was studied in media with glucose (0.5%) or glycerol (0.5%) as the carbon sources. Growth of the majority of the mutants in the medium with glycerol was inhibited by MFA at 0.2–0.4% whereas the growth of the wild type VKM Y-9 and of leu2 auxotroph L20105 (normal regulation of riboflavin synthesis) was not inhibited at all (Table 7). In the medium with glucose, MFA did not inhibit growth of most regulatory mutants. One regulatory mutant, 105-6-13, began to overproduce riboflavin in glucose medium with MFA (Table 8).

TABLE 7

Sensitivity of *Candida famata* regulatory mutants unable to overproduce riboflavin to different concentrations of monofluoroacetate during growth in Burkholder medium containing 0.5% glycerol

| *C. famata* strain | Concentration of monofluoroacetate, % | | | | | |
|---|---|---|---|---|---|---|
| | 0 | 0.2 | 0.4 | 0.6 | 0.8 | 1.0 |
| #105-6-1 | +++ | ++ | — | — | — | — |
| #105-6-2 | +++ | — | — | — | — | — |
| #105-6-3 | +++ | ++ | — | — | — | — |
| #105-6-4 | +++ | — | — | — | — | — |
| #105-6-8 | +++ | — | — | — | — | — |
| #105-6-11 | +++ | — | — | — | — | — |
| #105-6-13 | +++ | — | — | — | — | — |
| #105-6-14 | +++ | — | — | — | — | — |
| #105-6-22 | +++ | — | — | — | — | — |

TABLE 7-continued

Sensitivity of *Candida famata* regulatory mutants unable to overproduce riboflavin to different concentrations of monofluoroacetate during growth in Burkholder medium containing 0.5% glycerol

| *C. famata* strain | Concentration of monofluoroacetate, % | | | | | |
|---|---|---|---|---|---|---|
| | 0 | 0.2 | 0.4 | 0.6 | 0.8 | 1.0 |
| #105-6-27 | +++ | ++ | — | — | — | — |
| #105-6-30 | +++ | ++ | — | — | — | — |
| #105-6-33 | +++ | — | — | — | — | — |
| #4-126-28 | +++ | ++ | — | — | — | — |
| #4-126-30 | +++ | — | — | — | — | — |
| #4-126-31 | +++ | — | — | — | — | — |
| #4-126-35 | +++ | — | — | — | — | — |
| #8-15-9 | +++ | — | — | — | — | — |
| #8-15-2 | +++ | — | — | — | — | — |
| #8-15-12 | +++ | — | — | — | — | — |
| #5-133-9-4 | +++ | — | — | — | — | — |
| #5-133-9-5 | +++ | — | — | — | — | — |
| #5-133-9-10 | +++ | — | — | — | — | — |
| #5-133-9-17 | +++ | — | — | — | — | — |
| L20105 (leu2) | +++ | +++ | +++ | ++ | ++ | ++ |
| VKM Y-9 | +++ | +++ | +++ | +++ | +++ | ++ |

"+++"—strong growth
"++"—weak growth
"—" absence of growth

TABLE 8

Sensitivity of *Candida famata* regulatory mutants unable to overproduce riboflavin to different concentrations of monofluoroacetate during growth in Burkholder medium containing 0.5% glucose

| *C. famata* strain | Concentration of monofluoroacetate, % | | | | | |
|---|---|---|---|---|---|---|
| | 0 | 0.2 | 0.4 | 0.6 | 0.8 | 1.0 |
| #105-6-1 | +++ | +++ | +++ | ++ | ++ | ++ |
| #105-6-2 | +++ | +++ | ++ | ++ | ++ | ++ |
| #105-6-3 | +++ | +++ | +++ | ++ | ++ | ++ |
| #105-6-4 | +++ | +++ | +++ | ++ | ++ | ++ |
| #105-6-8 | +++ | +++ | +++ | ++ | ++ | ++ |
| #105-6-11 | +++ | +++ | +++ | ++ | ++ | ++ |
| #105-6-13 | +++ | ++ | — | — | — | — |
| #105-6-14 | +++ | ++ | ++ | ++ | ++ | ++ |

TABLE 8-continued

Sensitivity of *Candida famata* regulatory mutants unable to overproduce riboflavin to different concentrations of monofluoroacetate during growth in Burkholder medium containing 0.5% glucose

| *C. famata* strain | Concentration of monofluoroacetate, % | | | | | |
|---|---|---|---|---|---|---|
| | 0 | 0.2 | 0.4 | 0.6 | 0.8 | 1.0 |
| #105-6-22 | +++ | ++ | ++ | ++ | ++ | ++ |
| #105-6-27 | +++ | ++ | ++ | ++ | ++ | ++ |
| #105-6-30 | +++ | +++ | +++ | +++ | +++ | +++ |
| #105-6-33 | +++ | +++ | +++ | ++ | ++ | ++ |
| #4-126-28 | +++ | +++ | +++ | +++ | +++ | +++ |
| #4-126-30 | +++ | +++ | +++ | +++ | +++ | ++ |
| #4-126-31 | +++ | +++ | +++ | ++ | ++ | ++ |
| #4-126-35 | +++ | +++ | ++ | ++ | ++ | ++ |
| #8-15-9 | +++ | ++ | ++ | ++ | ++ | ++ |
| #8-15-2 | +++ | +++ | ++ | ++ | ++ | ++ |
| #8-15-12 | +++ | ++ | ++ | ++ | ++ | ++ |
| #5-133-9-4 | +++ | — | — | — | — | — |
| #5-133-9-5 | +++ | ++ | ++ | ++ | ++ | ++ |
| #5-133-9-10 | +++ | ++ | ++ | ++ | ++ | ++ |
| #5-133-9-17 | +++ | ++ | — | — | — | — |
| L20105 (leu2) | +++ | +++ | +++ | +++ | +++ | +++ |
| VKM Y-9 | +++ | +++ | +++ | +++ | +++ | +++ |

"+++"—strong growth
"++"—weak growth
"—" absence of growth

In the next experiments, the influence of cobalt and chromium ions on the growth and riboflavin synthesis of regulatory mutants having defects in derepression (derepression mutants) was studied. It was discovered that most of them are less sensitive to $Co^{2+}$ ions than the wild strain and do not overproduce flavins in the medium with this ion (Table 9). However, $Cr^{+6}$ ions (as $K_2Cr_2O_7$) at 0.15 mM are toxic for the derepression mutants whereas wild-type strains VKM Y-9 and L20105 (leu2) grow at this concentration quite satisfactory (Table 10). The addition of 0.3 M sucrose (used as an osmotic stabilizor during electrotransformation) did not change the general specific inhibitory effect of chromium bichromate on the growth of regulatory mutants whereas the growth of the wild-type strains was not inhibited (Table 11).

TABLE 9

Influence of different concentrations of $Co^{+2}$ ions on the growth and flavin production of *Candida famata* regulatory mutants unable to overproduce riboflavin

| *C. famata* strain | Concentration of $Co^{+2}$, g/ml | | | | | | | | Flavin fluorescence under different concentrations of $Co^{+2}$ | | | | | | | |
|---|---|---|---|---|---|---|---|---|---|---|---|---|---|---|---|---|
| | 0 | 10 | 15 | 20 | 25 | 30 | 40 | 60 | 0 | 10 | 15 | 20 | 25 | 30 | 40 | 50 |
| #105-6-1 | +++ | +++ | +++ | ++ | — | — | — | — | — | — | — | — | | | | |
| #105-6-2 | +++ | +++ | +++ | ++ | — | — | — | — | — | — | — | — | | | | |
| #105-6-3 | +++ | +++ | ++ | — | — | — | — | — | — | — | — | — | | | | |
| #105-6-4 | +++ | +++ | +++ | ++ | — | — | — | — | — | — | — | — | | | | |
| #105-6-8 | +++ | +++ | +++ | — | — | — | — | — | — | — | — | — | | | | |
| #105-6-11 | +++ | +++ | +++ | ++ | — | — | — | — | — | — | — | — | | | | |
| #105-6-13 | +++ | +++ | +++ | +++ | +++ | +++ | +++ | +++ | — | — | — | — | — | — | — | — |
| #105-6-14 | +++ | +++ | +++ | ++ | — | — | — | — | — | — | — | — | | | | |
| #105-6-22 | +++ | +++ | +++ | +++ | +++ | +++ | +++ | +++ | — | — | — | — | — | — | — | — |
| #105-6-27 | +++ | +++ | +++ | ++ | — | — | — | — | — | — | — | — | | | | |
| #105-6-30 | +++ | +++ | +++ | ++ | ++ | ++ | ++ | ++ | — | — | — | — | — | — | — | — |
| #105-6-33 | +++ | +++ | +++ | +++ | ++ | ++ | ++ | ++ | — | — | — | — | — | — | — | — |
| #4-126-28 | +++ | +++ | +++ | +++ | — | — | — | — | — | — | — | — | | | | |
| #4-126-30 | +++ | +++ | +++ | +++ | ++ | — | — | — | — | — | — | — | — | | | |
| #4-126-31 | +++ | +++ | +++ | ++ | ++ | — | — | — | — | — | — | — | — | | | |
| #4-126-35 | +++ | +++ | +++ | ++ | — | — | — | — | — | — | — | — | | | | |

TABLE 9-continued

Influence of different concentrations of $Co^{+2}$ ions on the growth and flavin production of *Candida famata* regulatory mutants unable to overproduce riboflavin

| C. famata strain | Concentration of $Co^{+2}$, g/ml | | | | | | | | Flavin fluorescence under different concentrations of $Co^{+2}$ | | | | | | | |
|---|---|---|---|---|---|---|---|---|---|---|---|---|---|---|---|---|
| | 0 | 10 | 15 | 20 | 25 | 30 | 40 | 60 | 0 | 10 | 15 | 20 | 25 | 30 | 40 | 50 |
| #8-15-9 | +++ | +++ | +++ | ++ | ++ | — | — | — | — | — | — | — | — | | | |
| #8-15-2 | +++ | +++ | +++ | +++ | +++ | +++ | +++ | +++ | — | — | — | — | — | — | — | — |
| #8-15-12 | +++ | +++ | +++ | +++ | +++ | +++ | +++ | +++ | — | — | — | — | — | — | — | — |
| #5-133-9-5 | +++ | +++ | +++ | +++ | +++ | +++ | +++ | +++ | — | — | — | — | — | — | — | — |
| #5-133-9-10 | +++ | +++ | +++ | +++ | ++ | ++ | — | — | — | — | — | — | — | — | — | — |
| #5-133-9-17 | +++ | +++ | +++ | +++ | ++ | ++ | — | — | — | — | — | — | — | — | — | — |
| L20105 (leu2) | +++ | +++ | ++ | — | — | — | — | — | — | + | + | | | | | |
| VKM Y-9 | +++ | +++ | ++ | — | — | — | — | — | — | + | + | | | | | |

"+++"—strong growth;
"++"—weak growth;
"—"—absence of growth;
"+"—fluorescence of samples (means riboflavin over synthesis);
"—"—absence of fluorescence

TABLE 10

Sensitivity of *Candida famata* regulatory mutants unable to overproduce riboflavin to different concentrations of $K_2Cr_2O_7$ during growth in Burkholder medium

| C. famata strain | Concentration of $K_2Cr_2O_7$, μM | | | | | | | |
|---|---|---|---|---|---|---|---|---|
| | 0 | 20 | 50 | 80 | 130 | 150 | 180 | 200 |
| #105-6-1 | +++ | +++ | ++ | — | — | — | — | — |
| #105-6-2 | +++ | +++ | +++ | +++ | — | — | — | — |
| #105-6-3 | +++ | +++ | +++ | +++ | ++ | — | — | — |
| #105-6-4 | +++ | — | — | — | — | — | — | — |
| #105-6-8 | +++ | +++ | — | — | — | — | — | — |
| #105-6-11 | +++ | ++ | ++ | — | — | — | — | — |
| #105-6-13 | +++ | +++ | +++ | +++ | +++ | ++ | ++ | — |
| #105-6-14 | +++ | ++ | — | — | — | — | — | — |
| #105-6-22 | +++ | +++ | ++ | — | — | — | — | — |
| #105-6-27 | +++ | +++ | ++ | — | — | — | — | — |
| #105-6-30 | +++ | +++ | +++ | +++ | — | — | — | — |
| #105-6-33 | +++ | +++ | +++ | +++ | — | — | — | — |
| #4-126-28 | +++ | +++ | +++ | +++ | — | — | — | — |
| #4-126-30 | +++ | +++ | +++ | +++ | — | — | — | — |
| #4-126-31 | +++ | +++ | +++ | +++ | — | — | — | — |
| #4-126-35 | +++ | +++ | +++ | +++ | — | — | — | — |
| #8-15-9 | +++ | — | — | — | — | — | — | — |
| #8-15-2 | +++ | +++ | +++ | +++ | ++ | — | — | — |
| #8-15-12 | +++ | +++ | +++ | +++ | ++ | — | — | — |
| #5-133-9-4 | +++ | +++ | +++ | +++ | — | — | — | — |
| #5-133-9-5 | +++ | +++ | +++ | +++ | +++ | — | — | — |
| #5-133-9-10 | +++ | +++ | — | — | — | — | — | — |
| #5-133-9-17 | +++ | ++ | — | — | — | — | — | — |
| L20105 (leu2) | +++ | +++ | +++ | +++ | +++ | +++ | — | — |
| VKM Y-9 | +++ | +++ | +++ | +++ | +++ | +++ | — | — |

"+++"—strong growth
"++"—weak growth
"—" absence of growth

TABLE 11

Sensitivity of *Candida famata* regulatory mutants unable to overproduce riboflavin to different concentrations of $K_2Cr_2O_7$ during growth in Burkholder medium containing 0.3 M sucrose

| C. famata strain | Concentration of $K_2Cr_2O_7$, μM | | | | | | | | | | | |
|---|---|---|---|---|---|---|---|---|---|---|---|---|
| | 0 | 50 | 60 | 70 | 80 | 100 | 120 | 140 | 160 | 180 | 200 | 400 |
| #105-6-1 | +++ | +++ | +++ | ++ | ++ | ++ | + | — | — | — | — | — |
| #105-6-2 | +++ | +++ | +++ | ++ | + | + | + | — | — | — | — | — |
| #105-6-3 | +++ | +++ | +++ | ++ | + | + | + | — | — | — | — | — |
| #105-6-4 | +++ | +++ | +++ | ++ | ++ | ++ | ++ | — | — | — | — | — |
| #105-6-8 | +++ | +++ | +++ | ++ | + | + | + | — | — | — | — | — |
| #105-6-11 | +++ | +++ | +++ | ++ | + | + | + | — | — | — | — | — |
| #105-6-13 | +++ | +++ | +++ | +++ | +++ | ++ | ++ | ++ | ++ | + | + | — |
| #105-6-14 | +++ | +++ | +++ | ++ | + | + | + | — | — | — | — | — |
| #105-6-22 | +++ | +++ | +++ | ++ | + | + | — | — | — | — | — | — |

TABLE 11-continued

Sensitivity of Candida famata regulatory mutants unable to overproduce riboflavin to different concentrations of K₂Cr₂O₇ during growth in Burkholder medium containing 0.3 M sucrose

| C. famata strain | Concentration of K$_2$Cr$_2$O$_7$, μM | | | | | | | | | | | |
|---|---|---|---|---|---|---|---|---|---|---|---|---|
| | 0 | 50 | 60 | 70 | 80 | 100 | 120 | 140 | 160 | 180 | 200 | 400 |
| #105-6-27 | +++ | ++ | ++ | ++ | + | + | + | — | — | — | — | — |
| #105-6-30 | +++ | +++ | +++ | +++ | ++ | + | + | — | — | — | — | — |
| #105-6-34 | +++ | +++ | +++ | +++ | + | + | + | — | — | — | — | — |
| #4-126-28 | +++ | +++ | +++ | +++ | ++ | + | + | — | — | — | — | — |
| #4-126-30 | +++ | +++ | +++ | ++ | + | + | + | — | — | — | — | — |
| #4-126-31 | +++ | +++ | +++ | +++ | + | + | + | — | — | — | — | — |
| #4-126-35 | +++ | +++ | +++ | ++ | + | + | + | — | — | — | — | — |
| #8-15-9 | +++ | +++ | ++ | ++ | ++ | + | + | + | + | — | — | — |
| #8-15-2 | +++ | +++ | +++ | ++ | ++ | + | + | + | + | — | — | — |
| #8-15-12 | +++ | +++ | ++ | ++ | ++ | + | + | + | + | — | — | — |
| #5-133-9-4 | +++ | +++ | ++ | + | + | + | + | — | — | — | — | — |
| #5-133-9-5 | +++ | +++ | ++ | ++ | ++ | + | + | — | — | — | — | — |
| #5-133-9-10 | +++ | +++ | ++ | ++ | + | + | + | — | — | — | — | — |
| #5-133-9-17 | +++ | +++ | ++ | ++ | + | + | + | — | — | — | — | — |
| L20105 (leu2) | +++ | +++ | +++ | +++ | +++ | +++ | +++ | +++ | ++ | — | — | — |
| VKM Y-9 | +++ | +++ | +++ | +++ | +++ | +++ | +++ | +++ | +++ | ++ | — | — |

"+++"—strong growth

"++"—weak growth

"+"—very weak growth

"—" absence of growth

The growth of the regulatory mutants after addition of both MFA and Cr+6 was studied. The following ratio between K₂Cr₂O₇ and MFA was used:
1. Cr, 2.5–100 μm; MFA, 0.05%;
2. Cr, 2.5–100 μm; MFA, 0.1%;
3. Cr, 2.5–100 μm; MFA, 0.2%.

After 5 days of replica plated colony cultivation on plates, the ratio of 100 μm of K₂Cr₂O₇ to 0.05% MFA provide total growth inhibition of all tested regulatory mutants of positive action whereas the wild-type strains (VKM Y-9 and L20105) still normally grew at this condition.

These observations open the ways for positive selection of transformants containing genes regulating derepression. As the mutants are selectively more sensitive to inhibition by chromium ions and MFA as well as by the mixture of these inhibitors, the transformants with restored regulatory genes of flavinogenesis will be picked up as the resistant colonies to the above inhibitors.

Example 46

The Assembly of the Cloned Structural Genes of C. famata Flavinogenesis on One Plasmid One vector comprising 5 C. famata fragments bearing the genes RIB1, RIB2, RIB5, RIB6 and RIB7 of riboflavin biosynthesis was constructed. The work was started by isolating fragments bearing genes RIB1, RIB2, RIB7 and the ARS element C.famata (CfARS 1614). At the site of joining these fragments and CfARS 1614 element, the restriction sites were absent, therefore the corresponding additional subcloning of the above mentioned fragments was carried out. From the plasmid pCR1Xb (FIG. 23) which contains the DNA fragment with RIB1 gene of ~2.5 kb, the KpnI-XbaI fragment of ~1.9 kb was isolated. From the plasmid PRp2-11 (FIG. 29), which contains the DNA fragment comprising the ~1.7 kb RIB2 gene, the ~1.55 kb EcoRI-XbaI fragment was cut out. From plasmid PRp7 (FIG. 19), which contains the DNA fragment with RIB7 gene of ~1.1 kb, the HindIII fragment was excised. Subsequently, the fragments KpnI-XbaI (~1.9 kb), EcoRI-XbaI (~1.55 kb) and HindIII (~1.1 kb) were eluted from agarose gel. Then fragments KpnI-XbaI and EcoRI-XbaI were blunted with T4 DNA polymerase. After blunting, these fragments were cloned in the unique SmaI site of the plasmid pCfARS1614. The new plasmids were designated as pRIB1 (insert of ~1.9 kb) and pR2 (insert of ~1.55 kb). HindIII fragment of ~1.1 kb (excised from the plasmid PRp7) was cloned in the unique HindIII site of the plasmid pCfARS1614. The new plasmid was designated pRIB7.

The restriction analysis of the obtained recombinant constructs was carried out. After treatment of pRIB1 plasmid simultaneously with endonucleases EcoRI and XbaI, three fragments of ~4.2 kb, ~1.9 kb and ~0.9 kb were isolated. After simultaneous treatment of plasmid pR2 with these enzymes, fragments of ~4.2 kb, ~1.55 kb and ~0.9 kb were obtained. Finally, after treatment of pRIB7 plasmid with HindIII endonuclease, two fragments of ~5.1 kb and ~1.1 kb were isolated.

For functional testing of the isolated constructs, electrotransformation of the riboflavin deficient mutants of C. famata 3-25 (rib1 leu2), 33-1n (rib2 leu2) and 8-70 (rib7 leu2) was carried out. It was shown that the plasmid pRIB1 does not complement riboflavin auxotrophy of 3-25 strain (rib1 leu2). Thus, the KpnI-XbaI fragment in this pRIB1 plamid does not contain the complete RIB1 gene. Plasmid pR2 complements riboflavin auxotrophy of 33-1n strain (rib2 leu2) with a transformation frequency $2.4 \times 10^4$ transformants/μg DNA. Plasmid pRIB7 complements the rib7 mutation of the strain 8-70 (rib7 leu2) with a transformation frequency of $1.7 \times 10^4$ transformants/μg DNA. Thus, the fragments of C famata carried by plasmids pR2 and pRIB7 bear the complete RIB2 and RIB7 genes, respectively.

Subcloning of the genomic DNA fragments which bear the RIB2 gene (EcoRI-XbaI fragment of ~1.55 kb) and those which bear the RIB7 gene (in the HindIII fragment of ~1.1 kb) was carried out. In such a way, the separation of the C. famata ARS element (CfARS1614) from the fragments containing the RIB2 and RIB7 genes was carried out. In further experiments, plasmid pCR1Xb comprising the complete RIB1 gene, was used as the basic vector.

The next step of this work included isolation of SalI-SmaI fragment from the plasmid pPR5 (FIG. 37). This fragment was eluted from the agarose gel. Vector pCR1Xb was linearized with XbaI endonuclease. Linearized vector pCR1Xb and the SalI-SmaI fragment were blunted with T4 DNA polymerase and were ligated. The resulting plasmid was designated as pR15, having a total size of ~9.1 kb. The restriction analysis of pR15 using endonuclease EcoRI was carried out. Five fragments of ~3.93 kb, ~2 kb, ~1.95 kb, ~0.6 kb and of ~0.55 kb were obtained.

Vector pR15 was linearized with endonuclease HindIII and dephosphorylated with alkaline phosphatase. The ~1.1 kb HindIII fragment which contains the C. famata RIB7 gene was inserted in this vector. The resulting plasmid was designated as pR157. Restriction analysis of this plasmid with endonuclease HindIII showed the expected fragments of ~9.1 kb and 1.1 kb. The total size of pR157 was ~10.2 kb.

Plasmid pR157 was linearized with SmaI and treated with alkaline phosphatase. Ligation of linearized and dephosphorylated vector pR157 with the blunted fragment of EcoRI-XbaI fragment of ~1.55 kb comprising the C. famata RIB2 gene was carried out. The resulting recombinant construct was designated as pR1572. Restriction analysis with endonuclease HindIII revealed 4 fragments of ~7.3 kb, ~2.9 kb, ~1.1 kb and ~0.8 kb. The total size of this plasmid consists ~11.75 kb.

Plasmid pF (FIG. 36) was used for isolation of the C. famata KpnI-EcoRI fragment conveying the RIB6 gene of ~4.5 kb. The KpnI-EcoRI fragment was eluted from agarose gel and blunted with T4 DNA polymerase. Vector pR1572 was linearized with endonuclease SacI, blunted and dephosphorylated. The linearized and dephosphorylated vector pR1572 will be ligated with the blunted fragment of C. famata DNA comprising the RIB6 gene.

Thus, the recombinant construct pR1572 bears four fragments of C famata DNA comprising genes RIB1, RIB2, RIB5 and RIB7 (FIG. 45).

Example 47

Cloning the C. famata RIB3 Gene

To clone the C. famata RIB3 gene, construction of a new genetic library of this species on the p2R vector was initiated. For this, the ligation of linearized and dephosphorylated vector p2R with Sau3AI restriction fragments of the total C. famata DNA was conducted. The resulting ligate was used for transformation of the strain Escherichia coli DH5α. Transformation was conducted using the electroporation method. Totally, more than 200,000 ampicillin resistant colonies of bacterial transformants were isolated (gene library of C. famata). The representation of inserts in this new library was tested. For this, plasmid DNA isolated from 24 individual bacterial colonies of the obtained library was tested for the presence of inserts in the isolated plasmids. Using electrophoresis of the native forms as well as restrictive fragments of these plasmids, it was shown that 12 of 24 plasmids bear the inserts. Thus, approximately 50% of bacterial colonies contain plasmids with inserts of C. famata chromosomal DNA.

Preparative amounts of plasmid DNA of the new C. famata gene library were accumulated. For this, the cells of ~200,000 bacterial colonies of the gene library were washed out from the plates and cultivated for 5 h in liquid medium LB containing ampicillin (100 μg/ml) in the total volume 800 ml with shaking. After cultivation, plasmid DNA was isolated from the cells of bacterial transformants (plasmid DNA of C. famata VKM Y-9 gene library on the vector p2R). Isolated plasmid DNA was dissolved in 4 ml sterile TE buffer. Spectrophotometric assay showed that the concentration of this plasmid DNA in TE buffer is approximately 1.5 μg/ml.

The resulting plasmid DNA of C. famata gene library was used for spheroplast transformation of the mutant P. guilliermondii RG1 (rib3 hisX). After two transformation experiments, 4 colonies of Rib$^+$ transformants were obtained.

However, none of these colonies contained plasmid DNA. So, transformation of the strain P. guilliermondii RG1 with the new C. famata gene library will be used for isolation of the recombinant construct carrying the C. famata genomic fragment comprising the RIB3 gene. The reasons for the failure to clone the RIB3 gene can be explained apparently by the fact that it is the largest gene of riboflavin synthesis, so its representation in the gene library has to be quite minor.

Example 48

Study of the Properties of the C. famata Regulatory Mutants Which Overproduce Riboflavin (Repression Mutants)

The sensitivity of the regulatory mutants of the yeast C. famata which overproduce riboflavin in iron rich medium probably due to defects in genes regulating repression (repression mutants), to different ions of heavy metals was studied. For this, the analyzed strains were streaked on the YPD plates and then were replica-plated on Burkholder synthetic medium containing leucine (40 μg/ml). The C. famata mutants L20105-40-1-11, L20105-40-1-17, L20105-3-2-1, L20105-3-2-8 and L20105-3-2-12 (all contained leu2 marker) accumulated 80–100 μg riboflavin/ml. The mutants #75, 4-48, 2-5 produced much higher amounts of riboflavin (200–250 μg/ml) but were prototrophs for leucine synthesis. Strain #75 was characterized by retarded growth comparing with other mutants. The strains VKM Y-9 (wild type) and L20105 (leu2) were used as the control strains.

Study of $CdSO_4 \times 8H_2O$ on the yeast growth showed that this compound is very toxic to all tested strains even at 2.5–3 μm. Mutants overproducing lower amounts of riboflavin appeared to be more sensitive to $CuSO_4$ (0.15 mM) than that of the strains producing higher amounts of riboflavin (inhibitory concentration 0.5 mM) (Table 12).

TABLE 12

Sensitivity of *Candida famata* regulatory mutants able to overproduce riboflavin to different concentrations of copper ions during growth on solid Burkholder medium

| C. famata strain | Concentration of $Cu^{+2}$, mM | | | | | | | | | | | | | | | | |
|---|---|---|---|---|---|---|---|---|---|---|---|---|---|---|---|---|---|
| | 0 | 0.05 | 0.1 | 0.15 | 0.2 | 0.25 | 0.3 | 0.35 | 4 | 0.45 | 0.5 | 0.55 | 0.6 | 0.65 | 0.7 | 0.75 | 8 |
| L20105-40-1-11 | +++ | ++ | ++ | — | — | — | — | — | — | — | — | — | — | — | — | — | — |
| L20105-40-1-17 | +++ | ++ | + | — | — | — | — | — | — | — | — | — | — | — | — | — | — |
| L20105-3-2-1 | +++ | ++ | + | — | — | — | — | — | — | — | — | — | — | — | — | — | — |
| L20105-3-2-4 | +++ | ++ | + | — | — | — | — | — | — | — | — | — | — | — | — | — | — |
| L20105-3-2-8 | +++ | ++ | + | — | — | — | — | — | — | — | — | — | — | — | — | — | — |
| L20105-3-2-12 | +++ | ++ | + | — | — | — | — | — | — | — | — | — | — | — | — | — | — |
| #75 | +++ | +++ | +++ | +++ | +++ | +++ | ++ | ++ | ++ | + | — | — | — | — | — | — | — |
| #4-48 | +++ | +++ | +++ | +++ | +++ | +++ | ++ | ++ | ++ | + | — | — | — | — | — | — | — |
| #2-5 | +++ | +++ | +++ | +++ | +++ | +++ | ++ | ++ | ++ | + | — | — | — | — | — | — | — |
| L20105 (leu2) | +++ | +++ | +++ | +++ | +++ | +++ | +++ | +++ | ++ | ++ | ++ | ++ | + | + | + | — | — |
| VKM Y-9 | +++ | +++ | +++ | +++ | +++ | +++ | +++ | +++ | ++ | ++ | ++ | ++ | + | + | — | — | — |

"+++"—strong growth
"++"—weak growth
"+"—very weak growth
"—" absence of growth

Results of the effect of $K_2Cr_2O_7$ on growth of tested strains in media with different carbon sources are presented in Table 13.

TABLE 13

Sensitivity of *Candida famata* regulatory mutants able to overproduce riboflavin to different concentrations of $K_2Cr_2O_7$ during growth on solid Burkholder medium containing 0.3 M sucrose

| C. famata strain | Concentration of $K_2Cr_2O_7$, $\mu$M | | | | | | | | | | |
|---|---|---|---|---|---|---|---|---|---|---|---|
| | 0 | 25 | 50 | 75 | 100 | 125 | 150 | 175 | 200 | 225 | 250 |
| L20105-40-1-11 | +++ | +++ | +++ | ++ | + | — | — | — | — | — | — |
| L20105-40-1-17 | +++ | +++ | +++ | ++ | + | — | — | — | — | — | — |
| L20105-3-2-1 | +++ | +++ | +++ | +++ | + | — | — | — | — | — | — |
| L20105-3-2-4 | +++ | +++ | +++ | +++ | + | — | — | — | — | — | — |
| L20105-3-2-8 | +++ | +++ | +++ | +++ | + | — | — | — | — | — | — |
| L20105-3-2-12 | +++ | +++ | +++ | +++ | + | — | — | — | — | — | — |
| #75 | +++ | +++ | ++ | ++ | — | — | — | — | — | — | — |
| #4-48 | +++ | +++ | +++ | +++ | ++ | ++ | ++ | — | — | — | — |
| #2-5 | +++ | +++ | +++ | +++ | ++ | ++ | ++ | — | — | — | — |
| L20105 (leu2) | +++ | +++ | +++ | +++ | +++ | +++ | +++ | ++ | — | — | — |
| VKM Y-9 | +++ | +++ | +++ | +++ | +++ | +++ | +++ | +++ | — | — | — |

"+++"—strong growth
"++"—weak growth
"+"—very weak growth
"—" absence of growth

In medium with 0.3 M sucrose, 125 $\mu$M $K_2Cr_2O_7$ totally inhibited growth of mutants with lower levels of riboflavin overproduction. 175 $\mu$M also inhibited growth of strains with higher riboflavin production (with exception of strain #75 where growth was inhibited already at 100 $\mu$M). In the medium with 0.5% glycerol, $K_2Cr_2O_7$ at 50 $\mu$M inhibited growth of weaker overproducers and at 65–100$\mu$M inhibited growth of more potent overproducers (Table 14).

TABLE 14

Sensitivity of *Candida famata* regulatory mutants able to overproduce riboflavin to different concentrations of $K_2Cr_2O_7$ during growth on solid Burkholder medium containing 0.5% glycerol

| C. famata strain | Concentration of $K_2Cr_2O_7$, $\mu$M | | | | | | | | | | | | | | | |
|---|---|---|---|---|---|---|---|---|---|---|---|---|---|---|---|---|
| | 0 | 25 | 30 | 35 | 40 | 45 | 50 | 55 | 60 | 65 | 70 | 75 | 85 | 100 | 125 | 150 |
| L20105-40-1-11 | +++ | ++ | + | | + | — | — | — | — | — | — | — | — | — | — | — |
| L20105-40-1-17 | +++ | ++ | + | | + | — | — | — | — | — | — | — | — | — | — | — |
| L20105-3-2-1 | +++ | ++ | + | | + | — | — | — | — | — | — | — | — | — | — | — |
| L20105-3-2-4 | +++ | +++ | + | | + | — | — | — | — | — | — | — | — | — | — | — |

TABLE 14-continued

Sensitivity of *Candida famata* regulatory mutants able to overproduce riboflavin to different concentrations of $K_2Cr_2O_7$ during growth on solid Burkholder medium containing 0.5% glycerol

| C. famata strain | Concentration of $K_2Cr_2O_7$, µM | | | | | | | | | | | | | | | |
|---|---|---|---|---|---|---|---|---|---|---|---|---|---|---|---|---|
| | 0 | 25 | 30 | 35 | 40 | 45 | 50 | 55 | 60 | 65 | 70 | 75 | 85 | 100 | 125 | 150 |
| L20105-3-2-8 | +++ | +++ | + | | + | — | — | — | — | — | — | — | — | — | — | — |
| L20105-3-2-12 | +++ | +++ | + | | + | — | — | — | — | — | — | — | — | — | — | — |
| #75 | +++ | +++ | +++ | +++ | | ++ | | ++ | | — | — | — | — | — | — | — |
| #4-48 | +++ | +++ | +++ | +++ | +++ | +++ | | ++ | | — | — | — | — | — | — | — |
| #2-5 | +++ | +++ | +++ | +++ | +++ | +++ | | ++ | | + | | + | — | — | — | — |
| L20105 (leu2) | +++ | +++ | +++ | +++ | +++ | +++ | +++ | +++ | +++ | ++ | ++ | ++ | ++ | ++ | — | — |
| VKM Y-9 | +++ | +++ | +++ | +++ | +++ | +++ | +++ | +++ | +++ | +++ | +++ | +++ | +++ | +++ | ++ | ++ |

"+++"—strong growth
"++"—weak growth
"+"—very weak growth
"—"absence of growth

In medium with glucose (0.5%), $K_2Cr_2O_7$ at 60–90 µM inhibited growth of both types of riboflavin overproducers (Table 15).

TABLE 15

Sensitivity of *Candida famata* regulatory mutants able to overproduce riboflavin to different concentrations of $K_2Cr_2O_7$ during growth on solid Burkholder medium containing 0.5% glucose

| C. famata strain | Concentration of $K_2Cr_2O_7$, µM | | | | | | | | | | | | | |
|---|---|---|---|---|---|---|---|---|---|---|---|---|---|---|
| | 0 | 25 | 30 | 35 | 40 | 45 | 50 | 60 | 70 | 80 | 90 | 100 | 125 | 150 |
| L20105-40-1-11 | +++ | +++ | +++ | ++ | + | + | + | — | — | — | — | — | — | — |
| L20105-40-1-17 | +++ | +++ | +++ | ++ | + | + | + | — | — | — | — | — | — | — |
| L20105-3-2-1 | +++ | +++ | +++ | ++ | + | + | + | — | — | — | — | — | — | — |
| L20105-3-2-4 | +++ | +++ | +++ | ++ | + | + | + | — | — | — | — | — | — | — |
| L20105-3-2-8 | +++ | +++ | +++ | ++ | + | + | + | — | — | — | — | — | — | — |
| L20105-3-2-12 | +++ | +++ | +++ | ++ | + | + | + | — | — | — | — | — | — | — |
| #75 | +++ | ++ | — | — | — | — | — | — | — | — | — | — | — | — |
| #4-48 | +++ | +++ | ++ | + | + | + | + | + | — | — | — | — | — | — |
| #2-5 | +++ | +++ | ++ | ++ | ++ | ++ | ++ | + | — | — | — | — | — | — |
| L20105 (leu2) | +++ | +++ | +++ | +++ | +++ | +++ | +++ | +++ | +++ | +++ | +++ | ++ | + | — |
| VKM Y-9 | +++ | +++ | +++ | +++ | +++ | +++ | +++ | +++ | +++ | +++ | +++ | +++ | ++ | + |

"+++"—strong growth
"++"—weak growth
"+"—very weak growth
"—" absence of growth $K_2Cr_2O_7$ at subinhibitory concentrations stimulated flavinogenesis of all tested strains, both riboflavin overproducers and wild-type strains. Finally, studies of the effect of $CoCl_2$ showed that this compound strongly inhibited growth of all tested riboflavin overproducers at 3.75–6.25 µg/ml (Table 16).

TABLE 16

Sensitivity of *Candida famata* regulatory mutants able to overproduce riboflavin to different concentrations of $Co^{+2}$ ions during growth on solid Burkholder medium

| C. famata strain | Concentration of $Co^{+2}$, µg/ml | | | | | | | | | | |
|---|---|---|---|---|---|---|---|---|---|---|---|
| | 0 | 1.25 | 2.5 | 3.75 | 5.0 | 6.25 | 7.5 | 8.75 | 10 | 11.25 | 12.5 |
| L20105-40-1-11 | +++ | +++ | ++ | + | — | — | — | — | — | — | — |
| L20105-40-1-17 | +++ | +++ | ++ | + | — | — | — | — | — | — | — |
| L20105-3-2-1 | +++ | +++ | ++ | + | — | — | — | — | — | — | — |
| L20105-3-2-9 | +++ | +++ | ++ | + | — | — | — | — | — | — | — |

TABLE 16-continued

Sensitivity of Candida famata regulatory mutants able to overproduce riboflavin to different concentrations of $Co^{+2}$ ions during growth on solid Burkholder medium

| C. famata strain | Concentration of $Co^{+2}$, µg/ml | | | | | | | | | | |
|---|---|---|---|---|---|---|---|---|---|---|---|
| | 0 | 1.25 | 2.5 | 3.75 | 5.0 | 6.25 | 7.5 | 8.75 | 10 | 11.25 | 12.5 |
| L20105-3-2-8 | +++ | +++ | ++ | + | + | — | — | — | — | — | — |
| L20105-3-2-12 | +++ | +++ | ++ | + | + | — | — | — | — | — | — |
| #75 | ++ | ++ | + | — | — | — | — | — | — | — | — |
| #4-48 | +++ | +++ | ++ | — | — | — | — | — | — | — | — |
| #2-5 | +++ | +++ | ++ | + | — | — | — | — | — | — | — |
| L20105 (leu2) | +++ | +++ | +++ | +++ | +++ | +++ | +++ | +++ | +++ | ++ | ++ |
| VKM Y-9 | +++ | +++ | +++ | +++ | +++ | +++ | +++ | +++ | +++ | +++ | +++ |

"+++"—strong growth
"++"—weak growth
"+"—very weak growth
"—" absence of growth

Development of the Strategy for Cloning Genes Regulating Depression of Riboflavin Production in C. famata Example 49

Transformation of Riboflavin Overproducers C. famata 2-5 and 4-48 with the C. famata Gene Library and Development of the Method for Positive Selection of the Transformants Having Lost the Ability to Overproduce Riboflavin The strategy for the cloning of the genes regulating derepression of riboflavin in C. famata was developed using regulatory mutants 2-5 and 4-48 which accumulate elevated amounts of riboflavin in the medium with high iron content. The method for positive selection of the transformants which, after transformation with C. famata gene library, would lose the ability to overproduce riboflavin in iron rich medium, was developed. For this, the difference in sensitivity to $Cr^{+6}$ ions (as $K_2Cr_2O_7$) between C. famata wild strain VKM Y-9 and overproducers of riboflavin 2-5 and 4-48 after their electroporation with the C. famata gene library constructed on pCfARS1614, was studied. As these mutants did not contain auxotrophic markers, it was not possible to determine transformation frequency in these experiments.

Toxicity of $Cr^{+6}$ was studied on agar plates containing different carbon sources (sucrose, glycerol, ethanol). Before the electroporated cells were plated on ethanol and glycerol medium, the cells were washed 3 times with 10 fold volumes of 0.6 M KCl and the suspension volumes were adjusted with 0.6 M KCl to 100 µl. On each plate containing glycerol (0.5%) or ethanol (1%), 0.6 M KCl and different concentrations (10–200 uM) of $K_2Cr_2O_7$, in a 30–60 µl suspension were spread. Where sucrose was used as a carbon source, this sugar was used at a 0.3M concentration, using it as both as a carbon source and osmotic stabilizer.

After 6 days of cultivation in the medium with ethanol, $K_2Cr_2O_7$ at 15–50 µM severely inhibited growth of mutants 2-5 and 4-48 whereas growth of the wild-type strain was almost uninhibited (Table 17).

TABLE 17

Sensitivity of cells of Candida famata wild type and regulatory mutants able to overproduce riboflavin on iron-rich medium after electroporation to different concentrations of $K_2Cr_2O_7$ during growth in Burkholder medium containing 1% ethanol.

| C. famata strain | Concentration of $K_2Cr_2O_7$, µM | | | | | | | |
|---|---|---|---|---|---|---|---|---|
| | 0 | 15 | 20 | 30 | 40 | 50 | 70 | 100 |
| VKM Y-9 | +++ | +++ | +++ | +++ | ++ | ++ | + | — |
| #2-5 | ++ | + | + | + | — | — | — | — |
| #4-48 | ++ | + | + | — | — | — | — | — |

"+++"—strong growth
"++"—weak growth
"+"—very weak growth
"—"—absence of growth

In the medium with glycerol, severe inhibition of the growth of the 2-5 and 4-48 mutants but not that of the wild-type strain was observed at 90–110 µM of $K_2Cr_2O_7$ (Table 18).

TABLE 18

Sensitivity of cells of Candida famata wild type and regulatory mutants able to overproduce riboflavin on iron-rich medium after electroporation to different concentrations of $K_2Cr_2O_7$ during growth in Burkholder medium containing 0.5% glycerol.

| C. famata strain | Concentration of $K_2Cr_2O_7$, µM | | | | | | | | |
|---|---|---|---|---|---|---|---|---|---|
| | 0 | 25 | 50 | 75 | 100 | 125 | 150 | 175 | 200 |
| VKM Y-9 | +++ | +++ | +++ | +++ | +++ | ++ | + | — | — |
| #2-5 | +++ | +++ | +++ | ++ | — | — | — | — | — |
| #4-48 | +++ | +++ | +++ | ++ | — | — | — | — | — |

"+++"—strong growth
"++"—weak growth
"+"—very weak growth

Growth of the regulatory mutants in the sucrose medium was inhibited at 120–140 µM $K_2Cr_2O_7$ (Table 19).

TABLE 19

Sensitivity of cells of *Candida famata* wild type and regulatory mutants able to overproduce riboflavin on iron-rich medium after electroporation to different concentrations of $K_2Cr_2O_7$ during growth in Burkholder medium containing 0.3 M sucrose.

| C. famata strain | Concentration of $K_2Cr_2O_7$, µM | | | | | | | | | | |
|---|---|---|---|---|---|---|---|---|---|---|---|
|  | 0 | 70 | 80 | 90 | 100 | 110 | 120 | 130 | 140 | 170 | 200 |
| VKM Y-9 | +++ | +++ | +++ | +++ | +++ | +++ | +++ | +++ | ++ | + | — |
| #2-5 | +++ | +++ | +++ | +++ | ++ | ++ | + | — | — | — | — |
| #4-48 | +++ | +++ | +++ | +++ | ++ | ++ | + | — | — | — | — |

"+++"—strong growth
"++"—weak growth
"+"—very weak growth
"—"—absence of growth

Next, the toxicity of $CdSO_4$ (0–25 µM) to regulatory mutants 2-5 and 4-48 and the *C. famata* wild strain was studied in the medium with sucrose (Table 20).

TABLE 20

Sensitivity of cells of *Candida famata* wild type and regulatory mutants able to overproduce riboflavin overproduction on iron-rich medium after electroporation to different concentrations of $3CdSO_4 \cdot 8H_2O$ during growth in Burkholder medium containing 0.3 M sucrose.

| C. famata strain | Concentration of $K_2Cr_2O_7$, µM | | | | | |
|---|---|---|---|---|---|---|
|  | 0 | 5 | 10 | 15 | 20 | 25 |
| VKM Y-9 | +++ | +++ | ++ | + | + | — |
| #2-5 | +++ | ++ | ++ | + | + | — |
| #4-48 | +++ | ++ | ++ | + | + | — |

"+++"—strong growth
"++"—weak growth
"+"—very weak growth
"—"—absence of growth

It was shown that all three strains appeared to be very sensitive to $Cd^{+2}$ ions without any differences between regulatory mutants and the wild-type strain.

Thus, it is possible to directly isolate transformants of 2-5 and 4-48 regulatory mutants which showed a restored wild type phenotype, by selection of such transformants which would be able to grow in the ethanol medium with high iron content and $K_2Cr_2O_7$ at concentrations from 30 to 60 µM or in sucrose medium at 120–130 µM of this toxic metal.

The total DNA from such resistant transformants showing a restored wild-type phenotype will be isolated. Subsequently, through *E. coli* retransformation, the plasmid DNA will be isolated therefrom. This work is already started.

Example 50

Heterologous Transformation of *P. guilliermondii* rib81 and rib80 Regulatory Mutants with the *C. famata* Gene Library The work directed to the cloning of *C famata* regulatory genes involved in riboflavin biosynthesis, using heterologous transformation of *P. guilliermondii* regulatory mutants rib81 leu2 (9-20 and 20-2) was carried out. Transformation was carried out using electroporation. Leucine prototrophic transformants were selected and those which did not accumulate elevated amounts of riboflavin were picked up. Transformation frequency in these experiments was 200–500/µg DNA. Nearly 30,000 leucine prototrophic transformants were studied. 9 of them did not accumulate elevated amounts of riboflavin on plates, similarly to the wild strains. Total DNA was isolated from them and after that, using *E. coli* DH5α retransformation, plasmid DNA. The detailed restriction analysis of all isolated plasmids was carried out.

5 analyzed transformants did not contain plasmid DNA, 2 colonies contained the initial plasmid vector without any inserts and 2 colonies contained plasmids comprising the initial vector and inserts of ~1.5 kb and ~3.0 kb. These plasmids were used for transformation of *P. guilliermondii* strain 9-20. However, the plasmids did not complement the regulatory mutation rib81 of the mutant 9-20.

The visual selection of the non-overproducing riboflavin transformants is rather arbitrary and uncertain. Therefore it was decided to develop the method for positive selection of the transformants using tentative differences in sensitivity to $K_2Cr_2O_7$ of wild-type *P. guilliermondii* and the regulatory mutants rib81 9-20 and 20-2. After 6 days of cultivation in the medium with 0.5% glycerol, it was shown that $K_2Cr_2O_7$ at 150–180 µM inhibited growth of regulatory mutant 9-20 more strongly than that of the wild strain (Table 21).

TABLE 21

Sensitivity of cells of *Pichia guilliermondii* wild type and regulatory mutants able to overproduce riboflavin on iron-rich medium (rib81) after electroporation to different concentrations of $K_2Cr_2O_7$ during growth in Burkholder medium containing 0.5% glycerol

| P. guilliermondii strain | Concentration of $K_2Cr_2O_7$, µM | | | | | | |
|---|---|---|---|---|---|---|---|
|  | 0 | 75 | 100 | 125 | 150 | 185 | 240 |
| ATCC9058 | +++ | +++ | +++ | +++ | +++ | ++ | — |
| #9-20 (leu2) | +++ | +++ | ++ | + | — | — | — |

"+++"—strong growth
"++"—weak growth
"+"—very weak growth
"—"—absence of growth

In the medium with 0.3 M sucrose, however, no differences in sensitivity to $Cr^{+6}$ ions (ranging from 100 to 600 µM) between regulatory mutants and the wild type was found (Table 22).

TABLE 22

Sensitivity of cells of *Pichia guilliermondii* wild type and regulatory mutants able to overproduce riboflavin on iron-rich medium (rib81) after electroporation to different concentrations of $K_2Cr_2O_7$ during growth in Burkholder medium containing 0.3 M sucrose.

| P. guilliermondii strain | Concentration of $K_2Cr_2O_7$, µM | | | | | | | | | | |
|---|---|---|---|---|---|---|---|---|---|---|---|
| | 100 | 150 | 200 | 250 | 300 | 350 | 400 | 450 | 500 | 550 | 600 |
| ATCC9058 | +++ | +++ | +++ | +++ | +++ | +++ | + | — | — | — | — |
| #9-20 (leu2) | +++ | +++ | +++ | +++ | +++ | +++ | + | — | — | — | — |

"+++"—strong growth
"++"—weak growth
"+"—very weak growth
"—"—absence of growth

So, the method for transformant selection using isolation of colonies resistant to 150–180 µM $K_2Cr_2O_7$ on plates with glycerol will be used for cloning the RIB81 gene analog in *C. famata*.

The work directed to the cloning of *C. famata* analog of *P. guilliermondii* regulatory gene RIB80 by heterologous transformation was begun. *P. guilliermondii* mutants rib80 leu2 (## 95, 131 and 190) were used as the host strains for transformation. Electroporated cells were plated on the medium without leucine. Each transformation resulted in a lot of small colonies on the plates which in fact remained leucine auxotrophs. Apparently, transformation to leucine prototrophy occurred at very low frequency. Therefore transformation was undertaken using the electroporation method. However, the colonies on plates without leucine were observed on both experimental (treated with DNA) and control (treated without DNA) plates. The number of colonies on plates using cells electroporated with DNA was greater than the number on the control plates. This suggests that there are real transformation events. To test this hypothesis, total and plasmid DNA from the corresponding colonies will be isolated and analyzed. Experiments on development of the method for positive selection of RIB80 transformants using differences in sensitivity to $K_2Cr_2O_7$ of the rib80 mutants and the wild-type strain will be conducted.

Example 51

Selection of Recipient Strains Suitable for Electrotransformation from the Regulatory Mutants of *C. famata* Unable to Overproduce Riboflavin Selection of *C. famata* mutants unable to overproduce riboflavin which retained this feature after electrotranformation was started. Altogether, 7 mutants were electrotransformed: 34, 126-30, 6-2, 9, 12, 6-3, 6-22. After electroporation, cells were plated on the medium containing $CoCl_2$. In such conditions, colonies of the strains able to overproduce riboflavin in iron-deficient medium, including revertants of riboflavin non-overproducing mutants, acquire yellow color. Only two strains, 126-30 and 6-2, retained white color after electroporation. They were tested for riboflavin oversynthesis in liquid medium treated with 8-hydroxyquiniline (for iron depletion). Only *C. famata* mutant 6-2 is suitable to be used as the recipient for the electroporation procedure. The mutant will be used as the recipient strain in transformation experiments with the *C. famata* gene library for cloning the regulatory gene(s) regulating derepression which are involved in riboflavin synthesis.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated polynucleotide molecule comprising an ARS nucleotide sequence, having the function of enhancing the transformation efficiency and the maintenance of vectors as stable extrachromosomal elements in *Candida famata*; said ARS nucleotide sequence having at least 95% sequence identity to the nucleotide sequence SEQ ID NO. 3.

2. A vector comprising the isolated polynucleotide molecule of claim 1.

3. An isolated or purified cell comprising the vector of claim 2.

4. The isolated polynucleotide molecule of claim 1 wherein said polynucleotide comprises the nucleotide sequence of SEQ ID NO. 3.

5. A vector comprising the isolated polynucleotide molecule of claim 4.

6. An isolated or purified cell comprising the vector of claim 5.

7. A plurality of cells of claim 6, wherein said cells are yeast cells comprising a gene library selected from the group consisting of (a) a gene library comprising vectors comprising *Pichia guilliermondii* ATCC 9058 DNA segments, PgARS elements, and CfARS elements, and (b) a gene library comprising vectors comprising *Candida famata* VKM Y-9 DNA segments, CfARS elements and PgARS elements.

8. The cell of claim 6 wherein said cell is a yeast cell.

9. The yeast cell of claim 8, wherein said yeast is a flavinogenic yeast.

10. The yeast cell of claim 9 wherein said yeast cell is *Candida* or *Pichia*.

11. The yeast cell of claim 10 wherein said yeast cell is *Candida famata* VKM Y-9 L20105 having NRRL deposit number Y-30292.

12. A method for the transformation of yeast cells comprising electroporating a cell suspension containing said yeast together with one or more nucleic acid constructs comprising one or more regulatory sequences and one or more genes or gene segments using one or more of resistance, field strength and pulse duration sufficient to transform said cells, wherein said constructs comprise a polynucleotide molecule of claim 1.

13. The method of claim 12 where said construct comprises the nucleotide sequence of SEQ ID NO. 3.

14. A method for the transformation of yeast cells comprising providing spheroplasts of said yeast cells, contacting a solution comprising said spheroplasts with one or more nucleic acid constructs comprising one or more regulatory sequences and one or more genes or gene segments and with one or more fusion agents, for a time sufficient to transform said spheroplasts, wherein said constructs comprise a polynucleotide molecule of claim 1.

15. The method of claim 14 where said construct comprises the nucleotide sequence of SEQ ID NO. 3.

16. A method for the transformation of *Candida famata* cells comprising electroporating a cell suspension containing said cells together with one or more nucleic acid constructs comprising one or more regulatory sequences and one or more genes or gene segments using one or more of resistance, field strength and pulse duration sufficient to transform said cells, wherein said field strength is from about 8 to about 15 kV/cm.

17. The method of claim 16, wherein said pulse duration is from about 1 ms to about 10 ms.

18. The method of claim 16, wherein said resistance is from about 13 ohms to about 720 ohms.

19. The method of claim 18, wherein said resistance is about 129 ohms.

* * * * *

SEQUENCE LISTING

```
<160> NUMBER OF SEQ ID NOS: 3

<210> SEQ ID NO 1
<211> LENGTH: 1493
<212> TYPE: DNA
<213> ORGANISM: Candida famata
<220> FEATURE:
<221> NAME/KEY: misc_feature
<222> LOCATION: (576)..(576)
<223> OTHER INFORMATION: May be any nucleotide
<220> FEATURE:
```

-continued

```
<221> NAME/KEY: misc_feature
<222> LOCATION: (626)..(626)
<223> OTHER INFORMATION: May be any nucleotide
<220> FEATURE:
<221> NAME/KEY: misc_feature
<222> LOCATION: (966)..(966)
<223> OTHER INFORMATION: May be any nucleotide
<220> FEATURE:
<221> NAME/KEY: misc_feature
<222> LOCATION: (1000)..(1000)
<223> OTHER INFORMATION: May be any nucleotide
<220> FEATURE:
<221> NAME/KEY: misc_feature
<222> LOCATION: (1084)..(1084)
<223> OTHER INFORMATION: May be any nucleotide
<220> FEATURE:
<221> NAME/KEY: misc_feature
<222> LOCATION: (1149)..(1149)
<223> OTHER INFORMATION: May be any nucleotide
<220> FEATURE:
<221> NAME/KEY: misc_feature
<222> LOCATION: (1174)..(1174)
<223> OTHER INFORMATION: May be any nucleotide
<220> FEATURE:
<221> NAME/KEY: misc_feature
<222> LOCATION: (1197)..(1197)
<223> OTHER INFORMATION: May be any nucleotide
<220> FEATURE:
<221> NAME/KEY: misc_feature
<222> LOCATION: (1223)..(1223)
<223> OTHER INFORMATION: May be any nucleotide
<220> FEATURE:
<221> NAME/KEY: misc_feature
<222> LOCATION: (1226)..(1226)
<223> OTHER INFORMATION: May be any nucleotide
<220> FEATURE:
<221> NAME/KEY: misc_feature
<222> LOCATION: (1251)..(1251)
<223> OTHER INFORMATION: May be any nucleotide
<220> FEATURE:
<221> NAME/KEY: misc_feature
<222> LOCATION: (1268)..(1268)
<223> OTHER INFORMATION: May be any nucleotide
<220> FEATURE:
<221> NAME/KEY: misc_feature
<222> LOCATION: (1280)..(1280)
<223> OTHER INFORMATION: May be any nucleotide
<220> FEATURE:
<221> NAME/KEY: misc_feature
<222> LOCATION: (1318)..(1318)
<223> OTHER INFORMATION: May be any nucleotide
<220> FEATURE:
<221> NAME/KEY: misc_feature
<222> LOCATION: (1347)..(1347)
<223> OTHER INFORMATION: May be any nucleotide
<220> FEATURE:
<221> NAME/KEY: misc_feature
<222> LOCATION: (1375)..(1375)
<223> OTHER INFORMATION: May be any nucleotide
<220> FEATURE:
<221> NAME/KEY: misc_feature
<222> LOCATION: (1379)..(1379)
<223> OTHER INFORMATION: May be any nucleotide
<220> FEATURE:
<221> NAME/KEY: misc_feature
<222> LOCATION: (1382)..(1382)
<223> OTHER INFORMATION: May be any nucleotide
<220> FEATURE:
<221> NAME/KEY: misc_feature
<222> LOCATION: (1385)..(1385)
<223> OTHER INFORMATION: May be any nucleotide
<220> FEATURE:
<221> NAME/KEY: misc_feature
<222> LOCATION: (1391)..(1391)
<223> OTHER INFORMATION: May be any nucleotide
<220> FEATURE:
<221> NAME/KEY: misc_feature
<222> LOCATION: (1410)..(1410)
<223> OTHER INFORMATION: May be any nucleotide
```

```
<220> FEATURE:
<221> NAME/KEY: misc_feature
<222> LOCATION: (1424)..(1424)
<223> OTHER INFORMATION: May be any nucleotide
<220> FEATURE:
<221> NAME/KEY: misc_feature
<222> LOCATION: (1428)..(1428)
<223> OTHER INFORMATION: May be any nucleotide
<220> FEATURE:
<221> NAME/KEY: misc_feature
<222> LOCATION: (1435)..(1435)
<223> OTHER INFORMATION: May be any nucleotide
<220> FEATURE:
<221> NAME/KEY: misc_feature
<222> LOCATION: (1437)..(1437)
<223> OTHER INFORMATION: May be any nucleotide
<220> FEATURE:
<221> NAME/KEY: misc_feature
<222> LOCATION: (1447)..(1447)
<223> OTHER INFORMATION: May be any nucleotide
<220> FEATURE:
<221> NAME/KEY: misc_feature
<222> LOCATION: (1457)..(1457)
<223> OTHER INFORMATION: May be any nucleotide
<220> FEATURE:
<221> NAME/KEY: misc_feature
<222> LOCATION: (1459)..(1459)
<223> OTHER INFORMATION: May be any nucleotide
<220> FEATURE:
<221> NAME/KEY: misc_feature
<222> LOCATION: (1472)..(1472)
<223> OTHER INFORMATION: May be any nucleotide
<220> FEATURE:
<221> NAME/KEY: misc_feature
<222> LOCATION: (1484)..(1484)
<223> OTHER INFORMATION: May be any nucleotide

<400> SEQUENCE: 1
cttgactgat tacgaattcg agctcggtac ccgggggatca tgaatgctag tcttttttaca      60
ctgaatattt ttttaacgat tttttaataa ttttgcaatc atttaagaaa aaccacaaat       120
ggttttccaa aatttaaatt gattttttag aaagtcctaa aaaatagaat cataccaaat       180
aaagaacaac ttaaagtcac tatgacaaat tcagaaatac aatcgtatga tccgttcatg       240
gataaagctg caaagtcaca agcaaggcta actaagatcc tctagggga tcctctagag       300
tcgactacgt cgttaaggcc gtttctgaca gagtaaaatt cttgagggaa ctttcaccat       360
tatgggaaat ggttcaagaa ggtattgact taaactccat caaatggtca ggtcattgag       420
tgttttttat ttgttgtatt tttttttttt tagagaaaat cctccaatat ataaattagg      480
aatcatagtt tcatgatttt tagagaaaat cctccaatat ataaattagg aatcatagtt      540
tcatgatttt ctgttacacc taacttttttg tgtggngccc tcctccttgt caatattaat     600
ctgttacacc taacttttttg tgtggngccc tcctccttgt caatattaat gttaaagtgc     660
aattcttttt ccttatcacg ttgagccatt agtatcaatt gttaaagtgc aattcttttt      720
ccttatcacg ttgagccatt agtatcaatt tgcttacctg tattcctttta catcctcctt     780
tttctccttc ttgataaatg tgcttacctg tattcctttta catcctcctt tttctccttc     840
ttgataaatg tatgtagatt gcgtatatag tttcgtctac cctatgaaca tattccattt     900
tatgtagatt gcgtatatag tttcgtctac cctatgaaca tattccattt tgtaatttcg     960
tgtcgnttct attatgaatt tcatttataa aggttatgtn tgtaatttcg ggcgttttcta   1020
ttatgaattt catttataaa gtttatgtcc aatatcataa aaaagagaa tcttttttaag   1080
caanggattt cttaactcaa atatcataaa aaaagagaat cttttttaagc aagggatttt  1140
cttaactttnt tcggggacgc atccccgctt cggnggactg gtggacccct aaatctnttc  1200
```

-continued

```
ggcgacagca tcccgacttc ggnggnactg tggaacccct aaatcccagt ntgatcctgc    1260
ttccaaanct tttactggtn ttcatgggcc taccccagtt ctgaacctgc atccaaanct    1320
tttactgctc ttcaagggct taccttntca ggcaggtcaa tgacaattca catcntgcnc    1380
anacnaaaaa nggcttttca gcaggtcaan gcaatttcac atcntgcnca aaaananagt    1440
ggcgatnggg tgacctntnt ttggcaacga tngggtgacc tatntttgca aac           1493
```

<210> SEQ ID NO 2
<211> LENGTH: 414
<212> TYPE: DNA
<213> ORGANISM: Pichia guilliermondii

<400> SEQUENCE: 2

```
tatgcacatt cgcacgccga ggtgcagcgt ttaggcgcgg ctcaacggaa gccaacggcc     60
gccacaaatt gtccggaaag tcgccgaaac tgatccactg gtaccacagc cccataagaa    120 cccccttaa tattaaaaac cgttcttcag ccacttttga tcacattgtt tgcagccgcc     180
cgttgctgcc atccaaacac cacgcgtccc ccgcacccct ttacggtgcc cactgcattg    240
gaatttgcat aaaacagcct cacgaagtgg attaatttt agagcactca agtcatcatg    300
ctgcaatctc tgcatcatga aatgactccc gttgatacag ggaactcaga ccgcaagcgg    360
cgaagagtca caagagcgtg tgatgtgtgt cgactctaga ggatccccgg gtac          414
```

<210> SEQ ID NO 3
<211> LENGTH: 487
<212> TYPE: DNA
<213> ORGANISM: Candida famata
<220> FEATURE:
<221> NAME/KEY: misc_feature
<222> LOCATION: (415)..(415)
<223> OTHER INFORMATION: May be any nucleotide

<400> SEQUENCE: 3

```
tgattacgaa ttcgagctcg gtacccgggg atcatgaatg ctagtctttt tacactgaat     60 attttttaa cgattttta ataattttgc aatcatttaa gaaaaaccac aaatggtttt     120
ccaaaattta aattgatttt ttagaaagtc ctaaaaaata gaatcatacc aaataaagaa    180
caacttaaag tcactatgac aaattcagaa atacaatcgt atgatccgtt catggataaa    240
gctgcaaagt cacaagcaag gctaactaag atcctctaga gtcgactacg tcgttaaggc    300
cgtttctgac agagtaaaat tcttgaggga actttcacca ttatgggaaa tggttcaaga    360
aggtattgac ttaaactcca tcaaatggtc aggtcattga gtgttttta tttgntgtat     420 ttttttttt ttagagaaaa tcctccaata tataaattag gaatcatagt ttcatgattt     480
tctgtta                                                               487
```